US006242616B1

(12) United States Patent
Smith, III et al.

(10) Patent No.: US 6,242,616 B1
(45) Date of Patent: Jun. 5, 2001

(54) SYNTHETIC TECHNIQUES AND INTERMEDIATES FOR POLYHYDROXY, DIENYL LACTONE DERIVATIVES

(75) Inventors: Amos B. Smith, III, Merion; Thomas J. Beauchamp, Media; Matthew J. LaMarche, Philadelphia, all of PA (US); Hirokazu Arimoto, Shizuoka (JP)

(73) Assignee: The Trustees of the University of Pennsylvania

( * ) Notice: Subject to any disclaimer, the term of this patent is extended or adjusted under 35 U.S.C. 154(b) by 0 days.

(21) Appl. No.: 09/455,649

(22) Filed: Dec. 7, 1999

Related U.S. Application Data

(63) Continuation-in-part of application No. 09/121,551, filed on Jul. 23, 1998, now Pat. No. 6,096,904, which is a continuation of application No. 09/021,878, filed on Feb. 11, 1998, now Pat. No. 6,031,133, and a continuation of application No. 08/759,817, filed on Dec. 3, 1996, now Pat. No. 5,789,605.

(51) Int. Cl.[7] ...................... C07D 309/30; C07D 309/10; C07D 309/32

(52) U.S. Cl. .................. 549/292; 549/416; 549/419; 549/273; 549/293; 549/294; 560/129; 568/579; 568/626

(58) Field of Search ................................. 549/292, 293, 549/294, 273, 416, 419; 560/129; 568/579, 626

(56) References Cited

FOREIGN PATENT DOCUMENTS 2280677    2/1995  (GB) .

OTHER PUBLICATIONS

Clark, D.L. et al., "Studies on the Alkylation of Chiral Enolates: Application toward the Total Synthesis of Discodermolide", *J. Org. Chem.*, 1993, 58, 5878–5879.
Evans, P.L. et al., "The Synthesis of a $C_9$–$C_{17}$ Lactone Fragment of Discodermolide", *Tetra. Lett.*, 1993, 34(50), 8163–8166.
Golec, J.M.C. et al., "The Synthesis of a $C_1$–$C_8$ Lactone Fragment of Discodermolide", *Tetra. Lett.*, 1993, 34(50), 8159–8162.
Golec, J.M.C. et al., "An Approach to the Synthesis of a $C_9$–$C_{15}$ Fragment of Discodermolide", *Tetra. Lett.*, 1993, 34(50), 8167–8168.
Golec, J.M.C. et al., "Total synthesis of discodermolide", *Chemical Abstracts*, 1995, 123, 831, Abstract No. 32864j.
Greene and Wuts, Protective Groups in Organic Synthesis, 2d Edition, John Wiley & Sons, New York, 1991.
Gunasekera et al., "Discodermolide: A New Bioactive Polyhydroxylated Lactone from the Marine Sponge *Discodermia dissoluta*", *J. Org. Chem.*, 1990, 55, 4912–4915.

Gunasekera, et al., "Discodermolide: A New Bioactive polyhydroxylated Lactone from the Marine Sponge *Discodermia dissoluta*", *J. Org. Chem.*, 1991, 56, 1346.
Hodges et al., "Reactions to Lithiooxazole", *J. Org. Chem.*, 1991, 56, 449–452.
Hodgson, et al., "Regio– and Stereo–Selective Reactions of Trimethylsilyl–Substituted Allyl–Chromium Reagents with Aldehydes", *Tetrahedron Letters*, 1992, 33, 4761–4762.
Hung et al., "Distinct binding and cellular properties of synthetic (+)–and (–)–discodermolides", *Chem. & Biol.*, 1994, 1(1), 67–71.
Hung et al., "(+)–Discodermolide binds to microtubules in stoichiometric ratio to tubulin dimers, blocks taxol binding and results in mitotic arrest", *Chem. & Biol.*, 1996, 3(4), 287–293.
Hung, D.T. et al., "Syntheses of Discodermolides Useful for Investigating Microtubule Binding and Stabilization", *J. Am. Chem. Soc.*, 1996, 118, 11054–11080.
Jacquesy et al., "Metabromation Du Dimethyl–2,6 Phenol Et De Son Ether Methylique En Milieu Superacide", *Tetrahedron*, 1981, 37, 747–751.
Kim et al., "Conversion of Acetals into Monothioacetals, α–Alkoxyazides and α–Alkoxyalkyl Thioacetates with Magnesium Bromide", *Tetra. lett.*, 1989, 30(48), 6697–6700.
Longley et al., "Discodermolide—A New, Marine–Derived Immunosuppressive Compound", *Transplantation*, 1991, 52(4), 650–656,657–661.
Longley et al., "Immunosuppression by Discodermolide", *Ann. N.Y. Acad. Sci.*, 1993, 696, 94–107.
Nerenberg et al., "Total Synthesis of the Immunosuppressive Agent (—)–Discodermolide", *J. Am. Chem. Soc.*, 1993, 115, 12621–12622.
Paterson, I. et al., "Studies Towards the Total Synthesis of the Marine–derived Immunosuppressant Discodermolide; Asymmetric Synthesis of a $C_1$–$C_8$ δ–lactone Subunit", *J. Chem. Soc. Chem. Commun.*, 1993, 1790–1792.
Paterson, I. et al., "Studies Towards the Total Synthesis of the Marine–derived Immunosuppressant Discodermolide; Asymmetric Synthesis of a $C_9$–$C_{24}$ Subunit", *Synlett*, 1995, 498–500.
Paterson, "α–Alkylation of Ketones, Esters and Lactons: Zinc Bromide–Catalysed Alkylation of o –Silylated Enolates, A Synthesis of (+)—AR–Turmerone", *Tetrahedron Letters*, 1979, 1519–1520.

(List continued on next page.)

*Primary Examiner*—C. S. Aulakh
(74) *Attorney, Agent, or Firm*—Woodcock Washburn Kurt Mackiewicz & Norris LLP

(57) ABSTRACT

Synthetic methods for lactone-containing compounds such as the discodermolides are provided, as are compounds which mimic the chemical and/or biological activity thereof, and methods and intermediates useful in their preparation.

14 Claims, 55 Drawing Sheets

OTHER PUBLICATIONS

Remington's Pharmaceutical Sciences, Mack Publishing Company, Easton, PA, 1980.

Roush et al., "Acyclic Diastereoselective Synthesis Using Tartrate Ester Modified Crotylboronates. Double Asymmetric Reactions with α–Methyl Chiral Aldehydes and Synthesis of the C(19)–C(29) Segment of Rifamycin S", *J. Am. Chem. Soc.*, 1990, 112, 6348–6359.

Smith et al., "Total Synthesis of (–)-Discodermolide", *J. Am. Chem. Soc.*, 1995, 117, 12011–12012.

Smith, A. B. et al., "Total Synthesis of (–)-Discodermolide Exploiting a Common Precursor", *J. Am. Chem. Soc.*, (Submission Copy), 1–60.

Solladie et al., "Asymmetric Synthesis of Polyhydroxylated Natural Products II. The C–1/C–12 Unit of Amphotericin B". *Tetra. Lett.*, 1987, 28(7), 797–800.

ter Haar et al., "Discodermolide, A Cytotoxic Marine Agent that Stabilizes Microtubules More Potently than Taxol", *Biochem.*, 1996, 35, 243–250.

Yang, G. et al., "The Synthsis of the C–9 to C–21 Sector of Discodermolide: An Efficient Route to the C13–14 Z–Trisubstituted Alkene", *Tetra. Lett.*, 1994, 35(16), 2503–2504.

Yang, G. et al., "An Alkylative Strategy to the C–13 to C–21 Sector of Discodermolide", *Tetra. Lett.*, 1994, 35(9), 1313–1316.

* Denote the repeating stereochemical triad

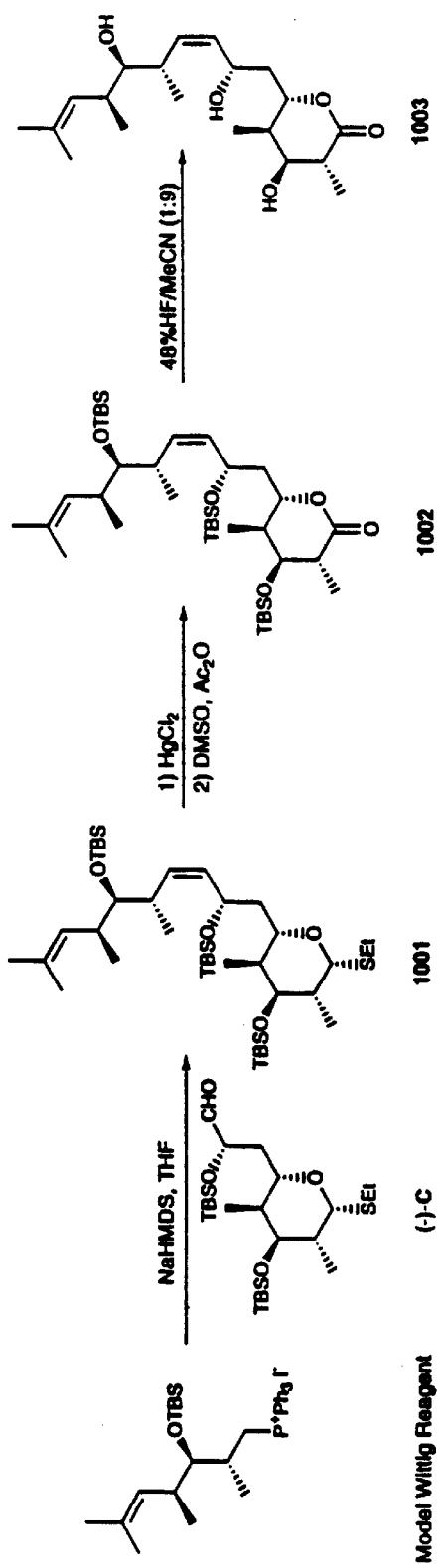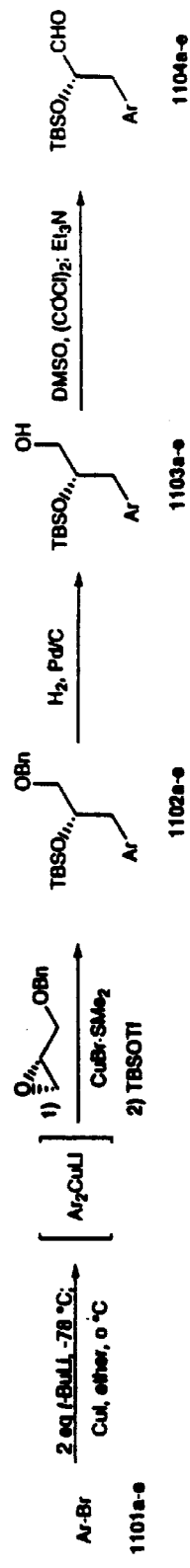

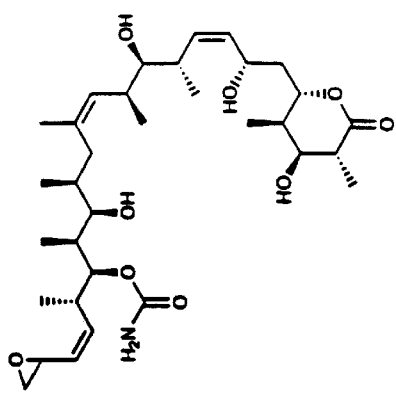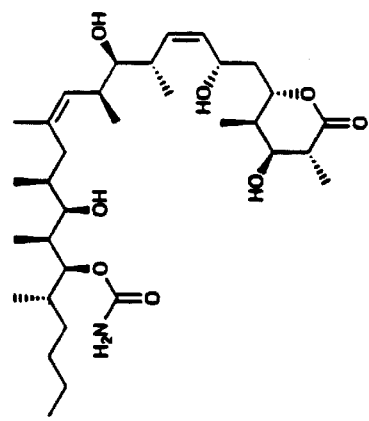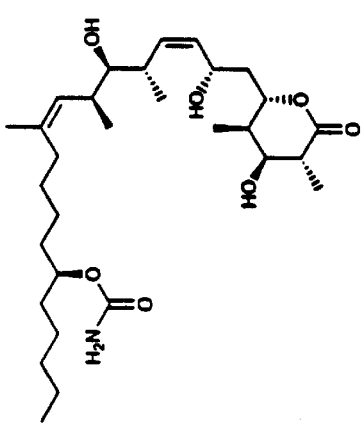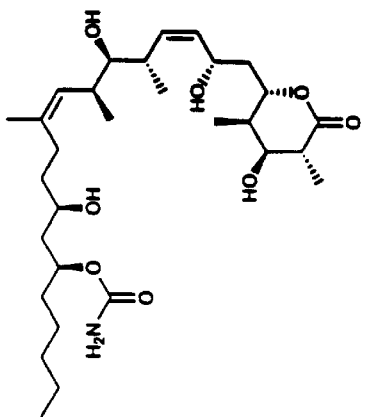
Figure 33

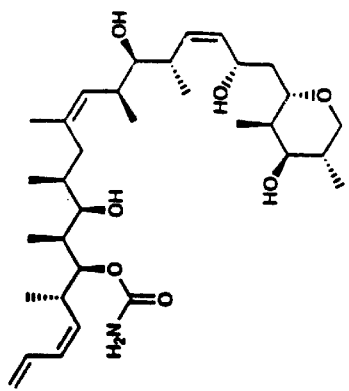
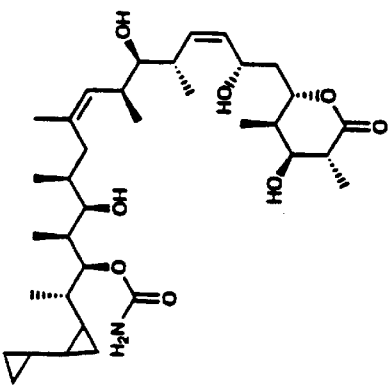
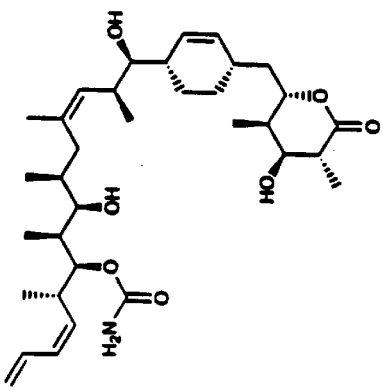
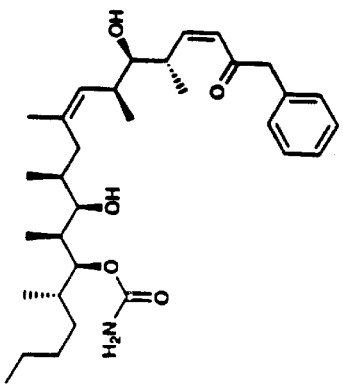
Figure 33A

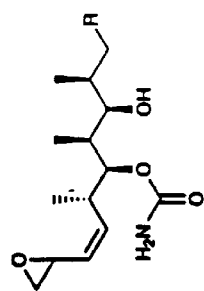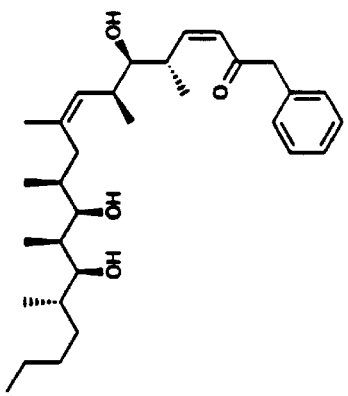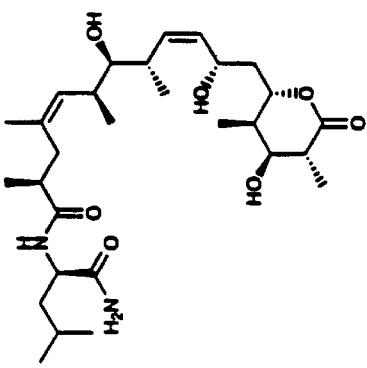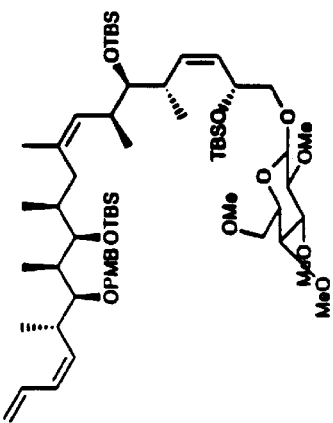
Figure 33B

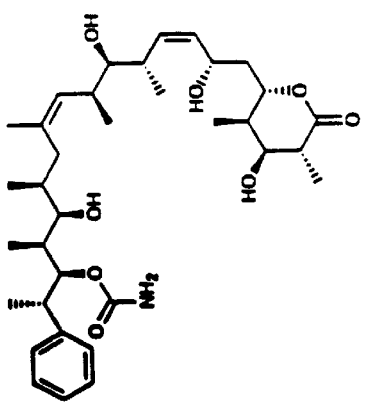
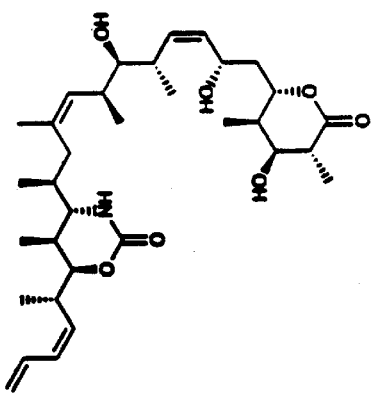
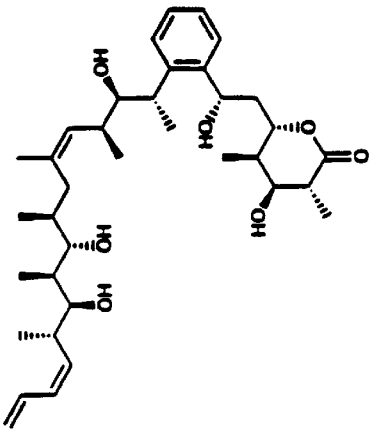
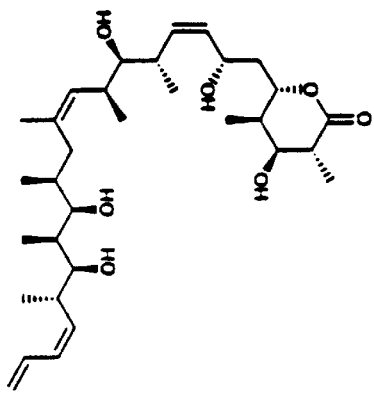
Figure 34A

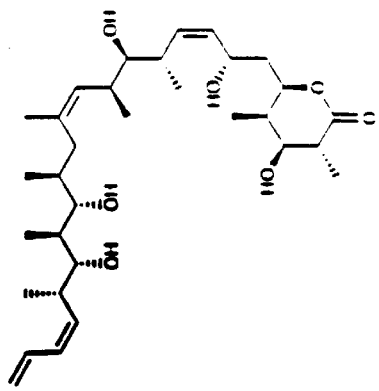
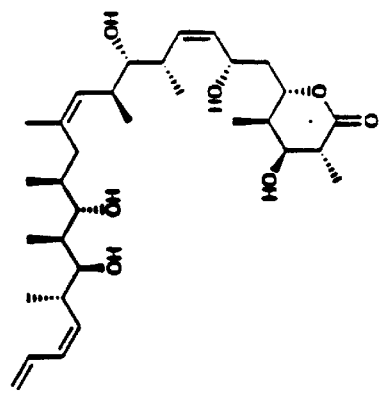
Figure 34B
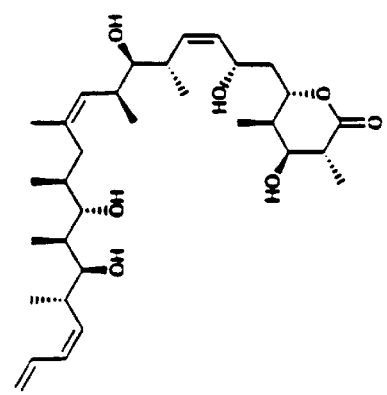
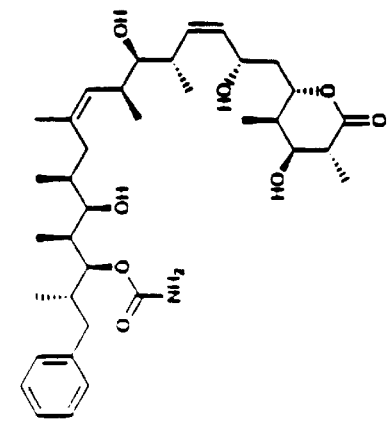

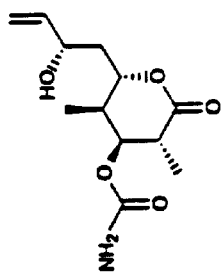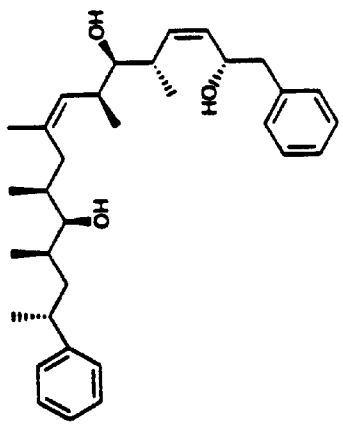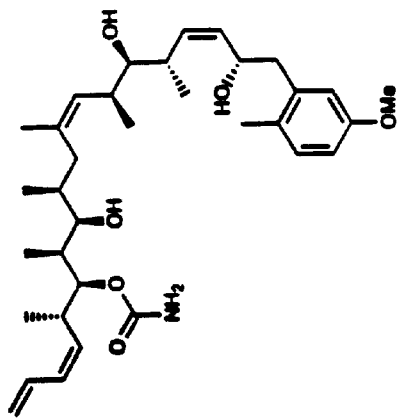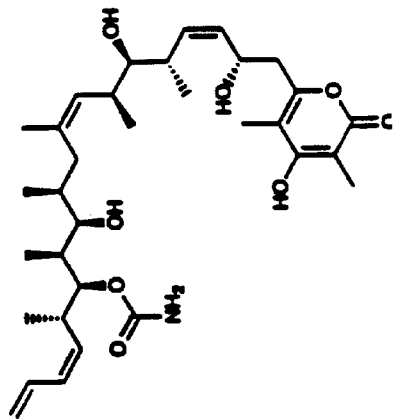
Figure 35

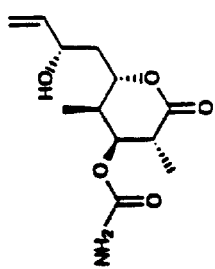
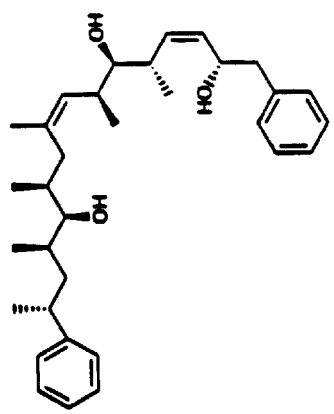
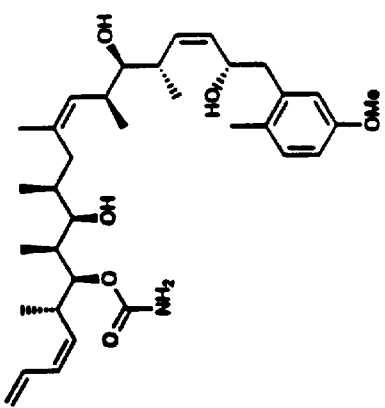
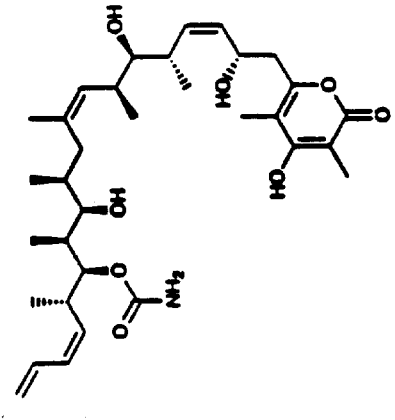
Figure 35A

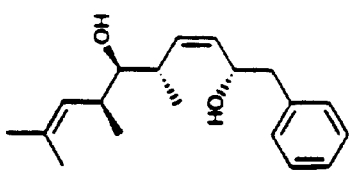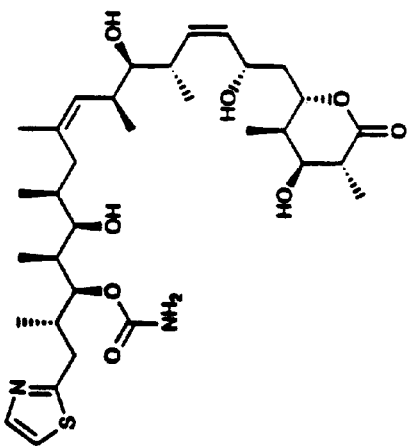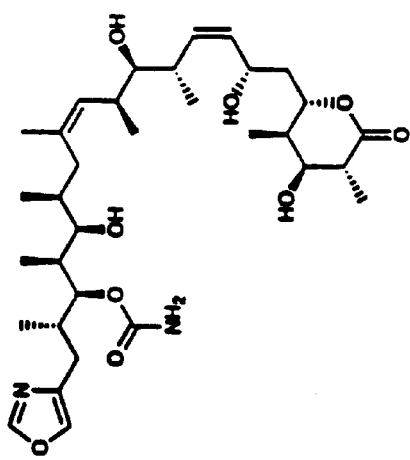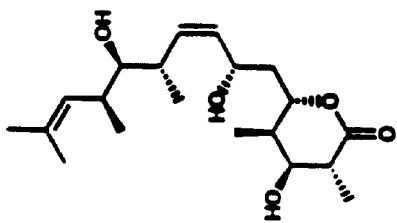
Figure 35B

Figure 40A
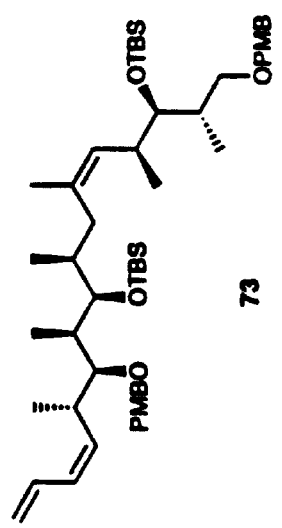
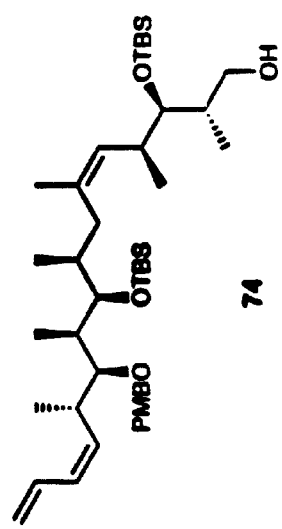

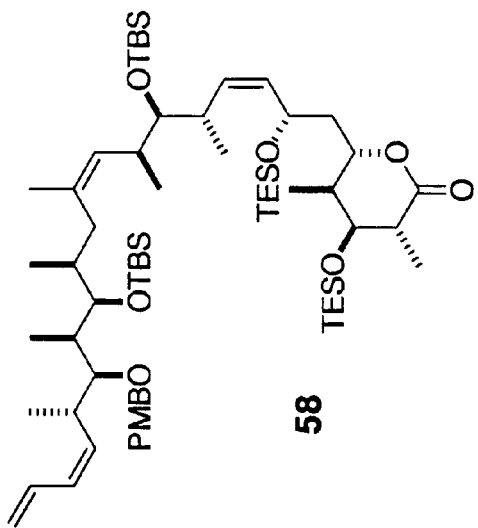
Figure 49
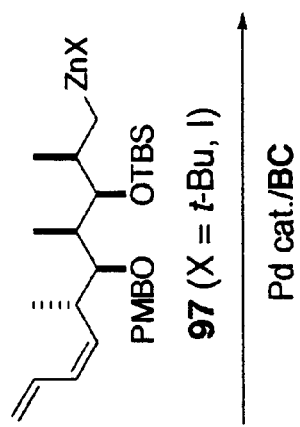
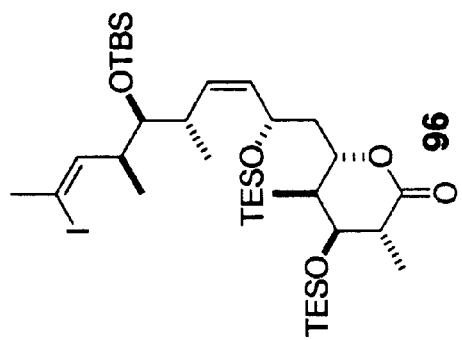

Figure 50
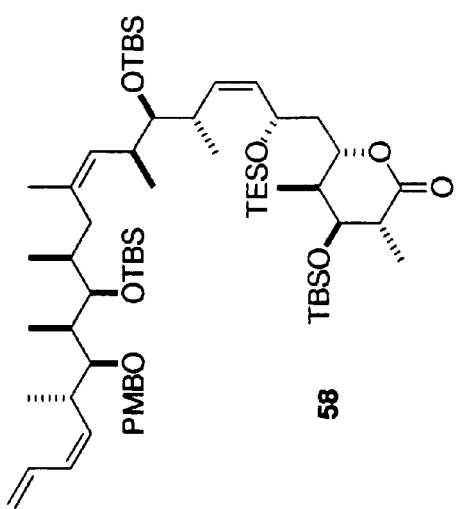
58
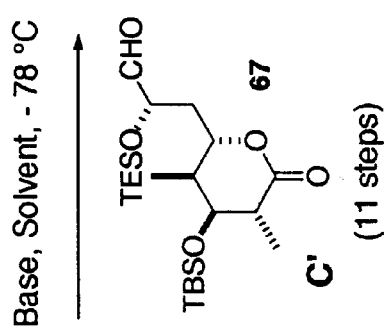
Base, Solvent, -78 °C
(11 steps)
C'  67
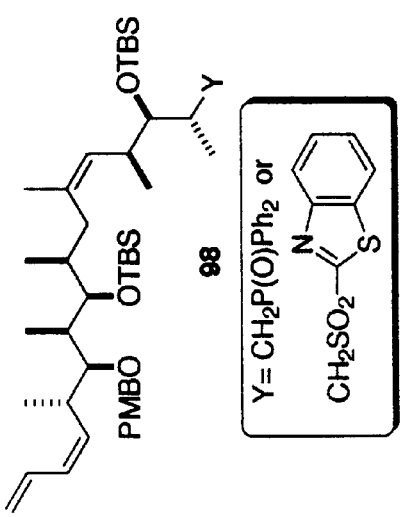
98
Y= CH₂P(O)Ph₂ or CH₂SO₂

SYNTHETIC TECHNIQUES AND INTERMEDIATES FOR POLYHYDROXY, DIENYL LACTONE DERIVATIVES

CROSS-REFERENCE TO RELATED APPLICATIONS

This is a continuation-in-part of U.S. patent application Ser. No. 09/121,551, filed Jul. 23, 1998 now U.S. Pat. No. 6,096,904.

RELATED APPLICATIONS DATA

This application is a continuation of U.S. patent application Ser. No. 08/759,817, filed Dec. 3, 1996 now U.S. Pat. No. 5,789,605 and a continuation of Ser. No. 09/021,878, filed Feb. 11, 1998 now U.S. Pat. No. 6,031,133.

GOVERNMENT SUPPORT

Certain of the inventors were supported by National Institutes of Health Grant GM-29028.

FIELD OF THE INVENTION

This invention relates to lactone-containing compounds such as discodermolide, to compounds which mimic the chemical and/or biological activity thereof, and to methods and intermediates useful in their preparation.

BACKGROUND OF THE INVENTION

In 1990, Gunasekera and co-workers at the Harbor Branch Oceanographic Institute reported the isolation of (+)-discodermolide (1), an architecturally novel metabolite of the marine sponge *Discodermia dissoluta* (0.002% w/w). (See, Gunasekera, et al., *J. Org. Chem.* 1990, 55, 4912. Correction: *J. Org. Chem.* 1991, 56, 1346).

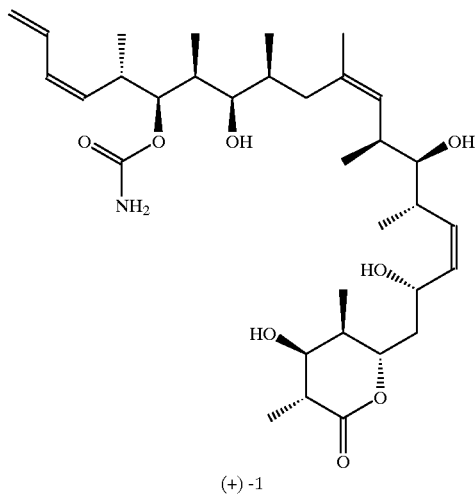

(+)-1

Initial studies revealed that (+)-discodermolide suppresses both the two-way mixed-lymphocyte reaction and the concanavalin A-induced mitogenesis of murine splenocytes in vitro with no associated cytotoxicity. Moreover, (+)-1 suppresses the in vivo graft-vs.-host splenomegaly response induced by injection of parental splenocytes into F1 recipient mice, with potency intermediate between those of cyclosporin A and FK506. (Longley, et al., *Transplantation* 1991, 52, 650; Longley, et al., *Transplantation* 1991, 52, 656; Longley, et al. *Ann. N.Y. Acad. Sci.* 1993, 696, 94).

These findings stimulated the recent discovery that (+)-1 arrests cell development at the M phase by binding and stabilizing mitotic spindle microtubules; thus discodermolide resembles taxol in its mode of action, but the microtubule binding affinity of 1 is much higher. (ter Haar, et al., *Biochemistry* 1996, 35, 243; Hung, et al., *Chemi. & Biol.* 1996, 3, 287). These and other results suggest that (+)-discodermolide holds considerable promise as an anti-cancer agent. The scarcity of natural material however has precluded a complete evaluation of its biological profile.

The absolute configuration of discodermolide remained undefined until Schreiber et al. synthesized both antipodes of 1. (Nerenberg, et al. *J. Am. Chem. Soc.* 1993, 115, 12621; Hung, et al., *Chem. & Biol.* 1994, 1, 67). Interestingly, the unnatural (−) antipode also displays significant immunosuppressant activity.

There is, therefore, a need for improved synthetic methods for the preparation of polyhydroxy, dienyl lactones such as the discodermolides, as well as a need for compounds having similar chemical and/or biological activity.

OBJECTS OF THE INVENTION

It is one object of the present invention to provide polyhydroxy, dienyl lactones and mimics thereof.

It is a further object to provide processes for the preparation of such compounds and their mimics.

It is another object of this invention to provide intermediates useful in such processes.

SUMMARY OF THE INVENTION

These and other objects are satisfied by the present invention, which, in one aspect, provides synthetic methods for the discodermolides and other polyhydroxylactones. In preferred embodiments, such methods involve contacting a phosphonium salt of formula I:

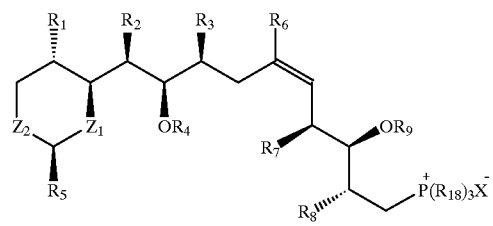

I with base and an alkylthiol of formula II:

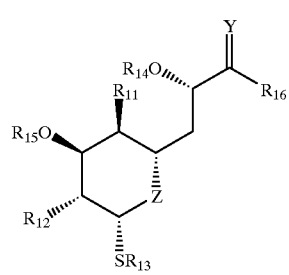

II to form a diene of formula III:

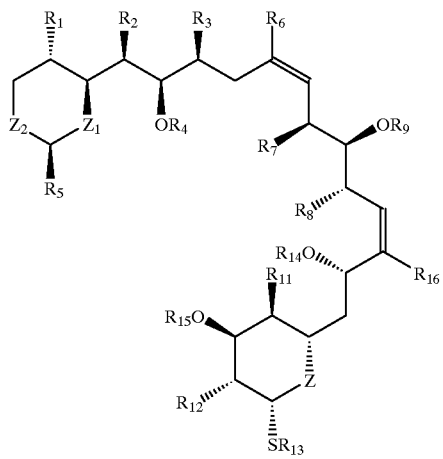

III wherein:

$R_1$, $R_2$, $R_3$, $R_7$, $R_8$, $R_{11}$, $R_{12}$ and $R_{13}$ are, independently, $C_1$–$C_{10}$ alkyl;

$R_6$ is H or $C_1$–$C_{10}$ alkyl;

X is a halogen;

Z, $Z_1$, and $Z_2$ are, independently, O, S or NR';

$R_4$, $R_9$, $R_{14}$, and $R_{15}$ are, independently, acid labile hydroxyl protecting groups;

$R_5$ is $C_6$–$C_{14}$ aryl;

Y is O, S or NR';

R' and $R_{16}$ are, independently, hydrogen or $C_1$–$C_6$ alkyl; and $R_{18}$ is $C_6$–$C_{14}$ aryl.

In another embodiment, compounds of formula I are contacted with compounds of the following formula XXIII:

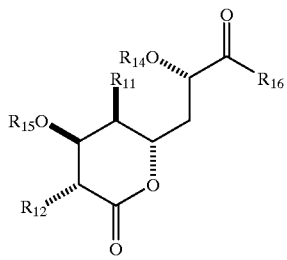

XXIII to form a diene of formula XXXXX:

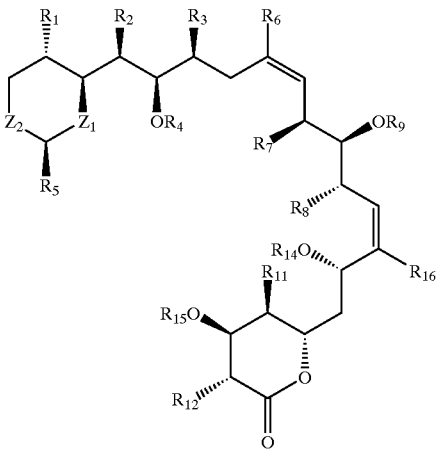

XXXXX

In another aspect, the methods of the invention involve producing an alkene of formula IV.

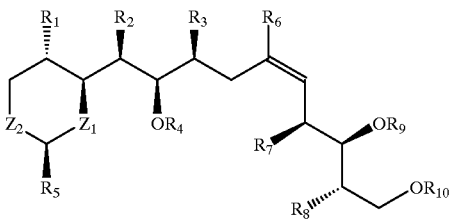

IV

This can be accomplished by contacting an organometallic reagent of formula Va:

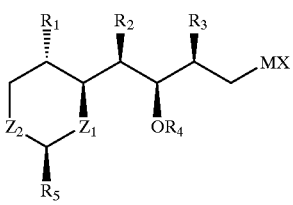

Va with a vinyl halide of formula VIa:

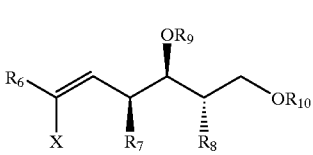

VIa wherein M is Li, Cu, Mg, or Zn and $R_{10}$ is an acid stable hydroxyl protecting group and all other variables are as defined above. Alternatively, a vinyl halide of formula Vb:

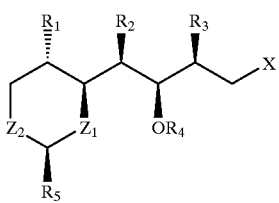

Vb can be contacted with an organometallic compound of formula VIb:

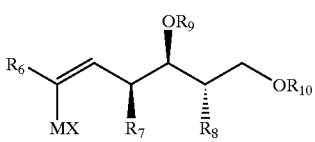

VIb

In yet another aspect, the methods of the invention involve compounds having formula VII.

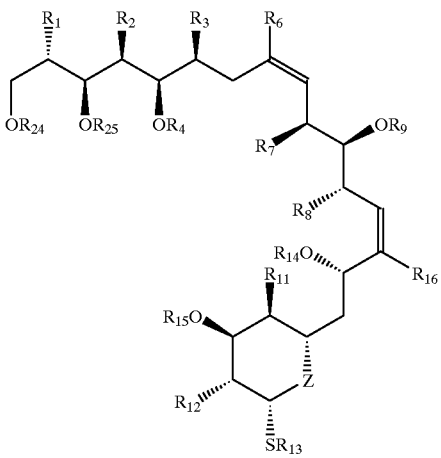

VII by contacting a diene of formula VIIIa:

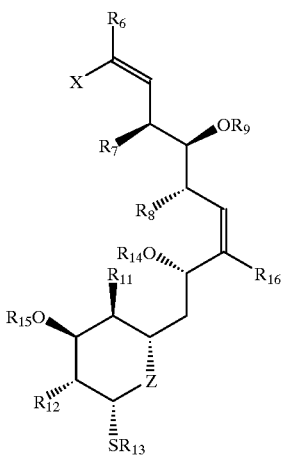

VIIIa with an organometallic compound having formula Va wherein $R_{24}$ is hydrogen and $R_{25}$ is hydrogen or an acid stable hydroxyl protecting group. Alternatively, an organometallic compound having formula VIIIb can be contacted with a vinyl halide having formula Vb.

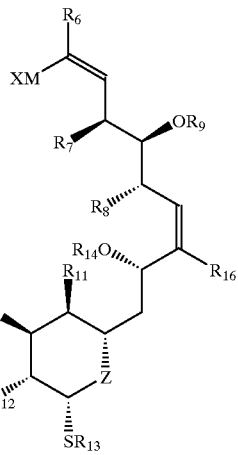

VIIIb

The methods of the invention also involve producing dienes having formula VIIIa by contacting phosphonium salts having formula IX:

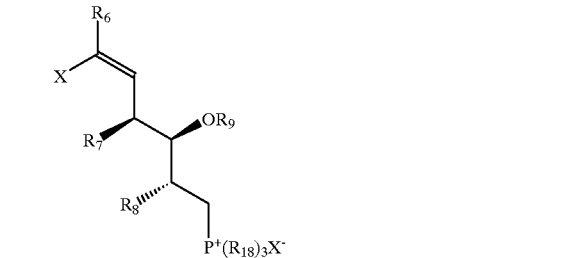

IX with base and alkylthiol compounds having formula II.

The present invention also provides synthetic intermediates which are useful in the preparation of polyhydroxylactones, including the compounds having formulas I–IX and X:

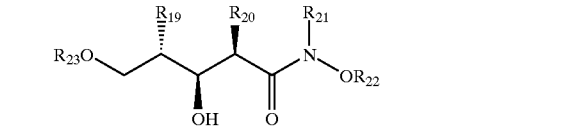

X wherein:

$R_{19}$, $R_{20}$, $R_{21}$ and $R_{22}$ are, independently, $C_1$–$C_{10}$ alkyl; and $R_{23}$ is $C_7$–$C_{15}$ aralkyl.

The present invention also provides compounds which mimic the chemical and/or biological activity of the discodermolides. In preferred embodiments, such compounds have formula XI:

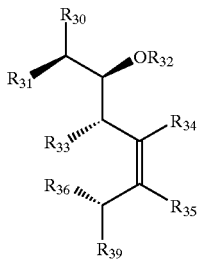

XI where
R$_{30}$ is substituted or unsubstituted C$_1$–C$_{10}$ alkyl or a moiety formula XII or XIII:

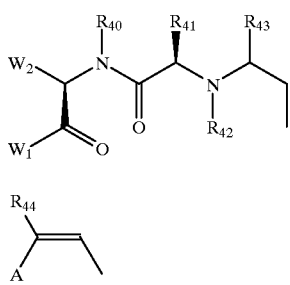

XII

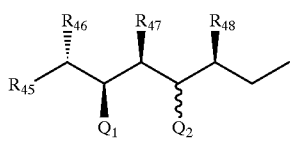

XIII where A is C$_1$–C$_{20}$ alkyl, —CH$_2$NH(T) or a moiety of formula XIV:

XIV wherein
T is peptide having 1 to about 10 amino acids;
R$_{32}$, R$_{40}$, R$_{42}$, R$_{43}$, R$_{46}$, R$_{47}$, and R$_{48}$ are, independently, hydrogen or C$_1$–C$_6$ alkyl;
R$_{41}$ is a side chain of an amino acid;
W$_1$ and W$_2$ are, independently, —OR$_{49}$ or —NHP$_1$;
P$_1$ is hydrogen or an amine protecting group;
R$_{33}$ and R$_{36}$ are, independently, hydrogen, C$_1$–C$_{10}$ alkyl, —OR$_{50}$, =O or together form —CH$_2$—CH$_2$—;
R$_{34}$ and R$_{35}$ are, independently, hydrogen or together form —C(H)=C(H)—C(H)=C(H)—;
R$_{39}$ is —OR$_{51}$ or —CH$_2$—R$_{51}$;
R$_{31}$ and R$_{44}$ are, independently, C$_1$–C$_{10}$ alkyl;
Q$_1$ and Q$_2$ are, independently, hydrogen, —OR$_Q$, —NHR$_{52}$, —OC(=O)NH$_2$ or together form —O—C(O)—NH—;
R$_Q$ is hydrogen or a hydroxyl protecting group;
R$_{51}$ is substituted or unsubstituted C$_6$–C$_{14}$ aryl, tetrahydropyranyl, furanosyl, pyranosyl (e.g., tetramethylfucosyl, tetramethylmannosyl, tetramethylgaractosyl and tetramethylglucosyl), C$_3$–C$_{10}$ lactonyl or 2-pyranonyl;
R$_{45}$ is C$_1$–C$_6$ alkenyl, C$_1$–C$_6$ alkyl, C$_6$–C$_{14}$ aryl, C$_2$–C$_{10}$ heterocycloalkyl, C$_3$–C$_{10}$ cycloalkyl, or C$_7$–C$_{15}$ aralkyl; and R$_{49}$, R$_{50}$, and R$_{52}$ are, independently, hydrogen or C$_1$–C$_6$ alkyl.

In another aspect, the present invention provides processes for preparing amides having formula XX:

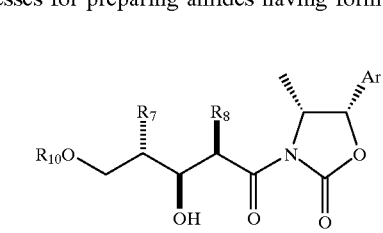

XX wherein Ar is C$_6$–C$_{14}$ aryl comprising the steps of contacting a compound having formula XXI:

XXI with a compound having formula XXII:

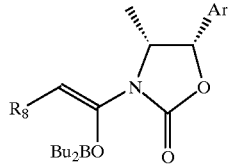

XXII for a time and under conditions effective to form the amide.

Also provided are processes for producing compounds of formula XXIII:

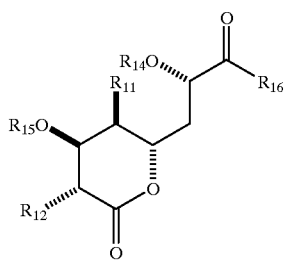

XXIII comprising the steps of contacting an aldehyde of formula XXIV:

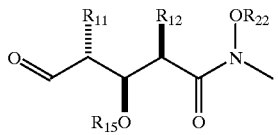

XXIV with an enol ether of formula XXV:

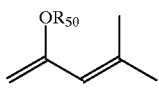

in the presence of a titanium salt for a time and under conditions effective to form an enone of formula XXVI:

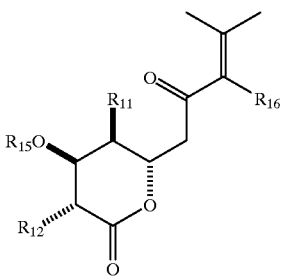
XXVI

Such enones are then contacted with a reducing agent for a time and under conditions effective to form a corresponding enol, which is contacted with a compound having formula R-L (wherein L is a leaving group) for a time and under conditions effective to form a protected enol. This protected enol is contacted with an oxidizing agent for a time and under conditions effective to oxidize the carbon—carbon double bond of the protected enol.

The invention also provides processes for producing halogenated olefins of formula XXVII:

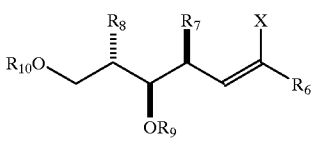
XXVII by contacting an aldehyde of formula XXVIII:

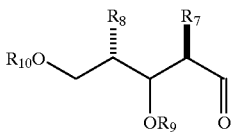
XXVIII with an α-halo sulfone of formula XXIX:

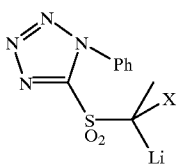
XXVIX for a time and conditions effective to from the halogenated olefin.

Also provided are processes for producing halogenated olefins of formula XXX:

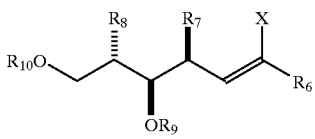
XXX comprising the steps of contacting a compound of formula XXXI:

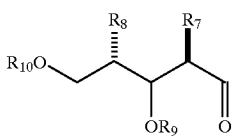
XXXI with triphenylphosphine and a carbon tetrahalide for a time and under conditions effective to form a dihalogenated olefin of formula XXXII:

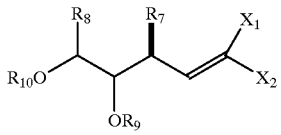
XXXII

Such a dihalogenated olefin is contacted with an organometallic compound (such as lithium dimethyl cuprate or an alkylzinc compound such as methyl zinc chloride or methyl zinc bromide) in the presence of a catalyst for a time and under conditions effective to form the halogenated olefin.

Additional processes of the invention are directed to synthesis of dienes of formula XXXIII:

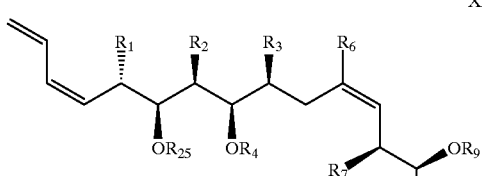
XXXIII

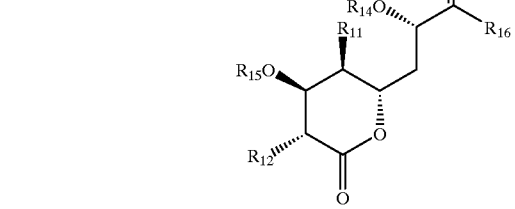

comprising contacting a phosphonium salt of formula XXXIV:

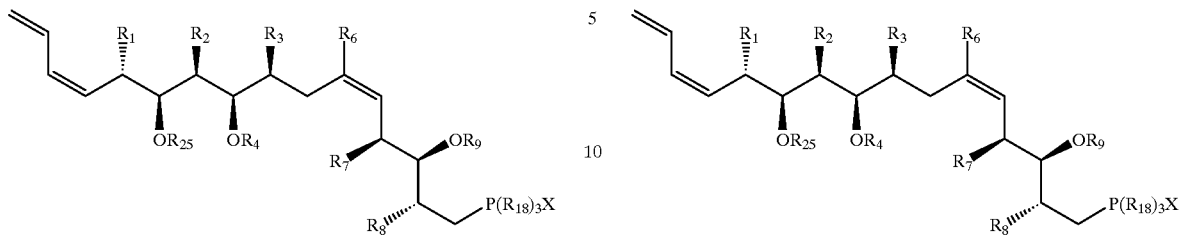
XXXIV with a base and a compound of formula XXXV.

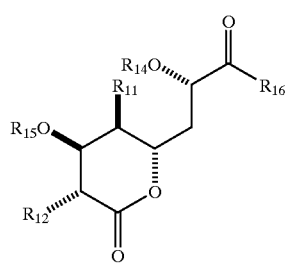
XXXV for a time and under conditions effective to form the diene.
The invention also provides processes for producing a compound of formula XXXVI:

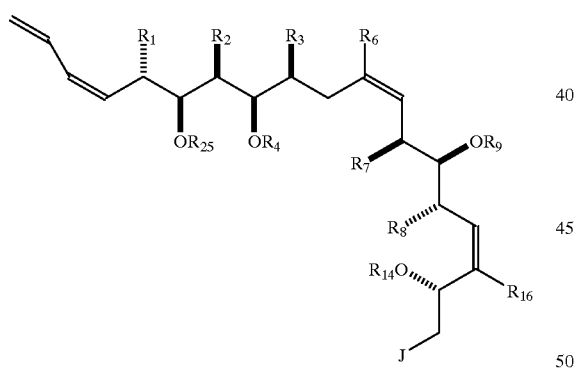
XXXVI comprising contacting a compound of the formula XXXVII:

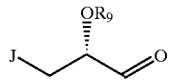
XXXVII wherein J is $C_1$–$C_{10}$ alkyl, $C_6$–$C_{14}$ aryl, $C_2$–$C_{10}$ heterocycloalkyl. or $C_2$–$C_{10}$ heterocycloalkenyl (preferably 4-methoxyphenyl, 4-hydroxyphenyl, 2-pyridyl, 3-pyridyl, or 4-pyridyl) with a phosphonium salt of formula XXXIV:

XXXIV and base.

The invention also provides synthetic intermediates having formulas XXXIII–XXXXV:

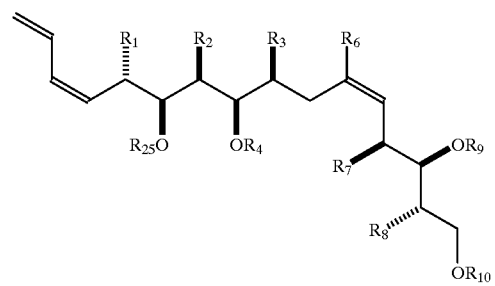
XXXIII

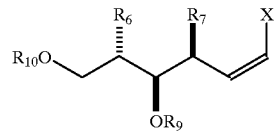
XXXIX

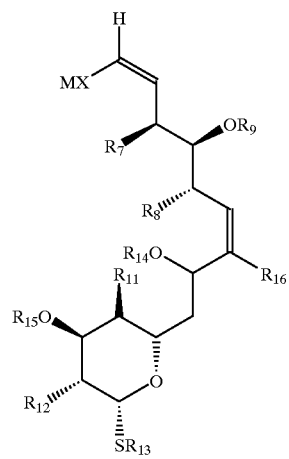
XXXX

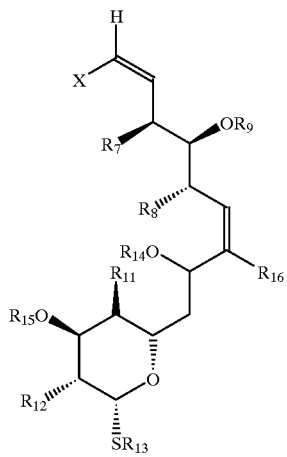

XXXXI

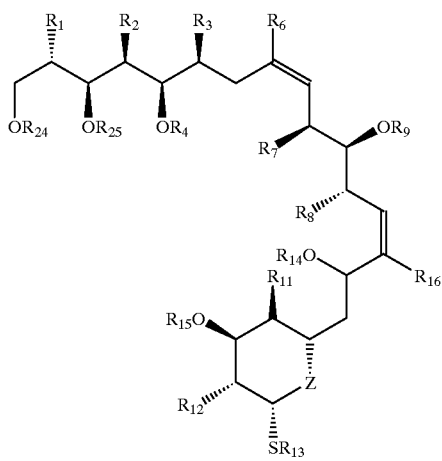

XXXXII

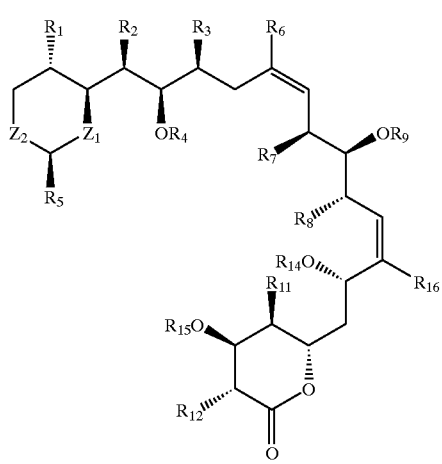

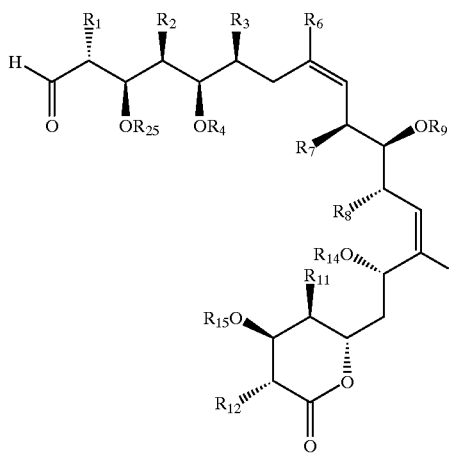

XXXXIV

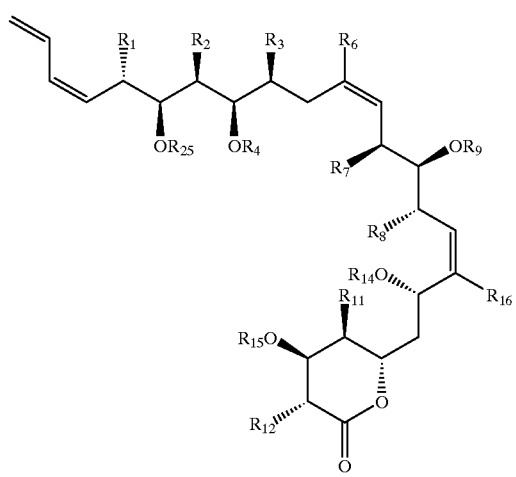

XXXXV

The present invention also provides methods for inhibiting mammalian cell proliferation by contacting mammalian cells with a compound according to the invention or by administering a compound according to the invention (or a pharmaceutical composition comprising such a compound) to a mammal suffering from undesired cell proliferation. Also provided are methods for inhibiting rejection of a transplanted organ in a mammal comprising administering a compound or composition according to the invention to a mammalian organ recipient.

The present invention also provides process for forming a halogenated olefin of formula:

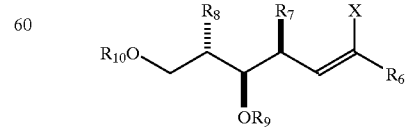

wherein:
R$_6$ is selected from H and C$_1$–C$_6$ alkyl;
R$_7$ and R$_8$ are independently C$_1$–C$_{10}$ alkyl;
R$_9$ is an acid labile hydroxyl protecting group;
R$_{10}$ is a protecting group labile to DDQ; and,
X is halogen;
the process comprising contacting an aldehyde of formula:

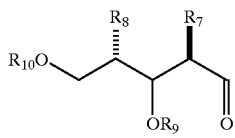

with a compound of formula R$_6$(R$_{18}$)$_3$PX and X$_2$ in the presence of base, wherein R$_{18}$ is C$_6$–C$_{14}$ aryl, for a time and conditions effective to form the halogenated olefin.

The present invention also provides a process for forming a triene of formula:

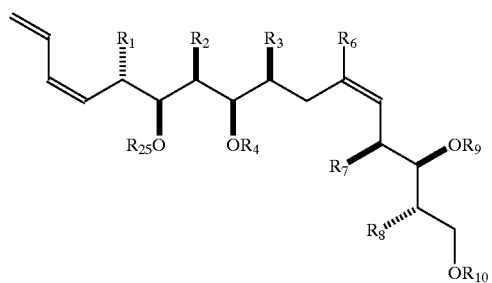

wherein:
R$_1$, R$_2$, R$_7$, and R$_8$ are independently C$_1$–C$_{10}$ alkyl;
R$_3$ and R$_6$ are independently selected from hydrogen and C$_1$–C$_6$ alkyl;
R$_4$ and R$_9$ are independently acid labile hydroxyl protecting groups;
R$_{25}$ is an acid stable hydroxyl protecting group; and
R$_{10}$ is a hydroxyl protecting group;
the process comprising contacting an aldehyde of formula:

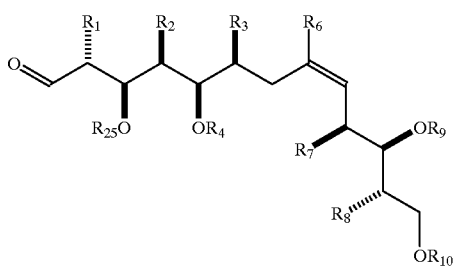

with a compound of formula Ph$_2$PCH$_2$CH=CH$_2$ in the presence of a base and a compound of formula Ti(O—R$_{27}$)$_4$, wherein R$_{27}$ is C$_{1-6}$ alkyl; followed by treatment with R$_{28}$X wherein R$_{28}$ is C$_{1-6}$ alkyl and X is a halogen, for a time and under conditions effective to form the triene.

The present invention also provides a process comprising contacting a triene of formula:

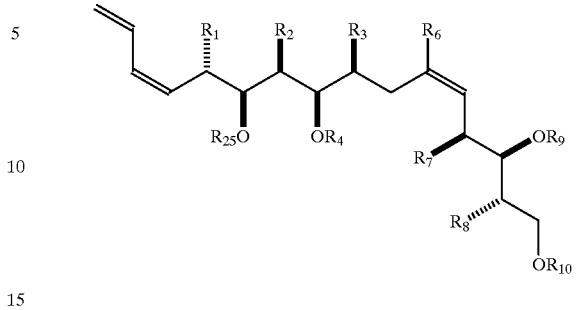

with a compound of formula:

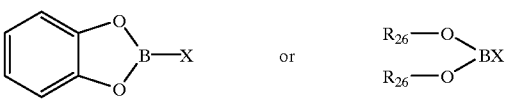

wherein X is a first halogen and R$_{26}$ is selected from C$_{6-14}$ aryl and C$_{1-6}$ alkyl, to form a triene alcohol of formula:

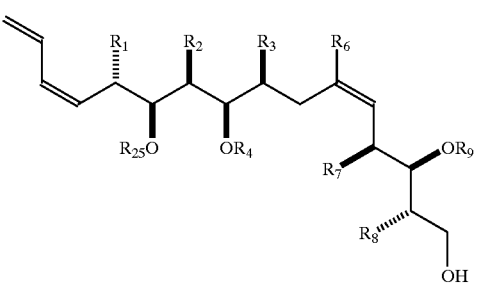

and;

contacting the triene alcohol with Y$_2$ in the presence of P(R$_{18}$)$_3$ and a base, wherein R$_{18}$ is C$_{6-14}$ aryl and Y is a second halogen, under conditions to form a compound of formula:

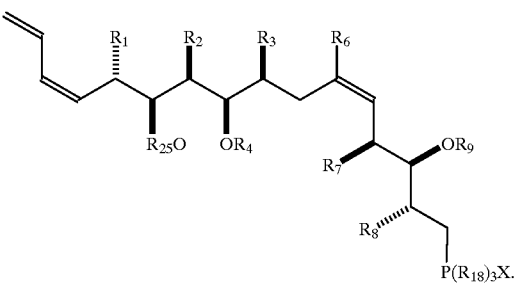

The present invention also provides a process of forming an aldehyde of formula:

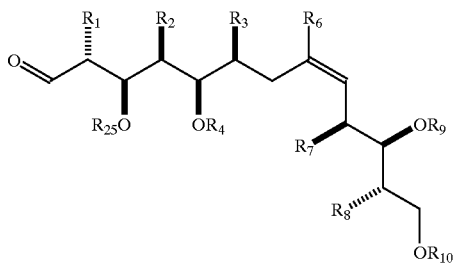

the process comprising contacting a compound of formula:

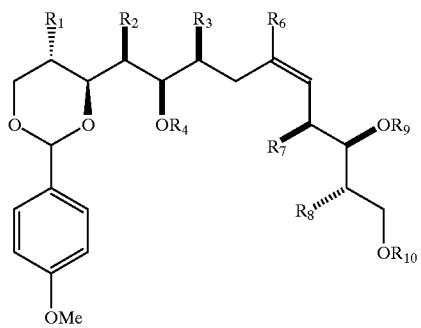

wherein:

$R_1$, $R_2$, $R_7$, and $R_8$ are independently $C_1-C_{10}$ alkyl;

$R_3$ and $R_6$ are independently selected from hydrogen and $C_1-C_6$ alkyl;

$R_4$ and $R_9$ are independently acid labile hydroxyl protecting groups; and $R_{10}$ is a trityl group;

with hydride to form an alcohol of formula:

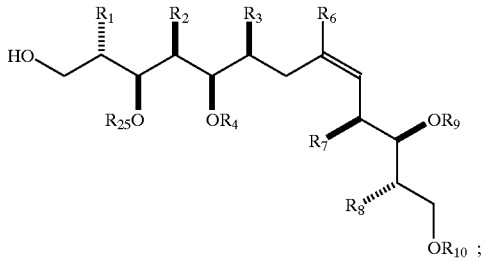

oxidizing the alcohol to form the aldehyde.

The present invention also provides a process for forming a tetraene of formula:

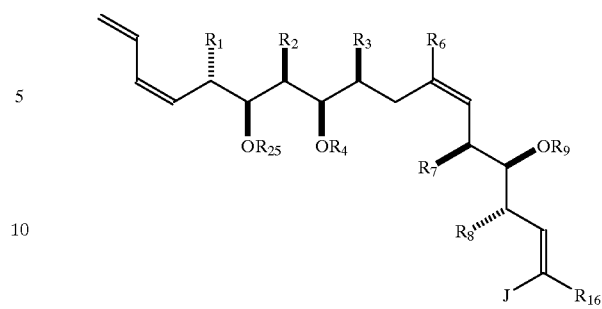

wherein:

$R_1$, $R_2$, $R_7$, and $R_8$ are independently $C_1-C_{10}$ alkyl;

$R_3$, $R_6$, and $R_{16}$ are independently selected from hydrogen and $C_1-C_6$ alkyl;

$R_4$ and $R_9$ are independently an acid labile hydroxyl protecting group;

$R_{25}$ is an acid stable hydroxyl protecting group; and

J is selected from:

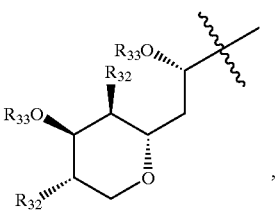

,

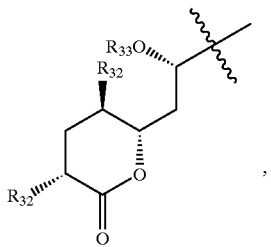

,

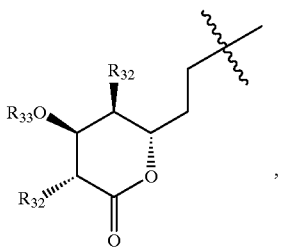

,

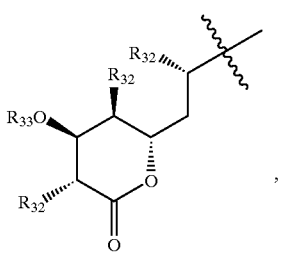

,

-continued

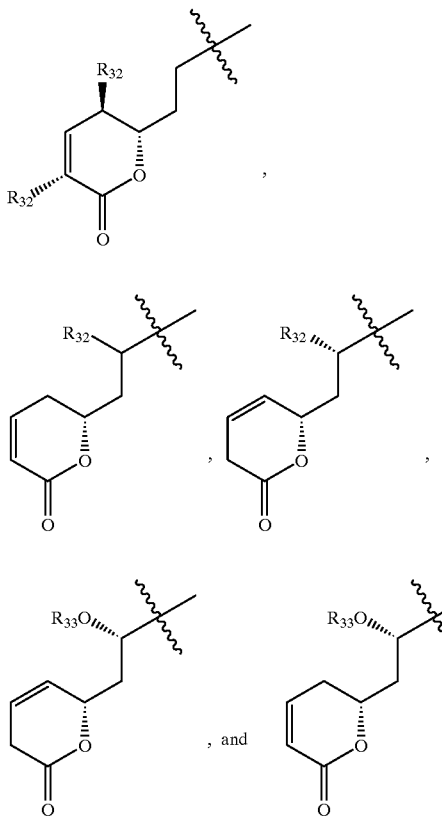

wherein $R_{32}$ is $C_1$–$C_6$ alkyl and $R_{33}$ is an acid labile hydroxyl protecting group;
the process comprising contacting a compound of the formula:

J-CHO with a phosphonium salt of the formula:

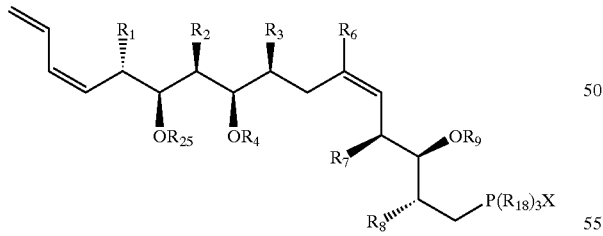

wherein $R_{18}$ is $C_6$–$C_{14}$ aryl, in the presence of a base for a time and under conditions effective to form the tetraene.

The present invention also provides a process for forming a tetraene of formula:

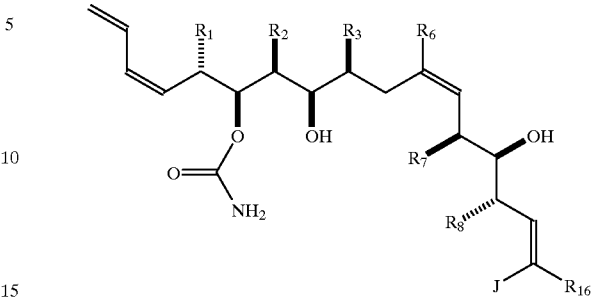

wherein:

$R_1$, $R_2$, $R_7$ and $R_8$ are independently $C_1$–$C_{10}$ alkyl;

$R_3$, $R_6$, and $R_{16}$ are independently selected from hydrogen and $C_1$–$C_6$ alkyl; and J is selected from:

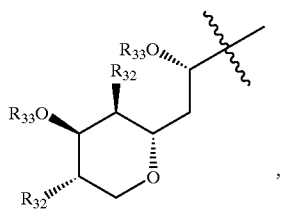

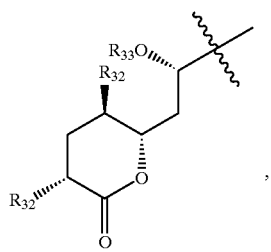

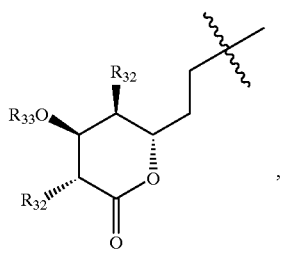

-continued

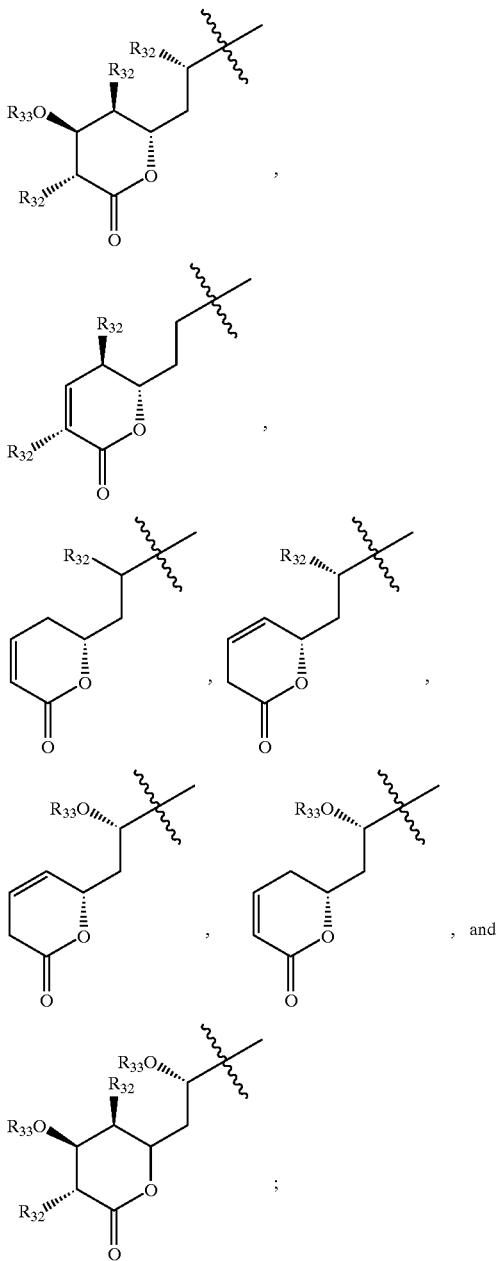

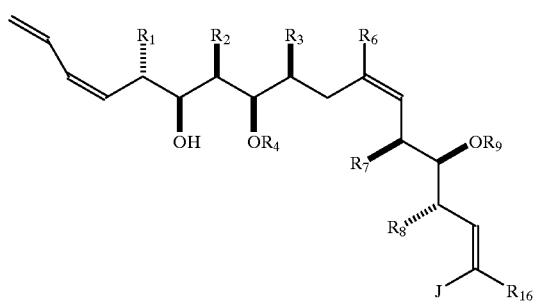

wherein $R_{32}$ is $C_1$–$C_6$ alkyl and $R_{33}$ is H;
the process comprising contacting an alcohol of formula:

wherein $R_4$, $R_9$, and $R_{33}$ are acid labile hydroxyl protecting groups, with an isocyanate of the formula:

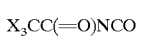

$$X_3CC(=O)NCO$$

wherein X is a halogen, to form a carbamate intermediate;

contacting the carbamate intermediate with neutral alumina to form a carbamate of formula:

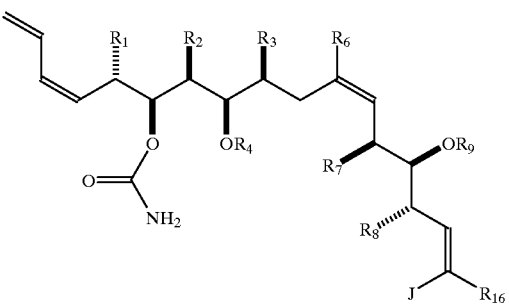

and;

removing the acid labile hydroxyl protecting groups by contacting the carbamate with acid in a protic solvent to form the tetraene.

The present invention also provides several processes for forming an alcohol of formula:

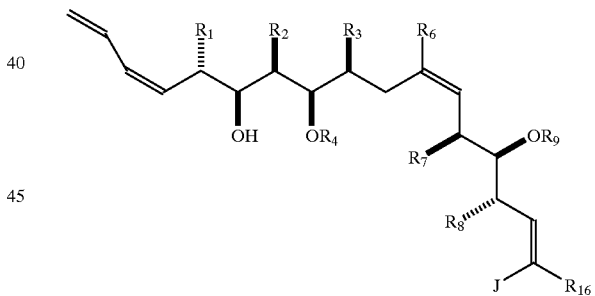

In one process, the process comprises contacting a compound of formula:

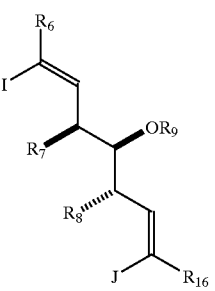

with a compound of formula:

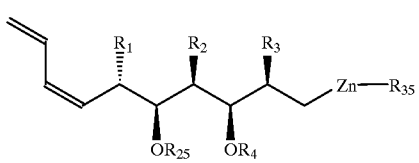

wherein $R_{25}$ is an acid stable protecting hydroxyl protecting group, and $R_{35}$ is selected from $C_4$ alkyl and a halogen, in the presence of a metal coupling catalyst for a time and under conditions effective to form a coupling product of formula:

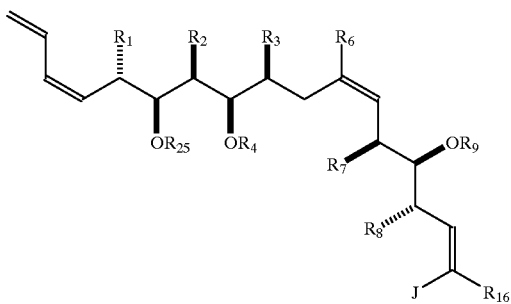

and deprotecting the coupling product to form the alcohol.

In another process, the alcohol is formed by contacting a compound of formula:

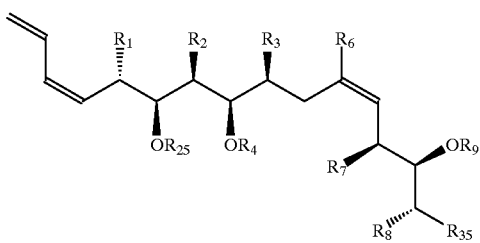

wherein:

$R_{25}$ is an acid stable protecting hydroxyl protecting group;
$R_{35}$ is selected from $CH_2P(R_{18})_3X$, CHO, —P(=O)Ph$_2$, and

—CH$_2$SO$_2$

X is a halogen; and
$R_{18}$ is $C_{6-14}$ aryl;
with a compound of formula:

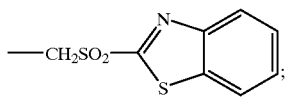

in the presence of a base to form a coupling product of formula:

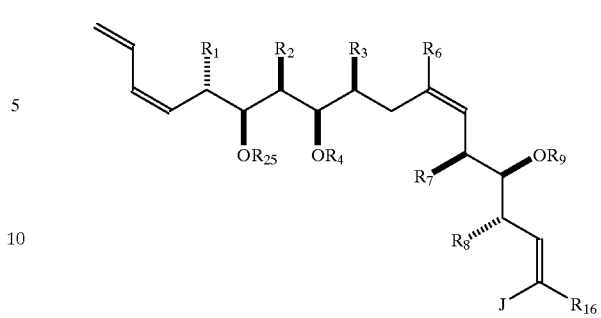

and deprotecting the coupling product to form the alcohol.

The present invention also provides a process for forming an alcohol of formula:

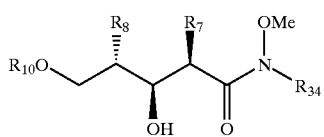

wherein:

$R_7$ and $R_8$ are independently $C_1$–$C_{10}$ alkyl;
$R_{10}$ is an acid stable hydroxyl protecting group;
$R_{34}$ is selected from $(CH_2)_n C_6$–$C_{14}$ aryl and $(CH_2OCH_2)$ $C_6$–$C_{14}$ aryl, wherein the aryl is substituted with 0–3 $R_{35}$;
$R_{35}$ is selected from F, $CF_3$, Br, Cl, and $NO_2$; and
n is selected from 0 and 1;
the process comprising contacting a compound of formula:

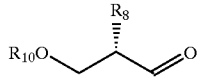

with the enolate of a compound of formula:

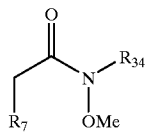

in the presence of Lewis acid for a time and under conditions effective to form the alcohol.

The present invention also provides intermediate compounds of formula:

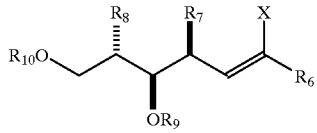

wherein:

$R_6$ is $C_1$–$C_4$ alkyl;
$R_7$ and $R_8$ are independently $C_1$–$C_{10}$ alkyl;
$R_9$ is an acid labile hydroxyl protecting group;
$R_{10}$ is an acid stable hydroxyl protecting group; and
X is halogen.

The present invention also provides intermediate compounds of formula:

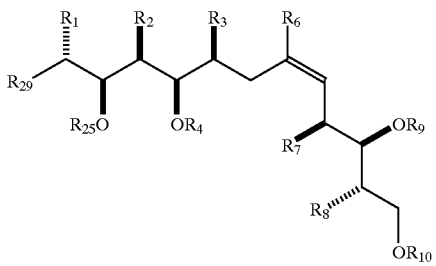

wherein:

$R_1$, $R_2$, $R_7$, and $R_8$ are independently $C_1$–$C_{10}$ alkyl;

$R_3$ and $R_6$ are independently selected from hydrogen and $C_1$–$C_6$ alkyl;

$R_4$ and $R_9$ are independently acid labile hydroxyl protecting groups;

$R_{25}$ is an acid stable hydroxyl protecting group; and $R_{10}$ is a trityl group; and $R_{29}$ is selected from OH, CHO, and —CH=CH—CH=CH$_2$.

The present invention also provides a compound of formula:

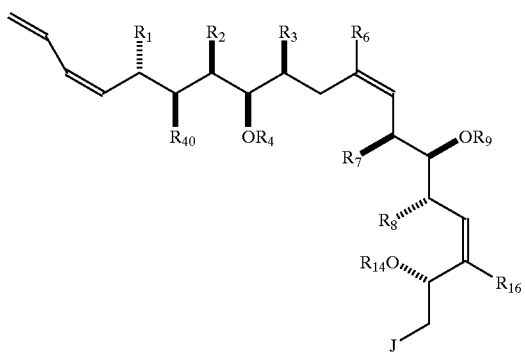

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl;

$R_4$, $R_9$, and $R_{14}$ are acid labile protecting groups;

$R_{40}$ is selected from $OR_{28}$ and $OC(=O)NH_2$;

$R_{25}$ is an acid stable protecting group; and

J is selected from:

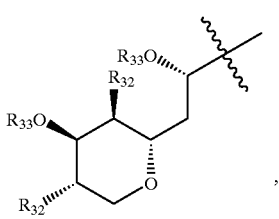

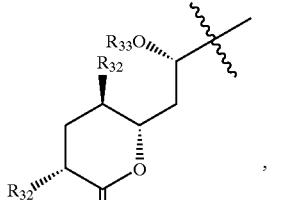

,

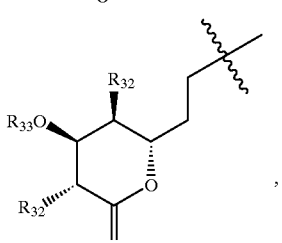

,

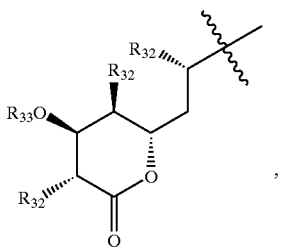

,

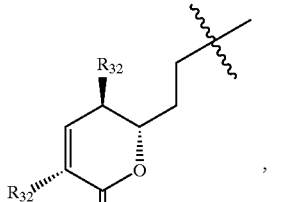

,

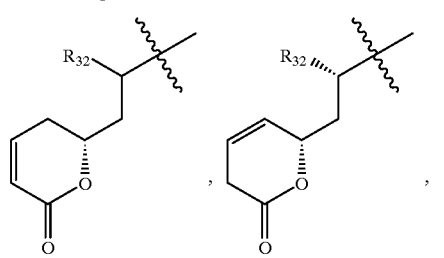

,

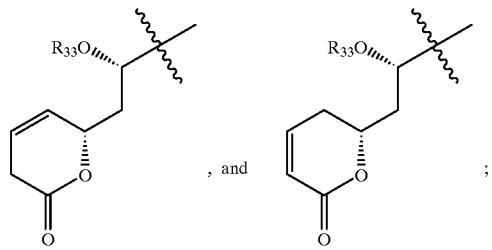

;

wherein $R_{32}$ is $C_1$–$C_6$ alkyl and $R_{33}$ is selected from H and an acid labile hydroxy protecting group.

BRIEF DESCRIPTION OF THE DRAWINGS

The numerous objects and advantages of the present invention may be better understood by those skilled in the art by reference to the accompanying figures, in which:

FIG. 30 shows a synthetic scheme for compound 1003.

FIG. 31 shows a synthetic scheme for compound 1104 (Ar=2,4-dimethyl-3-methoxyphenyl (a), 2-methyl-5-methoxyphenyl (b), 2,4-dimethyl-5-methoxyphenyl (c), 2,4-dimethylphenyl (d), and 4-methylphenyl (e)).

FIGS. 33–36 show representative compounds of the invention.

FIG. 49 shows a synthetic scheme for compound 94.

FIG. 50 shows a synthetic scheme for compound 58.

DETAILED DESCRIPTION OF THE PREFERRED EMBODIMENTS

It has been found in accordance with the present invention that the synthesis of polyhydroxy, dienyl lactones such as the discodermolides can be achieved by highly convergent and stereocontrolled synthetic procedures.

Figure 1:
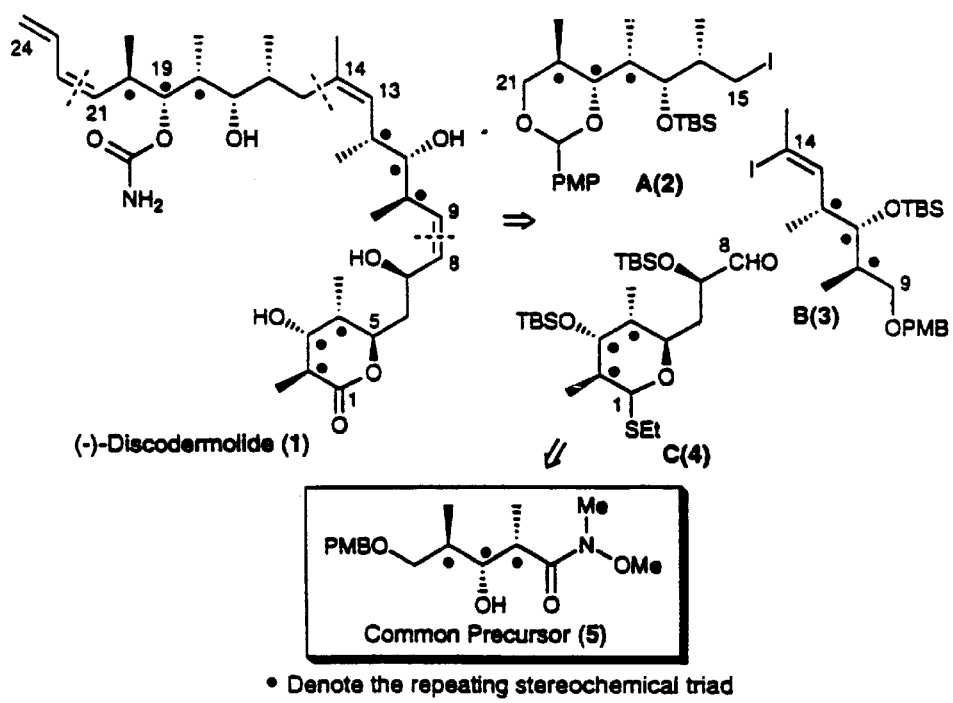
FIG. 1 shows a retrosynthetic analysis for (−)-discodermolide 1.

As shown in FIG. 1 for the (−)-discodermolide antipode, our analysis revealed a repeating triad of contiguous stereocenters, separated by Z-olefinic linkages at C(8,9) and C(13,14). Disconnections at C(8,9), C(14,15) and C(21,22) generated fragments A, B and C, each deriving in turn from a common precursor (5) containing the recurring stereochemical triad.

Figure 2:
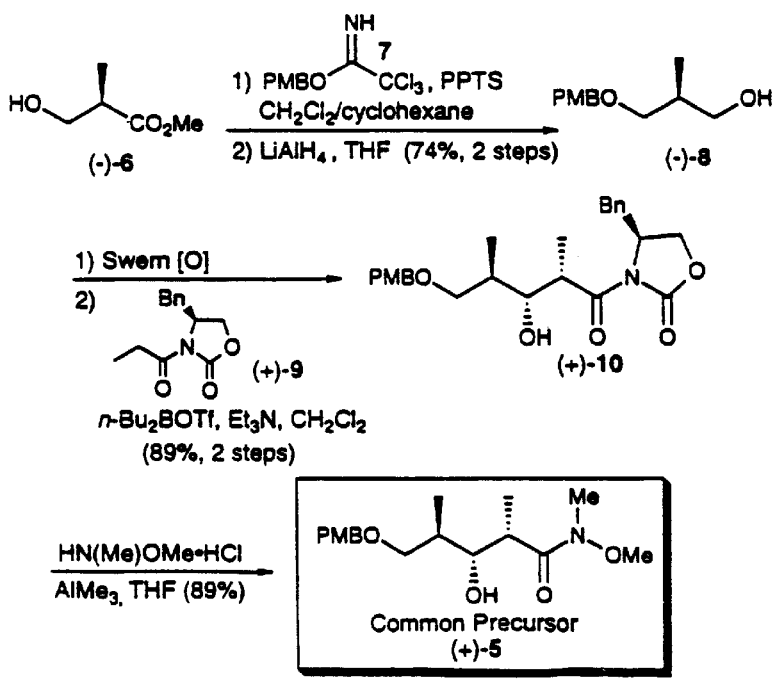
FIG. 2 shows a synthetic scheme for compound (+)-5.

As shown in FIG. 2, precursor 5 was prepared by a synthetic procedure whereby hydroxy ester (−)-6 was protected as the p-methoxybenzyl (PMB) ether by treatment with the Bundle trichloroimidate reagent 7 under acidic conditions. Reduction with $LiAlH_4$ provided the alcohol (−)-8 after distillation. Swern oxidation, Evans aldol condensation, and Weinreb amide formation completed the construction of common precursor (+)-5. This concise five-step synthesis could be routinely carried out on a 50-g scale in 59% overall yield.

Figure 37:
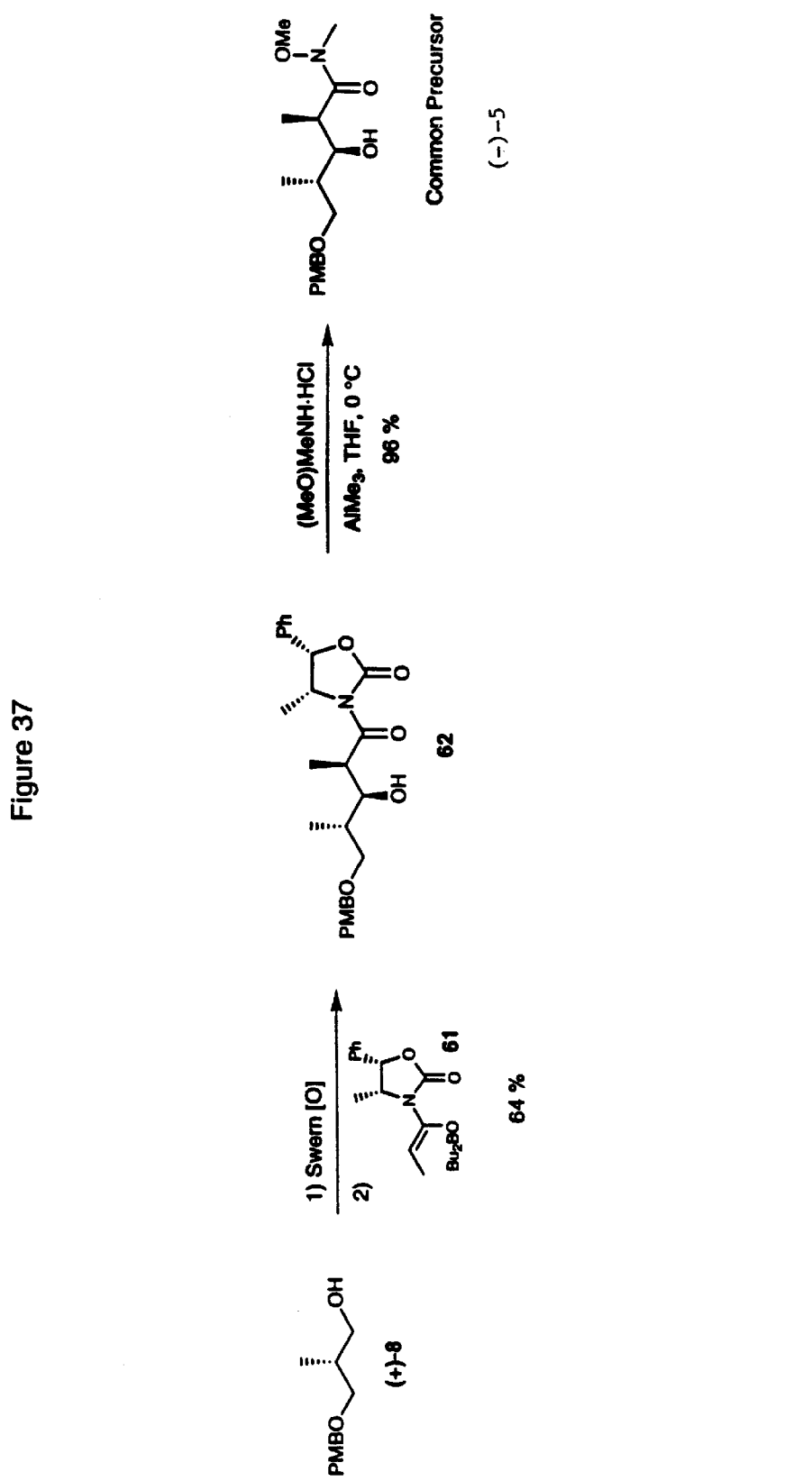
FIG. 37 shows a synthetic scheme for compound (−)-5.

Alternatively, as shown in FIG. 37, Swern oxidation of (+)-8 followed by the addition norephedrine derived oxazolidinone 61 results in a crystalline product 62 which, in turn, can be converted to common precursor (−)-5.

Figure 3:
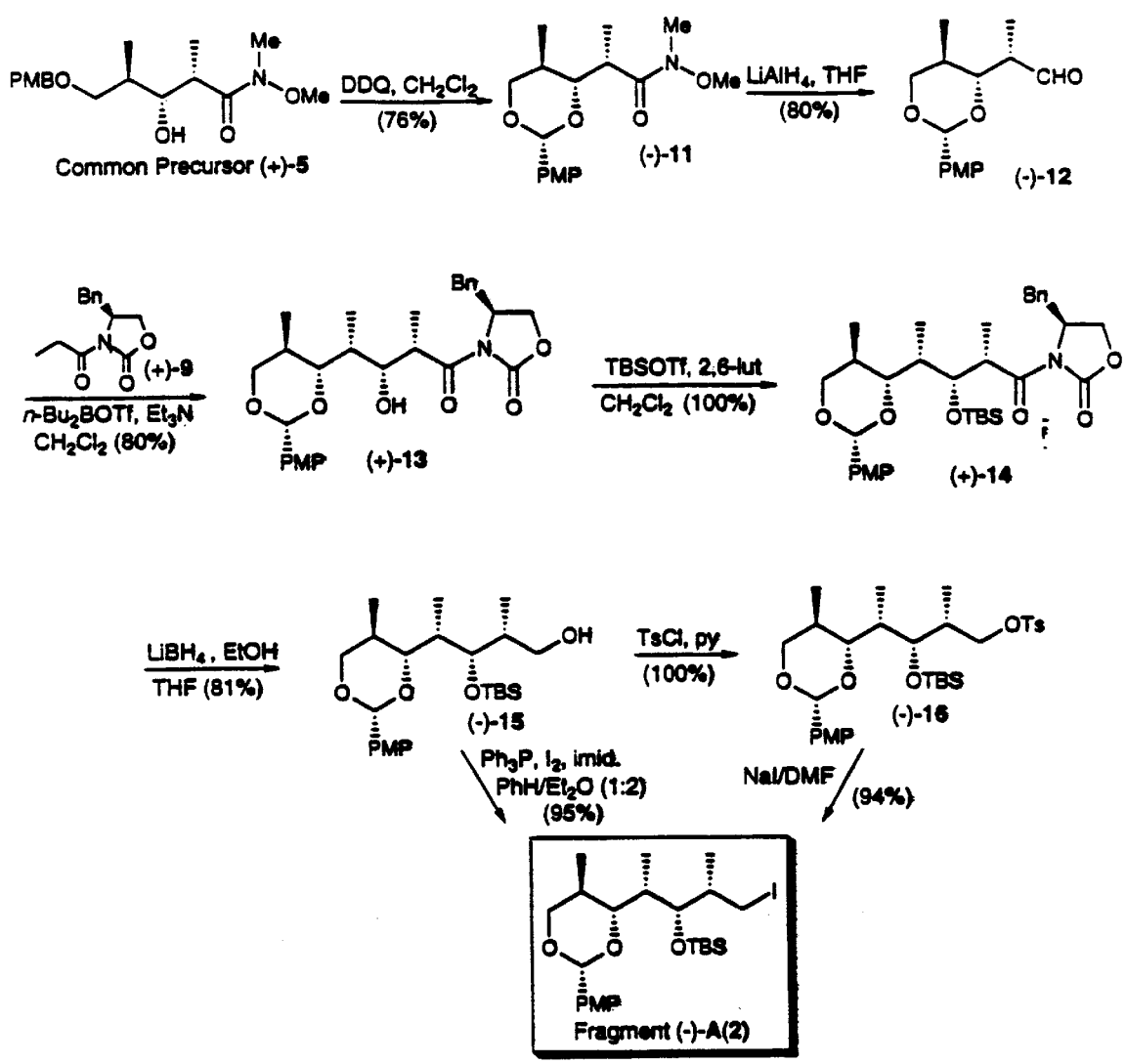
FIG. 3 shows a synthetic scheme for fragment A.

In view of the polypropionate structure of the A fragment, we performed a second asymmetric aldol reaction, as shown in FIG. 3. Initial formation of the p-methoxybenzylidene acetal (−)-11 from common precursor (−)-5 (78% yield) was designed to allow selective deprotection of C(21) and C(19) hydroxyls for introduction of the terminal diene and carbamate moieties. Following reduction of amide (−)-11 to the aldehyde (80% yield), (aldol reaction with oxazolidinone (+)-9 (80% yield) provided alcohol (+)-13 which incorporated the five stereocenters of subunit A. The structure of (+)-13 was confirmed by single-crystal X-ray analysis. Protection of the secondary alcohol as the TBS ether and removal of the chiral auxiliary ($LiBH_4$,EtOH,THF) afforded primary alcohol (−)-15 (81% yield, two steps), which could be efficiently converted either to tosylate (−)-16 or iodide (−)-A.

Figure 4:
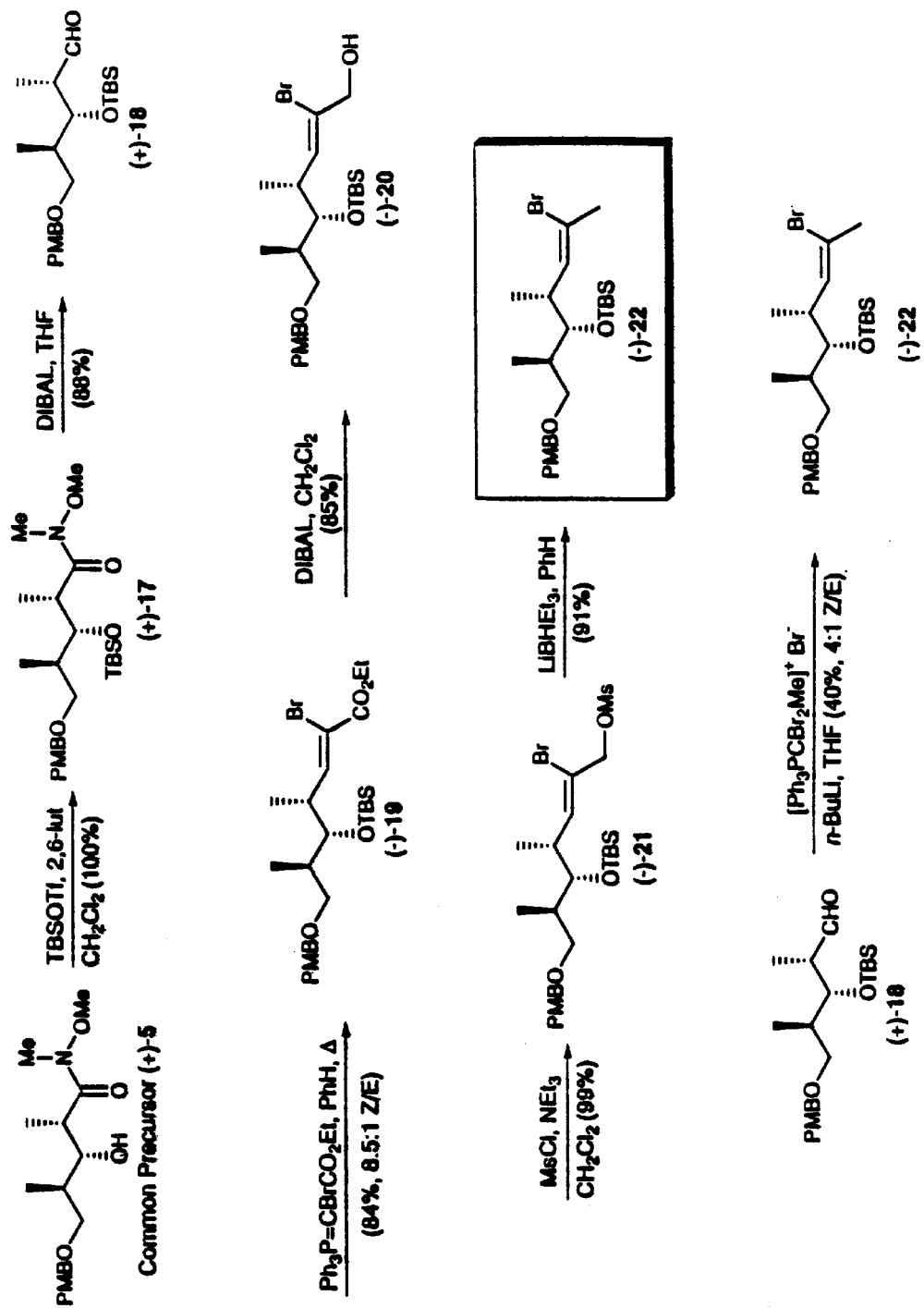
FIG. 4 shows a synthetic scheme for compound 22.

As outlined in FIG. 1, our strategy required a Z vinylic halide B for coupling with fragment A. Beginning again with the common precursor (+)-5, TBS protection (FIG. 4) followed by reduction of the Weinreb amide [DIBAL (2 equiv), THF, −78° C.] (Kim, et al., *Tetrahedron Lett.* 1989, 30, 6697) afforded aldehyde (+)-18 in 88% yield for the two steps. We adopted a stepwise approach to introduction of the vinyl halide, whereby (+)-18 was converted to the Z α-bromo unsaturated ester (−)-19 ($Ph_3PCBrCO_2Et$, PhH, reflux; 75% yield after chromatography). Reduction to allylic alcohol (−)-20 followed by mesylation and displacement with $LiBHEt_3$ then furnished Z vinyl bromide (−)-22 in 77% overall yield from 19.

Figure 9:
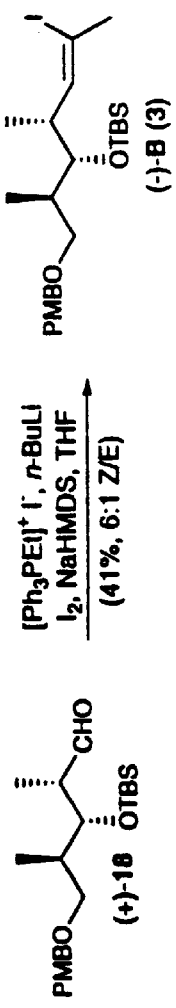
FIG. 9 shows a synthetic scheme for fragment B.
Figure 39:
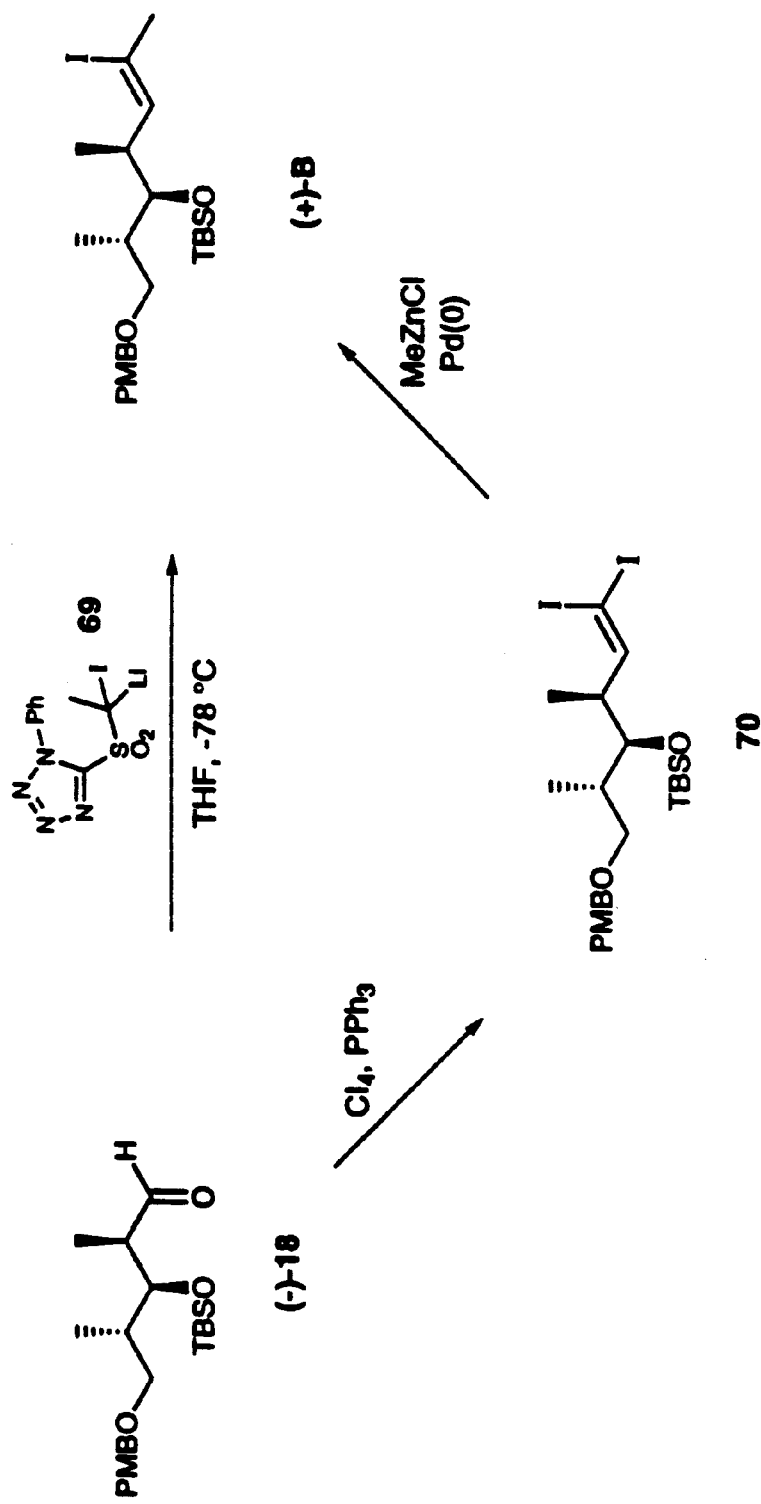
FIG. 39 shows a synthetic scheme for compound (+)-B.

One preferred synthetic strategy utilized a vinyl iodide as the desired B segment. Synthesis of (−)-B was achieved by direct olefination of aldehyde (+)-18 (41%, 6:1 Z/E) (FIG. 9), followed by chromatographic removal of the undesired E product. Alternatively, the B segment can be prepared by the two routes shown in FIG. 39. The first involves an α-iodo sulfone 69 to effect a one-step installation of the vinyl iodide. The second exploits the enhanced reactivity of the trans iodide of diiodide 70.

Figure 5:
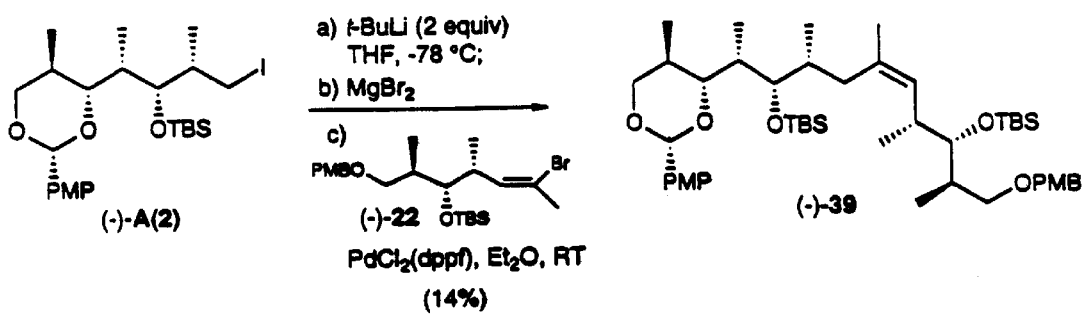
FIG. 5 shows a synthetic scheme for compound 39.
Figure 6:
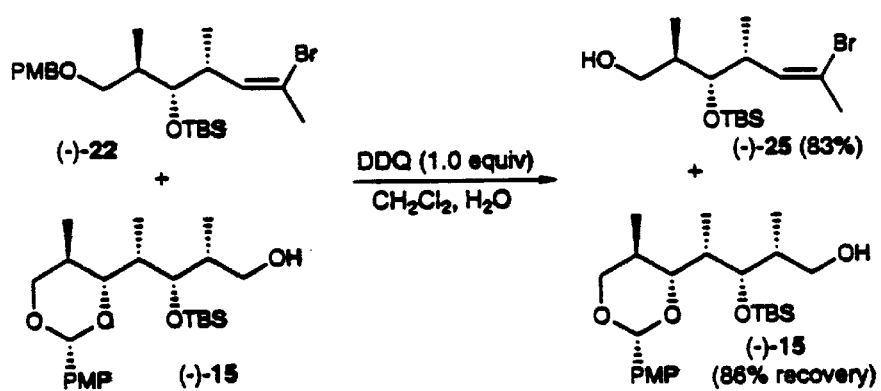
FIG. 6 shows a synthetic scheme for compounds 15 and 25.

Our preferred synthetic strategy involves selective removal of a primary PMB ether in the presence of a PMP acetal in the AB coupling product ((−)-39, FIG. 5). A 1:1 mixture of PMB ether (−)-22 and PMP acetal (−)-15 was exposed to DDQ (1.1 equiv) in $CH_2Cl_2/H_2O$ (FIG. 6). The acetal (−)-15 largely remained intact while the debenzylated alcohol (−)-25 was formed in 83% yield.

Figure 7:
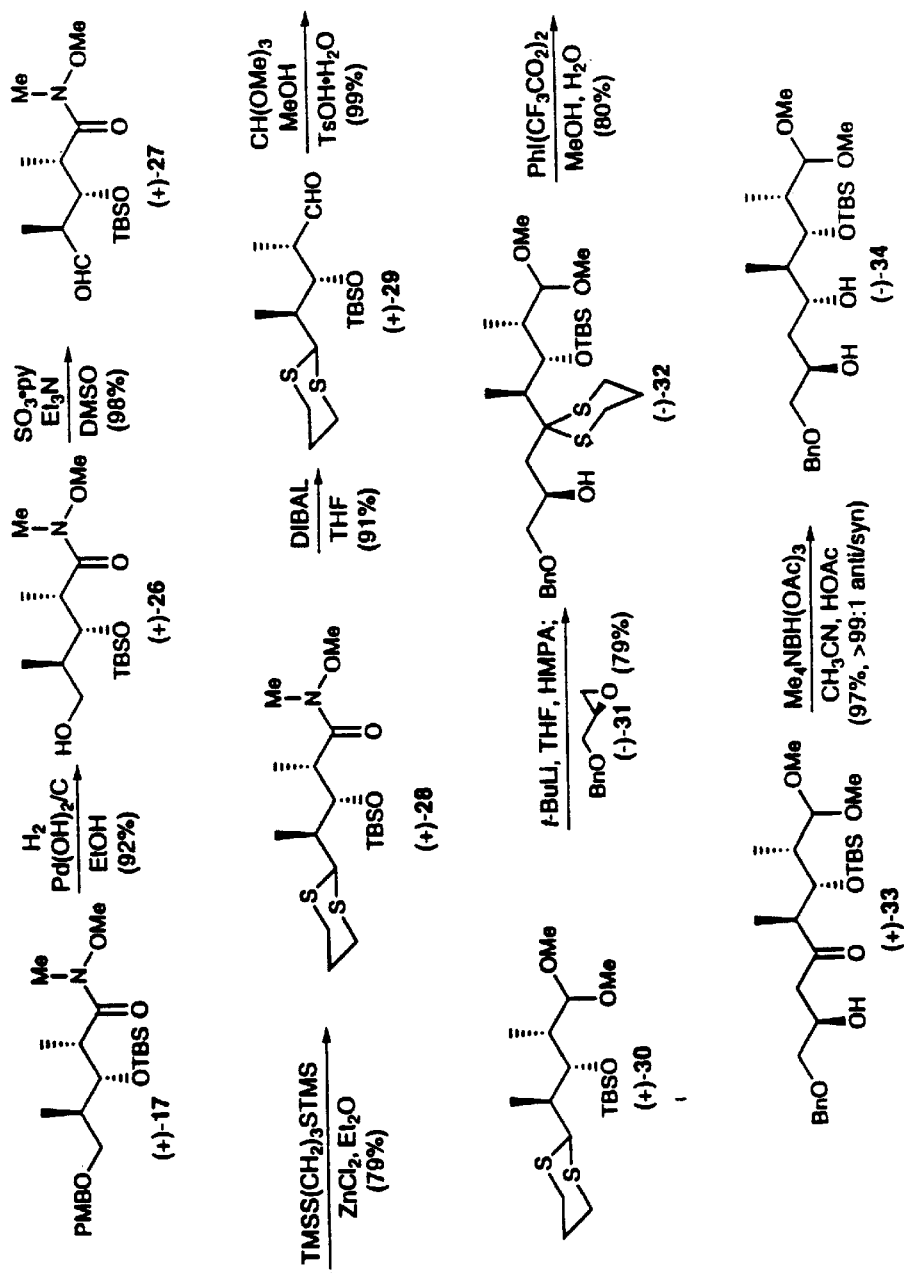
FIG. 7 shows a synthetic scheme for compound 34.

As shown in FIG. 7, we again utilized the TBS ether (+)-17 for the preparation of C from common precursor (+)-5. Oxidative cleavage of the PMB group (DDQ, $CH_2Cl_2$, $H_2O$) provided alcohol 26 in variable (60–86%) yields, accompanied by the corresponding lactone. Hydrogenolysis with Pearlman's catalyst afforded (+)-26 in 92% yield. Exposure of the alcohol to $SO_3$.pyr furnished aldehyde (+)-27 (98% yield), which in turn was converted to dithiane (+)-28 (79%). In the latter step, our modification of the Evans protocol for dithiane generation [$(TMSSCH_2)_2CH_2$, $ZnCl_2$, $Et_2O$] minimized elimination of the TBS ether to form the α,β-unsaturated amide. Following reduction to aldehyde (+)-29 with DIBAL (91% yield), dimethyl acetal formation gave (+)-30 (99%). The coupling of dithiane 30 with R-(−)-glycidyl benzyl ether [(−)-31] then afforded alcohol (−)-32 in 79% yield. Unmasking of the ketone moiety [$(CF_3CO_2)_2IPh$, 80%] and Evans stereocontrolled reduction (97%) provided the anti diol (−)-34, which embodied all of the stereocenters in fragment C.

Figure 8:
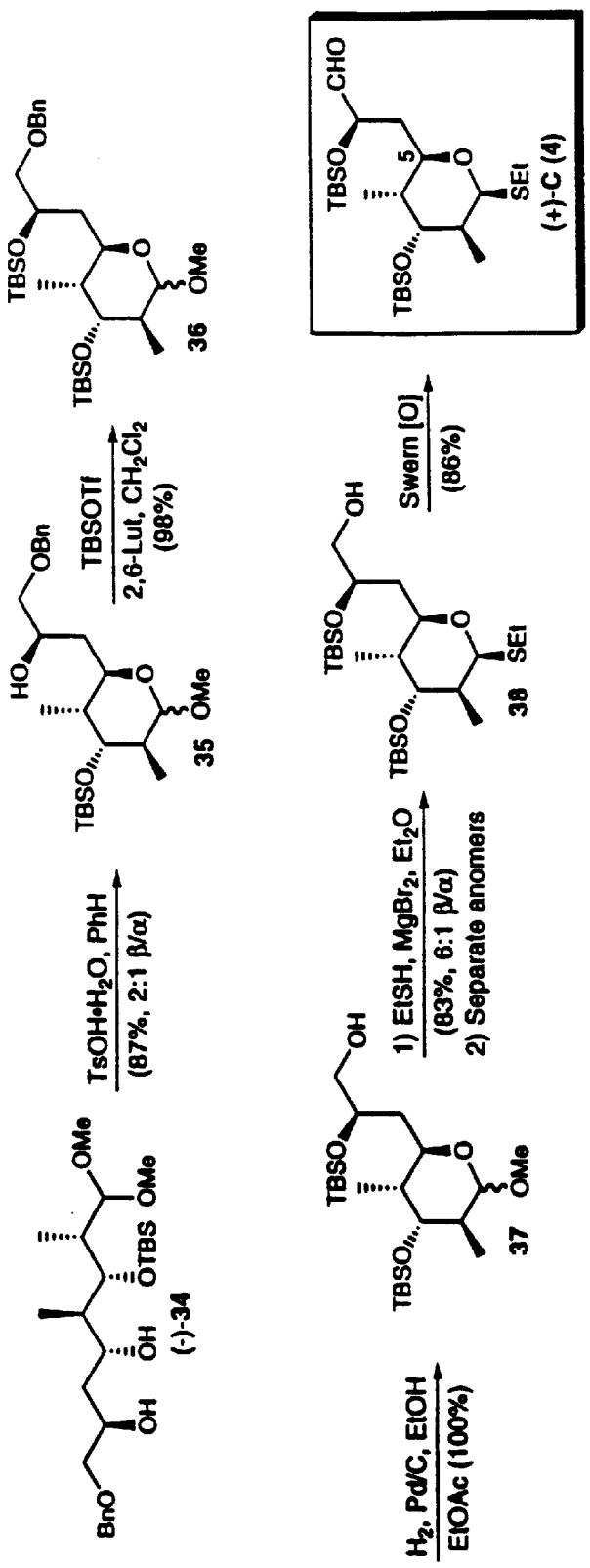
FIG. 8 shows a synthetic scheme for fragment C.

Acid-catalyzed cyclization of (−)-34 (TsOH, room temperature) provided methoxy pyran 35 in 87% yield as a 1:2 mixture of α and β anomers (FIG. 8). Debenzylation ($H_2$, Pd/C) of 36 afforded alcohol 37 quantitatively. Exposure to EtSH and $MgBr_2$ in $Et_2O$ then gave a separable 6:1 mixture of β ethyl hemithioacetal (+)-38 and its α anomer in 83% yield. Swern oxidation of (+)-38 furnished the final fragment (+)-C in 86% yield.

Figure 10:
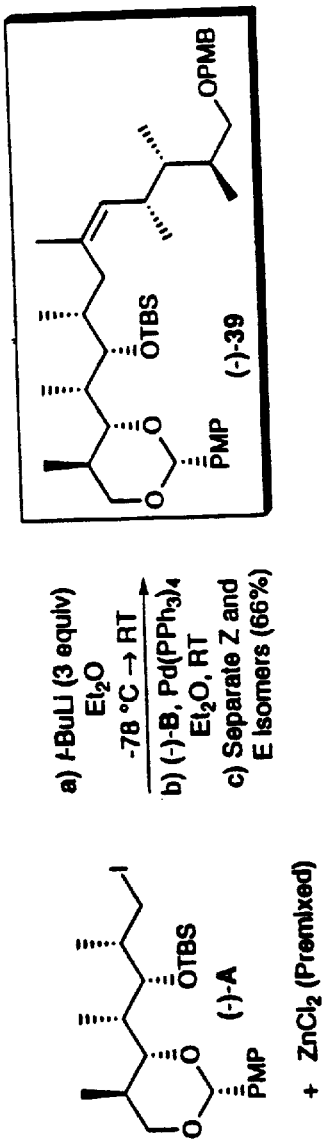
FIG. 10 shows a synthetic scheme for compound 39.

Reaction of (−)-B with the organozinc derivative of (−)-A (FIG. 10) was achieved by premixing iodide A with dried solid $ZnCl_2$ (ether, −78° C.) before addition of t-BuLi. It is believed that three equivalents of t-BuLi are required for complete consumption of (−)-A, probably because the first equivalent reacts with $ZnCl_2$. This modification increased the yield to 66% after flash chromatography.

Figure 11:
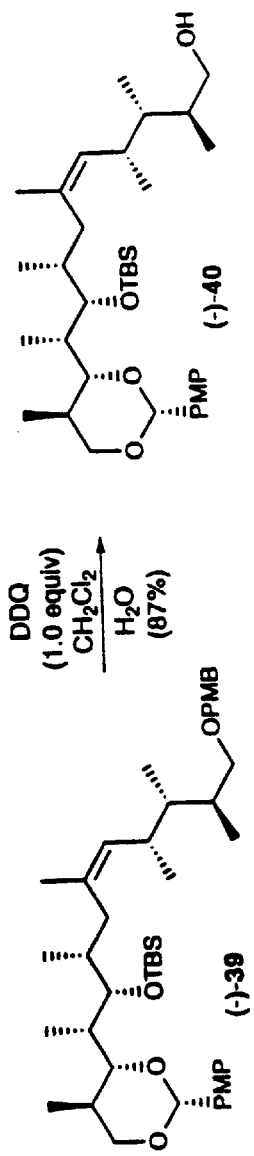
FIG. 11 shows a synthetic scheme for compound 40.
Figure 12:
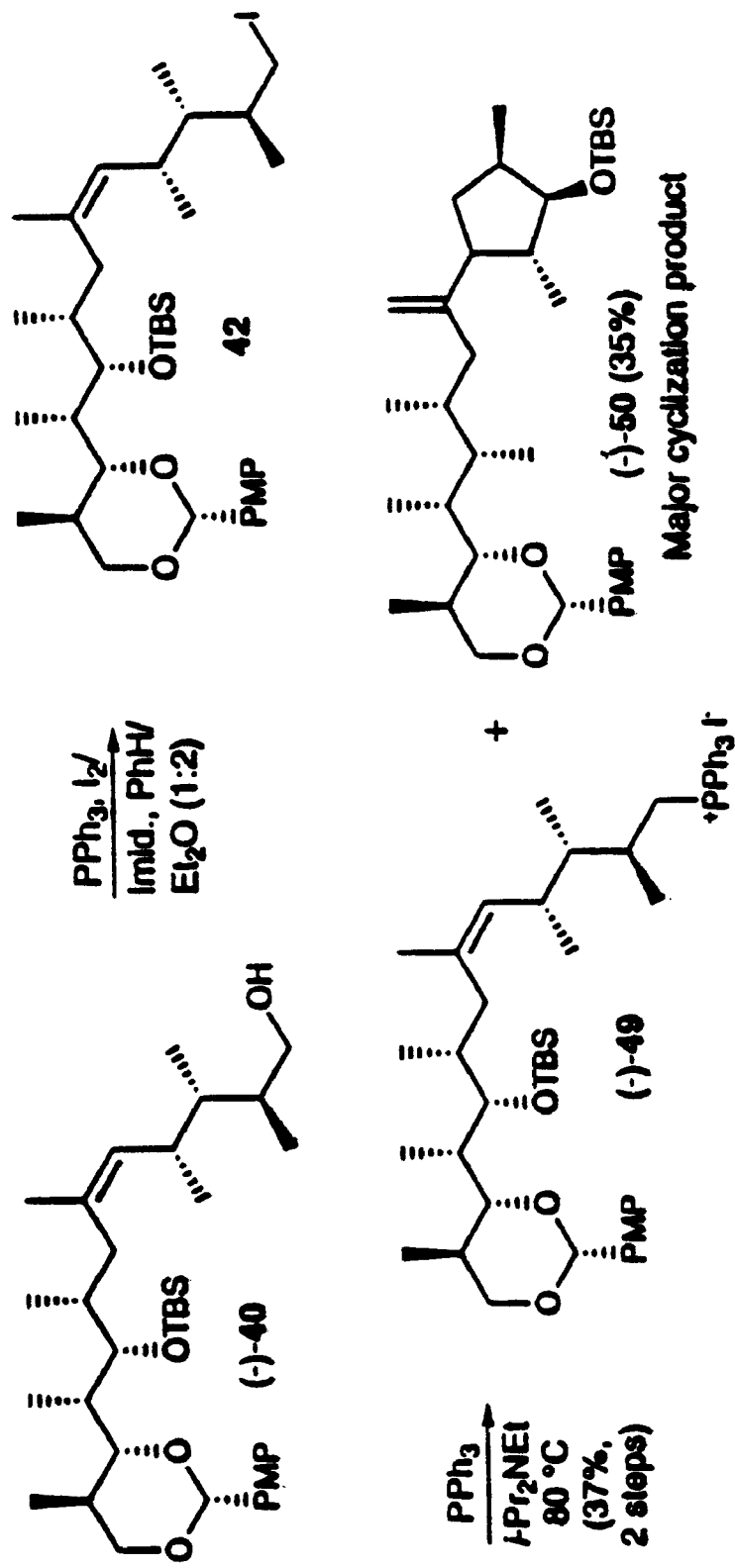
FIG. 12 shows a synthetic scheme for compound 49.
Figure 13:
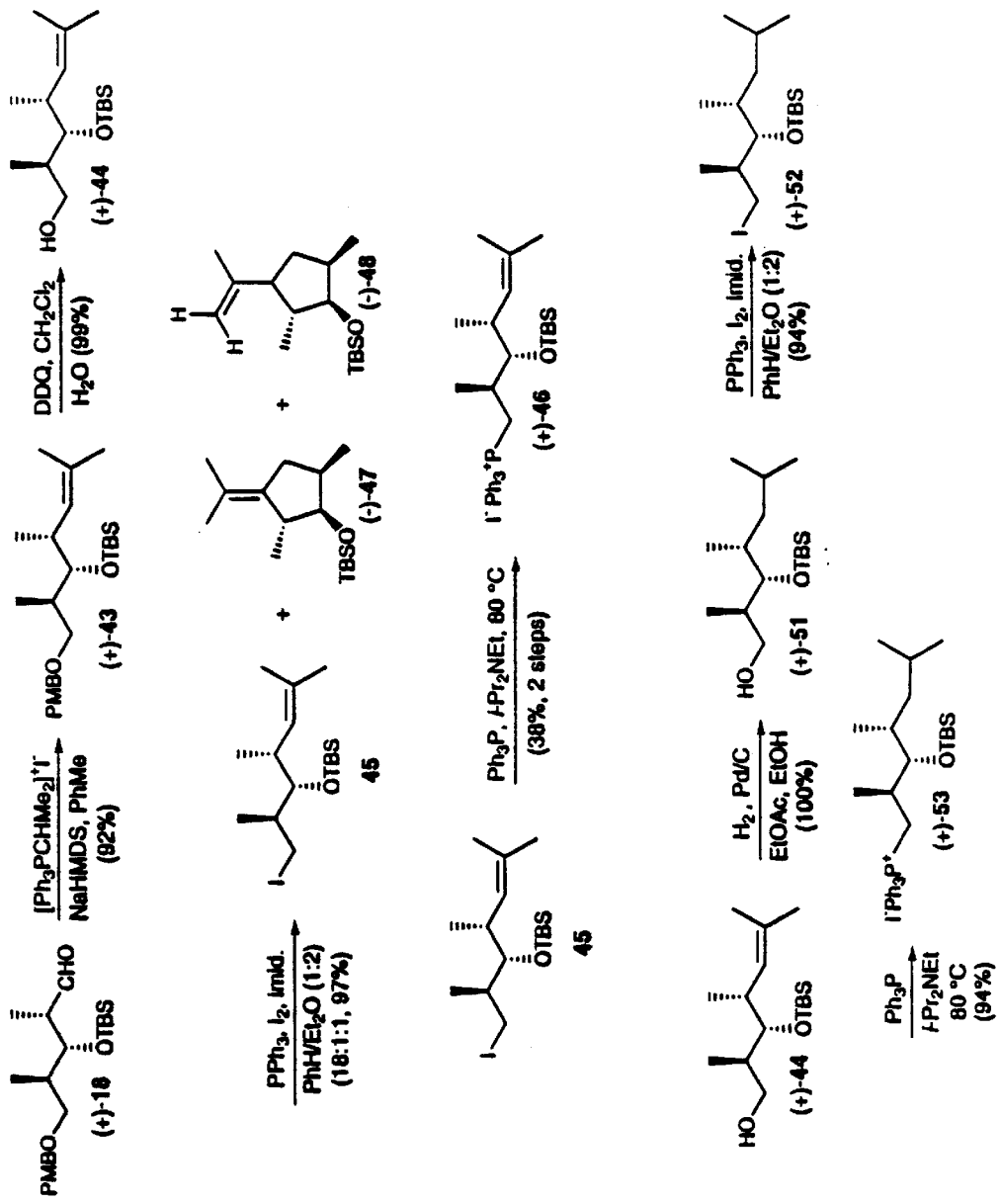
FIG. 13 shows a synthetic scheme for compounds 53 and 46.

Conversion of the Z trisubstituted olefin (−)-39 to the phosphonium iodide (−)-49 began with selective removal of the PMB group, as in our model study (DDQ, $CH_2Cl_2$, $H_2O$), furnishing (−)-40 in 87% yield (FIG. 11). As shown in FIG. 12, alcohol (−)-40 furnished the requisite iodide 42 almost exclusively, as indicated by NMR examination of the crude material. The very sensitive iodide was used without purification. Thorough mixing of iodide 42 with I—$Pr_2NEt$ (3 equiv) followed by exposure to excess $PPh_3$ (15 equiv) without solvent at 80° C. generated (−)-49 in 37% yield for the two steps. The major by-product was characterized as (−)-50 (35% yield). The unsaturated model alcohol (+)-44 similarly afforded the Wittig salt (+)-46 in low yield (FIG. 13), whereas the saturated derivative (+)-51 gave phosphonium iodide (+)-53 almost quantitatively.

Our preferred method to prepare compound 49 entails the mixing of iodide 42 with I—$Pr_2NEt$ (0.5 equiv.) and $PPh_3$ (4 equiv.) in benzene/toluene (7:3) and subjecting this mixture to an applied pressure of 10–15 Kbar.

Figure 14:
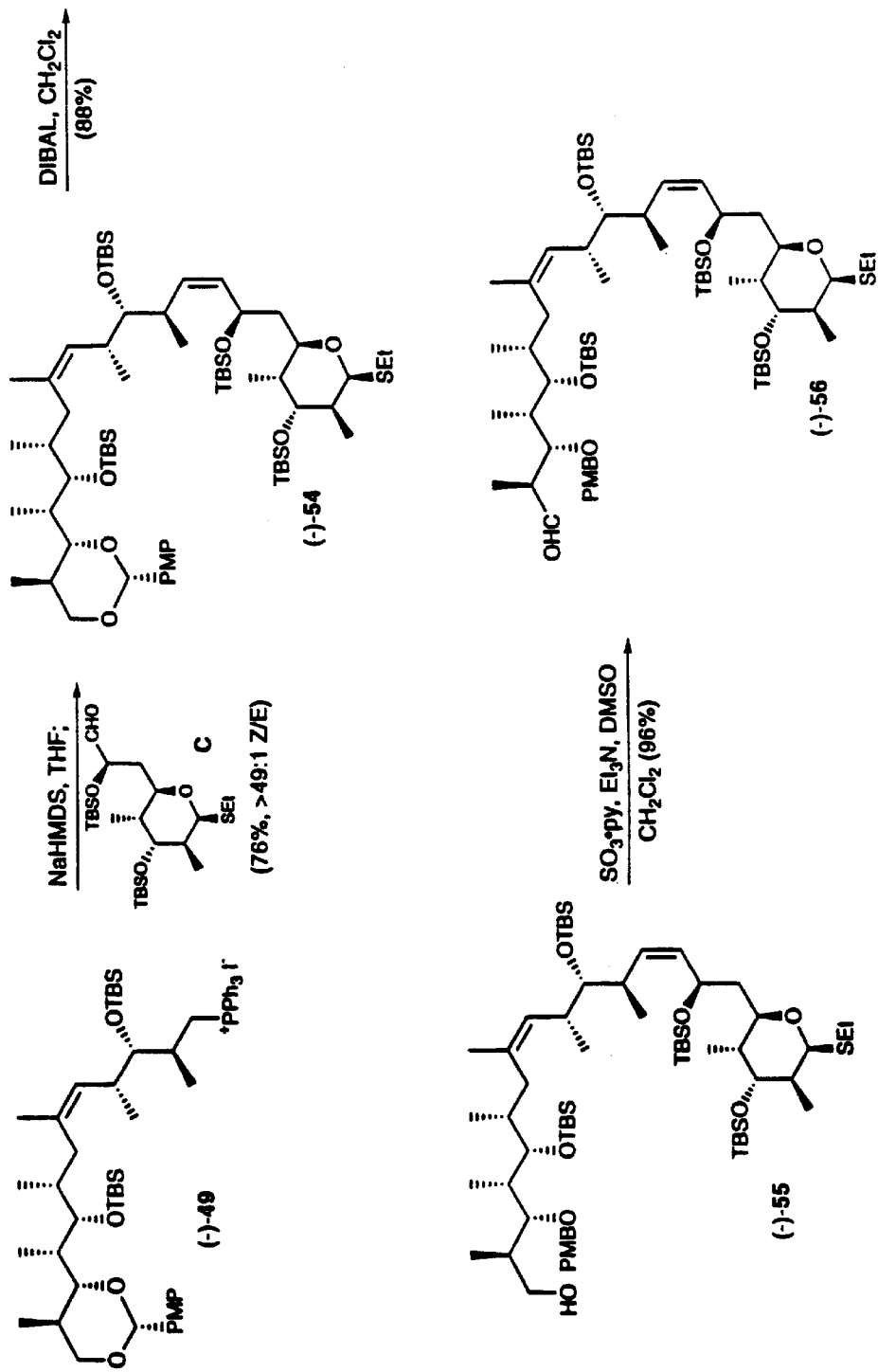
FIG. 14 shows a synthetic scheme for compound 56.
Figure 15:
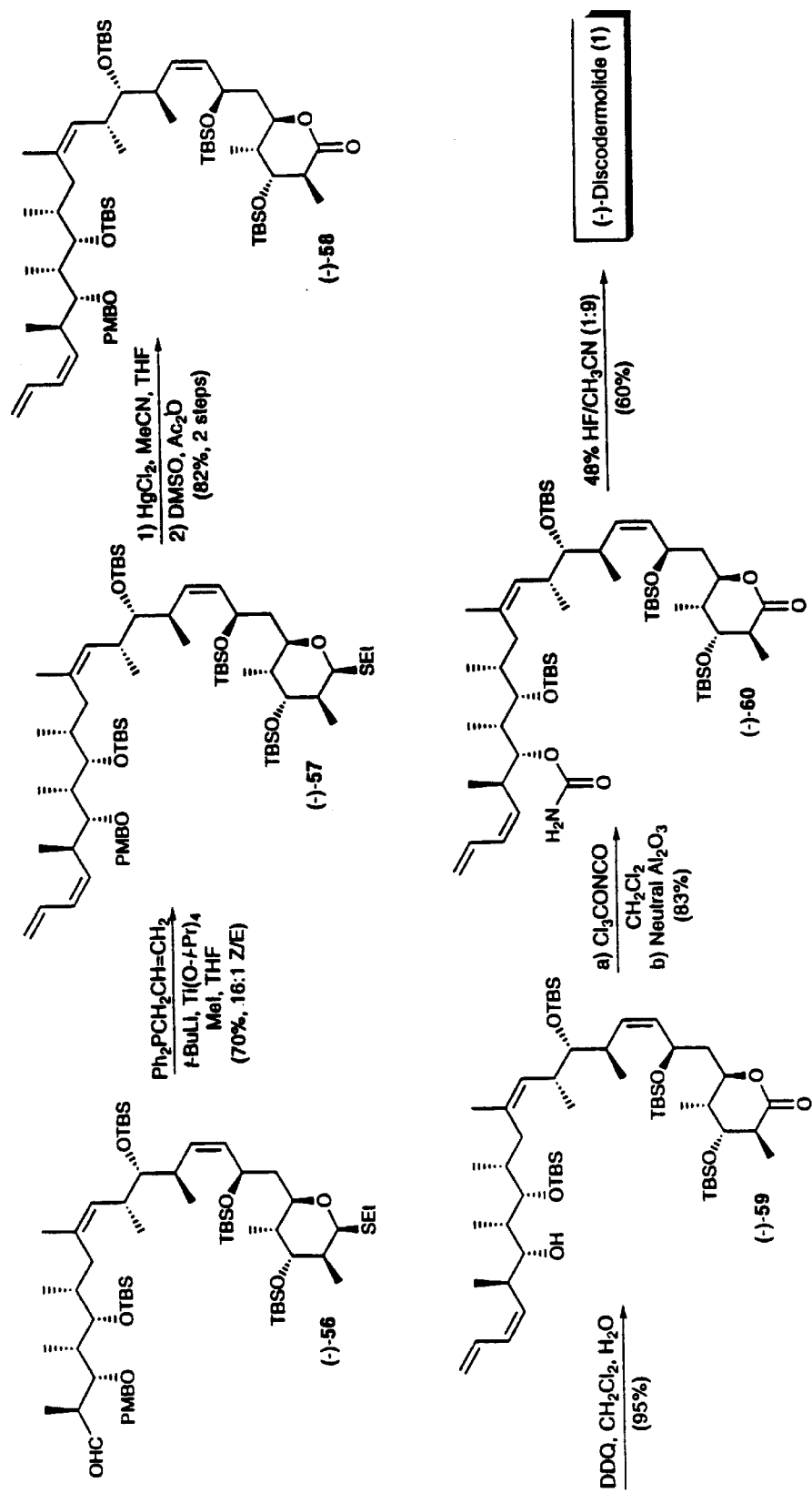
FIG. 15 shows a synthetic scheme for compound 1.

As shown in FIG. 14, assembly of the discodermolide backbone entailed Wittig coupling of aldehyde C with the ylide derived from AB phosphonium salt (−)-49 to install the C(8,9) Z alkene in (−)-54 (>49:1 Z/E, 76% yield). DIBAL reduction (88% yield) followed by oxidation of the resultant primary alcohol (−)-55 then produced aldehyde (−)-56 (96%). The terminal Z diene (−)-57 was elaborated via the Yamamoto protocol in 70% yield with excellent selectivity (16:1 Z/E). After flash chromatography, hydrolysis of the hemithio acetal and mild DMSO/$Ac_2O$ oxidation provided lactone (−)-58 in 82% yield for the two steps. Removal of the PMB group (DDQ, $CH_2Cl_2$, $H_2O$, 95% yield) and carbamate formation ($Cl_3CONCO$, $CH_2Cl_2$, neutral $Al_2O_3$, 83%) afforded tris(TBS ether) (−)-60. Final deprotection with 48% HF/$CH_3CN$ (1:9) furnished (−)-discodermolide, identical with an authentic sample (FIG. 15).

Figure 38:
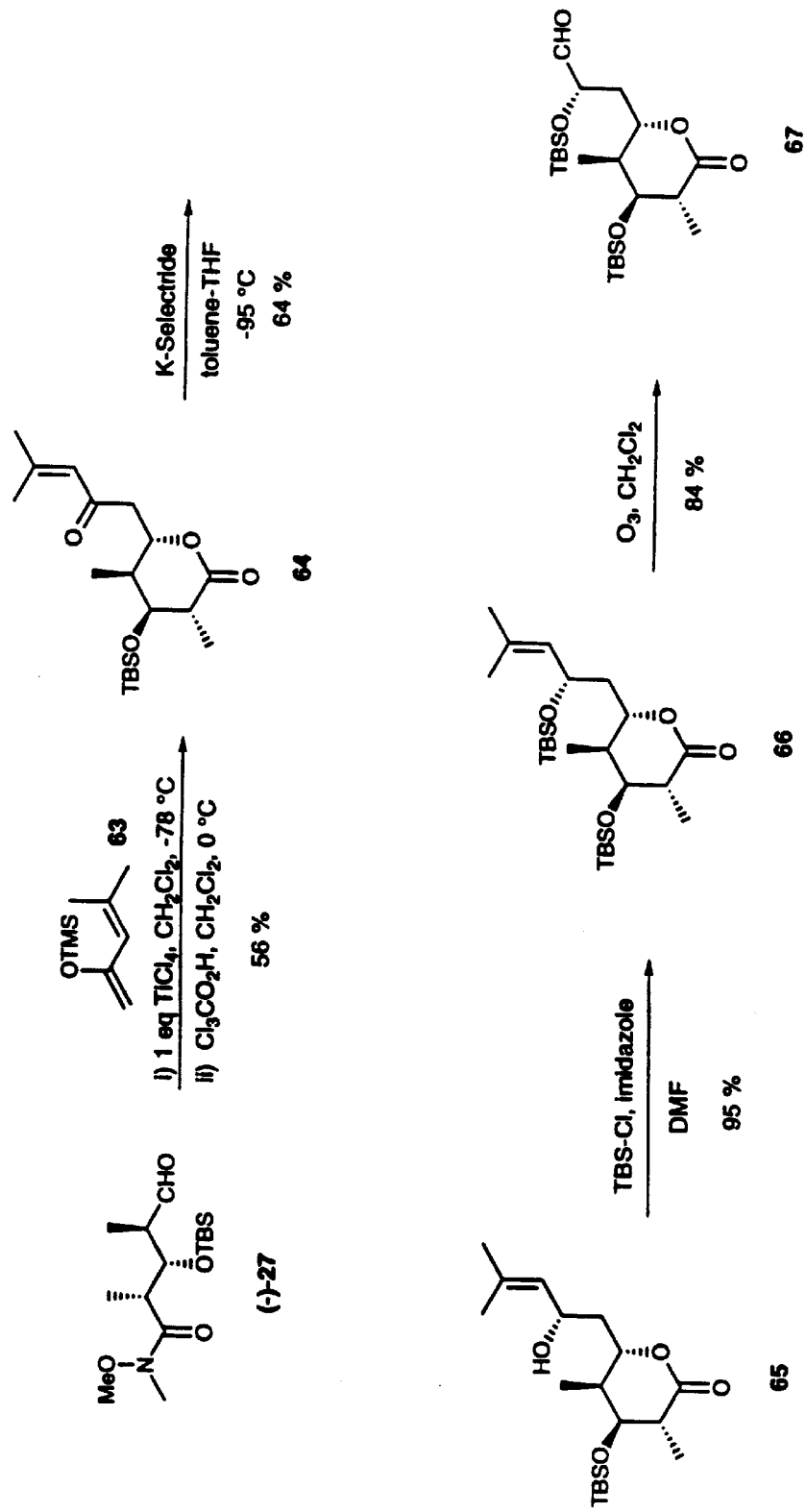
FIG. 38 shows a synthetic scheme for compound 67.
Figure 42:
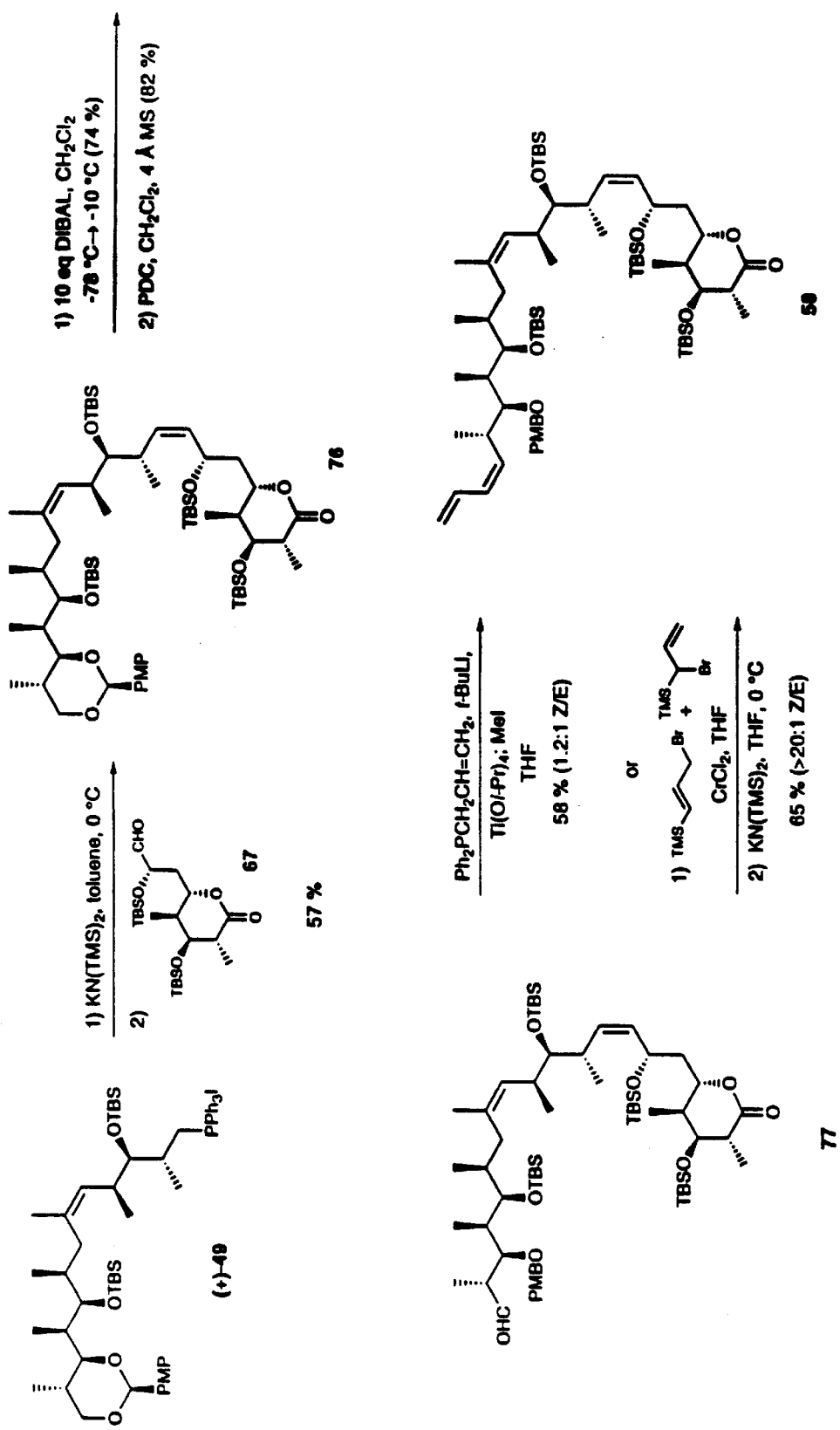
FIG. 42 shows a synthetic scheme for compound 58.

Alternatively, lactone 58 can be prepared by the Wittig coupling of aldehyde 67 with the ylide derived from 49, as shown in FIG. 42. Regioselective ring opening of benzylidene acetal 76 with DIBAL followed by oxidation with pyridinium dichromate affords aldehyde 77. Application of the Yamamoto olefination protocol affords compound 58. Alternatively, the diene installation can be effected using an alkyl chromium reagent generated by the procedure of Hodgson, et al., *Tetrahedron Letters* 1992, 33, 4761. The aldehyde 67 can be prepared by from compound (−)-27 (prepared generally according to the procedure of Smith, et al., *J. Am. Chem. Soc.* 1995, 117, 12011) by effecting a Mukaiyama aldol reaction between aldehyde 27 and enol ether 63 to form enone 64. Reduction of enone 64 furnished a 9:1 mixture of carbinols, favoring the desired isomer. Protection of the newly formed carbinol with TBSCl and subsequent ozonolysis of the trisubstituted olefin provides 67 in approximately 80% overall yield, as shown in FIG. 38.

Figure 40:
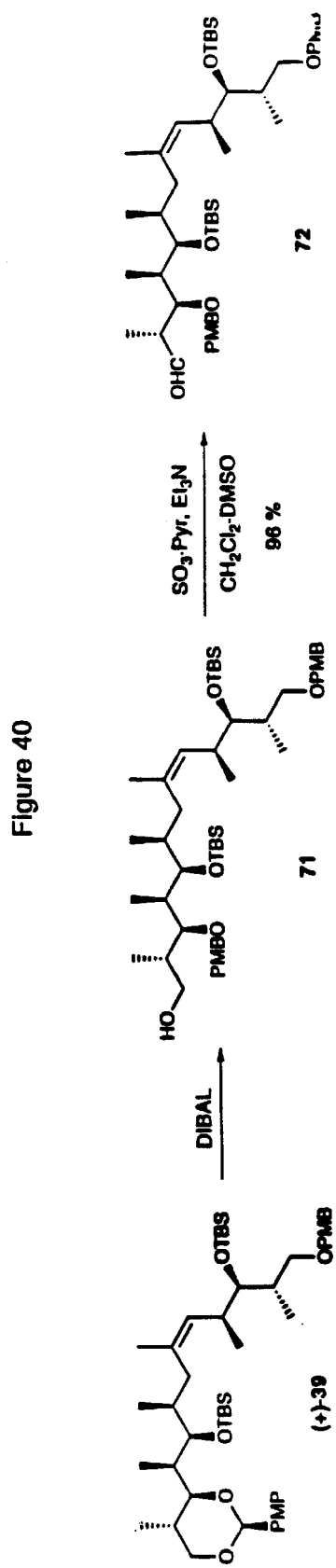
FIG. 40 shows a synthetic scheme for compound 58.
Figure 40B:
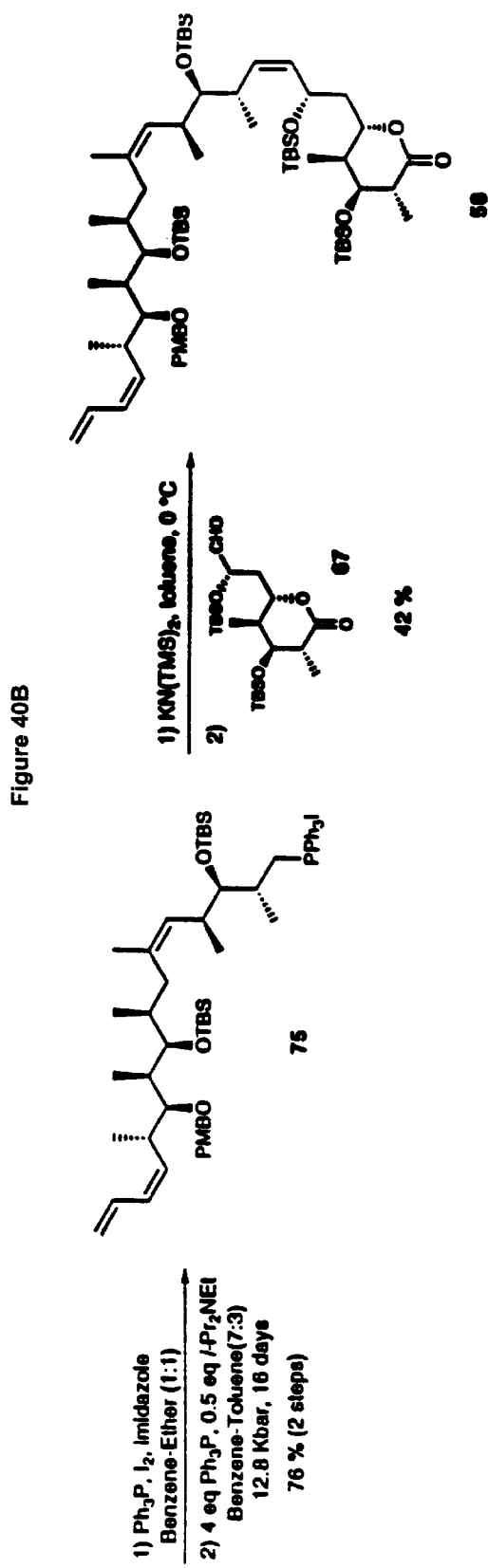

Alternatively, the discodermolide backbone can be synthesized by installing the terminal diene before Wittig coupling with Fragment C. As shown in FIG. 40, regioselective ring opening of benzylidine acetal 39 with DIBAL-H followed by oxidation and application of the Yamamoto olefination protocol provides diene 73. Selective removal of the less hindered PMB using DDQ/$H_2O$ is followed by conversion to the primary iodide and phosphonium salt 75. Alternatively, the primary PMB can be enhanced for either a dimethoxy benzyl ether or silyl protecting group earlier in the sequence. Application of Dauben's high pressure conditions results in approximately 75% yield of the desired phosphonium salt. Further assembly of the discodermolide backbone entails Wittig coupling of aldehyde 67 with the ylide derived from phosphonium salt 75 to afford 58. Further manipulation as indicated above (FIG. 15) provides (+)-discodermolide.

Figure 43:
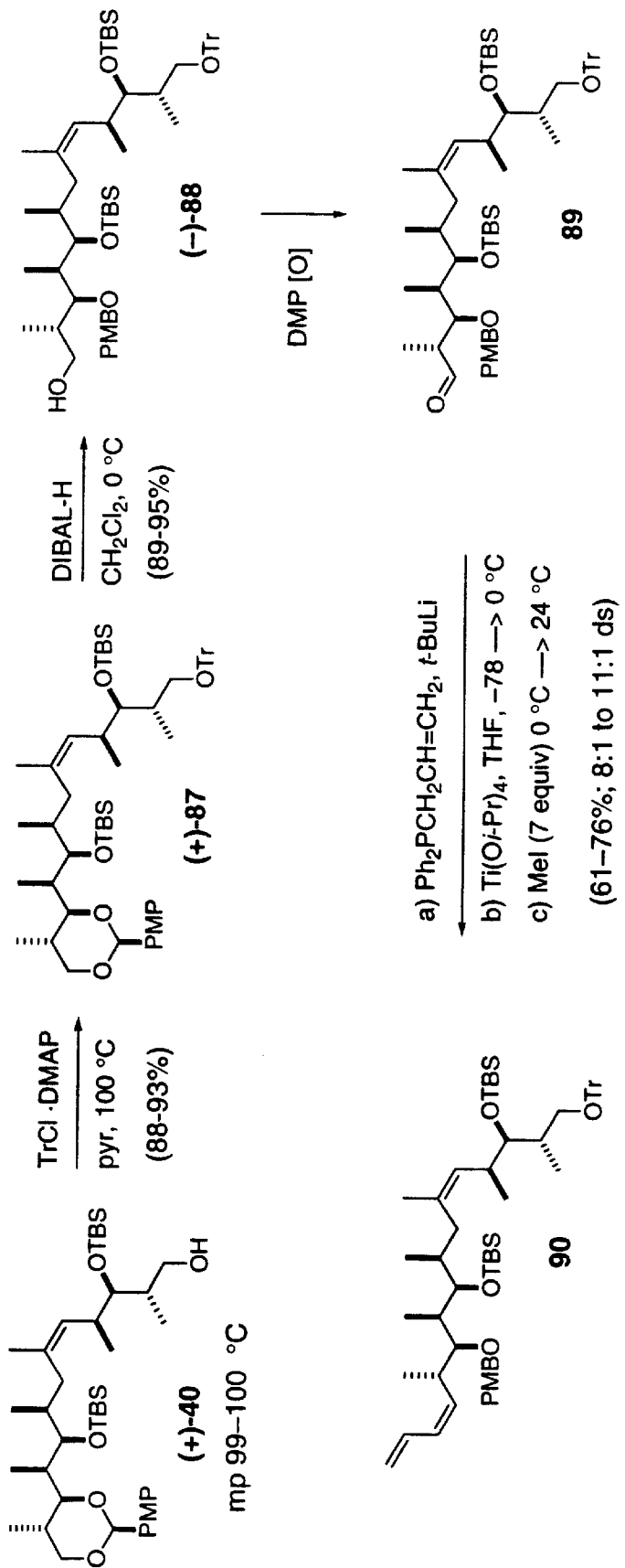
FIG. 43 shows a synthetic scheme for compound (+)-B.
Figure 44:
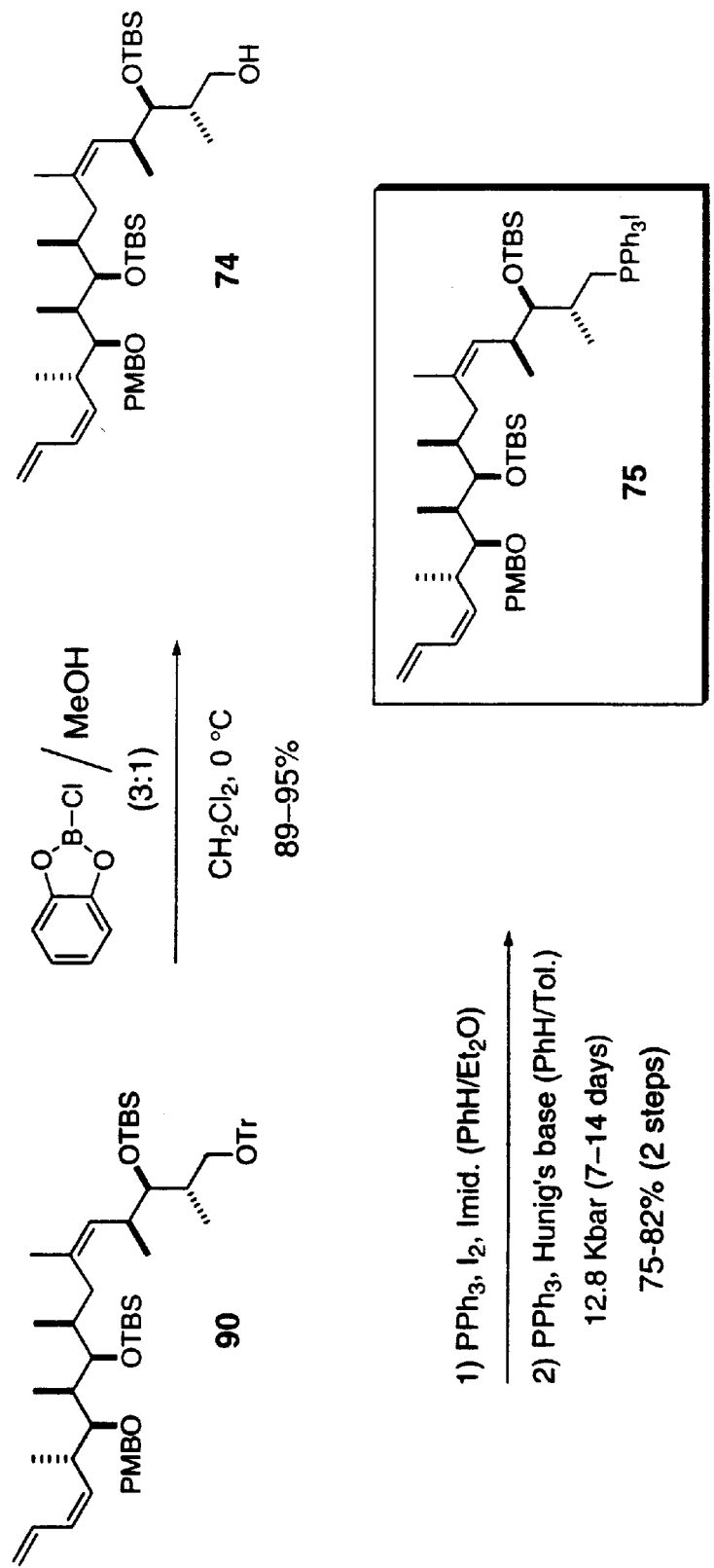
FIG. 44 shows a synthetic scheme for compound 89.

Another preferred route to phosphonium salt 75 is depicted in FIGS. 43 and 44. Starting from alcohol 40, trityl ether 87 may be prepared by contacting with trityl chloride andN,N-dimethyl-pyridine (DMAP) in hot pyridine (FIG. 43) Reductive opening of the anisylidine acetal functionality of 87 with DIBALH provides the primary alcohol 88. Oxidation of 88 with Dess-Martin Periodane (DMP) followed by Yamamoto olefination provides diene 90 with approximately a 8–11:1 diastereoselectivity.

The trityl protecting group of 90 is preferably removed utilizing a modified Boeckman protocol, as described, for example, in Boeckman, R. K., Jr.; Potenza, J. C. *Tetrahedron Lett.* 1985, 26, 1411, the disclosure of which is hereby incorporated by reference in its entirety, to provide alcohol 74. (FIG. 44). Wittig salt 75 may be prepared via conversion of alcohol 74 to the corresponding iodide employing a modified Corey protocol ($PPh_3$, I2, PhH/Et2O) and subjection of the unstable iodide to excess $PPh_3$ at high pressure (12.8 Kbar) in a buffered, non-polar medium (Hunig's base, toluene/benzene).

Figure 45:
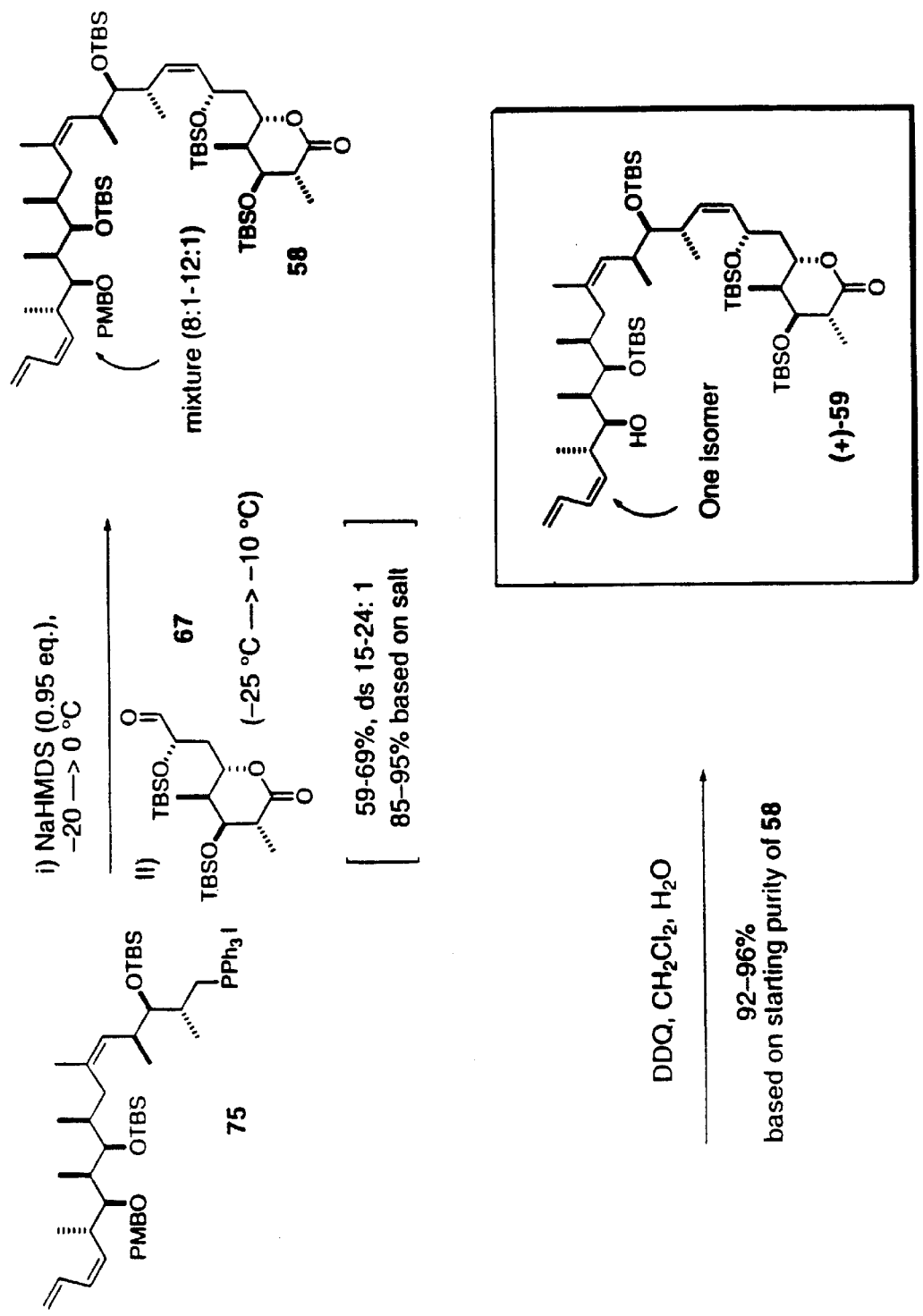
FIG. 45 shows a synthetic scheme for compound 75.
Figure 46:
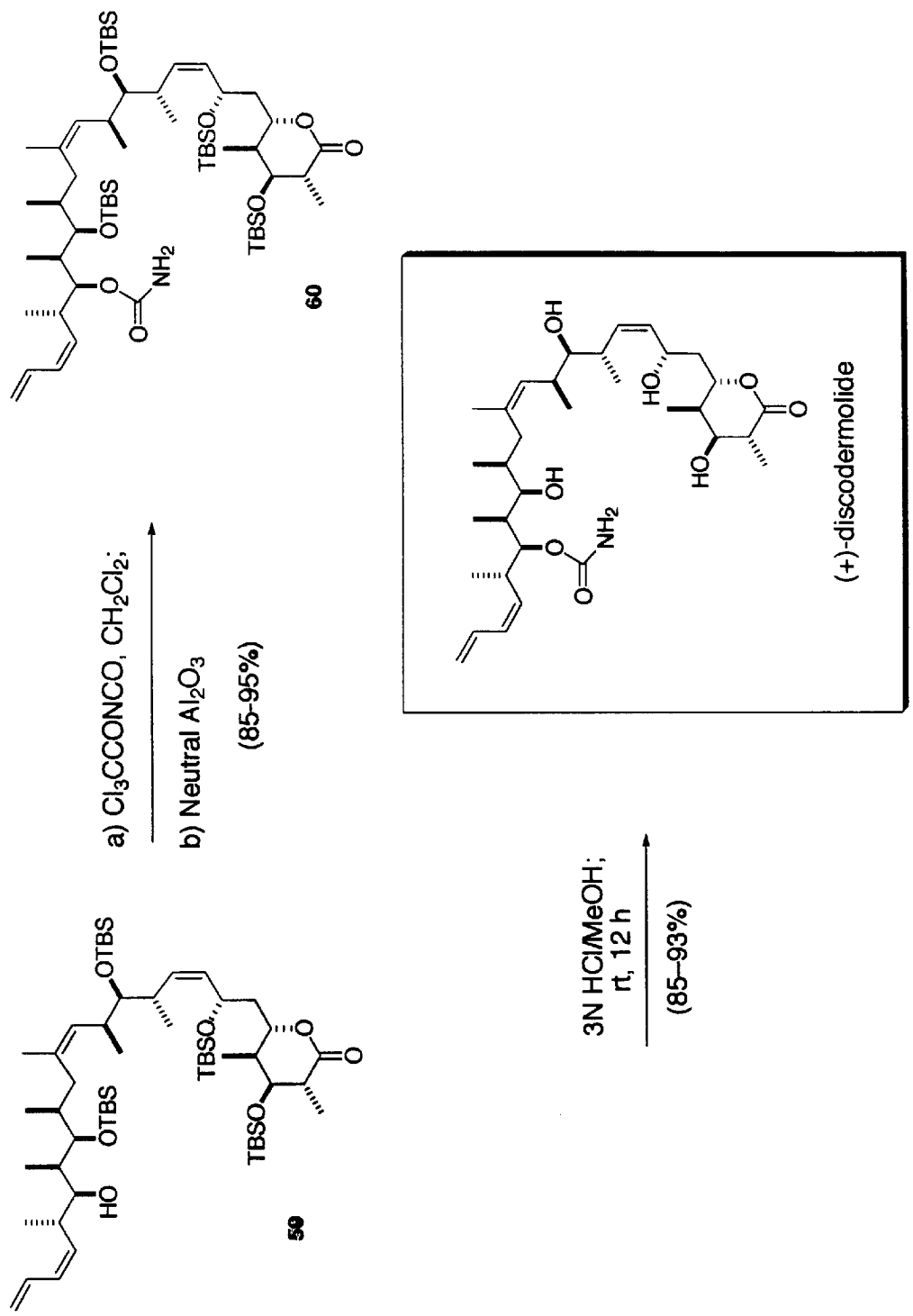
FIG. 46 shows a synthetic scheme for compound (+)-59.

Treatment of tetraene 58 (a mixture of diene isomers; ca 8–12:1) with DDQ results in oxidative removal of the PMB ether and, selective destruction of the trans-diene impurity preferably yields diastereomerically pure alcohol 59 after flash chromatography (FIG. 45).

Alcohol 59 may be subjected to the Kocovsky protocol to yield the carbamate 60 (Scheme 46). Carbamate 60 is preferably taken onto the natural product (+)-discodermolide by slow addition of acid, for example, 3N HCl to a methanol solution of 60 over a suitable time period such as 12 hours. Discodermolide may be purified by flash chromatography followed by crystallization from, for example, neat acetonitrle.

Figure 47:
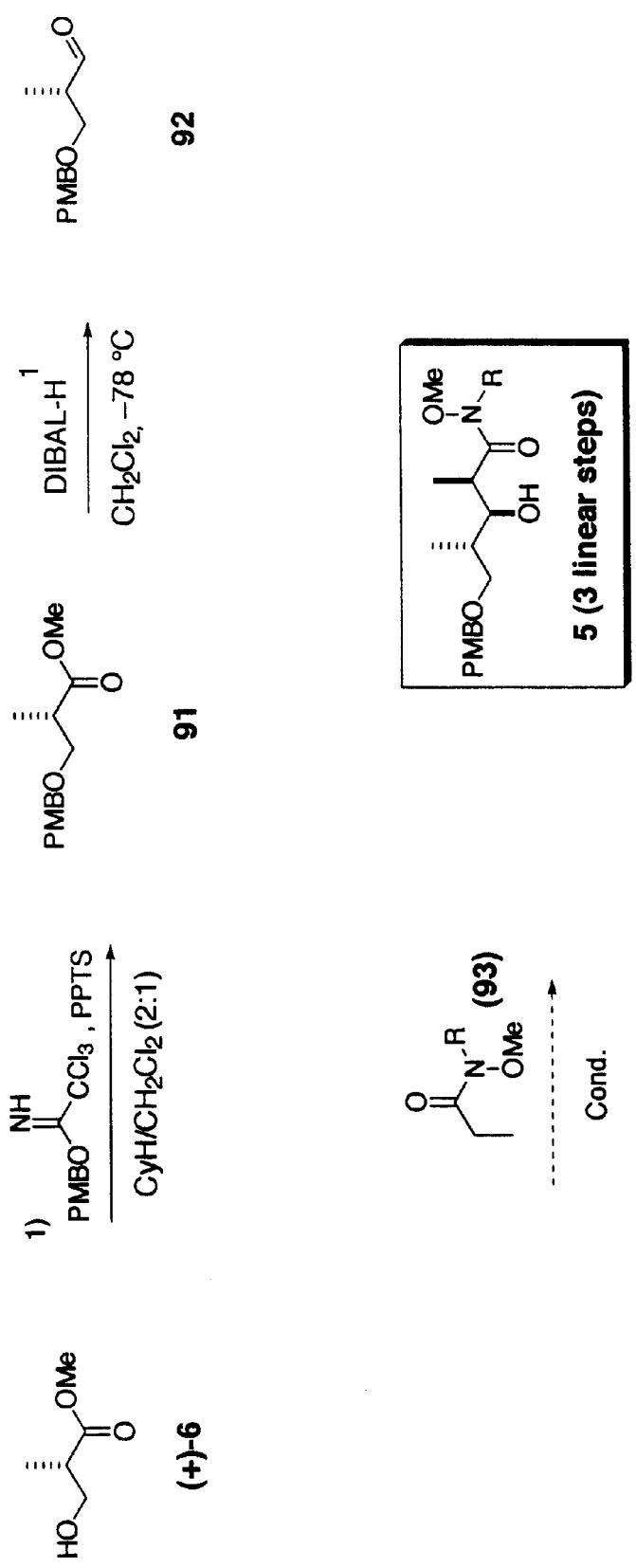
FIG. 47 shows a synthetic scheme for (+)-discodermolide.
Figure 48:
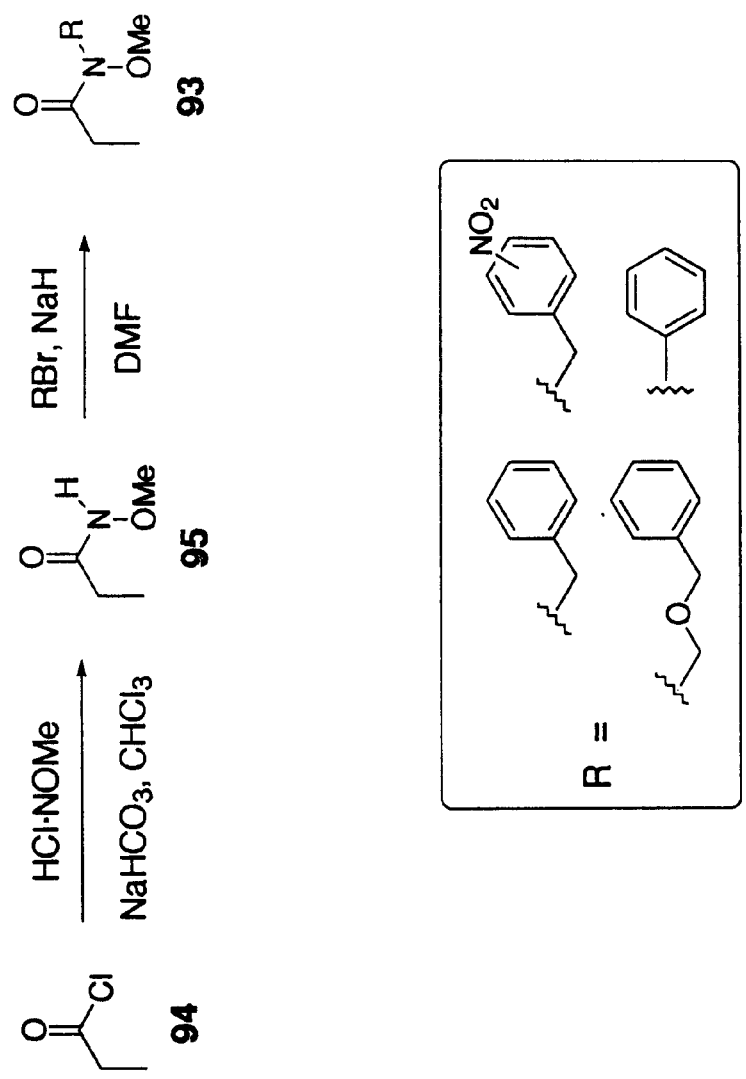
FIG. 48 shows a synthetic scheme for compound 95.

An Aldol reaction between aldehyde 92 and the corresponding enolate of amide 93 yields the common precursor in three steps (FIG. 47). Amide 93 can be easily prepared from the commercially available acid chloride 94 (FIG. 48).

Alternative synthetic routes to tetraene 58 are depicted in FIGS. 49 and 50. A palladium catalyzed coupling between vinyl iodide 96 and organozinc 97 yields 58 (FIG. 49). Alternatively 58 can be constructed via the coupling of 98 with aldehyde 67 (FIG. 50).

Alkyl groups according to the invention include but are not limited to straight chain and branched chain hydrocarbons such as methyl, ethyl, propyl, pentyl, isopropyl, 2-butyl, isobutyl, 2-methylbutyl, and isopentyl moieties having 1 to about 10 carbon atoms, preferably 1 to about 6 carbon atoms. Cycloalkyl groups are cyclic hydrocarbons having 3 to about 10 carbon atoms such as cyclopentyl and cyclohexyl groups. Heterocycloalkyl groups are cycloalkyl groups which include at least one heteroatom (i.e., an atom which is not carbon, such as O, S, or N) in their cyclic backbone. Alkenyl groups according to the invention are straight chain or branched chain hydrocarbons that include one or more carbon—carbon double bonds. Preferred alkenyl groups are those having 2 to about 10 carbon atoms. Alkyl, cycloalkyl, heterocycloalkyl, and alkenyl groups according to the invention optionally can be unsubstituted or can bear one or more substituents such as, for example, halogen hydroxyl, amine, and epoxy groups.

Aryl groups according to the invention are aromatic and heteroaromatic groups having 6 to about 14 carbon atoms, preferably from 6 to about 10 carbon atoms, including, for example, naphthyl, phenyl, indolyl, and xylyl groups and substituted derivatives thereof, particularly those substituted with amino, nitro, hydroxy, methyl, methoxy, thiomethyl, trifluoromethyl, mercaptyl, and carboxy groups. Alkaryl groups are groups that contain alkyl and aryl portions and are covalently bound to other groups through the alkyl portion, as in a benzyl group.

The target compounds and intermediates of the present invention may contain protecting groups. Protecting groups are known per se as chemical functional groups that can be selectively appended to and removed from functionality, such as hydroxyl and amine groups, present in a chemical compound to render such functionality inert to certain chemical reaction conditions to which the compound is exposed. See, e.g., Greene and Wuts, Protective Groups in Organic Synthesis, 2d edition, John Wiley & Sons, New York, 1991. Numerous hydroxyl protecting groups are known in the art, including the acid-labile t-butyldimethylsilyl, diethylisopropylsilyl, and triethylsilyl groups and the acid-stable aralkyl (e.g., benzyl), triisopropylsilyl, and t-butyldiphenylsilyl groups. Useful amine protecting groups include the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (I-Noc) groups.

As used herein, the term "oxidatively labile group" is intended to include all groups known to be removed by an oxidizing agent. An example of an oxidizing agent includes, but is not limited to, 2,3-dichloro-5,6-dicyano-1,4-benzoquinone (DDQ).

The term amino acid as used herein is intended to include all naturally-occurring and synthetic amino acids known in the art. In general, amino acids have structure $H_2N-CH(R_C)-C(O)OH$ where $R_C$ is the amino acid side chain. Representative, naturally-occurring side chains are shown in Table 1.

TABLE 1

| | |
|---|---|
| $CH_3-$ | $CH_3-CH_2-S-CH_2-CH_2-$ |
| $HO-CH_2-$ | $HO-CH_2-CH_2-$ |
| $C_6H_5-CH_2-$ | $CH_3-CH_2(OH)-$ |
| $HO-C_6H_5-CH_2-$ | $HO_2C-CH_2-NH_2C(O)-CH_2-$ |
| 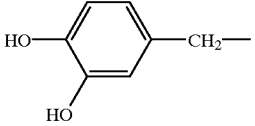 | 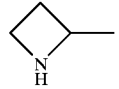 |
| 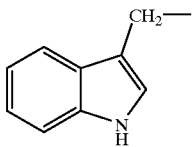 | $HCO_2-CH_2-CH_2-$ |
| | $NH_2C(O)-CH_2-CH_2-$ |
| | $(CH_3)_2-CH-$ |
| | $(CH_3)_2-CH-CH_2-$ |
| | $CH_3-CH_2-CH_2-$ |
| | $H_2N-CH_2-CH_2-CH_2-$ |
| 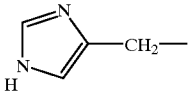 | $H_2N-C(NH)-NH-CH_2-CH_2-CH_2-$ |
| | $H_2N-C(O)-NH-CH_2-CH_2-CH_2-$ |
| | $CH_3-CH_2-CH(CH_3)-$ |
| | $CH_3-CH_2-CH_2-CH_2-$ |
| $HS-CH_2-$ | $H_2N-CH_2-CH_2-CH_2-CH_2-$ |
| $HO_2C-CH(NH_2)-CH_2-S-S-CH_2-$ | |
| $CH_3-CH_2-$ | |
| $CH_3-S-CH_2-CH_2-$ | |

Hydrophobic amino acid side chains are preferred, including the $CH_3-$, $C_6H_5-CH_2-$, $CH_3-CH_2-$, $CH_3-S-$ $CH_2$—$CH_2$—, $(CH_3)_2$—$CH$—, $(CH_3)_2$—$CH$—$CH_2$—, $CH_3$—$CH_2$—$CH(CH_3)$—, and $CH_3$—$CH_2$—$CH_2$—$CH_2$— side chains. Peptides according to the invention are linear, branched, or cyclic chemical structures containing at least 2 covalently bound amino acids.

Certain compounds of the invention contain amino groups and, therefore, are capable of forming salts with various inorganic and organic acids. Such salts are also within the scope of this invention. Representative salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts can be formed by conventional means, such as by reacting the free base form of the product with one or more equivalents of the appropriate acid in a solvent or medium in which the salt is insoluble, or in a solvent such as water which is later removed in vacuo or by freeze drying. The salts also can be formed by exchanging the anions of an existing salt for another anion on a suitable ion exchange resin.

All processes described herein are contemplated to be run on any scale, including milligram, gram, kilogram, and commercial scale. Preferred processes according to the invention include contacting a phosphonium salt of formula I with base and an alkylthiol of formula II:

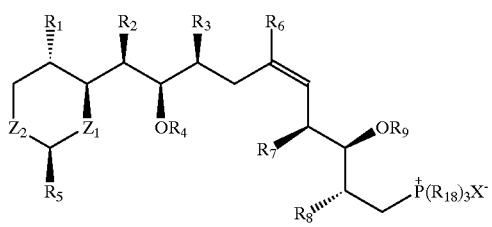

I

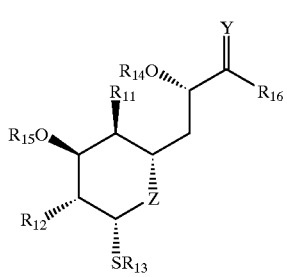

II to form a diene of formula III:

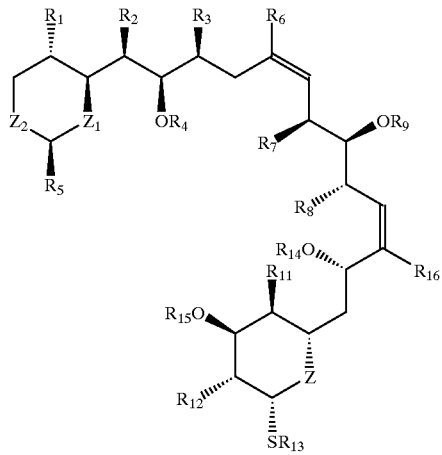

III wherein:

$R_1$, $R_2$, $R_3$, $R_7$, $R_8$, $R_{11}$, $R_{12}$ and $R_{13}$ are, independently, $C_1$–$C_{10}$ alkyl;

X is a halogen;

$R_6$ is selected from the group consisting of H and $C_1$–$C_{10}$ alkyl;

Z, $Z_1$, and $Z_2$ are, independently, O, S or NR';

$R_4$, $R_9$, $R_{14}$, and $R_{15}$ are, independently, acid labile hydroxyl protecting groups;

$R_5$ is $C_6$–$C_{14}$ aryl;

Y is O, S or NR';

R' and $R_{16}$ are, independently, hydrogen or $C_1$–$C_6$ alkyl; and $R_{18}$ is $C_6$–$C_{14}$ aryl.

Such procedures preferably are run in solvents such as tetrahydrofuran at −78° C.–0° C. Suitable bases for such procedures include sodium hexamethyldisilazide, potassium hexamethyldisilazide, and n-butyllithium with hexamethylphosphoramide.

Phosphonium salts of formula I can be prepared by reacting a corresponding halogen of formula XXXXVI:

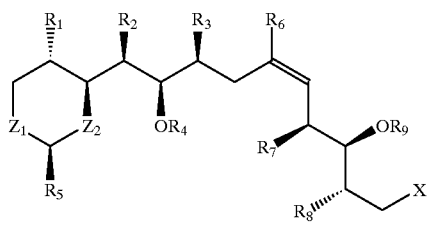

XXXXVI with $P(R_{18})_3$ in an for a time and under conditions effective to produce the salt. This reaction preferably is conducted in a aromatic hydrocarbon organic solvent such as toluene or benzene. A mixture of benzene and toluene in a ratio of 7:3 is preferred at a pressure of about 5 Kbar to about 20 Kbar.

The methods of the invention involve also are directed to the synthesis of alkenes of formula IV:

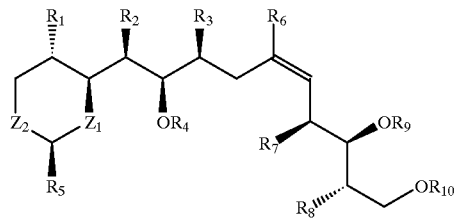

IV by contacting organometallic reagents of formula Va:

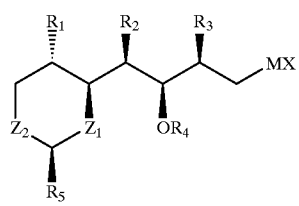

Va with vinyl halides of formula VIa:

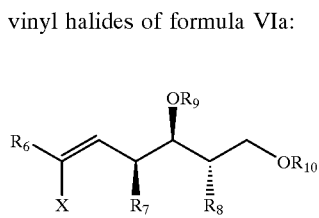

VIa wherein M is Li, Cu, Mg, or Zn, and $R_{10}$ is an acid stable hydroxyl protecting group. Alternatively, a vinyl halide of formula Vb:

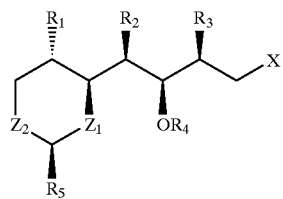

Vb is contacted with an organometallic compound of formula VIb:

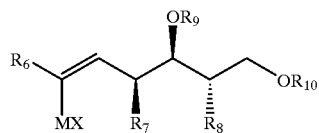

VIb

Such reactions preferably are performed in the presence of a palladium-containing catalyst such as $Pd(PPh_3)_4$, $Pd(Cl_2)(PPh_3)_2$, $Pd(Cl_2)(dppf)_2$.

In yet another aspect, the synthetic methods of the invention are directed to the preparation of compounds having formula VII:

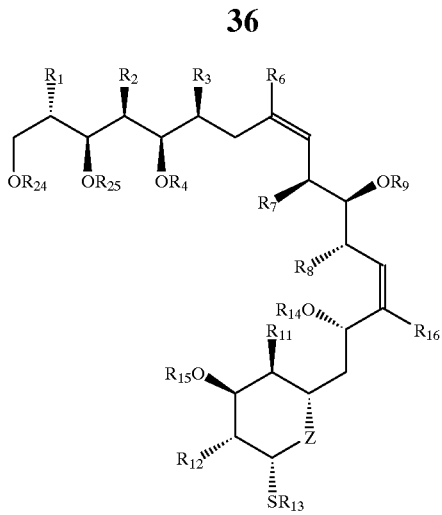

VII by contacting a diene of formula VIIIa:

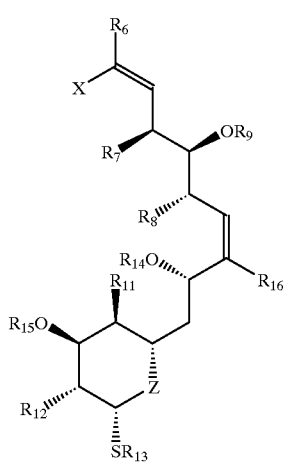

VIIIa with an organometallic compound having formula Va wherein $R_{24}$ is hydrogen and $R_{25}$ is hydrogen or an acid stable hydroxyl protecting group. Alternatively, an organometallic compound having formula VIIIb is contacted with a vinyl halide having formula Vb.

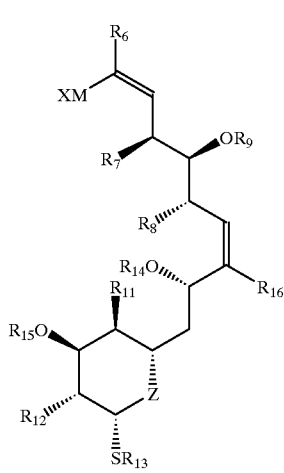

VIIIb

The reaction of compounds having formulas V and VIII preferably is performed in ether in the presence of a palladium- or nickel-containing catalyst.

The methods of the invention also involve producing dienes having formula VIIIa by contacting phosphonium salts having formula IX:

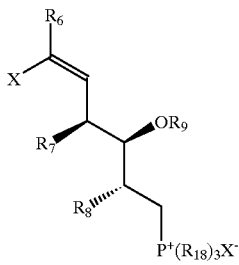

IX with a base such as sodium hexamethyl disilazide and an alkylthiol compound having formula II. Such procedures preferably are run in solvents such as tetrahydrofuran at −78° C.–0° C. Suitable bases for such procedures include sodium hexamethyldisilazide, potassium hexamethyldisilazide, and n-butyllithium with hexamethylphosphoramide.

The methods of the invention also involve producing compounds of formula XXIII:

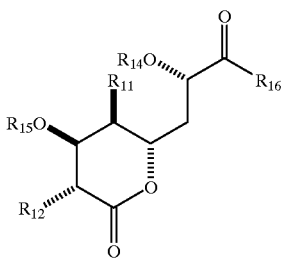

XXIII by contacting an aldehyde of formula XXIV:

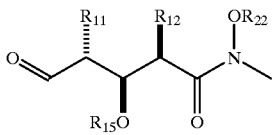

XXIV with an enol ether of formula XXV:

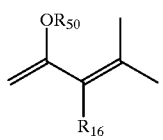

XXV in the presence of a titanium salt and an organic acid to form an enone of formula XXVI:

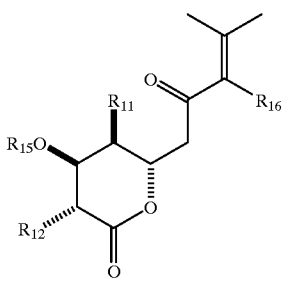

XXVI

Preferably, the reaction between aldehyde 27 and the enol ether 62 is a Mukaiyama aldol reaction wherein the Lewis acid is a titanium salt (such as $TiCl_4$) or some other Ti(IV) of Sn(IV) Lewis acid (such as $SnCl_4$) and the organic acid is trichloroacetic acid, trifluoroacetic acid, sulfuric acid, or pyridinium p-toluenesulfonate. Following the aldol reaction, enone 64 is contacted with a reducing agent to form the corresponding enol 65. Preferably, the reducing agent is potassium tri-sec-butylborohydride or sodium tri-sec-butylborohydride (commercially available in THF as K-Selectride® and N-Selectride®, respectively) but may include chiral reducing agents such as lithium B-isopinocampheyl-9-borabicyclo[3.3.1]nonyl hydride (commercially available in THF as Alpine-Hydride®.

According to the present invention, enol 65 is then contacted with a compound having formula R-L wherein R is an acid labile protecting group and L is a leaving group. Preferably, R-L is t-butyldimethylsilyl chloride or t-butyldimethysilyl triflate.

The protected enol is then oxidized with an oxidizing agent such as $O_3$ or the reagent combination of $NaIO_4$ with catalytic $OsO_4$ for a time and under conditions effective to oxidize the carbon—carbon double bond of the protected enol.

The methods of the present invention are also directed to the synthesis of diene having formula XXXIII:

XXXIII

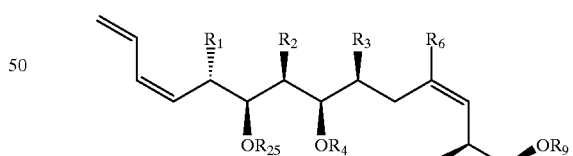
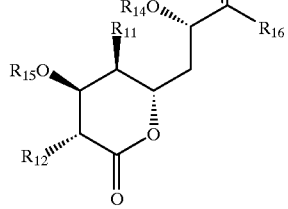

by contacting phosphonium salts of formula XXXIV:

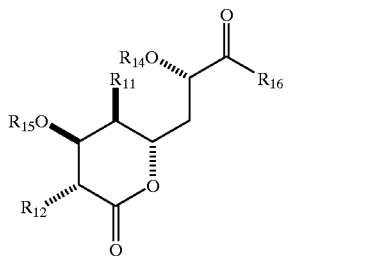

XXXIV with base and a compound of formula XXXV:

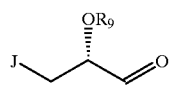

XXXV

Suitable bases for such procedures include potassium hexamethyldisilazide, sodium hexamethyldisilazide, n-butyllithium and potassium t-butoxide. A preferred solvent is toluene, preferably at a temperature of −78° C.–0° C.

Phosphonium salts of formula XXXIV can be prepared by reacting a corresponding halogen of formula XXXXVII:

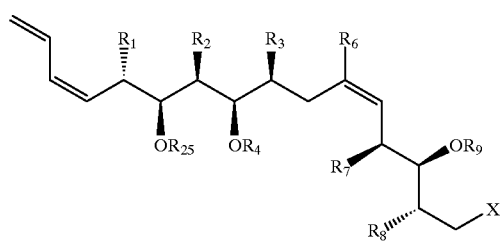

XXXXVII with $P(R_{18})_3$ in an for a time and under conditions effective to produce the salt. This reaction preferably is conducted in a aromatic hydrocarbon organic solvent such as toluene or benzene. A mixture of benzene and toluene in a ratio of 7:3 is preferred at a pressure of about 5 Kbar to about 20 Kbar.

Further processes of the invention involve producing compound having formula XXXVI:

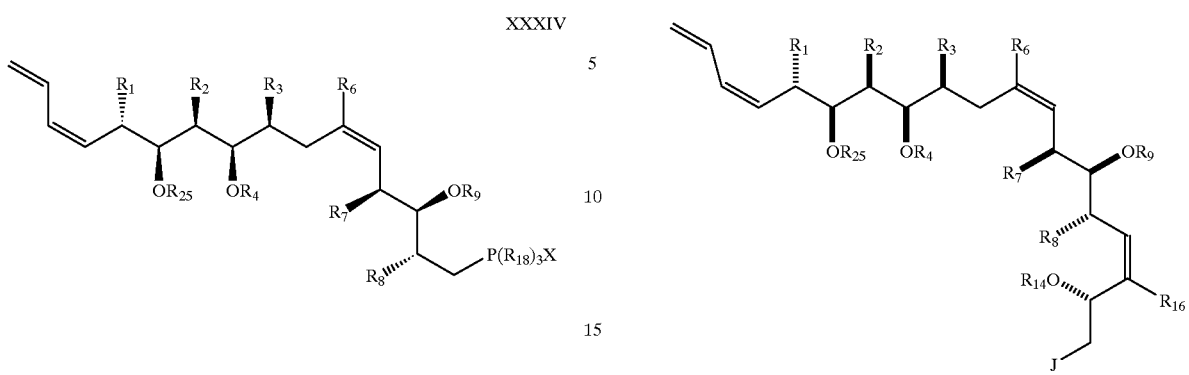

XXXVI by contacting a compound of formula XXXVII:

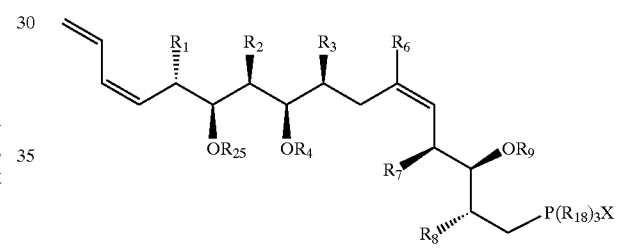

XXXVII with base and a phosphonium salt of formula XXXIV:

XXXIV

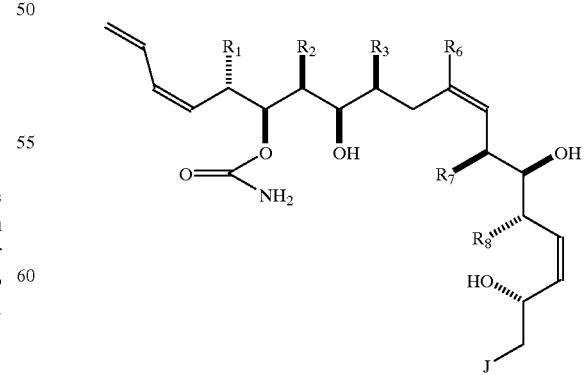

Preferred bases include sodium hexamethyldisilazide, potassium hexamethyldisilazide, n-butyllithium with hexamethylphosphoramide, and potassium t-butoxide. A preferred solvent is toluene, preferably at a temperature of −78° C.–0° C.

According to methods of the invention, removal of the acid stable protective group and carbamate formation followed by final deprotection furnishes compounds having formula:

Although preferred synthetic methods are those directed to (+)-discodermolide and compounds having like stereochemistry, those skilled in the art will recognize that the methods disclosed herein can be readily adapted to the synthesis of antipodal compounds such as, for example, (−)-discodermolide, and vice versa. All such synthetic methods are within the scope of the present invention.

The present invention provides compounds which mimic the chemical and/or biological activity of the discodermolides. In preferred embodiments, such compounds have formula XI:

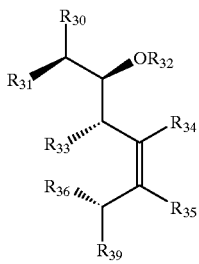

XI where
$R_{30}$ is substituted or unsubstituted $C_1$–$C_{10}$ alkyl or a moiety formula XII or XIII:

XII

XIII where A is $C_1$–$C_{20}$ alkyl, —$CH_2NH(T)$ or a moiety of formula XIV:

XIV wherein
T is peptide having 1 to about 10 amino acids;
$R_{32}$, $R_{40}$, $R_{42}$, $R_{43}$, $R_{46}$, $R_{47}$, and $R_{48}$ are, independently, hydrogen or $C_1$–$C_6$ alkyl;
$R_{41}$ is a side chain of an amino acid;
$W_1$ and $W_2$ are, independently, —$OR_{49}$ or —$NHP_1$;
$P_1$ is hydrogen or an amine protecting group;
$R_{33}$ and $R_{36}$ are, independently, hydrogen, $C_1$–$C_{10}$ alkyl, —$OR_{50}$, =O or together form —$CH_2$—$CH_2$—;
$R_{34}$ and $R_{35}$ are, independently, hydrogen or together form —C(H)=C(H)—C(H)=C(H)—;
$R_{39}$ is —$OR_{51}$ or —$CH_2$—$R_{51}$;
$R_{31}$ and $R_{44}$ are, independently, $C_1$–$C_{10}$ alkyl;
$Q_1$ and $Q_2$ are, independently, hydrogen, —$OR_Q$, —$NHR_{52}$, —$OC(=O)NH_2$ or together form —O—C(O)—NH—;
$R_Q$ is hydrogen or a hydroxyl protecting group;
$R_{51}$ is substituted or unsubstituted $C_6$–$C_{14}$ aryl, tetrahydropyranyl, furanosyl, pyranosyl, $C_3$–$C_{10}$ lactonyl or 2-pyranonyl;
$R_{45}$ is $C_1$–$C_6$ alkenyl, $C_1$–$C_6$ alkyl, $C_6$–$C_{14}$ aryl, $C_2$–$C_{10}$ heterocycloalkyl, $C_3$–$C_{10}$ cycloalkyl, or $C_7$–$C_{15}$ aralkyl; and
$R_{49}$, $R_{50}$, and $R_{52}$ are, independently, hydrogen or $C_1$–$C_6$ alkyl.

Some preferred compounds having formula XI are shown in FIGS. 33–36.

In other aspects, the present invention provides a process for forming a halogenated olefin of formula:

wherein:
$R_6$ is selected from H and $C_1$–$C_6$ alkyl;
$R_7$ and $R_8$ are independently $C_1$–$C_{10}$ alkyl;
$R_9$ is an acid labile hydroxyl protecting group;
$R_{10}$ is an oxidatively labile protecting group; and,
X is halogen;

the process comprising contacting an aldehyde of formula:

with a compound of formula $(R_{18})_3PCHXR_6$ in the presence of base, wherein $R_{18}$ is $C_6$–$C_{14}$ aryl, for a time and conditions effective to form the halogenated olefin.

Preferred conditions include cooling a suspension of $R_6Ph_3PX$ in an aprotic solvent, such as tetrahydrofuran, at about 0° C. to −25° C., and contacting the suspension with a strong base such as an alkyl metal. Suitable strong bases include, but are not limited to alkyl lithiums, such as butyl lithium, t-butyl lithium, and the like. The solution may be added to a precooled solution of $X_2$, preferably at a rate such that the temperature of the resultant solution does not exceed −70° C. An additional base, such as sodium hexamethyl disilazide, is preferably added over approximately a 10 to 60 minute period followed by introduction of the aldehyde.

In certain preferred embodiments, $R_6$, $R_7$, and $R_8$ are independently $C_1$–$C_4$ alkyl, and $R_{18}$ is phenyl. In certain more preferred embodiments, $R_6$, $R_7$, and $R_8$ are methyl, X is iodine, $R_2$ is tert-butyldimethylsilyl, and $R_{10}$ is paramethoxybenzyl.

The present invention also provides process for forming a triene of formula:

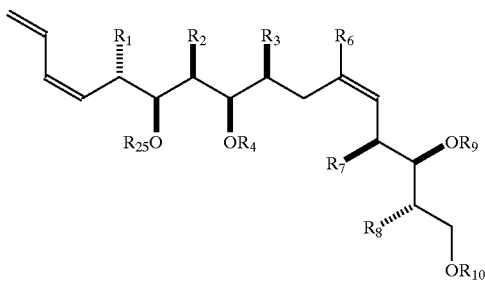

wherein:

R$_1$, R$_2$, R$_7$, and R$_8$ are independently C$_1$–C$_{10}$ alkyl;

R$_3$ and R$_6$ are independently selected from hydrogen and C$_1$–C$_6$ alkyl;

R$_4$ and R$_9$ are independently acid labile hydroxyl protecting groups;

R$_{25}$ is an oxidatively labile hydroxyl protecting group; and;

R$_{10}$ is a hydroxy protecting group;

the process comprising contacting an aldehyde of formula:

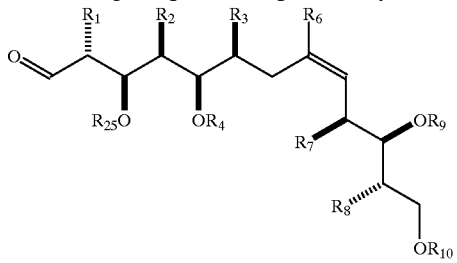

with a compound of formula Ph$_2$PCH$_2$CH=CH$_2$ in the presence of a base and a compound of formula Ti(O—R$_{27}$)$_4$, wherein R$_{27}$ is C$_{1-6}$ alkyl; followed by treatment with R$_{28}$X wherein R$_{28}$ is C$_{1-6}$ alkyl and X is a halogen, for a time and under conditions effective to form the triene.

Preferable conditions include precooling a solution of Ph$_2$PCH$_2$CH=CH$_2$ in an aprotic solvent, such as tetrahydrofuran, to a temperature of below 0° C., more preferably below −70° C., followed by the addition over a suitable time period of a strong base such as an alkyl metal. Strong bases may include, but are not limited to alkyl lithiums, such as butyl lithium, t-butyl lithium, and the like. The solution is preferably treated with Ti(O—R$_{27}$)$_4$ and stirred for a suitable period, followed by the introduction of the aldehyde. An excess of R$_{28}$X is then added and the solution warmed over a suitable time period to afford the triene.

In certain preferred embodiments, R$_1$, R$_2$, R$_7$, and R$_8$ are independently C$_1$–C$_4$ alkyl; R$_{10}$ is selected from triphenyl methyl, dimethoxyl benzyl, and dimethoxybenzyl-O-methyl; the base is C$_1$–C$_6$ alkyl lithium; R$_{27}$ is isopropyl, R$_{28}$ is methyl; and X is iodine.

In another embodiment, the process for forming the triene further comprising contacting the triene with a borane compound of formula:

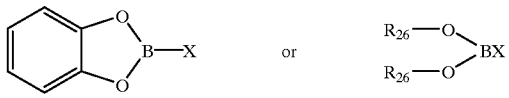

wherein X is a first halogen and R$_{26}$ is selected from C$_{6-14}$ aryl and C$_{1-6}$ alkyl, to form a triene alcohol of formula:

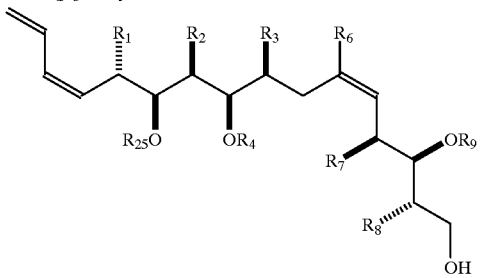

and;

contacting the triene alcohol with a halogen such as iodine in the presence of base and P(R$_{18}$)$_3$ to form the corresponding iodide, followed by further treatment of the resulting iodide with Hunig's base and P(R$_{10}$)$_3$ under conditions to form a phosphonium salt of formula:

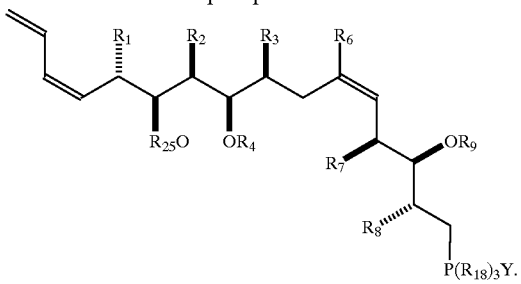

Preferable conditions include adding a protic solvent to a solution of the borane and a polar solvent. Preferable protic solvent include, but are not limited to, alcoholic solvents such as methanol. Preferable polar solvents include, but are not limited to, chlorinated solvents. The solution may be added over a suitable period of time to a solution of trityl ether to provide the triene alcohol. The triene alcohol is preferably stirred in a solution of P(R$_{18}$)$_3$ and a base, to which Y$_2$ is added. In certain embodiments, R$_{18}$ is phenyl, the base is imidazole and Y$_2$ is iodine. The resultant compound is preferably stirred in a solution to which an amine base, such as Hunig's base, is added followed by P(R$_{18}$)$_3$. The resultant solution may be subjected to elevated pressure for a period of time sufficient to form the phosphonium salt.

In certain embodiments, the aldehyde of formula:

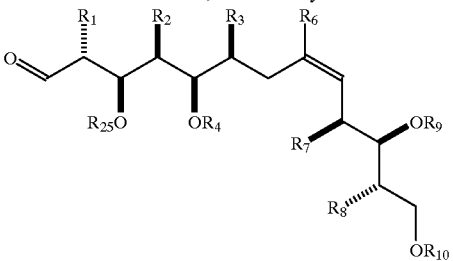

is formed by a process comprising contacting a compound of formula:

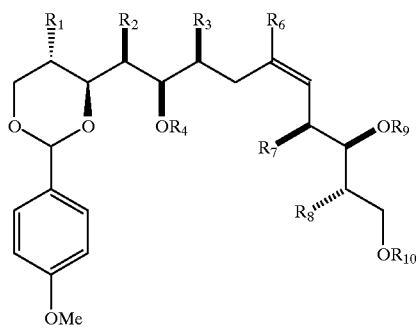

wherein:
R$_1$, R$_2$, R$_7$, and R$_8$ are independently C$_1$–C$_{10}$ alkyl;
R$_3$ and R$_6$ are independently selected from hydrogen and C$_1$–C$_6$ alkyl;
R$_4$ and R$_9$ are independently acid labile hydroxyl protecting groups; and
R$_{10}$ is a trityl group;
with hydride to form an alcohol of formula:

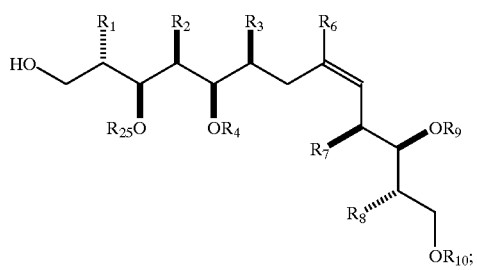

and oxidizing the alcohol to form the aldehyde.

The formation of the alcohol as well as the oxidation may be performed, for example, at reduced temperatures such as about 0° C. or lower. In certain embodiments, the hydride is diisobutylaluminum hydride (DIBAL-H) and the oxidation is accomplished through treatment of the alcohol with Dess-Martin periodinane.

The present invention further provides a process for forming a tetraene of formula:

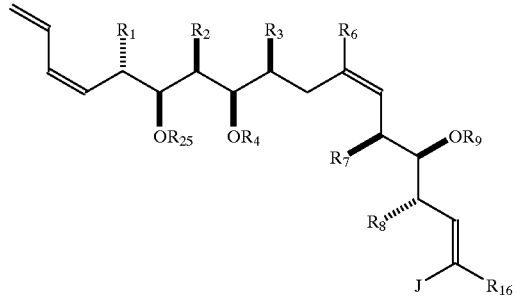

wherein:
R$_1$, R$_2$, R$_7$, and R$_8$ are independently C$_1$–C$_{10}$ alkyl;
R$_3$, R$_6$, and R$_{16}$ are independently selected from hydrogen and C$_1$–C$_6$ alkyl;
R$_4$ and R$_9$ are independently an acid labile hydroxyl protecting group;

R$_{25}$ is an acid stable hydroxyl protecting group; and
J is selected from:

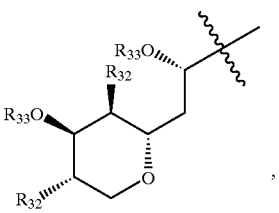

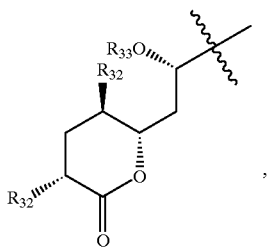

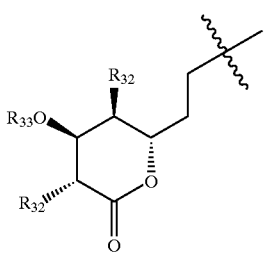

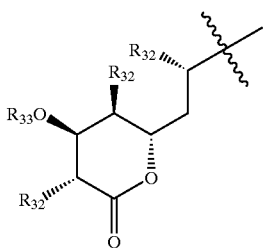

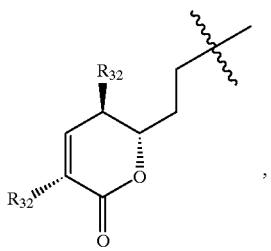

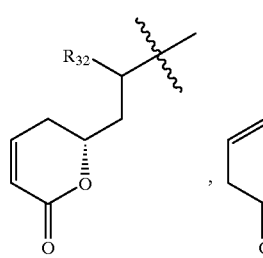

-continued

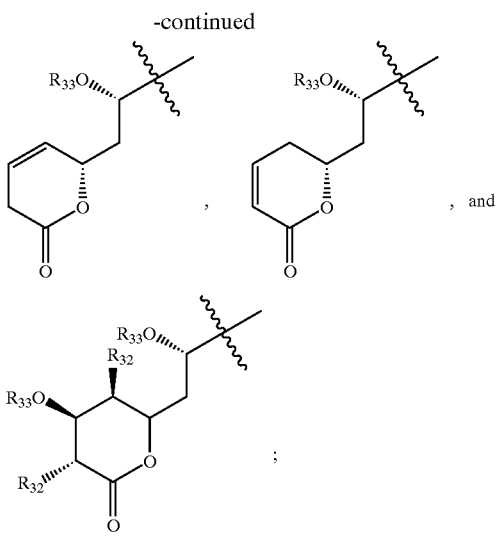

wherein $R_{32}$ is $C_1$–$C_6$ alkyl and $R_{33}$ is an acid labile hydroxyl protecting group;
the process comprising contacting a compound of the formula:

J-CHO with a phosphonium salt of the formula:

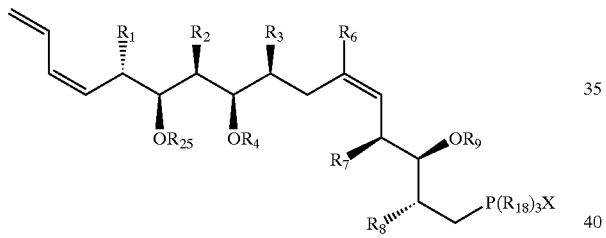

wherein $R_{18}$ is $C_6$–$C_{14}$ aryl, in the presence of a base for a time and under conditions effective to form the tetraene. In certain preferred embodiments, the process according to claim 11 wherein $R_1$, $R_2$, $R_7$, and $R_8$ are independently $C_1$–$C_4$ alkyl, $R_3$ and $R_6$ are independently selected from hydrogen and $C_1$–$C_4$ alkyl, and $R_{32}$ is $C_{14}$ alkyl.

The present invention also provides a process for forming a tetraene of formula:

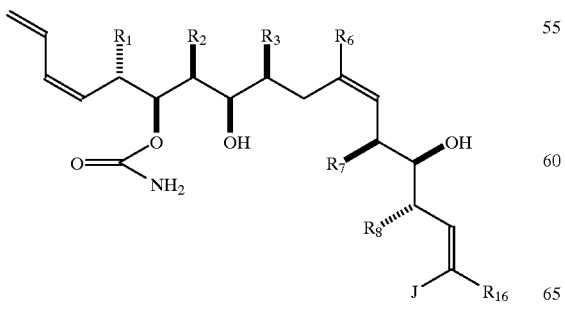

wherein:

$R_1$, $R_2$, $R_7$, and $R_8$ are independently $C_1$–$C_{10}$ alkyl;

$R_3$, $R_6$, and $R_{15}$ are independently selected from hydrogen and $C_1$–$C_6$ alkyl; and J is selected from:

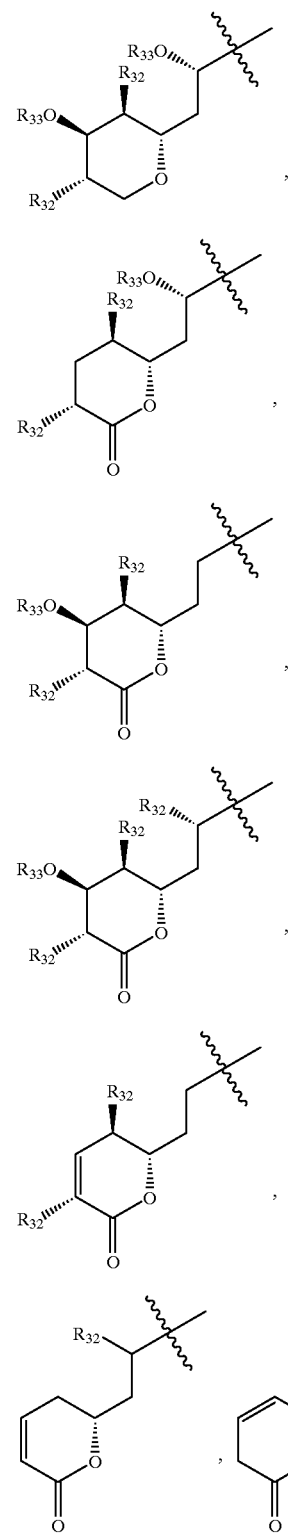

-continued

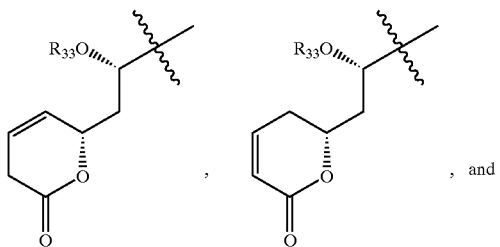, and

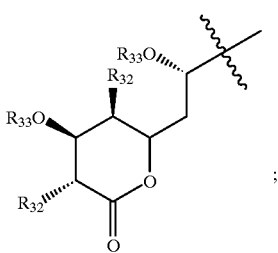;

wherein $R_{32}$ is $C_1$–$C_6$ alkyl and $R_{33}$ is H;
the process comprising contacting an alcohol of formula:

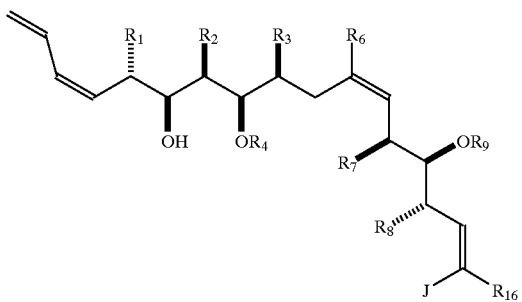

wherein $R_4$, $R_9$, and $R_{33}$ are acid labile hydroxyl protecting groups, with an isocyanate of the formula:

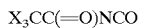

X$_3$CC(=O)NCO wherein X is a halogen, to form a carbamate intermediate; contacting the carbamate intermediate with neutral alumina to form a carbamate of formula:

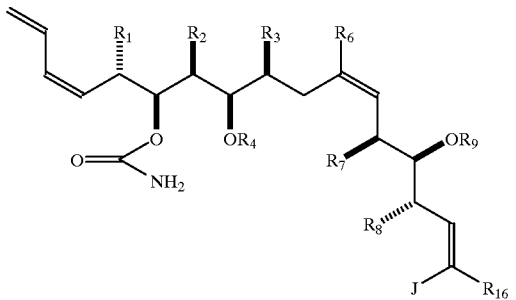

and;
removing the acid labile hydroxyl protecting groups by contacting the carbamate with acid in a protic solvent to form the tetraene.

A solution of the alcohol in a polar solvent may be contacted with the isocyanate at room temperature for a period of about 15 to 45 minutes followed by loading the solution directly onto neutral alumina. After a suitable period of time, for example, several hours, the material may be flushed from the column with an suitable solvent system. In certain preferred embodiments, the acid labile protecting group is removed with aqueous hydrochloric acid in an alcoholic solvent. More preferably, the addition of acid is performed in portions and over a period of time which minimizes precipitation.

In certain preferred embodiments, the alcohol is formed by contacting a compound of formula:

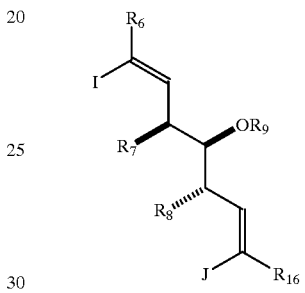

with a compound of formula:

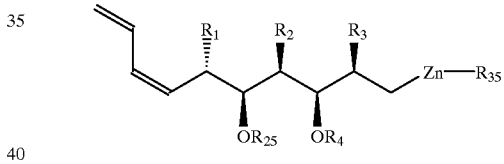

wherein $R_{25}$ is an oxidatively labile protecting hydroxyl protecting group, and $R_{35}$ is selected from $C_1$–$C_4$ alkyl and a halogen, in the presence of a metal coupling catalyst for a time and under conditions effective to form a coupling product of formula:

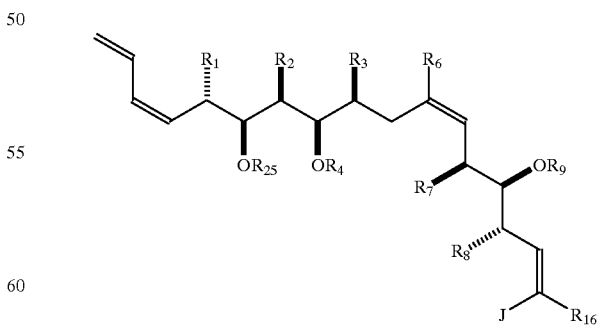

and deprotecting the coupling product to form the alcohol.
In certain preferred embodiments, $R_1$, $R_2$, $R_7$, and $R_8$ are independently $C_1$–$C_4$ alkyl, $R_3$, $R_6$, and $R_{16}$ are independently selected from hydrogen and $C_1$–$C_4$ alkyl, J is:

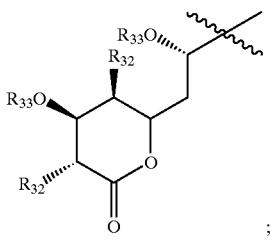

the isocyanate is Cl₃CC(=O)NCO, the acid is HCl, and the polar solvent is an alcohol selected from methanol, ethanol, and isopropanol. In other preferred embodiments, the alcohol is formed by contacting a compound of formula:

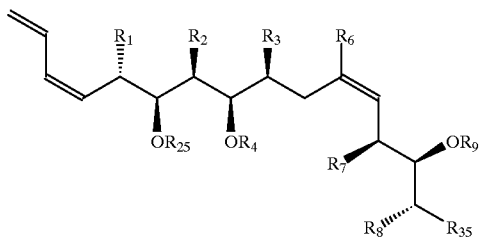

wherein:
  $R_{25}$ is an oxidatively labile protecting group;
  $R_{35}$ is selected from $CH_2P(=O)Ph_2$ and

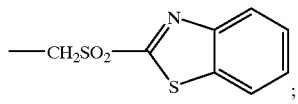

X is a halogen; and
$R_{18}$ is $C_{6-14}$ aryl;
with a compound of formula:

J-C(O)R¹⁶;

in the presence of a base to form a coupling product of formula:

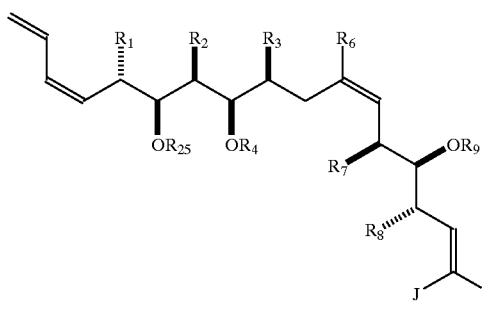

and deprotecting the coupling product (removing $R_{25}$) to form the alcohol. In certain more preferred embodiments, the protic solvent is an alcohol selected from methanol, ethanol, and isopropanol.

In other embodiments, the present invention provides a process for forming an alcohol of formula:

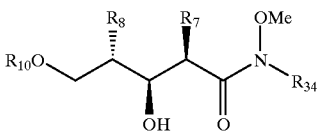

wherein:
  $R_7$ and $R_8$ are independently $C_1$–$C_{10}$ alkyl;
  $R_{10}$ is an acid stable hydroxyl protecting group;
  $R_{34}$ is selected from $(CH_2)_nC_6$–$C_{14}$ aryl and $(CH_2OCH_2)C_6$–$C_{14}$ aryl, wherein the aryl is substituted with 0–3 $R_{35}$;
  $R_{35}$ is selected from F, CF₃, Br, Cl, and NO₂; and
  n is selected from 0 and 1;
the process comprising contacting a compound of formula:

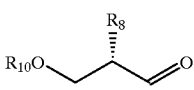

with the enolate of a compound of formula:

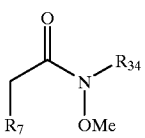

in the presence of Lewis acid for a time and under conditions effective to form the alcohol.

The present invention also provides a compound of formula:

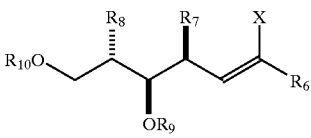

wherein:
  $R_6$ is $C_1$–$C_4$ alkyl;
  $R_7$ and $R_8$ are independently $C_1$–$C_{10}$ alkyl;
  $R_9$ is an acid labile hydroxyl protecting group;
  $R_{10}$ is an acid stable hydroxyl protecting group; and
  X is halogen.

The present invention also provides a compound of formula:

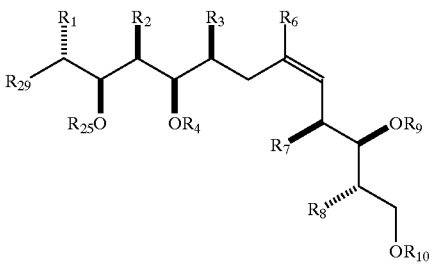

wherein:
  $R_1$, $R_2$, $R_7$, and $R_8$ are independently $C_1$–$C_{10}$ alkyl;
  $R_3$ and $R_6$ are independently selected from hydrogen and $C_1$–$C_6$ alkyl;

$R_4$ and $R_9$ are independently acid labile hydroxyl protecting groups;

$R_{25}$ is an oxidatively labile hydroxyl protecting group; and $R_{10}$ is a trityl group; and $R_{29}$ is selected from OH, CHO, and —CH=CH—CH=CH$_2$. In certain preferred compounds, $R_1$, $R_2$, $R_7$, and $R_8$ are methyl, and $R_3$ and $R_6$ are independently selected from hydrogen and methyl.

In other embodiments, the present invention provides a compound of formula:

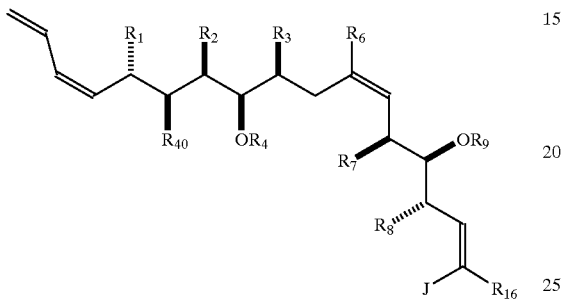

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl;

$R_4$, $R_9$, and $R_{14}$ are acid labile protecting groups;

$R_{40}$ is selected from $OR_{25}$ and $OC(=O)NH_2$;

$R_{25}$ is an acid stable protecting group; and

J is selected from:

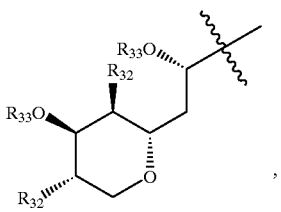,

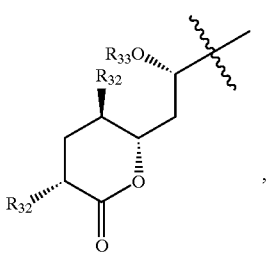,

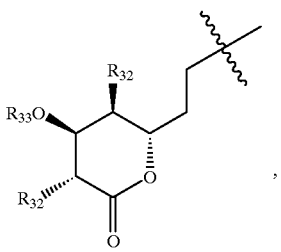,

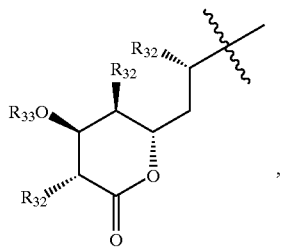,

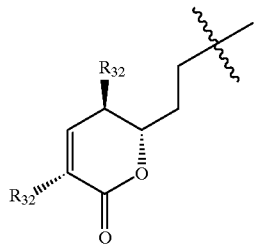,

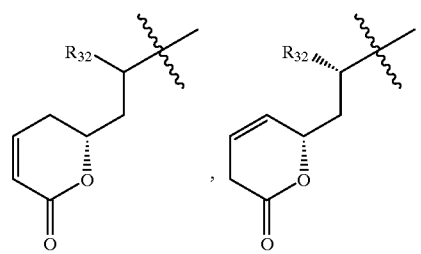,

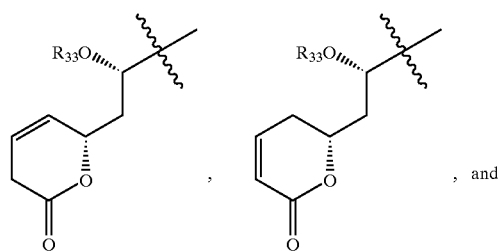, and

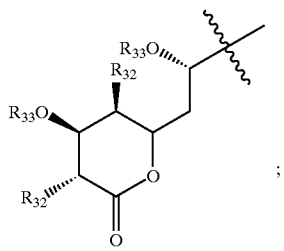;

wherein $R_{32}$ is $C_1$–$C_6$ alkyl and $R_{33}$ is selected from H and an acid labile hydroxy protecting group.

The compounds of the present invention can be admixed with carriers, excipients, and/or diluents to form novel compositions. Such compositions can be used in prophylactic, diagnostic, and/or therapeutic techniques. By administering an effective amount of such a composition, prophylactic or therapeutic responses can be produced in a human or some other type mammal. It will be appreciated that the production of prophylactic or therapeutic responses includes the initiation or enhancement of desirable responses, as well as the mitigation, cessation, or suppression of undesirable responses. The compositions of the invention are expected to find use, for example, in the inhibition of undesired cell proliferation (e.g., cancer) and in the inhibition of rejection in organ transplantation procedures. (See, e.g., Longley, et al., *Transplantation* 1991, 52, 650 and 656).

Compositions of the invention can be prepared by any of the methods well known in the pharmaceutical art, for example, as described in *Remington's Pharmaceutical Sciences* (Mack Pub. Co., Easton, Pa., 1980). The compositions can include a compound of the invention as an active ingredient in admixture with an organic or inorganic carrier or excipient suitable, for example, for oral administration. Other suitable modes of administration will be apparent to those skilled in the art. The compound of the invention can be compounded, for example, with the usual non-toxic, pharmaceutically acceptable carriers for tablets, pellets, capsules, solutions, suppositories, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The compound of the invention is included in the pharmaceutical composition in an amount sufficient to produce the desired effect upon the process or condition of diseases.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in appropriately soluble (e.g., gelatin) capsules; preferred materials in this connection also include lactose or milk sugar as well as high molecular weight polyethylene glycols.

When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, glycerin and various like combinations thereof.

For parenteral administration, suspensions containing a compound of the invention in, for example, aqueous propylene glycol can be employed. The suspensions should be suitably buffered (preferably pH>8) if necessary and the liquid diluent first rendered isotonic. The aqueous suspensions are suitable for intravenous injection purposes. The preparation of such suspensions under sterile conditions is readily accomplished by standard pharmaceutical techniques well-known to those skilled in the art. Additionally, it is possible to administer the compounds of the invention topically and this may preferably be done by way of creams, jellies, gels, pastes, ointments and the like, in accordance with standard pharmaceutical practice.

The compounds of the invention can be employed as the sole active agent in a pharmaceutical composition or can be used in combination with other active ingredients, e.g., other agents useful in diseases or disorders.

The amount of active ingredient that is to be combined with the carrier materials to produce a single dosage form will vary depending upon the host treated and the particular mode of administration. The specific dose level for any particular patient will depend on a variety of factors including the activity of the specific compound employed, the age, body weight, general health, sex, diet, time of administration, route of administration, rate of excretion, drug combination, and the severity of the particular disease undergoing therapy. In some instances, dosage levels below the lower limit of the aforesaid range may be more than adequate, while in other cases still larger doses may be employed without causing any harmful side effects provided that such higher dose levels are first divided into several small doses for administration throughout the day. The concentrations of the active ingredient in therapeutic compositions will vary depending upon a number of factors, including the dosage of the drug to be administered, the chemical characteristics (e.g., hydrophobicity) of the active ingredient, and the route of administration. Typical dose ranges are from about 285 $\mu$g/kg of body weight per day in three divided doses; a preferred dose range is from about 42 $\mu$g/kg to about 171 $\mu$g/kg of body weight per day. The preferred dosage to be administered is likely to depend on such variables as the type and extent of progression of the disease or disorder, the overall health status of the particular patient, the relative biological efficacy of the compound selected, and formulation of the compound excipient, and its route of administration, as well as other factors, including bioavailability, which is in turn influenced by several factors well known to those skilled in the art.

Additional objects, advantages, and novel features of this invention will become apparent to those skilled in the art upon examination of the following examples thereof, which are not intended to be limiting.

All reactions were carried out in oven-dried or flame-dried glassware under an argon atmosphere, unless otherwise noted. All solvents were reagent grade. Diethyl ether and tetrahydrofuran (THF) were freshly distilled from sodium/benzophenone under argon before use. Dichloromethane, benzene and diisopropyl amine were freshly distilled from calcium hydride before use. Triethylamine and diisopropylethylamine were distilled from calcium hydride and stored over potassium hydroxide. Hexamethylphosphoramide was freshly distilled from calcium hydride. Anhydrous pyridine, dimethylformamide and dimethyl sulfoxide were purchased from Aldrich and used without purification. n-Butyllithium and t-butyllithium were purchased from Aldrich and standardized by titration with diphenylacetic acid.

Unless stated otherwise all reactions were magnetically stirred and monitored by thin layer chromatography using 0.25 mm E. Merck pre-coated silica gel plates. Flash column chromatography was performed with the indicated solvents using silica gel-60 (particle size 0.040–0.062 mm) supplied by E. Merck. Yields refer to chromatographically and spectroscopically pure compounds, unless otherwise stated.

All melting points were determined on a Bristoline heated-stage microscope or a Thomas-Hoover apparatus and are corrected. The IR and NMR were obtained for $CHCl_3$ and $CDCl_3$ solutions respectively unless otherwise noted. Infrared spectra were recorded with a Perkin-Elmer Model 283B spectrometer using polystyrene as an external standard. Proton NMR spectra were recorded on a Bruker AM-500 spectrometer. Carbon-13 NMR spectra were recorded on a Bruker AM-500 or AM-250 spectrometer. Chemical shifts are reported relative to internal tetramethylsilane (d 0.00) for proton and chloroform $\delta 77.0$) or benzene ($\delta 128.0$) for carbon-13. Optical rotations were obtained with a Perkin-Elmer model 241 polarimeter in the solvent indicated. High-resolution mass spectra were obtained at the University of Pennsylvania Mass Spectrometry Service Center on either a VG micromass 70/70H high resolution double-focusing electron impact/chemical ionization spectrometer or a VG ZAB-E spectrometer. Microanalyses were performed by Robertson Laboratories, Madison, N.J. Single-crystal X-ray diffraction structure determination were performed at the University of Pennsylvania using an Enraf Nonius CAD-4 automated diffractometer. High performance liquid chromatography (HPLC) was performed using a Ranin component analytical/semi-prep system.

EXAMPLE 1

Alcohol (−)-8 p-Methoxybenzyl alcohol (200 g, 1.45 mol) was added to a suspension of NaH (60% in mineral oil; 5.82 g, 0.146 mol) in anhydrous ether (450 mL) over 1 h at room temperature. The mixture was stirred for 1 h and cooled to 0° C. Trichloroacetonitrile (158 mL, 1.58 mol) was then introduced over 80 min. After 1.5 h the solution was concentrated with the water bath temperature maintained below 40° C. The residue was treated with a mixture of pentane (1.5 L) and MeOH (5.6 mL), stirred at room temperature for 30 min, and filtered through a short Celite column. Concentration gave the trichloroimidate (394.3 g) as a red oil which was used without further purification.

A solution of (R)-(−)-Roche ester (124.7 g, 1.06 mol) in $CH_2Cl_2$/cyclohexane (1:2, 1.5 L) was cooled to 0° C. and treated with trichloroimidate (364.3 g) and PPTS (13.3 g, 52.9 mmol). After 3 h, the mixture was warmed to room temperature, stirred for 40 h, and concentrated. Filtration through a short silica column (20% ethyl acetate/hexane) afforded the ester (303.5 g) as a slight yellow oil.

The ester (303.5 g) was divided into three portions for the next reaction. In each preparation, solution of crude ester (112.8 g) in anhydrous THF (1.0 L) was cooled to 0° C. and $LiAlH_4$ (1.0 M in THF, 560 mL, 0.560 mol) was added over 1 h. The mixture was warmed gradually to room temperature and stirred for 24 h. After dilution with ether (1.0 L) the mixture was cooled to 0° C. and quenched carefully with saturated aqueous Rochelle's salt (20 mL). The resultant mixture was then transferred to a 4-L flask, diluted with ether (1.0 L), and treated with additional Rochelle's solution (ca. 300 mL) with shaking until a solid precipitated. The solution was filtered, concentrated, and the residue (including the aqueous layer) was diluted with ether (700 mL), dried over $Na_2SO_4$, filtered and concentrated. The crude products of the three reactions were combined and distilled under vacuum, furnishing (−)-8 (142.7 g, 74% yield for two steps) as a colorless oil: $[\alpha]^{23}_D$ −16.9° ©1.28, $CHCl_3$); IR ($CHCl_3$) 3510 (m), 3015 (s), 2965 (s), 2940 (s), 2920 (s), 2870 (s), 2840 (m), 1618 (s), 1590 (m), 1517 (s), 1470 (s), 1445 (m), 1423 (m), 1365 (m), 1305 (s), 1250 (s), 1178 (s), 1092 (s), 1037 (s), 826 (m), 814 (m), 718 (w), 710 (w) $cm^{-1}$; $^1H$ NMR (500 MHZ, $CDCl_3$) d 7.23 (d, J=8.6 Hz, 2 H), 6.86 (d, J=8.6 Hz, 2 H), 4.43 (ABq, $J_{AB}$=11.7 Hz, $\Delta\delta_{AB}$=13.2 Hz, 2 H), 3.78 (s, 3 H), 3.61–3.54 (m, 2 H), 3.53 (ddd, J=9.1, 4.7, 0.8 Hz, 1 H), 3.38 (dd, J=9.1, 7.9 Hz, 1 H), 2.60 (br s, 1 H), 2.08–1.98 (m, 1 H), 0.90 (d, J=7.0 Hz, 3 H); $^{13}C$ NMR (125 MHZ, $CDCl_3$) d 159.2, 130.2, 129.2, 113.8, 75.0, 73.01 67.7, 55.2, 35.6, 13.4; high resolution mass spectrum (CI, $NH_3$) m/z 210.1252 [M+; calcd for $C_{12}H_{18}O_3$: 210.1256].

Anal. Calcd for $C_{12}H_{18}O_3$: C, 68.54; H, 8.63. Found: C, 68.41; H, 8.60.

EXAMPLE 2

Aldol (+)-10

A solution of DMSO (40.0 mL, 564 mmol) in $CH_2Cl_2$ (1.0 L) was cooled to −78° C. and oxalyl chloride (23.0 mL, 263 mmol) was added over 1 h. After an additional 15 min, a cooled (−78° C.) solution of alcohol (−)-8 (38.0 g, 181 mmol) in $CH_2Cl_2$ (50 mL) was introduced via a cannula over 15 min (20 mL rinse) and the resultant milky mixture was stirred 0.5 h further at −78° C. I—$Pr_2NEt$ (150 mL, 861 mmol) was then added over 15 min. The mixture was stirred for 30 min, slowly warmed to room temperature (70 min), and quenched with aqueous $NaHSO_4$ (1.0 M, 1.0 L). The organic phase was concentrated, diluted with ether (500 mL), washed with water (6×500 mL), dried over $MgSO_4$, filtered and concentrated to give the corresponding aldehyde (38.0 g) as a colorless oil.

A solution of oxazolidinone (+)-9 (44.3 g, 190 mmol) in $CH_2Cl_2$ (500 mL) was cooled to 0° C. n-$Bu_2BOTf$ (1.0 M in $CH_2Cl_2$, 199.0 mL, 199 mmol) was introduced over 0.5 h, followed by addition of $NEt_3$ (30.2 mL, 217 mmol) over 10 min. The mixture was stirred at 0° C. for 0.5 h and cooled to −78° C. A precooled (−78° C.) solution of the above aldehyde in $CH_2Cl_2$ (100 mL) was then added via a cannula over 30 min (2×20 mL rinse). After 2 h at −78° C. and 2 h at 0° C., the reaction was quenched with pH 7 phosphate buffer (200 mL). The mixture was slowly treated with a solution of 30% $H_2O_2$ in MeOH (1:2, 600 mL) at 0° C., stirred overnight at room temperature, and concentrated. The residue was extracted with ethyl acetate (3×250 mL) and the combined extracts were washed with saturated aqueous $NaHCO_3$ and water (500 mL each), dried over $MgSO_4$, filtered and concentrated. Flash chromatography (30% ethyl acetate/hexane) provided (+)-10 (70.9 g, 89% yield from 8) as a colorless oil: $[\alpha]^{23}_D$ +278° ©0.49, $CHCl_3$); IR ($CHCl_3$) 3470 (w, br), 3020 (m), 2980 (m), 2940 (m), 2920 (m), 2880 (m), 1790 (s), 1705 (m), 1620 (m), 1590 (w), 1520 (m), 1485 (w), 1460 (m), 1390 (m), 1360 (m), 1305 (w), 1230 (br, s), 1110 (m), 1080 (m), 1035 (m), 985 (m), 970 (m), 820 (w), 695 (w) $cm^{-1}$; $^1H$ NMR (500 MHZ, $CDCl_3$) d 7.33–7.30 (m, 2 H), 7.27–7.19 (m, 5 H), 6.85 (d, J=8.7 Hz, 2 H), 4.67–4.63 (m, 1 H), 4.42 (apparent s, 2 H), 4.14 (apparent d, J=5.0 Hz, 2 H), 3.93 (qd, J=6.9, 3.4 Hz, 1 H), 3.85 (ddd, J=8.2, 3.1, 3.1 Hz, 1 H), 3.78 (s, 3 H), 3.69 (d, J=2.8 Hz, 1 H), 3.54 (apparent t, J=9.3 Hz, 1 H), 3.54 (dd, J=21.1, 9.2 Hz, 1 H), 3.28 (dd, J=13.4, 3.2 Hz, 1 H), 2.76 (dd, J=13.4, 9.6 Hz, 1 H), 1.98–1.93 (m, 1 H), 1.25 (d, J=6.9 Hz, 3 H), 0.94 (d, J=7.0 Hz, 3 H); $^{13}C$ NMR (125 MHZ, $CDCl_3$) $\delta$176.1, 159.2, 153.0, 135.3, 129.9, 129.3, 129.2, 128.8, 127.2, 113.7, 75.3, 74.5, 73.1, 66.0, 55.5, 55.2, 40.6, 37.7, 35.9, 13.5, 9.7; high resolution mass spectrum (CI, $NH_3$) m/z 442.2243 [(M+H)+; calcd for $C_{25}H_{32}NO_6$: 442.2229].

Anal. Calcd for $C_{25}H_{31}NO_6$: C, 68.01; H, 7.08. Found: C, 67.81; H, 7.26.

EXAMPLE 3

Common Precursor (+)-5

A suspension of N,O-Dimethylhydroxylamine hydrochloride (46.9 g, 481 mmol) in THF (250 mL) was cooled to 0° C. and $AlMe_3$ (2.0 M in hexane, 240 mL, 480 mmol) was added over 30 min. The resultant solution was warmed to room temperature, stirred for 0.5 h and then cooled to −30° C. A solution of oxazolidinone (+)-10 (70.9 g, 161 mmol) in THF (150 mL) was introduced over 20 min via cannula (20 mL rinse). After 3 h, the solution was poured slowly into a mixture of aqueous HCl (1.0 N, 1.2 L) and $CH_2Cl_2$ (1.0 L) at 0° C. and the mixture was shaken vigorously for 1 h. The aqueous phase was extracted with $CH_2Cl_2$ (2×500 mL) and the combined organic extracts were washed with water (3×1.0 L), dried over $MgSO_4$, filtered and concentrated. The crude material was taken up in ethyl acetate/hexane (1:3, 150 mL) with vigorous stirring to precipitate most of the chiral auxiliary. Filtration, concentration and flash chromatography (20% acetone/hexane) afforded (+)-5 (46.2 g, 88% yield) as a colorless oil: $[\alpha]^{23}_D$ +144° (c0.41, CHCl$_3$); IR (CHCl$_3$) 3470 (m, br), 3010 (s), 2975 (s), 2945 (s), 2915 (s), 2870 (s), 2845 (m), 1680 (s), 1590 (w), 1515 (s), 1465 (s), 1425 (m), 1390 (m), 1365 (m), 1310 (m), 1250 (s), 1180 (s), 1150 (m), 1090 (s), 1040 (s), 1000 (s), 825 (m) cm$^{-1}$; $^1$H NMR (500 MHZ, CDCl$_3$) δ7.25 (d, J=8.6 Hz, 2 H), 6.86 (d, J=8.7 Hz, 2 H), 4.44 (ABq, J$_{AB}$=11.6 Hz, Δδ$_{AB}$=17.1 Hz, 2 H), 3.95 (d, J=2.8 Hz, 1 H), 3.79 (s, 3 H), 3.70 (ddd, J=8.2, 3.2, 3.2 Hz, 1 H), 3.66 (s, 3 H), 3.62 (dd, J=9.0, 4.0 Hz, 1 H), 3.53 (dd, J=9.1, 5.9 Hz, 1 H), 3.17 (s, 3 H), 3.04 (m, 1 H), 1.91–1.84 (m, 1 H), 1.17 (d, J=7.0 Hz, 3 H), 0.98 (d, J=6.9 Hz, 3 H); $^{13}$C NMR (125 MHZ, CDCl$_3$) d 178.0, 159.0, 130.6, 129.1, 113.7, 113.6, 73.8, 72.8, 72.6, 61.3, 55.1, 36.5, 36.0, 14.2, 10.4; high resolution mass spectrum (CI, NH$_3$) m/z 326.1962 [(M+H)$^+$; calcd for C$_{17}$H$_{28}$NO$_5$: 326.1967].

Anal. Calcd for C$_{17}$H$_{27}$NO$_5$: C, 62.74; H, 8.36. Found: C, 62.74; H, 8.24.

EXAMPLE 4

Weinreb Amide (–)-11

A mixture of common precursor (+)-5 (337.3 mg, 1.04 mmol), 4 Å molecular sieves (344 mg), and CH$_2$Cl$_2$ (10 mL) was cooled to 0° C. and treated with DDQ (310.3 mg, 1.37 mmol). After 1.5 h, the mixture was filtered through a short Celite column (50% ethyl acetate/hexane). The filtrate was washed with saturated aqueous NaHCO$_3$ and water (100 mL each), dried over MgSO$_4$, filtered and concentrated. Flash chromatography (30% ethyl acetate/hexane) provided (–)-11 (255.6 mg, 76% yield) as a colorless oil: $[\alpha]^{23}_D$ –339° (c0.520, CHCl$_3$); IR (CHCl$_3$) 3010 (s), 2970 (s), 2940 (m), 2880 (m), 2840 (m), 1663 (s), 1620 (s), 1592 (w), 1520 (s), 1466 (s), 1447 (m), 1425 (m), 1393 (s), 1375 (s), 1307 (m), 1253 (s), 1178 (s), 1120 (s), 1083 (s), 1035 (s), 1015 (m), 1000 (s), 930 (w), 830 (m), 700 (w), 660 (w), 620 (w) cm$^{-1}$; $^1$H NMR (500 MHZ, CDCl$_3$) d 7.41 (d, J=8.8 Hz, 2 H), 6.87 (d, J=8.8 Hz, 2 H), 5.46 (s, 1 H), 4.04 (dd, J=11.3, 4.7 Hz, 1 H), 3.82 (dd, J=9.8, 6.5 Hz, 1 H), 3.79 (s, 3 H), 3.71 (s, 3 H), 3.51 (apparent t, J=11.2 Hz, 1 H), 3.19 (s, 3 H), 3.21–3.14 (m, 1 H), 1.98–1.92 (m, 1 H), 1.27 (d, J 7.0 Hz, 3 H), 0.75 (d, J 6.8 Hz, 3 H); $^{13}$C NMR (125 MHZ, CDCl$_3$) d 175.8, 159.8, 131.2, 127.2, 113.5, 100.7, 82.8, 72.8, 61.3, 55.3, 39.0, 33.8, 32.6, 13.1, 12.4; high resolution mass spectrum (CI, NH$_3$) m/z 323.1736 [M$^+$; calcd for C$_{17}$H$_{25}$NO$_5$: 323.1732].

Anal. Calcd for C$_{17}$H$_{25}$NO$_5$: C, 63.14; H, 7.79. Found: C, 63.18; H, 7.74.

EXAMPLE 5

Aldehyde (–)-12

A solution of amide (–)-11 (2.07 g, 6.40 mmol) in THF (70 mL) was cooled to –78° C. and LiAlH$_4$ (1.0 M in THF, 3.40 mL, 3.40 mmol) was added over 15 min. After 10 min at –78° C. and 10 min at 0° C., the mixture was quenched with MeOH (1.0 mL), and partitioned between ethyl acetate and saturated aqueous Rochelle's salt (100 mL each). The organic phase was washed with brine (100 mL), dried over MgSO$_4$, filtered and concentrated. Flash chromatography (15% ethyl acetate/hexane) gave (–)-12 (1.38 g, 80% yield) as a colorless oil: $[\alpha]^{23}_D$ –7.8° (c0.46, CHCl$_3$); IR (CHCl$_3$) 3015 (m), 2970 (m), 2940 (m), 2840 (m), 1735 (s), 1725 (s), 1615 (m), 1590 (w), 1520 (s), 1460 (s), 1390 (m), 1370 (m), 1305 (m), 1250 (s), 1170 (s), 1115 (s), 1085 (s), 1035 (s), 990 (m), 960 (m), 830 (m) cm$^{-1}$; $^1$H NMR (500 MHZ, CDCl$_3$) d 9.74 (apparent s, 1 H), 7.32 (d, J=8.8 Hz, 2 H), 6.84 (d, J=8.7 Hz, 2 H), 5.46 (s, 1 H), 4.13 (dd, J=11.5, 4.8 Hz, 1 H), 4.05 (dd, J=10.4, 2.6 Hz, 1 H), 3.77 (s, 3 H), 3.56 (apparent t, J=11.1 Hz, 1 H), 2.56 (qd, J=7.1, 2.6 Hz, 1 H), 2.15–2.03 (m, 1 H), 1.23 (d, J=7.1 Hz, 3 H), 0.80 (d, J=6.7 Hz, 3 H); $^{13}$C NMR (125 MHZ, CDCl$_3$) δ204.0, 159.9, 130.7, 127.2, 113.5, 100.9, 81.6, 72.8, 55.2, 47.4, 30.3, 11.9, 7.1; high resolution mass spectrum (CI, NH$_3$) m/z 265.1432 [(M+H)$^+$; calcd for C$_{15}$H$_{21}$O$_4$: 265.1439].

EXAMPLE 6

Aldol (+)-13

A solution of oxazolidinone (+)-9 (21.6 g, 92.7 mmol) in CH$_2$Cl$_2$ (200 mL) was cooled to 0° C. and n-Bu$_2$BOTf (1.0 M in CH$_2$Cl$_2$, 86.1 mL, 86.1 mmol) was added over 0.5 h, followed by addition of NEt$_3$ (15.7 mL, 112.5 mmol) over 10 min. The mixture was stirred at 0° C. for 1 h and cooled to –78° C. A solution of aldehyde (–)-12 (17.5 g, 66.2 mmol) in CH$_2$Cl$_2$ (50 mL) was added over 10 min. After additional 20 min at –78° C. and 1 h at 0° C., the reaction was quenched with pH 7 phosphate buffer (100 mL) and MeOH (300 mL), then slowly treated with a solution of 30% H$_2$O$_2$ in MeOH (1:1, 100 mL) at 0° C. After 1 h, saturated aqueous Na$_2$S$_2$O$_3$ (100 mL) was added. The mixture was concentrated and the residue was extracted with ethyl acetate (3×250 mL). The combined extracts were washed with saturated aqueous Na$_2$S$_2$O$_3$, aqueous NaHCO$_3$ (10%), brine (200 mL each), dried over MgSO$_4$, filtered and concentrated. Flash chromatography (10% ethyl acetate/hexane) provided (+)-13 (26.3 g, 80% yield) as white crystals: mp 98–100° C.; $[\alpha]^{23}_D$ +13.5° (c1.19, CHCl$_3$); IR (CHCl$_3$) 3690 (w), 3520 (w, br), 3020 (m), 2980 (m), 2940 (m), 2880 (w), 2850 (m), 1790 (s), 1695 (m), 1620 (m), 1595 (w), 1525 (m), 1505 (w), 1490 (w), 1465 (m), 1390 (s), 1365 (m), 1310 (m), 1260–1210 (m, br), 1175 (m), 1120 (s), 1085 (m), 1040 (m), 1020 (m), 985 (m), 970 (m), 930 (w), 830 (m), 700 (m) cm$^{-1}$; $^1$H NMR (500 MHZ, CDCl$_3$) d 7.35 (d, J=8.7 Hz, 2 H), 7.31 (d, J=7.6 Hz, 2 H), 7.27 (d, J=7.2 Hz, 1 H), 7.19 (d, J=7.7 Hz, 2 H), 6.84 (d, J=8.7 Hz, 2 H), 5.45 (s, 1 H), 4.67–4.62 (m, 1 H), 4.14 (apparent d, J=5.3 Hz, 2 H), 4.08 (dd, J=11.4, 4.8 Hz, 1 H), 4.07 (apparent t, J=4.1 Hz, 1 H), 4.04–3.99 (m, 1 H), 3.76 (s, 3 H), 3.61 (dd, J=9.9, 2.2 Hz, 1 H), 3.51 (apparent t, J=11.1 Hz, 1 H), 3.33 (d, J=1.3 Hz, 1 H), 3.21 (dd, J=13.4, 3.4 Hz, 1 H), 2.76 (dd, J=13.4, 9.4 Hz, 1 H), 2.12–2.06 (m, 1 H), 1.92–1.86 (m, 1 H), 1.31 (d, J=6.9 Hz, 3 H), 1.07 (d, J=7.0 Hz, 3 H), 0.74 (d, J=6.7 Hz, 3 H); $^{13}$C NMR (125 MHZ, CDCl$_3$) δ177.1, 160.0, 152.7, 135.0, 131.0, 129.4, 128.9, 127.40, 127.39, 113.6, 101.2, 85.8, 74.5, 73.0, 66.0, 55.2, 54.9, 39.8, 37.7, 35.7, 30.4, 12.8, 11.7, 7.8; high resolution mass spectrum (CI, NH$_3$) m/z 497.2410 [M$^+$; calcd for C$_{28}$H$_{35}$NO$_7$: 497.2413].

Anal. Calcd for C$_{28}$H$_{35}$NO$_7$: C, 67.58; H, 7.09. Found: C, 67.42; H, 7.02.

EXAMPLE 7

Acetal (+)-14

A solution of alcohol (+)-13 (26.3 g, 52.9 mmol) and 2,6-lutidine (11.1 mL, 95.3 mmol) in CH$_2$Cl$_2$ (150 mL) was cooled to –20° C. and TBSOTf (20.5 mL, 79.3 mmol) was added over 30 min. After additional 2 h at 0° C., the mixture was diluted with ether (300 mL), washed with aqueous NaHSO$_4$ (1.0 M, 200 mL), brine (200 mL), dried over MgSO$_4$, filtered and concentrated. Flash chromatography (gradient elution, 5%→10% ethyl acetate/hexane) afforded (+)-14 (32.4 g, 100% yield) as a colorless oil: [α]$^{23}_D$ +20.3°©1.32, CHCl$_3$); IR (CHCl$_3$) 3025 (m), 2970 (m), 2940 (m), 2864 (m), 1788 (s), 1705 (m), 1620 (m), 1597 (w),1524 (m), 1503 (w), 1470 (m), 1447 (w), 1430 (w), 1395 (s), 1358 (m), 1307 (m), 1255 (s), 1135 (m), 1120 (s), 1075 (m), 1030 (m), 985 (m), 976 (m), 930 (m) 865 (m), 838 (s), 813 (m), 790 (m), 700 (m) cm$^{-1}$; $^1$H NMR (500 MHZ, CDCl$_3$) d 7.38 (d, J=8.7 Hz, 2 H), 7.30–7.12 (m, 5 H), 6.82 (d, J=8.7 Hz, 2 H), 5.44 (s, 1 H), 4.30 (dddd, J=13.4, 7.3, 5.1, 5.1 Hz, 1 H), 4.11 (dd, J=7.1, 4.0 Hz, 1 H), 4.02 (dd, J=11.2, 4.7 Hz, 1 H), 3.97 (dq, J=7.0, 7.0 Hz, 1 H), 3.80 (dd, J=8.9, 2.3 Hz, 1 H), 3.740 (apparent t, J=4.9 Hz, 1 H), 3.738 (s, 3 H), 3.48 (apparent t, J=11.1 Hz, 1 H), 3.27 (apparent t, J=8.2 Hz, 1 H), 3.15 (dd, J=13.4, 3.2 Hz, 1 H), 2.59 (dd, J=13.4, 9.8 Hz, 1 H), 2.05 (apparent qd, J=7.4, 4.2 Hz, 1 H), 2.02–1.94 (m, 1 H), 1.19 (d, J=6.9 Hz, 1 H), 1.04 (d, J=7.5 Hz, 3 H), 0.92 (s, 9 H), 0.73 (d, J=6.7 Hz, 3 H), 0.05 (s, 3 H), 0.04 (s, 3 H); $^{13}$C NMR (125 MHZ, CDCl$_3$) d 175.6, 159.9, 152.4, 135.5, 132.0, 129.4, 128.8, 127.8, 127.2, 113.4, 100.7, 80.7, 74.6, 73.1, 65.3, 55.3, 55.2, 41.4, 40.9, 37.4, 30.6, 26.0, 18.1, 15.0, 12.7, 11.5, −4.0, −4.6; high resolution mass spectrum (CI, NH$_3$) m/z 612.3340 [(M+H)$^+$; calcd for C$_{34}$H$_{50}$NO$_7$Si: 612.3356].

Anal. Calcd for C$_{34}$H$_{49}$NO$_7$Si: C, 66.74; H, 8.07. Found: C, 66.69; H, 7.98.

EXAMPLE 8

Alcohol (−)-15

A solution of acetal (+)-14 (32.0 g, 52.3 mmol) in THF (600 mL) was cooled to −30° C. and EtOH (6.14 mL, 105 mmol) was added, followed by addition of LiBH$_4$ (2.0 M in THF, 52.3 mL, 105 mmol) over 15 min. After additional 1 h at 0° C. and 12 h at room temperature, the mixture was diluted with ether (1.0 L), quenched carefully with aqueous NaOH (1.0 N, 200 mL) and stirred for 2 h at room temperature. The layers were separated and the organic phase was washed with brine (500 mL), dried over Na$_2$SO$_4$, filtered and concentrated. Flash chromatography (20% ethyl acetate/hexane) provided (−)-15 (18.7 g, 81% yield) as a colorless oil: [α]$^{23}_D$ −36.1° ©1.15, CHCl3); IR (CHCl$_3$) 3630 (w), 3480 (w, br), 3010 (m), 2960 (s), 2940 (s), 2885 (m), 2860 (s), 1620 (m), 1594 (w), 1523 (m), 1468 (s), 1445 (w), 1430 (w), 1395 (m), 1365 (m), 1307 (m), 1255 (s), 1175 (m), 1165 (m),1150 (m), 1120 (s), 1080 (s), 1030 (s), 990 (m), 968 (m), 910 (s), 860 (m), 833 (s), 700 (m), 645 (m) cm$^{-1}$; $^1$H NMR (500 MHZ, CDCl$_3$) d 7.36 (d, J=8.7 Hz, 2 H), 6.85 (d, J=8.8 Hz, 2 H), 5.38 (s, 1 H), 4.08 (dd, J=11.2, 4.7 Hz, 1 H), 3.84 (dd, J=6.7, 1.9 Hz, 1 H), 3.77 (s, 3 H), 3.53 (dd, J=9.9, 1.8 Hz, 1 H), 3.55–3.52 (m, 1 H), 3.47 (apparent t, J=11.1 Hz, 1 H), 3.44 (dd, J=10.3, 6.2 Hz, 1 H), 2.08–1.97 (m, 2 H), 1.94 (dqd, J=7.1, 7.1, 1.7 Hz, 1 H), 1.76 (br s, 1 H), 1.02 (d, J=7.1 Hz, 3 H), 0.88 (s, 9 H), 0.84 (d, J=6.9 Hz, 3 H), 0.73 (d, J=6.7 Hz, 3 H), 0.03 (s, 3 H), 0.00 (s, 3 H); $^{13}$C NMR (125 MHZ, CDCl$_3$) d 159.8, 131.4, 127.3, 113.5, 101.0, 82.9, 74.3, 73.3, 66.3, 55.2, 38.7, 37.8, 30.7, 26.1, 18.3, 12.2, 11.1, 10.7, −4.0, −4.2; high resolution mass spectrum (CI, NH$_3$) m/z 439.2889 [(M+H)$^+$; calcd for C$_{24}$H$_{43}$O$_5$Si: 439.2879].

Anal. Calcd for C$_{24}$H$_{42}$O$_5$Si: C, 65.71; H, 9.65. Found: C, 65.51; H 9.54.

EXAMPLE 9

Tosylate (−)-16

A solution of alcohol (−)-15 (5.00 g, 11.4 mmol) in anhydrous pyridine (30 mL) was cooled to 0° C. and treated with TsCl (3.91 g, 20.5 mmol). After 30 min at 0° C. and 5 h at room temperature, the reaction was quenched with saturated aqueous NaHCO$_3$ (20 mL). The mixture was diluted with ether (200 mL), washed with aqueous NaHSO$_4$ (1.0 M), aqueous NaHCO$_3$ (10%), brine (200 mL each), dried over MgSO$_4$, filtered and concentrated. Flash chromatography (10% ethyl acetate/hexane) provided (−)-15 (6.76 g, 100% yield) as white solid: mp 71–72° C.; [α]$^{23}_D$ −23.2° ©1.42, CHCl$_3$); IR (CHCl$_3$) 3020 (m), 3000 (m), 2960 (s), 2935 (s), 2880 (m), 2855 (s), 1617 (m), 1600 (m), 1590 (m), 1518 (m), 1495 (w), 1462 (s), 1390 (m), 1360 (s), 1302 (m), 1250 (s), 1190 (s), 1178 (s), 1120 (s), 1098 (s), 1085 (s), 1070 (s, 1032 (s), 963 (s), 900 (m), 830 (s), 810 (s), 653 (m); $^1$H NMR (500 MHZ, CDCl$_3$) d 7.70 (d, J=8.3 Hz, 2 H), 7.34 (d, J=8.7 Hz, 2 H), 7.25 (d, J=8.8 Hz, 2 H), 6.86 (d, J=8.7 Hz, 2 H), 5.36 (s, 3 H), 4.07 (dd, J=11.2, 4.7 Hz, 1 H), 3.85 (dd, J=7.3, 2.7 Hz, 1 H), 3.79 (s, 3 H), 3.71 (dd, J=7.1, 1.7 Hz, 1 H), 3.48 (dd, J=9.9, 1.4 Hz, 1 H), 3.45 (apparent t, J=11.1 Hz, 1 H), 2.40 (s, 3 H), 2.15 (dqd, J=13.9, 7.0, 1.7 Hz, 1 H), 2.05–1.96 (m, 1 H), 1.83 (dqd, J=7.1, 7.1, 1.6 Hz, 1 H), 0.94 (d, J=7.1 Hz, 3 H), 0.82 (s, 9 H), 0.81 (d, J=7.7 Hz, 3 H), 0.69 (d, J=6.7 Hz, 3 H), −0.04 (s, 3 H), −0.11 (s, 3 H); $^{13}$C NMR (125 MHZ, CDCl$_3$) d 159.8, 144.6, 133.2, 131.3, 129.7, 127.9, 127.3, 113.5, 100.9, 82.0, 73.7, 73.2, 73.0, 55.2, 38.4, 35.5, 30.6, 26.0, 21.6, 18.3, 12.2, 10.6, 10.3, −3.9, −4.3; high resolution mass spectrum (FAB, NBA) m/z 593.2955 [(M+H)$^+$; calcd for C$_{31}$H$_{49}$O$_7$SSi: 593.2968].

EXAMPLE 10

Fragment (−)-A. From Tosylate (−)-16:

A solution of Tosylate (−)-16 (6.76 g, 11.4 mmol) in anhydrous DMF (50 mL) was treated with NaI (17.1 g, 114.0 mmol), heated at 60° C. for 1.5 h, and cooled to room temperature. The mixture was diluted with ether (200 mL), washed with water (200 mL), saturated aqueous Na$_2$S$_2$O$_3$ (100 mL), brine (200 mL), dried over MgSO$_4$, filtered and concentrated. Flash chromatography (3% ethyl acetate/ hexane) provided (−)-A (5.87 g, 94 % yield) as a colorless oil.

From Alcohol (−)-15:

A solution of alcohol (−)-15 (4.70 g, 10.7 mmol), PPh$_3$ (4.21 g, 16.1 mmol) and imidazole (1.09 g, 16.1 mmol) in benzene/ether (1:2, 75 mL) was treated with I2 ( 4.08 g, 16.1 mmol) under vigorous stirring. The mixture was stirred 1 h then diluted with ether (200 mL), washed with saturated Na$_2$S$_2$O$_3$, brine (100 mL each), dried over MgSO$_4$, filtered and concentrated. Flash chromatography (2% ethyl acetate/ hexane) furnished (−)-A (5.56 g, 95% yield) as a colorless oil: [α]$^{23}_D$ −39.3° ©2.01, CHCl$_3$); IR (CHCl$_3$) 3015 (m), 2960 (s), 2940 (s), 2860 (m), 1620 (w), 1520 (m), 1465 (m), 1430 (w), 1390 (m), 1305 (w), 1255 (s), 1230 (m), 1215 (m), 1205 (m), 1170 (m), 1120 (m), 1070 (m), 1035 (m), 990 (w), 970 (w), 930 (w), 830 (m) cm$^{-1}$; $^1$H NMR (500 MHZ, CDCl$_3$) d 7.39 (d, J=8.7 Hz, 2 H), 6.86 (d, J=8.8 Hz, 2 H), 5.40 (s, 1 H), 4.09 (dd, J=11.2, 4.7 Hz, 1 H), 3.85 (dd, J=7.1, 1.9 Hz, 1 H), 3.79 (s, 3 H), 3.48 (dd, J=8.2, 1.5 Hz, 1 H), 3.47 (apparent t, J=11.1 Hz, 1 H), 3.18–3.12 (m, 2 H), 2.11–2.00 (m, 2 H), 1.84 (ddq, J=7.1, 7.1, 1.6 Hz, 1 H), 1.02 (d, J=7.1 Hz, 3 H), 0.98 (d, J=6.7 Hz, 3 H), 0.89 (s, 9 H), 0.72 (d, J=6.7 Hz, 3 H), 0.06 (s, 3 H); $^{13}$C NMR (125 MHZ, CDCl$_3$) d 159.8, 131.4, 127.4, 113.4, 100.9, 82.4, 75.5, 73.2, 55.3, 39.6, 38.7, 30.7, 26.2, 18.4, 14.7, 14.5, 12.2, 10.7, −3.7, −3.8; high resolution mass spectrum (CI, NH$_3$) m/z 548.1833 [(M)$^+$; calcd for C$_{24}$H$_{41}$O$_4$Si: 548.1819].

Anal. Calcd for C$_{24}$H$_{41}$O$_4$ISi: C, 52.55; H, 7.53. Found: C, 52.77; H, 7.68.

EXAMPLE 11

Amide (+)-17

A solution of common precursor (+)-5 (12.1 g, 37.2 mmol) and 2,6-lutidine (7.80 mL, 70.0 mmol) in $CH_2Cl_2$ (90 mL) was cooled to 0° C. and tert-Butyldimethylsilyl trifluoromethanesulfonate (12.8 mL, 55.8 mmol) was added over 10 min. After 1.5 h, the mixture was diluted with $Et_2O$ (100 mL), washed with aqueous $NaHSO_4$ (1.0 M), brine (200 mL each), dried over $MgSO_4$, filtered and concentrated. Flash chromatography (10% ethyl acetate/hexanes) provided (+)-17 (16.4 g, 100% yield) as a colorless oil: $[\alpha]^{23}_D$ +9.49° ©1.47, $CHCl_3$); IR ($CHCl_3$) 3018 (s), 2970 (s), 2945 (s), 2900 (m), 2870 (s), 1658 (s),1620 (m), 1592 (w), 1520 (s), 1470 (s), 1448 (m), 1425 (m), 1393 (m), 1367 (m), 1308 (m), 1255 (s), 1213 (s), 1185 (m), 1178 (m), 1115 (s), 1084 (s), 1042 (s), 1000 (s), 940 (w), 928 (w), 871 (s), 839 (s), 770 (s), 726 (s), 664 (m) $cm^{-1}$; $^1H$ NMR (500 MHZ, $CDCl_3$) d 7.21 (d, J=8.7 Hz, 2 H), 6.83 (d, J=8.7, 2 H), 4. 36 (ABq, $J_{AB}$=11.6 Hz, LAB=17.3 Hz, 2 H), 3.92 (dd, J=8.2, 3.0 Hz, 1 H), 3.77 (s, 3 H), 3.55 (s, 3 H), 3.54 (dd, J=9.2, 2.5 Hz, 1 H), 3.13 (dd, J=9.2, 7.8 Hz, 1 H), 3.09 (s, 3 H), 3.15–3.09 (m, 1 H), 1.92–1.87 (m, 1 H), 1.09 (d, J=7.0 Hz, 3 H), 0. 98 (d, J=7.0 Hz, 3 H), 0.88 (s, 9 H), 0.04 (apparent s, 6 H); $^{13}C$ NMR (125 MHZ, $CDCl_3$) d 176.8, 159.1, 130.9, 129.2, 113.7, 76.0, 72.7, 71.9, 61.1, 55.2, 39.3, 38.9, 26.1, 18.4, 15.3, 15.0, –3.87, –3.93; high resolution mass spectrum (CI, $NH_3$) m/z 440.2823 $[(M+H)^+$; calcd for $C_{23}H_{42}NO_5Si$: 440.2832].

Anal. Calcd for $C_{23}H_{41}NO_5Si$: C, 62.83; H, 9.40. Found: C, 63.05; H, 9.32.

EXAMPLE 12

Aldehyde (+)-18

A solution of amide (+)-17 (9.19 g, 20.9 mmol) in THF (350 mL) was cooled to –78° C. and DIBAL (1.0 M in hexane, 44.0 mL, 44.0 mmol) was added over 30 min. After 0.5 h at –78° C., the reaction was quenched with MeOH (10 mL). The mixture was diluted with ether (500 mL), washed with saturated aqueous Rochelle's salt, brine (300 mL each), dried over $MgSO_4$, filtered and concentrated. Flash chromatography (10% ethyl acetate/hexane) gave (+)-18 (7.05 g, 89% yield) as a colorless oil: $[\alpha]^{23}_D$ +23.2°©1.49, $CHCl_3$); IR ($CHCl_3$) 2960 (s), 2930 (s), 2860 (s), 1730 (s), 1610 (m), 1583 (w), 1510 (m), 1460 (m), 1373 (m), 1360 (w), 1300 (m), 1245 (s), 1170 (m), 1085 (m), 1033 (s), 933 (w), 835 (s) $cm^{-1}$; $^1H$ NMR (500 MHZ, $CDCl_3$) d 9.67 (d, J=0.9 Hz, 1 H), 7.22 (d, J=8.7 Hz, 2 H), 6.86 (d, J=8.7 Hz, 2 H), 4.37 (ABq, $J_{AB}$=11.6 Hz, $\Delta\delta_{AB}$=23.6 Hz, 2 H), 4.18 (dd, J=6.1, 3.7 Hz, 1 H), 3. 78 (s, 3 H), 3.41 (dd, J=9.2, 5.7 Hz, 1 H), 3.31 (dd, J=9.2, 6.0 Hz, 1 H), 2.47 (qdd, J=7.1, 3.7, 0.9 Hz, 1 H), 2.03–1.95 (m, 1 H), 1.08 (d, J=7.0 Hz, 3 H), 0.94 (d, J=7.0 Hz, 3 H), 0.84 (s, 9 H), 0.04 (s, 3 H), –0.03 (s, 3 H); $^{13}C$ NMR (125 MHZ, $CDCl_3$) d 204.8, 159.2, 130.5, 129.2, 113.8, 72.7, 72.4, 71.7, 55.3, 50.0, 38.3, 25.9, 18.2, 14.3, 8.4, –4.1, –4.4; high resolution mass spectrum (FAB, NBA) m/z 403.2304 $[(M+Na)^+$; calcd for $C_{21}H_{36}O_4SiNa$: 403.2280].

EXAMPLE 13

Bromo Ester 19

A solution of aldehyde (+)-18 (822.1 mg, 2.16 mmol) in benzene (20 mL) was treated with $Ph_3P=CBrCO_2Et$ (2.28 g, 5.34 mmol), heated at reflux for 40 h and cooled to room temperature. The mixture was filtered through a short silica column (20% ethyl acetate/hexane) and concentrated. Flash chromatography (3% ethyl acetate/hexane) afforded Z-Bromo ester (–)-19 (861.4 mg, 75% yield) and E-Bromo Ester (+)-19 (101.0 mg, 8.8% yield).

Z-Bromo Ester (–)-19: Colorless oil; $[\alpha]^{23}_D$ –6.38° ©1.85, $CHCl_3$); IR ($CHCl_3$) 2960 (s), 2940 (s), 2860 (s), 1725 (s), 1618 (m), 1590 (w), 1515 (s), 1468 (m), 1390 (m), 1370 (m), 1303 (m), 1250 (s, br), 1176 (m), 1090 (s), 1037 (s), 1008 (m), 950 (m), 940 (m), 840 (s) $cm^{-1}$; $^1H$ NMR (500 MHZ, $C_6D_6$) d 7.45 (d, J=9.7 Hz, 1 H), 7.26 (d, J=8.6 Hz, 2 H), 6.80 (d, J=8.7 Hz, 2 H), 4.37 (ABq, $J_{AB}$=11.6 Hz, $\Delta\delta_{AB}$=19.3 Hz, 2 H), 3.99, (dq, J=10.8, 7.1 Hz, 1 H), 3.94 (dq, J=10.8, 7.1 Hz, 1 H), 3.82 (apparent t, J=5.4 Hz, 1 H), 3.41 (dd, J=9.1, 6.3 Hz, 1 H), 3.31 (s, 3 H), 3.30 (dd, J=9.2, 6.5 Hz, 1 H), 3.13–3.06 (m, 1 H), 2.05 (apparent septet, J=6.9 Hz, 1 H), 1.013 (d, J=7.0 Hz, 3 H), 1.006 (d, J=6.8 Hz, 3 H), 0.97 (s, 9 H), 0.92 (apparent t, J=7.1 Hz, 3 H), 0.06 (s, 3 H), 0.05 (s, 3 H); $^{13}C$ NMR (125 MHZ, $CDCl_3$) d 162.5, 159.1, 149.6, 130.8, 129.0, 114.9, 113.7, 75.5, 72.6, 72.2, 62.4, 55.3, 40.2, 38.9, 26.0, 18.3, 14.2, 14.1, 13.7, –4.0, –4.2; high resolution mass spectrum (CI, $NH_3$) m/z 546.2270 $[(M+NH_4)^+$; calcd for $C_{25}H_{45}NO_5BrSi$: 546.2251].

Anal. Calcd for $C_{25}H_{41}O_5BrSi$: C, 56.70; H, 7.80. Found: C, 56.96; H, 7.86.

E-Bromo Ester (+)-19. Colorless oil; $[\alpha]^{23}_D$ +3.2° ©1.65, $CHCl_3$); IR ($CHCl_3$) 2965 (s), 2940 (s), 2905 (m), 2890 (m), 2865 (s), 1720 (s), 1617 (m), 1590 (w), 1518 (s), 1468 (s), 1375 (s), 1350 (m), 1305 (m), 1250 (s, br), 1177 (m), 1090 (s), 1035 (s), 1007 (m), 950 (m), 840 (s), 675 (w) $cm^{-1}$; $^1H$ NMR (500 MHZ, $CDCl_3$) d 7.23 (d, J=8.6 Hz, 2 H), 6.86 (d, J=8.7 Hz, 2 H), 6.56 (d, J=10.6 Hz, 1 H), 4.39 (apparent s, 2 H), 4.24 (dq, J=10.8, 7.1 Hz, 1 H), 4.22 (dq, J=10.8, 7.1 Hz, 1 H), 3.79 (s, 3 H), 3.61 (dd, J=5.5, 5.0 Hz, 1 H), 3.43 (dd, J 9.2, 5.5 Hz, 1 H), 3.39–3.32 (m, 1 H), 3.24 (dd, J 9.1, 7.2 Hz, 1 H), 1.98–1.90 (m, 1 H), 1.30 (apparent t, J=7.1 Hz, 1 H), 1.00 (d, J=6.7 Hz, 3 H), 0.94 (d, J=7.0 Hz, 3 H), 0.89 (s, 9 H), 0.05 (s, 3 H), 0.03 (s, 3 H); $^{13}C$ NMR (125 MHZ, $CDCl_3$) d 162.8, 159.1, 151.9, 130.8, 129.1, 113.7, 110.2, 76.3, 72.6, 72.2, 62.1, 55.2, 38.8, 26.1, 18.3, 14.7, 14.1, 13.9, –4.06, –4.10; high resolution mass spectrum (CI, $NH_3$) m/z 529.1982 $[(M+H)^+$; calcd for $C_{25}H_{42}BrO_5Si$: 529.1985].

Anal. Calcd for $C_{25}H_{41}O_5BrSi$: C, 56.70; H, 7.80. Found: C, 56.83; H, 7.99.

EXAMPLE 14

Allylic Alcohol (–)-20

A solution of ester (–)-19 (858.4 mg, 1.62 mmol) in $CH_2Cl_2$ (16 mL) was cooled to –78° C. and DIBAL (1.0 M in hexane, 3.60 mL, 3.60 mmol) was added over 10 min. After 5 min at –78° C. and 10 min at room temperature, the reaction was quenched with MeOH (200 mL), followed by addition of saturated aqueous Rochelle's salt dropwise with stirring until a solid precipitated. The solution was separated by decanting (3×30 mL rinse, ethyl acetate) and the combined organic solutions were dried over $MgSO_4$, and concentrated. Flash chromatography (10% ethyl acetate/ hexane) provided (–)-20 (674.5 mg, 85% yield) as a colorless oil: $[\alpha]^{23}_D$ –15.5° ©2.51, $CHCl_3$); IR ($CHCl_3$) 3600 (w), 3420 (w, br), 3010 (s), 2960 (s), 2940 (s), 2890 (m), 2860 (s), 1618 (m), 1590 (w), 1520 (s), 1470 (m), 1380 (m), 1315 (m), 1307 (m), 1255 (s), 1178 (m), 1085 (s), 1039 (s), 1010 (m), 972 (m), 940 (m), 840 (s), 675 (m), 660 (m) $cm^{-1}$; $^1H$ NMR (500 MHZ, $CDCl_3$) d 7.24 (d, J=8.7 Hz, 2 H), 6.87 (d, J=8.7 Hz, 2 H), 5.88 (br d, J=9.3 Hz, 1 H), 4.39

(ABq, $J_{AB}$=11.6 Hz, to.=18.3 Hz, 2 H), 4.16 (apparent d, J=5.6 Hz, 2 H), 3.79 (s, 3 H), 3.59 (apparent t, J=5.3 Hz, 1 H), 3.48 (dd, J=9.2, 5.3 Hz, 1 H), 3.23 (dd, J=9.2, 7.7 Hz, 1 H), 2.82–2.76 (m, 1 H), 2.00–1.92 (m, 1 H), 0.98 (d, J=6.9 Hz, 3 H), 0.97 (d, J=6.8 Hz, 3 H), 0.88 (s, 9 H), 0.024 (s, 3 H), 0.016 (s, 3 H); $^{13}$C NMR (125 MHZ, CDCl$_3$) d 159.1, 134.1, 130.9, 129.1, 125.1, 113.7, 76.5, 72.6, 72.3, 68.4, 55.3, 39.1, 38.7, 26.1, 18.4, 14.9, 14.3, −3.9, −4.0; high resolution mass spectrum (CI, NH$_3$) m/z 487.1873 [(M+H)$^+$; calcd for $C_{23}H_{40}O_4BrSi$: 487.1879].

Anal. Calcd for $C_{23}H_{39}O_4BrSi$: C, 56.66; H, 8.06. Found: C, 56.72; H, 8.07.

EXAMPLE 15

Mesylate (−)-21

A solution of alcohol (−)-20 (6.85 g, 14.1 mmol) in CH$_2$Cl$_2$ (150 mL) was cooled to 0° C. and MsCl (2.20 mL, 28.4 mmol) was added over 2 min. After 10 min, the reaction was quenched with aqueous NaHSO$_4$ (1.0 M, 100 mL). The organic phase was washed with water (100 mL), dried over MgSO$_4$, and concentrated. Flash chromatography (10% ethyl acetate/hexane) afforded (−)-21 (7.85 g, 99% yield) as a colorless oil: $[\alpha]^{23}_D$ −14.6° (©1.40, CHCl$_3$); IR (CHCl$_3$) 3020 (m), 2960 (s), 2940 (s), 2880 (m), 2860 (s), 1730 (w), 1610 (m), 1583 (m), 1510 (s), 1460 (m), 1410 (m), 1362 (s), 1300 (m), 1250 (s), 1220 (s), 1175 (s), 1080 (s), 1032 (s), 1002 (m), 960 (m), 937 (s), 835 (s)cm$^{-1}$; $^1$H NMR (500 MHZ, CDCl$_3$) d 7.23 (d, J=8.6 Hz, 2 H), 6.86 (d, J=8.6 Hz, 2 H), 6.07 (d, J=9.4 Hz, 1 H), 4.74 (d, J=0.4 Hz, 2 H), 4.38 (ABq, $J_{AB}$=11.7 Hz, $\Delta\delta_{AB}$=25.5 Hz, 2 H), 3.79 (s, 3 H), 3.61 (apparent t, J=5.2 Hz, 1 H), 3.44 (dd, J=9.2, 5.7 Hz, 1 H), 3.22 (dd, J=9.2, 7.3 Hz, 1 H), 3.01 (s, 3 H), 2.84–2.77 (m, 1 H), 1.99–1.91 (m, 1 H), 0.98 (d, J=6.8 Hz, 3 H), 0.96 (d, J=7.0 Hz, 3 H), 0.88 (s, 9 H), 0.03 (s, 3 H), 0.02 (s, 3 H); $^{13}$C NMR (125 MHZ, CDCl$_3$) d 159.1, 140.9, 130.8, 129.1, 116.7, 113.8, 76.1, 74.2, 72.6, 72.1, 55.3, 39.6, 38.8, 38.5, 26.0, 18.3, 14.7, 14.3, −3.9, −4.0; high resolution mass spectrum (CI, NH$_3$) m/z 582.1911 [(M+NH$_4$)$^+$; calcd for $C_{24}H_{45}NO_6BrSSi$: 582.1920].

EXAMPLE 16

Vinyl Bromide (−)-22

A solution of mesylate (−)-21 (6.43 g, 11.4 mmol) in benzene (120 mL) was treated with LiBHEt$_3$ (1.0 M in THF, 25.0 mL, 25.0 mmol) at room temperature. After 0.5 h, the reaction was quenched with aqueous NaOH (1.0 N, 50 mL). The mixture was diluted with ethyl acetate (200 mL), washed with brine (2×200 mL), dried over MgSO$_4$, filtered and concentrated. Flash chromatography (5% ethyl acetate/hexane) provided (−)-22 (4.86 g, 91%) as a colorless oil: [α]$^{23}_D$ −16.9° (©1.69, CHCl$_3$) ; IR (CHCl$_3$) 3005 (m), 2965 (s), 2935 (s), 2860 (s), 1660 (w), 1610 (m), 1585 (w), 1510 (m), 1460 (m), 1425 (w), 1377 (m), 1360 (m), 1300 (m), 1250 (s), 1180 (m), 1170 (m), 1075 (s), 1030 (m), 860 (m), 835 (s), 805 (m), 660 (w) cm$^{-1}$; $^1$H NMR (500 MHZ, CDCl$_3$) d 7.24 (d, J=8.6 Hz, 2 H), 6.86 (d, J=8.6 Hz, 2 H), 5.47 (apparent dd, J=9.0, 1.2 Hz, 1 H), 4.39 (ABq, $J_{AB}$=11.7 Hz, $\Delta\delta_{AB}$=15.8 Hz, 2 H), 3.79 (s, 3 H), 3.56 (apparent t, J=5.4 Hz, 1 H), 3.50 (dd, J=9.1, 5.1 Hz, 1 H), 3.22 (dd, J=8.8, 8.1 Hz, 1 H), 2.74–2.67 (m, 1 H), 2.21 (d, J=1.1 Hz, 3 H), 1.99–1.91 (m, 1 H), 0.98 (d, J=6.9 Hz, 3 H), 0.94 (d, J=6.8 Hz, 3 H), 0.88 (s, 9 H), 0.01 (s, 3 H), 0.00 (s, 3 H); $^{13}$C NMR (125 MHZ, CDCl$_3$) d 159.1, 133.4, 131.0, 129.1, 120.6, 113.7, 76.7, 72.6, 72.5, 55.3, 39.7, 38.7, 28.8, 26.1, 18.4, 14.8, 14.4, −3.96, −4.01; high resolution mass spectrum (FAB, NBA) m/z 493.1763 [(M+Na)$^+$; calcd for $C_{23}H_{39}O_3BrSiNa$: 493.1750].

EXAMPLE 17

Vinyl Silane (−)-23

A solution of vinyl bromide (−)-22 (83.2 mg, 0.177 mmol) in THF (2.0 mL) was cooled to −78° C. and n-BuLi (1.6 M in hexane, 260 ml, 416 mmol) was added over 10 min. After 1 h at −78° C. and 15 min at room temperature, the reaction was quenched with H$_2$O (200 mL). The mixture was concentrated and dissolved in ethyl acetate (30 mL), washed with water (30 mL), dried over MgSO$_4$, filtered and concentrated. Flash chromatography (5% ethyl acetate/hexane) provided (−)-23 (47.9 mg, 69% yield) as a colorless oil: $[\alpha]^{23}_D$ −61.5° (©0.615, CHCl$_3$); IR (CHCl$_3$) 3680 (w), 3470 (m, br), 1614 (m), 1588 (w), 1513 (s), 1465 (m), 1442 (m), 1415 (m), 1360 (m), 1302 (m), 1250 (s), 1176 (m), 1120 (m), 1077 (m), 1032 (m), 992 (m), 830 (s), 820 (s), 805 (s) cm$^{-1}$; $^1$H NMR (500 MHZ, CDCl$_3$) d 7.22 (d, J=8.7 Hz, 2 H), 6.85 (d, J=8.7 Hz, 2 H), 6.22 (dq, J=10.5, 1.6 Hz, 1 H), 4.42 (ABq, $J_{AB}$=11.4 Hz, $\Delta\delta_{AB}$=18.8 Hz, 2 H), 3.78 (s, 3 H), 3.65 (br s, 1 H), 3.56 (dd, J=9.1, 4.0 Hz, 1 H), 3.44 (dd, J=8.8, 2.9 Hz, 1 H), 3.42 (apparent t, J=8.8 Hz, 1 H), 2.45 (dqd, J=10.3, 6.6, 2.7 Hz, 1 H), 1.95–1.87 (m, 1 H), 1.78 (d, J=1.6 Hz, 3 H), 0.91 (d, J=6.7 Hz, 3 H), 0.87 (s, 9 H), 0.80 (d, J=7.0 Hz, 3 H), 0.09 (s, 3 H), 0.08 (s, 3 H); $^{13}$C NMR (125 MHZ, CDCl$_3$) d 159.4, 147.7, 130.8, 129.7, 129.4, 113.9, 79.9, 76.4, 73.3, 55.3, 38.1, 36.3, 27.1, 26.6, 17.8, 13.4, 13.1, −3.4, −3.7; high resolution mass spectrum (CI, NH$_3$) m/z 393.2821 [(M+H)$^+$; calcd for $C_{23}H_{41}O_3Si$: 393.2824].

Anal. Calcd for $C_{23}H_{40}O_3Si$: C, 70.36; H, 10.27. Found: C, 70.58; H, 10.57.

EXAMPLE 18 trans Olefin (+)-24

A solution of vinyl bromide (−)-22 (27.8 mg, 0.0591 mmol) in ether (600 μL) was cooled to −78° C., and t-BuLi (1.7 M in pentane, 103 μL, 0.175 mmol) was added over 2 min. After 10 min at −78° C. and 5 min at room temperature, the reaction was quenched with MeOH (100 mL). The mixture was filtered through a short silica plug, and concentrated. Flash chromatography (1% ethyl acetate/hexane) provided (+)-24 (21.9 mg, 94% yield) as a colorless oil; $[\alpha]^{23}_D$ +19.3° (©1.10, CHCl$_3$); IR (CHCl$_3$) 3000 (m), 2960 (s), 2935 (s), 2880 (m), 2860 (s), 1612 (m), 1587 (w), 1510 (s), 1462 (m), 1440 (m), 1405 (w), 1375 (m), 1360 (m), 1300 (m), 1250 (s), 1170 (m), 1090 (s), 1034 (s), 1002 (m), 970 (m), 934 (w), 850 (m), 832 (s), 720 (m) cm$^{-1}$; $^1$H NMR (500 MHZ, C$_6$D$_6$) d 7.24 (d, J=8.7 Hz, 2 H), 6.80 (d, J=8.6 Hz, 2 H), 5.43 (ddq, J=15.3, 7.8, 1.4 Hz, 1 H), 5.34 (dqd, J=15.4, 6.3, 0.7 Hz, 1 H), 4.38 (ABq, $J_{AB}$=11.7 Hz, A5A=30.7 Hz, 2 H), 3.58 (apparent t, J=5.2 Hz, 1 H), 3.57 (dd, J=9.0, 5.1 Hz, 1 H), 3.36 (dd, J=9.0, 7.2 Hz, 1 H), 3.30 (s, 3 H), 2.39 (ddq, J=6.8, 6.8, 6.8 Hz, 1 H), 2.17–2.10 (m, 1 H), 1.58 (apparent d, J=6.1 Hz, 3 H), 1.07 (d, J=7.2 Hz, 3 H), 1.05 (d, J=6.9 Hz, 3 H), 1.00 (s, 9 H), 0.10 (s, 3 H), 0.08 (s, 3 H); $^{13}$C NMR (125 MHZ, CDCl$_3$) d 159.0, 135.6, 131.1, 129.1, 123.9, 113.7, 78.4, 72.6, 72.5, 55.3, 40.4, 37.9, 26.2, 26.1, 18.4, 18.0, 15.9, 15.1, −3.8, −4.1; high resolution mass spectrum (CI, NH$_3$) m/z 393.2836 [(M+H)$^+$; calcd for $C_{23}H_{41}O_3Si$: 393.2824].

EXAMPLE 19

Alcohol (−)-25

A solution of PMB ether (−)-22 (50.0 mg, 0.106 mmol) and PMB acetal (−)-15 (46.5 mg, 0.106 mmol) in CH$_2$Cl$_2$ (2.0 mL) was cooled to 0° C., then treated with $H_2O$ (100 mL) and DDQ (26.5 mg, 0.117 mmol). After 30 min, the mixture was diluted with ether (60 mL), washed with saturated aqueous $NaHCO_3$ (60 mL), brine (3×60 mL), dried over $MgSO_4$, filtered and concentrated. Flash chromatography (gradient elution, 5%→10% ethyl acetate/hexane) afforded (−)-25 (31.0 mg, 83% yield) and recovered (−)-15 (40.0 mg, 86% recovery).

(−)-25: $[\alpha]^{23}_D$ −13.3° ©0.99, $CHCl_3$); IR ($CHCl_3$) 3640 (w), 3520 (m), 3000 (m), 2960 (s), 2940 (s), 2890 (m), 2860 (s), 1660 (w), 1472 (m), 1465 (m), 1440 (m), 1407 (m), 1390 (m), 1380 (m), 1360 (m), 1258 (s), 1072 (s), 1023 (s), 1005 (s), 980 (m), 937 (m), 847 (s) $cm^{-1}$; $^1H$ NMR (500 MHZ, $CDCl_3$) d 5.50 (apparent dd, J=9.0, 1.1 Hz, 1 H), 3.65 (dd, J=11.0, 4.8 Hz, 1 H), 3.59 (dd, J=11.0, 5.7 Hz, 1 H), 3.56 (apparent t, J=5.2 Hz, 1 H), 2.80–2.72 (m,1 H), 2.25 (d, J=1.0 Hz, 3 H), 2.20 (br s, 1 H),1.86–1.78 (m, 1 H), 0.99 (d, J=7.1 Hz, 3 H), 0.98 (d, J=6.9 Hz, 3 H), 0.90 (s, 9 H), 0.09 (s, 3 H), 0.05 (s, 3 H); $^{13}C$ NMR (125 MHZ, $CDCl_3$) d 132.6, 121.7, 79.7, 65.6, 40.9, 38.8, 28.9, 26.1, 18.3, 15.5, 15.0, −3.9, −4.0; high resolution mass spectrum (CI, $NH_3$) m/z 351.1087 [$M^+$; calcd for $C_{15}H_{31}O_2BrSi$: 351.1093].

EXAMPLE 20

Alcohol (+)-26

A solution of amide (+)-17 (323.5 mg, 0.738 mmol) in EtOH (8.0 mL) was stirred for 5 h under $H_2$ atmosphere in the presence of Pearlman's catalyst (20% $Pd(OH)_2/C$, 104.1 mg), then filtered and concentrated. Flash chromatography (10 mL silica, 20% ethyl acetate/hexane) provided (+)-26 (216.7 mg, 92% yield) as a colorless oil: $[\alpha]^{23}_D$ +16.1° ©2.60, $CHCl_3$); IR ($CHCl_3$) 3480 (m, br), 3000 (s), 2958 (s), 2935 (s), 2880 (s), 2860 (s), 1635 (s), 1460 (s), 1415 (m), 1390 (s), 1360 (m), 1285 (w), 1255 (s), 1174 (m), 1148 (m), 1093 (s), 1070 (s), 1047 (s), 1033 (s), 990 (s), 935 (m), 905 (w), 860 (s), 830 (s) $cm^{-1}$; $^1H$ NMR (500 MHZ, $CDCl_3$) d 4.05 (dd, J=9.1, 3.1 Hz, 1 H), 3.69 (s, 3 H), 3.55–3.50 (m, 1 H), 3.23 (ddd, J=10.1, 10.1, 2.8 Hz, 1 H), 3.13 (s, 3 H), 3.09 (br m, 1 H), 2.81 (br m, 1 H), 1.91–1.83 (m, 1 H), 1.14 (d, J=7.0 Hz, 3 H), 0.879 (d, J=7.0 Hz, 3 H), 0.879 (s, 9 H), 0.08 (s, 3 H), 0.06 (s, 3 H); $^{13}C$ NMR (125 MHZ, $CDCl_3$) d 177.3, 75.2, 64.9, 61.5, 40.8, 38.2, 32.2, 26.0, 18.2, 15.9, 12.8, −4.1, −4.3; high resolution mass spectrum (CI, $NH_3$) m/z 320.2265 [$(M+H)^+$; calcd for $C_{15}H_{34}NO_4Si$: 320.2256].

EXAMPLE 21

Aldehyde (+)-27

A solution of alcohol (+)-26 (8.80 g, 27.5 mmol) and $NEt_3$ (15.3 mL, 110 mmol) in $CH_2Cl_2$ (50 mL) was cooled to −10° C. and treated with $SO_3$.pyr (13.1 g, 82.6 mmol) in DMSO (100 mL). After 20 min at room temperature, the mixture was diluted with ether (300 mL), washed with aqueous $NaHSO_4$ (1.0 M, 200 mL), brine (4×200 mL), dried over $MgSO_4$, filtered and concentrated. Flash chromatography (20% ethyl acetate/hexane) afforded (+)-27 (8.55 g, 98% yield) as a colorless oil: $[\alpha]^{23}_D$ +51.2° ©1.00, $CHCl_3$); IR ($CHCl_3$) 3010 (m), 2960 (s), 2940 (s), 2895 (m), 2865 (m), 1750 (m), 1720 (s), 1647 (s), 1460 (s), 1420 (m), 1390 (s), 1360 (m), 1255 (s), 1180 (m), 1105 (m), 1077 (m), 1040 (s), 995 (s), 936 (m), 853 (s), 837 (s), 710 (m), 657 (m) $cm^{-1}$; $^1H$ NMR (500 MHZ, $CDCl_3$) d 9.68 (d, J=1.6 Hz, 1 H), 4.22 (dd, J=8.9, 2.6 Hz, 1 H), 3.68 (s, 3 H), 3.10 (apparent s, 4 H), 2.46 (qdd, J=7.1, 2.6, 1.5 Hz, 1 H), 1.16 (d, J=6.9 Hz, 3 H), 1.10 (d, J=7.0 Hz, 3 H), 0.88 (s, 9 H), 0.092 (s, 3 H), 0.088 (s, 3 H); $^{13}C$ NMR (125 MHZ, $CDCl_3$) d 203.2, 175.6, 75.1, 61.5, 52.1, 39.6, 32.1, 25.9, 18.2, 15.4, 10.2, −4.07, −4.11; high resolution mass spectrum (CI,$NH_3$) M/Z 318.2096 [$(M+H)^+$; $C_{15}H_{32}NO_4Si$: 318.2100].

EXAMPLE 22

Dithiane (+)-28

A solution of $ZnCl_2$ (dried at 140° C. for 1 h under vacuum, 170.5 mg, 1.25 mmol) in ether (6.0 mL) was cooled to 0° C. and $(TMSSCH_2)_2CH_2$ (175.0 μL, 0.628 mmol) was added. The resultant white milky suspension was treated with aldehyde (+)-27 (180.0 mg, 0.567 mmol) in ether (6.0 mL). The mixture was stirred for 4.5 h at 0° C. and 1.5 h at room temperature, then partitioned between ethyl acetate (50 mL) and aqueous ammonia (30 mL). The organic phase was washed with brine (2×30 mL), dried over $MgSO_4$, filtered and concentrated. Flash chromatography (10% ethyl acetate/hexane) provided (+)-28 (182.9 mg, 79% yield) as a white solid: mp 55–57° C.; $[\alpha]^{23}_D$ +18.5° ©1.44, $CHCl_3$); IR ($CHCl_3$) 3015 (m), 2970 (s), 2945 (s), 2910 (m), 2870 (m), 1665 (s), 1475 (m), 1470 (m), 1437 (m), 1430 (m), 1420 (m), 1390 (m), 1365 (m), 1320 (w), 1280 (m), 1260 (m), 1120 (m), 1115 (m), 1097 (m), 1080 (m), 1065 (m), 1040 (m), 1000 (m), 940 (w), 925 (w), 910 (w), 877 (m), 838 (s), 815 (m), 800 (m), 700 (w), 675 (w), 660 (w) $cm^{-1}$; $^1H$ NMR (500 MHZ, $CDCl_3$) d 4.33 (d, J=4.2 Hz, 1 H), 4.23 (dd, J=7.1, 3.6 Hz, 1 H), 3.68 (s, 3 H), 3.15 (s, 3 H), 2.98 (dq, J=6.8, 3.7 Hz, 1 H), 2.90 (ddd, J=14.1, 12.2, 2.5 Hz, 1 H), 2.83–2.77 (m, 3 H), 2.09–2.03 (m, 1 H), 1.94 (ddq, J=7.2, 7.2, 4.3 Hz, 1 H), 1.88–1.76 (m, 1 H), 1.08 (d, J=7.2 Hz, 3 H), 1.07 (d, J=6.9 Hz, 3 H), 0.90 (s, 9 H), 0.13 (s, 3 H), 0.02 (s, 3 H); $^{13}C$ NMR (125 MHZ, $CDCl_3$) d 176.2, 73.2, 61.0, 50.8, 44.2, 38.6, 31.3, 30.3, 26.2, 18.4, 12.9, 11.0, −4.1, −4.2; high resolution mass spectrum (CI, $NH_3$) m/z 408.2081 [$(M+H)^+$; calcd for $C_{18}H_{38}NO_3S_2Si$: 408.2062].

Anal. Calcd. for $C_{18}H_{37}NO_3S_2Si$: C, 53.03; H, 9.15. Found: C, 53.06; H, 9.31.

EXAMPLE 23

Aldehyde (+)-29

A solution of dithiane (+)-28 (1.05 g, 2.58 mmol) in THF (40 mL) was cooled to −78° C. and DIBAL (1.0 M in hexane, 5.15 mL, 5.15 mmol) was added over 15 min. After 10 min at −78° C., the mixture was quenched with MeOH (2.0 mL) and partitioned between ether and saturated aqueous Rochelle's salt (50 mL each). The organic phase was washed with brine (30 mL), dried over $MgSO_4$, filtered and concentrated. Flash chromatography (10% ethyl acetate/hexane) provided (+)-29 (822 mg, 91% yield) as white solid: mp 54–55° C.; $[\alpha]^{23}_D$ +50.8° ©1.19, $CHCl_3$); IR ($CHCl_3$) 2965 (s), 2940 (s), 2910 (s), 2865 (s), 2720 (w), 1730 (s), 1475 (m), 1467 (m), 1428 (m), 1418 (m), 1390 (m), 1365 (m), 1280 (m), 1260 (s), 1190 (m), 1150 (m), 1104 (s), 1070 (m), 1030 (s), 1007 (m), 953 (m), 940 (m), 910 (m), 835 (s), 810 (m), 675 (m) $cm^{-1}$; $^1H$ NMR (500 MHZ, $CDCl_3$) d 9.70 (s, 1 H), 4.44 (dd, J=8.3, 2.2 Hz, 1 H), 4.38 (d, J=3.7 Hz, 1 H), 2.93 (ddd, J=14.1, 12.3, 2.6 Hz, 1 H), 2.84–2.80 (m, 3 H), 2.43 (qd, J=7.1, 2.2 Hz, 1 H), 2.13–2.07 (m, 1 H), 2.02 (dqd, J=8.2, 7.1, 3.7 Hz, 1 H), 1.88–1.79 (m, 1 H), 1.10 (d, J=6.9 Hz, 3 H), 1.05 (d, J=7.1 Hz, 3 H), 0.87 (s, 9 H), 0.16 (s, 3 H), −0.01 (s, 3 H); $^{13}C$ NMR (125 MHZ, $CDCl_3$) d 204.6, 71.1, 51.0, 49.7, 43.5, 31.3, 30.3, 26.2, 26.0, 18.4, 12.9, 6.8, −3.9, −4.3; high resolution mass spectrum (CI, $NH_3$) m/z 349.1678 [$(M+H)^+$; calcd for $C_{16}H_{33}O_2S_2Si$: 349.1691].

Anal. Calcd for $C_{16}H_{32}O_2S_2Si$: C,55.12; H, 9.25. Found: C, 55.08; H, 9.28.

EXAMPLE 24

Dimethoxy Acetal (+)-30

A solution of aldehyde (+)-29 (792 mg, 2.27 mmol) in $HC(OMe)_3/MeOH$ (48 mL, 1:5) was treated with $TsOH.H_2O$ (8.6 mg, 0.045 mmol) at room temperature. After 30 min, $NEt_3$ (1.0 mL) was added and the mixture was concentrated. Flash chromatography (10% ethyl acetate/hexane) provided (+)-30 (886 mg, 99% yield) as a white solid: mp 58–59° C.; $[\alpha]^{23}_D$ +27.1° ©2.85, $CHCl_3$); IR ($CHCl_3$) 2960 (s), 2940 (s), 2905 (s), 2860 (m), 2835 (m), 1473 (m), 1463 (m), 1432 (m), 1425 (m), 1415 (m), 1387 (m), 1362 (m), 1340 (w), 1278 (m), 1252 (s), 1190 (m), 1158 (m), 1104 (s), 1070 (m), 1050 (m), 1030 (s), 1005 (m), 963 (m), 938 (m), 908 (m), 873 (m), 834 (s), 810 (m) $cm^{-1}$; $^1H$ NMR (500 MHZ, $CDCl_3$) d 4.41 (d, J=3.1 Hz, 1 H), 4.23 (d, J=8.6 Hz, 1 H), 4.02 (dd, J=8.6, 1.3 Hz, 1 H), 3.29 (s, 3 H), 3.26 (s, 3 H), 2.93 (ddd, J=14.0, 12.4, 2.5 Hz, 1 H), 2.85–2.78 (m, 3 H), 2.11–2.05 (m, 1 H), 1.93–1.77 (m, 3 H), 1.00 (d, J=7.2 Hz, 3 H), 0.91 (s, 9 H), 0.85 (d, J=6.9 Hz, 3 H), 0.17 (s, 3 H), 0.09 (s, 3 H); $^{13}C$ NMR (125 MHZ, $CDCl_3$) d 105.0, 71.5, 53.0, 51.5, 51.2, 43.8, 37.4, 31.3, 30.2, 26.3, 18.8, 12.9, 8.1, –3.8, –4.3; high resolution mass spectrum (FAB, NBA) m/z 417.1934 [(M+Na)$^+$; calcd for $C_{18}H_{38}O_3S_2SiNa$: 417.1930].

Anal. Calcd for $C_{18}H_{38}O_3S_2Si$: C, 54.78; H, 9.70. Found: C, 54.80; H, 9.66.

EXAMPLE 25

Hydroxy Acetal (−)-32

A solution of dithiane (+)-30 (3.60 g, 9.12 mmol) in 10% HMPA/THF (60 mL) was cooled to −78° C. and treated with t-BuLi (1.7 M in pentane, 5.63 mL, 9.58 mmol) dropwise over 15 min. The mixture was stirred 1 h at −78° C. and 1 h at −42° C., then recooled to −78° C. A solution of benzyl R-(−)-glycidyl ether (1.65 g, 10.0 mmol) in 10% HMPA/THF (12 mL) was added via cannula. After 0.5 h, the reaction mixture was warmed to −42° C. for 0.5 h and quenched with saturated aqueous $NH_4Cl$ (20 mL). The mixture was diluted with ether (200 mL), washed with water, brine (200 mL each), dried over $MgSO_4$, filtered and concentrated. Flash chromatography (10% ethyl acetate/hexane) afforded (−)-32 (4.04 g, 79% yield) as a colorless oil: $[\alpha]^{23}_D$ −5.9° ©2.1, $CHCl_3$); IR ($CHCl_3$) 3450 (w, br), 3020 (m), 2960 (s), 2940 (s), 2910 (m), 2860 (m), 2840 (m), 1605 (w), 1500 (w), 1475 (m), 1468 (m), 1458 (m), 1440 (m), 1430 (m), 1393 (m), 1387 (m), 1365 (m), 1280 (w), 1255 (m), 1233 (m), 1203 (m), 1167 (w), 1153 (w), 1110 (s), 1060 (m), 1045 (m), 1030 (m), 1010 (m), 980 (w), 940 (m), 910 (w), 860 (m), 837 (s), 800 (m), 695 (m), 670 (m), 660 (m) $cm^{-1}$; $^1H$ NMR (500 MHZ, $CDCl_3$) d 7.35–7.25 (m, 5 H), 4.64 (dd, J=4.0, 1.1 Hz, 1 H), 4.57 (ABq, $J_{AB}$=12.1 Hz, $\Delta\delta_{AB}$=17.8 Hz, 2 H), 4.21 (d, J=7.7 Hz, 1 H), 4.14–4.09 (m, 1 H), 3.48 (dd, J=9.5 1 6.0 Hz, 1 H), 3.47 (dd, J=9.6, 5.0 Hz, 1 H), 3.37 (d, J=0.7 Hz, 1 H), 3.36 (s, 3 H), 3.29 (s, 3 H), 3.08 (ddd, J=14.4, 11.4, 2.9 Hz, 1 H), 2.95 (ddd, J=14.4, 11.3, 3.1 Hz, 1 H), 2.71–2.64 (m, 2 H), 2.59 (dqd, J=6.7, 6.7, 0.9 Hz, 1 H), 2.49 (dd, J=15.6, 7.9 Hz, 1 H), 2.30 (dq, J=4.0, 7.3 Hz, 1 H), 2.27 (dd, J=15.6, 2.3 Hz, 1 H), 2.04–2.00 (m, 1 H), 1.86–1.78 (m, 1 H), 1.18 (d, J=7.4 Hz, 3 H), 0.94 (d, J=6.8 Hz, 3 H), 0.90 (s, 9 H), 0.08 (s, 3 H), 0.07 (s, 3 H); $^{13}C$ NMR (125 MHZ, $CDCl_3$) d 138.2, 128.4, 127.6, 106.9, 74.4, 73.3, 70.0, 67.9, 55.7, 53.6, 52.6, 47.2, 39.4, 38.5, 26.3, 26.1, 26.0, 25.0, 18.3, 9.8, 9.5, −3.9, −4.9; high resolution mass spectrum (FAB, NBA) m/z 581.2763 [(M+Na)$^+$; calcd for $C_{28}H_{50}O_5S_2SiNa$: 581.2767].

EXAMPLE 26

Ketone (+)-33

A solution of hydroxy acetal (−)-32 (3.94 g, 7.05 mmol) in $H_2O$/MeOH (1:9, 75 mL) was treated with $(CF_3CO_2)_2,Ph$ (4.55 g, 10.6 mmol) at 0° C. After 5 min, the mixture was quenched with saturated $NaHCO_3$ (20 mL) and extracted with ether (200 mL). The organic phase was washed with brine (200 mL), dried over $MgSO_4$, filtered and concentrated. Flash chromatography (20% ethyl acetate/hexane) furnished (+)-33 (2.66 g, 80% yield) as a colorless oil. $[\alpha]^{23}_D$ +36° ©0.36, $CHCl_3$); IR ($CHCl_3$) 3580 (w, br), 3005 (m), 2960 (s), 2930 (s), 2900 (m), 2860 (m), 1710 (m), 1463 (m), 1455 (m), 1387 (m), 1362 (m), 1253 (m), 1220 (m), 1105 (s), 1070 (s),1053 (s), 1030 (s), 1002 (m), 938 (m), 866 (m), 830 (s), 808 (m), 690 (m), 660 (m) $cm^{-1}$; $^1H$ NMR (500 MHZ, $CDCl_3$) d 7.34–7.25 (m, 5 H), 4.54 (apparent s, 2 H), 4.40–4.25 (m, 1 H), 4.23 (dd, J=7.6, 1.9 Hz, 1 H), 4.19 (d, J=8.0 Hz, 1 H), 3.46 (dd, J=9.7, 4.9 Hz, 1 H), 3.43 (dd, J=9.7, 5.9 Hz, 1 H), 3.27 (s, 3 H), 3.25 (s, 3 H), 3.01 (d, J=3.8 Hz, 1 H), 2.76 (dd, J=18.0, 8.7 Hz, 1 H), 2.74 (dq, J=7.1, 7.1 Hz, 1 H), 2.62 (dd, J=17.9, 3.2 Hz, 1 H), 1.83 (dqd, J=8.0, 7.0, 1.9 Hz, 1 H), 0.97 (d, J=7.1 Hz, 3 H), 0.88 (d, J=6.9 Hz, 3 H), 0.83 (s, 9 H), 0.06 (s, 3 H), −0.05 (s, 3 H); $^{13}C$ NMR (125 MHZ, $CDCl_3$) d 213.0, 138.0, 128.4, 127.71, 127.68, 105.0, 73.4, 73.3, 71.8, 66.5, 52.9, 52.6, 52.3, 46.5, 37.9, 26.1, 18.4, 12.7, 8.8, −4.1, −4.8; high resolution mass spectrum (FAB, NBA) m/z 491.2821 [(M+Na)$^+$; calcd for $C_{25}H_{44}O_6SiNa$: 491.2805].

EXAMPLE 27

Diol (−)-34

A solution of $Me_4NBH(OAc)_3$ (1.80 g, 6.84 mmol) in $HOAc/CH_3CN$ (1:1, 10.0 mL) was cooled to −40° C. and ketone (+)-33 (536 mg, 1.14 mmol) in $CH_3CN$ (5 mL) was added. After 12 h at −20° C., the mixture was treated with saturated aqueous Rochelle's salt (20 mL) and extracted with $CH_2Cl_2$ (3×50 mL). The combined organic extracts were washed with saturated $NaHCO_3$, brine (100 mL each), dried over $MgSO_4$, filtered and concentrated. Flash chromatography (1:1:1, $CH_2Cl_2$/ether/hexane) provided (−)-34 (519 mg, 97% yield) as a colorless oil: $[\alpha]^{23}_D$ −7.78° ©0.900, $CHCl_3$); IR ($CHCl_3$) 3680 (w), 3460 (m, br), 3015 (m), 2960 (s), 2940 (s), 2900 (s), 2865 (s), 1470 (m), 1460 (m),1390 (m), 1365 (m), 1260 (m), 1230 (m), 1208 (m), 1112 (s), 1065 (s), 1030 (m), 1010 (m), 942 (m), 865 (m), 838 (m), 698 (m) $cm^{-1}$; $^1H$ NMR (500 MHZ, $CDCl_3$) d 7.33–7.30 (m, 4 H), 7.29–7.25 (m, 1 H), 4.55 (ABq, $J_{AB}$=12.0 Hz, A5AB=15.7 Hz, 2 H), 4.16–4.11 (m, 1 H), 4.13 (d, J=7.8 Hz, 1 H), 4.07 (dd, J=4.8, 1.6 Hz, 1 H), 3.73 (br s, 1 H), 3.68 (dddd, J=9.3, 9.3, 2.4, 2.4 Hz, 1H), 3.50 (dd, J=9.6, 4.5 Hz, 1 H), 3.42 (dd, J=9.4, 7.0 Hz, 1 H), 3.38 (s, 3 H), 3.29 (s, 3 H), 3.09 (d, J=4.0 Hz, 1 H), 1.90 (dqd, J=7.0, 7.0, 1.5 Hz, 1 H), 1.76 (br dd, J=13.6, 8.5 Hz, 1 H), 1.68 (dqd, J=9.6, 6.9, 5.0 Hz, 1 H), 1.49 (ddd, J=14.3, 9.0, 2.9 Hz, 1 H), 0.894 (d, J=7.9 Hz, 3 H), 0.886 (s, 9 H), 0.80 (d, J=7.0 Hz, 3 H), 0.055 (s, 3 H), 0.048 (s, 3 H); $^{13}C$ NMR (125 MHZ, $CDCl_3$) d 138.2, 128.4, 127.7, 127.6, 107.3, 74.5, 73.3, 71.0, 70.9, 67.8, 55.2, 52.1, 45.9, 37.3, 36.9, 25.9, 18.2, 11.6, 10.6, −4.3, −4.7; high resolution mass spectrum (FAB, NBA) m/z 493.2951 [(M+Na)$^+$; calcd for $C_{25}H_{46}O_6SiNa$: 493.2962].

EXAMPLE 28

Alcohol (−)-35

A solution of (−)-34 (123.3 mg, 0.262 mmol) in benzene (10 mL) was treated with TsOH.H$_2$O (2.0 mg, 0.0105 mmol) at room temperature. After 20 min, the mixture was quenched with NEt$_3$ (1.0 mL) and concentrated. Flash chromatography (2% ether/CH$_2$Cl$_2$) afforded 35 (100.1 mg, /a=2:1, 87% yield) as a colorless oil.

β Anomer (35): [α]$^{23}_D$ −3.3° ©2.25, CHCl$_3$); IR (CHCl$_3$) 3680 (w), 3580 (w), 3490 (w), 3010 (m), 2960 (s), 2930 (s), 2880 (m), 2860 (s), 1603 (w), 1525 (w), 1515 (w), 1493 (m), 1470 (m), 1460 (m), 1450 (m), 1387 (m), 1360 (m), 1347 (m), 1330 (m), 1253 (s), 1225 (m), 1200 (m), 1143 (m), 1110 (s), 1070 (s), 1045 (s), 1020 (s), 1015 (m), 1003 (m), 985 (m), 950 (m), 870 (m), 853 (m), 833 (s), 807 (m), 800 (m), 790 (m), 690 (m), 670 (m), 657 (m) cm$^{-1}$; $^1$H NMR (500 MHZ, CDCl$_3$) d 7.34–7.25 (m, 5 H), 4.69 (d, J=2.4 Hz, 1 H), 4.55 (ABq, J$_{AB}$=12.0 Hz, Δδ$_{AB}$=14.6 Hz, 2 H), 4.17–4.12 (m, 1 H), 3.78 (ddd, J=9.7, 9.7, 2.5 Hz, 1 H), 3.60 (apparent t, J=2.7 Hz, 1 H), 3.51 (dd, J=9.5, 4.1 Hz, 1 H), 3.42 (s, 3 H), 3.39 (dd, J=9.5, 7.0 Hz, 1 H), 2.86 (d, J=3.8 Hz, 1 H), 1.88 (apparent qt, J=7.1, 2.7 Hz, 1 H), 1.76 (ddd, J=14.4, 8.9, 2.6 Hz, 1 H), 1.72–1.65 (m, 1 H), 1.53 (ddd, J=14.4, 9.3, 2.9 Hz, 1 H), 0.90 (d, J=8.2 Hz, 3 H), 0.89 (s, 9 H), 0.78 (d, J=6.8 Hz, 3 H), 0.04 (s, 3 H), 0.02 (s, 3 H); $^{13}$C NMR (125 MHZ, CDCl$_3$) d 138.2, 128.4, 127.7, 101.2, 76.7, 74.7, 73.3, 73.0, 67.4, 56.6, 41.1, 36.0, 34.7, 25.9, 18.1, 13.7, 9.7, −4.6, −4.9; high resolution mass spectrum (FAB, NBA) m/z 461.2693 [(M+Na)$^+$; calcd for C$_{24}$H$_{42}$O$_5$SiNa: 461.2699].

α Anomer (35): [α]$^{23}_D$ +48° ©0.54, CHCl$_3$); IR (CHCl$_3$) 3670 (w), 3570 (w), 3480 (w, br), 3005 (m), 2960 (s), 2930 (s), 2880 (m), 2855 (s), 1600 (w), 1527 (w), 1515 (w), 1495 (w), 1460 (m), 1360 (m), 1253 (s), 1225 (m), 1212 (m), 1200 (m), 1170 (m), 1148 (m), 1106 (s), 1087 (s), 1048 (s), 1030 (s), 963 (m), 872 (m), 833 (s), 788 (m), 690 (m) cm$^{-1}$; $^1$H NMR (500 MHZ, CDCl$_3$) d 7.34–7.24 (m, 5 H), 4.55 (ABq, J$_{AB}$=12.1 Hz, Δδ$_{AB}$=14.4 Hz, 2 H), 4.30 (d, J=2.9 Hz, 1 H), 4.12–4.07 (m, 1 H), 4.01 (ddd, J=9.2, 9.2, 2.7 Hz, 1 H), 3.51 (apparent t, J=4.4 Hz, 1 H), 3.50 (dd, J=9.5, 4.2 Hz, 1 H), 3.39 (dd, J=15 9.5, 7.1 Hz, 1 H), 3.28 (s, 3 H), 2.86 (d, J=3.2 Hz, 1 H), 1.85 (qdd, J=7.3, 5.2, 2.9 Hz, 1 H), 1.76 (dqd, J=9.3, 6.9, 4.0 Hz, 1 H), 1.71 (ddd, J=14.5, 9.0, 2.8 Hz, 1 H), 1.55 (ddd, J=14.4, 9.2, 2.9 Hz, 1 H), 0.96 (d, J=7.3 Hz, 3 H), 0.88 (s, 9 H), 0.81 (d, J=6.8 Hz, 3 H), 0.03 (s, 3 H), −0.01 (s, 3 H); $^{13}$C NMR d 138.2, 128.4, 127.7, 101.2, 76.7, 74.7, 73.3, 73.0, 67.4, 56.7, 41.1, 36.0, 34.7, 25.9, 18.1, 13.7, 9.7, −4.6, −4.9; high resolution mass spectrum (FAB, NBA) m/z 461.2715 [(M+Na)$^+$; calcd for C$_{24}$H$_{42}$O$_5$SiNa: 461.2699].

EXAMPLE 29

Methyl Pyranoside 36

A solution of 35 (281.2 mg, β/α=2:1, 0.642 mmol) and 2,6-lutidine (224.0 μL, 1.92 mmol) in CH$_2$Cl$_2$ (6.0 mL) was cooled to 0° C. and TBSOTf (295.0 μL, 1.28 mmol) was added over 5 min. After 1 h at 0° C., the mixture was diluted with ethyl acetate (100 mL), washed with aqueous NaHSO$_4$ (1.0 M, 50 mL), brine (100 mL), dried over MgSO$_4$, filtered and concentrated. Flash chromatography (5% ethyl acetate/hexane) provided 36 (344.6 mg, β/α=2:1, 97% yield) as a colorless oil.

α anomer: [α]$^{23}_D$ +50.0° ©1.44, CHCl$_3$); IR (CHCl$_3$) 2960 (s), 2935 (s), 2885 (s), 2860 (s), 1490 (w), 1460 (m), 1388 (m), 1378 (m), 1360 (m), 1250 (s), 1190 (m), 1145 (m), 1105 (s), 1085 (s), 1050 (s), 1025 (s), 1002 (s), 963 (m), 934 (m), 867 (m), 833 (s), 690 (m) cm$^{-1}$; $^1$H NMR (500 MHZ, CDCl$_3$) d 7.32–7.25 (m, 5 H), 4.51 (ABq, J$_{AB}$=12.1 Hz, Δδ$_{AB}$=19.7 Hz, 2 H), 4.23 (d, J=4.8 Hz, 1 H), 4.03 (dddd, J=8.0, 5.3, 5.3, 2.5 Hz, 1 H), 3.87 (ddd, J=9.9, 7.8, 1.8 Hz, 1 H), 3.53 (dd, J=7.2, 4.8 Hz, 1 H), 3.39 (dd, J=9.8, 5.6 Hz, 1 H), 3.37 (dd, J=10.0, 5.2 Hz, 1 H), 3.33 (s, 3 H), 1.79 (dqd, J=7.1, 7.1, 4.9 Hz, 1 H), 1.71–1.64 (m, 2 H), 1.53 (ddd, J=14.4, 8.8, 1.9 Hz, 1 H), 0.94 (d, J=7.0 Hz, 3 H), 0.89 (s, 9 H), 0.865 (s, 9 H), 0.862 (d, J=6.9 Hz, 3 H), 0.07 (s, 3 H), 0.04 (s, 3 H), 0.03 (s, 3 H), 0.005 (s, 3 H); $^{13}$C NMR (125 MHZ, CDCl$_3$) d 138.5, 128.3, 127.6, 127.5, 103.8, 75.5, 73.2, 72.8, 69.8, 69.1, 55.7, 38.9, 38.5, 37.6, 26.0, 25.8, 18.18, 18.16, 15.1, 12.9, −3.9, −4.6, −4.7, −4.8; high resolution mass spectrum (FAB, NBA) m/z 575.3552 [(M+Na)$^+$; calcd for C$_{30}$H$_{56}$O$_5$Si$_2$Na: 575.3564].

β anomer: [α]$^{23}_D$ +13.3° ©1.38, CHCl$_3$); IR (CHCl$_3$) 3003 (m), 2960 (s), 2935 (s), 2880 (s), 2860 (s), 1495 (w), 1470 (m), 1464 (m), 1390 (m), 1360 (m), 1350 (m), 1330 (w), 1253 (s), 1155 (s), 1140 (s), 1120 (s), 1090 (s), 1045 (s), 1022 (s), 1002 (s), 953 (m), 933 (m), 850 (s), 830 (s), 690 (m), 658 (m) cm$^{-1}$; $^1$H NMR (500 MHZ, CDCl$_3$) d 7.32–7.22 (m, 5 H), 4.74 (d, J=2.4 Hz, 1 H), 4.50 (ABq, J$_{AB}$=13.2 Hz, Δδ$_{AB}$=17.8 Hz, 2 H), 4.23–4.18 (m, 1 H), 3.74 (ddd, J=10.6, 10.6, 1.3 Hz, 1 H), 3.60 (apparent t, J=2.7 Hz, 1 H), 3.48 (s, 3 H), 3.38 (dd, J=9.8, 4.5 Hz, 1 H), 3.35 (dd, J=9.8, 5.7 Hz, 1 H), 1.88 (qdd, J=7.1, 2.7, 2.7 Hz, 1 H), 1.66 (ddd, J=14.0, 10.1, 1.6 Hz, 1 H), 1.63–1.55 (m, 1 H), 1.49 (ddd, J=14.0, 10.8, 1.8 Hz, 1 H), 0.91 (d, J=7.1 Hz, 3 H), 0.89 (s, 9 H), 0.88 (s, 9 H), 0.785 (d, J=6.8 Hz, 3 H), 0.07 (s, 3 H), 0.045 (s, 3 H), 0.040 (s, 3 H), 0.02 (s, 3 H); $^{13}$C NMR (125 MHZ, CDCl$_3$) d 138.5, 128.2, 127.6, 127.4, 100.6, 76.9, 75.8, 73.2, 71.7, 67.9, 56.7, 41.1, 38.4, 35.0, 26.1, 25.8, 18.2, 18.1, 14.0, 9.7, −3.9, −4.5, −5.0; high resolution mass spectrum (FAB, NBA) m/z 575.3560 [(M+Na)$^+$; calcd for C$_{30}$H$_{56}$O$_5$Si$_2$Na: 575.3564].

EXAMPLE 30

Primary Alcohol 37

A solution of 36 (331.6 mg, 0.600 mmol) in EtOH/EtOAc (1:8, 9 mL) was treated with Pd/C (10% wet, E101 NE/W, 51.2 mg) under H$_2$ atmosphere for 3 h, then filtered and concentrated. Flash chromatography (10% ethyl acetate/hexane) provided 37 (276.6 mg, β/α=2:1, 99% yield) as a colorless oil.

β anomer: [α]$^{23}_D$ +16.9° ©2.52, CHCl$_3$); IR (CHCl$_3$) 3680 (w), 3590 (w, br), 3450 (w, br), 3000 (m), 2960 (s), 2925 (s), 2880 (m), 2855 (s), 1470 (m), 1462 (m), 1388 (m), 1360 (m), 1253 (s), 1222 (m), 1200 (m), 1150 (m),1130 (m), 1110 (s), 1098 (m), 1065 (s), 1046 (s), 1023 (s), 1002 (m), 980 (m), 952 (m), 894 (m), 865 (m), 850 (m), 830 (s), 663 (m), 657 (m) cm$^{-1}$; $^1$H NMR (500 MHZ, CDCl$_3$) d 4.73 (d, J=2.5 Hz, 1 H), 4.09–4.05 (m, 1 H), 3.64 (ddd, J=10.5, 10.5, 1.3 Hz, 1 H), 3.60 (apparent t, J=2.5 Hz, 1 H), 3.62–3.59 (m, 1 H), 3.47 (s, 3 H), 3.47–3.42 (m, 1 H), 1.95–1.85 (m, 2 H), 1.82 (ddd, J=14.3, 9.2, 1.5 Hz, 1 H), 1.60 (dqd, J=10.2, 6.8, 2.5 Hz, 1 H), 1.45 (ddd, J=14.3, 10.7, 2.6 Hz, 1 H), 0.895 (d, J=7.5 Hz, 3 H), 0.887 (apparent s, 18 H), 0.785 (d, J=6.8 Hz, 3 H), 0.09 (s, 3 H), 0.08 (s, 3 H), 0.04 (s, 3 H), 0.02 (s, 3 H); $^{13}$C NMR (125 MHZ, CDCl$_3$) d 100.8, 76.8, 72.2, 69.5, 67.6, 56.8, 41.0, 38.2, 34.9, 25.9, 25.8, 18.1, 14.0, 9.7, −4.2, −4.6, −4.7, −5.0; high resolution mass spectrum (FAB, NBA) m/z 485.3080 [(M+Na)$^+$; calcd for C$_{23}$H$_{50}$O$_5$SiNa: 485.3094].

α anomer: [α]$^{23}_D$ +54.9° ©1.20, CHCl$_3$) ; IR (CHCl$_3$) 3670 (w), 3590 (w) 3440 (w, br), 3000 (m), 2960 (s), 2925

(s), 2880 (m), 2855 (s), 1463 (m), 1390 (m), 1360 (m), 1255 (s), 1225 (m), 1192 (m), 1168 (m), 1143 (m), 1102 (s), 1083 (s), 1045 (s), 1030 (m), 1002 (m), 963 (m), 932 (m), 862 (m), 833 (s) cm$^{-1}$; $^1$H NMR (500 MHZ, CDCl$_3$) d 4.25 (d, J=4.2 Hz, 1 H), 3.89 (dddd, J=6.5, 4.6, 4.6, 4.6 Hz, 1 H), 3.80 (ddd, J=9.1, 9.1, 2.3 Hz, 1 H), 3.61 (br dd, J=10.9, 3.4 Hz, 1 H), 3.51 (dd, J=6.5, 4.6 Hz, 1 H), 3.52–3.48 (m, 1 H), 3.33 (s, 3 H), 2.15 (s, br, 1 H), 1.81 (dqd, J=6.9, 6.9, 4.2 Hz, 1 H), 1.72–1.60 (m, 3 H), 0.94 (d, J=7.1 Hz, 3 H), 0.882 (s, 9 H), 0.879 (s, 9 H), 0.845 (d, J=6.8 Hz, 3 H), 0.09 (s, 3 H), 0.08 (s, 3 H), 0.02 (s, 3 H), 0.00 (s, 3 H); $^{13}$C NMR (125 MHZ, CDCl$_3$) d 104.0, 72.7, 71.3, 70.0, 67.6, 55.7, 38.7, 38.5, 37.3, 25.8, 18.13, 18.08, 15.2, 13.1, −4.4, −4.6, −4.7; high resolution mass spectrum (FAB, NBA) m/z 485.3081 [(M+Na)$^+$; calcd for C$_{23}$H$_{50}$O$_5$Si$_2$Na: 485.3094].

EXAMPLE 31

Alcohol 38

A solution of 37 (276.6 mg, 0.598 mmol) in Et$_2$O (40 mL) was treated with EtSH (8.90 mL, 120 mmol) and MgBr$_2$.Et$_2$O (1.54 g, 5.96 mmol) at room temperature. After 60 h, the mixture was diluted with ethyl acetate (50 mL), washed with brine (2×100 mL), dried over MgSO$_4$, filtered and concentrated. Flash chromatography (3% acetone/hexane) provided 38α (34.4 mg, 12% yield) and 38β (211.3 mg, 71% yield).

β anomer: colorless oil; $[\alpha]^{23}_D$ +16.6° ©1.18, CHCl$_3$); IR (CHCl$_3$) 3595 (m), 3400 (m, br), 3000 (m), 2960 (s), 2930 (s), 2855 (s), 1655 (w), 1612 (s), 1588 (m), 1510 (s), 1462 (s), 1375 (m), 1360 (m), 1300 (m), 1250 (s, br), 1170 (m), 1080 (s, br), 1030 (s), 1002 (m), 967 (m), 835 (s) cm$^{-1}$; $^1$H NMR (500 MHZ, CDCl$_3$) d 5.08 (d, J=2.3 Hz, 1 H), 4.04–4.00 (m, 1H), 3.62 (ddd, J=10.4, 10.4, 1.0 Hz, 1 H), 3.60 (ddd, J=11.1, 11.1, 4.2 Hz, 1 H), 3.56 (apparent t, J=2.7 Hz, 1 H), 3.43 (ddd, J=11.7, 7.9, 4.1 Hz, 1 H), 2.70 (dq, J=12.7, 7.4 Hz, 1 H), 2.67 (dq, J=12.8, 7.5 Hz, 1 H), 1.95 (dd, J=7.9, 4.8 Hz, 1 H), 1.86 (qdd, J=7.1, 2.7, 2.7 Hz, 1 H), 1.79 (ddd, J=14.4, 9.0, 1.4 Hz, 1 H), 1.66–1.59 (m, 1 H), 1.57 (s, 3 H), 1.45 (ddd, J=14.4, 10.5, 2.7 Hz, 1 H), 1.27 (apparent t, J=7.4 Hz, 1 H), 0.99 (d, J=7.1 Hz, 3 H), 0.90 (s, 9 H), 0.89 (s, 9 H), 0.79 (d, J=6.8 Hz, 3 H), 0.083 (s, 3 H), 0.075 (s, 3 H), 0.04 (s, 3 H), 0.03 (s, 3 H); $^{13}$C NMR (125 MHZ, CDCl$_3$) d 81.0, 76.2, 75.0, 69.8, 67.6, 41.9, 38.3, 34.5, 25.9, 25.8, 25.2, 18.1, 15.2, 14.4, 11.5, −4.2, −4.56, −4.63, −4.9; high resolution mass spectrum (FAB, NBA) m/z 515.3037 [(M+Na); calcd for C$_{24}$H$_{52}$O$_4$SSi$_2$Na: 515.3023].

α anomer: colorless oil; $[\alpha]^{23}_D$ +94.5° ©0.33, CHCl$_3$); IR (CHCl$_3$) 3680 (w), 3580 (w), 3440 (w, br), 3010 (m), 2960 (s), 2930 (s), 2880 (m), 2860 (m), 1513 (w), 1470 (m), 1462 (m), 1390 (m), 1380 (m), 1360 (m), 1257 (s), 1225 (m), 1200 (m), 1114 (m), 1070 (s), 1047 (s), 1022 (m), 1002 (m), 957 (m), 860 (m), 833 (m), 705 (s), 660 (m) cm$^{-1}$; $^1$H NMR (500 MHZ, CDCl$_3$) d 4.76 (d, J=3.1 Hz, 1 H), 4.04 (ddd, J=9.8, 9.8, 1.8 Hz, 1 H), 3.84 (dddd, J=5.0, 5.0, 5.0, 5.0 Hz, 1 H), 3.57 (dd, J=11.0, 4.2 Hz, 1 H), 3.53 (apparent t, J=4.0 Hz, 1 H), 3.47 ( dd, J=11.0, 4.7 Hz, 1 H), 2.57 (dq, J=12. 8, 7.5 Hz, 1 H), 2.54 (dq, J=12.8, 7.5 Hz, 1 H), 1.97–1.91 (m, 1 H), 1.75 (ddd, J=14.7, 6.1 Hz, 2.0, 1 H), 1.72–1.65 (m, 1 H), 1.60 (ddd, J=14.9, 10.0, 5.1 Hz, 1 H), 1.60–1.50 (br, 1 H), 1.23 (apparent t, J=7.4 Hz, 3 H), 1.06 (d, J=7.1 Hz, 3 H), 0.92 (s, 9 H), 0.89 (s, 9 H), 0.85 (d, J=6.9 Hz, 3 H), 0.12 (s, 3 H), 0.08 (s, 3 H), 0.05 (s, 3 H), 0.02 (s, 3 H); $^{13}$C NMR (125 MHZ, CDCl$_3$) d 85.3, 73.8, 71.5, 69.2, 67.5, 40.6, 38.2, 36.4, 26.4, 26.1, 25.9, 18.2, 18.1, 17.5, 14.7, 13.9, −4.2, −4.4, −4.8; high resolution mass spectrum (FAB, NBA) m/z 515.3045 [(M+Na)$^+$; calcd for C$_{24}$H$_{52}$O$_4$SSi$_2$Na: 515.3023].

EXAMPLE 32

Fragment (+)-C

A solution of DMSO (100 μL, 1.42 mmol) in CH$_2$Cl$_2$ (2.0 mL) was cooled to −78° C. and oxalyl chloride (55.0 μl, 0.630 mmol) was introduced dropwise. After 15 min. a cooled (−78° C.) solution of 38α (104.8 mg, 0.213 mmol) in CH$_2$Cl$_2$ (1.0 mL) was introduced via cannula (2×500 μL rinse). The resultant milky solution was stirred for 15 min at −78° C. and I—Pr$_2$NEt (370 μl, 2.12 mmol) was added dropwise. The reaction mixture was stirred for 0.5 h, slowly warmed to room temperature (15 min), and quenched with aqueous NaHSO$_4$ (1.0 M, 4.0 mL). The organic phase was diluted with ether (30 mL), washed with brine (3×30 mL), dried over MgSO$_4$, filtered and concentrated. Flash chromatography (2% ethyl acetate/hexane) furnished (+)-C (88.8 mg, 86% yield) as a colorless oil: $[\alpha]^{23}_D$ +11.2° ©1.42, CHCl$_3$); IR (CHCl$_3$) 2960 (s), 2935 (s), 2880 (s), 2860 (s), 1735 (s), 1470 (m), 1460 (m), 1380 (m), 1360 (m), 1320 (m), 1295 (w), 1265 (s), 1153 (m), 1120 (m), 1080 (m), 1060 (s), 1043 (s), 1025 (s), 1003 (s), 970 (m), 950 (m), 935 (m), 903 (m), 865 (m), 835 (s), 800 (m), 690 (m) cm$^{-1}$; $^1$H NMR (500 MHZ, CDCl$_3$) d 9.56 (d, J=0.9 Hz, 1 H), 5.07 (d, J=2.3 Hz, 1 H), 4.35 (ddd, J=7.9, 2.2, 0.6 Hz, 1 H), 3.70 (ddd, J=10.3, 10.3, 1.5 Hz, 1 H), 3.57 (apparent t, J=2.7 Hz, 1 H), 2.71–2.60 (m, 2 H), 1.86 (apparent qt, J=7.1, 2.7 Hz, 1 H), 1.78 (ddd, J=14.1, 10.4, 7.8 Hz, 1 H), 1.72–1.66 (m, 1 H), 1.67 (ddd, J=10.3, 3.9, 1.8 Hz, 1 H), 1.25 (apparent t, J=7.4 Hz, 3 H), 1.00 (d, J=7.2 Hz, 3 H), 0.90 (s, 9 H), 0.89 (s, 9 H), 0.78 (d, J=6.8 Hz, 3 H), 0.10 (s, 3 H), 0.04 (s, 6 H), 0.03 (s, 3 H); $^{13}$C NMR (125 MHZ, CDCl$_3$) d 202.6, 81.2, 76.1, 74.9, 73.7, 41.9, 35.8, 34.4, 25.82, 25.79, 25.2, 18.2, 18.1, 15.3, 14.3, 11.5, −4.2, −4.5, −4.9, −5.2; high resolution mass spectrum (CI, NH$_3$) m/z 491.3058 [(M+H)$^+$; calcd for C$_{24}$H$_{51}$O$_4$SSi$_2$: 491.3046].

EXAMPLE 33

Fragment (−)-B

From vinyl bromide (−)-22: A solution of (−)-22 (3.78 g, 8.04 mmol) in HMPA/DMF (2:1, 6 mL) was added to a mixture of KI (4.15 g, 250 mmol), NiBr$_2$ (34.9 mg, 0.160 mmol), and Zn powder (23.2 mg, 0.355 mmol). The mixture was stirred at room temperature for 15 min then heated to 90° C. The green color mixture turned black-brown after 5 min and dark green after 1 h. After additional 1 h at 90° C., the mixture was cooled to room temperature, diluted with ethyl acetate (200 mL), washed with brine (4×200 mL), dried over MgSO$_4$, filtered and concentrated. Flash chromatography (2% ethyl acetate/hexane) provided B (3.59 g, containing 13% unreacted vinyl bromide) as a colorless oil.

From aldehyde (+)-18: A suspension of EtPh$_3$P$^+$I$^-$ (15.1 g, 36.1 mmol) in THF (200 mL) was treated with n-BuLi (1.6 M in hexane, 23.0 mL, 36.8 mmol) at room temperature over 10 min. After an additional 10 min, the resultant red solution was added via cannula to a cooled (−78° C.) solution of I2 (8.02 g, 31.6 mmol) in THF (300 mL) over 15 min. The yellow slurry formed was stirred at −78° C. for 5 min and at −23° C. for 10 min. NaHMDS (1.0 M in THF, 31.0 mL, 31.0 mmol) was added over 8 min and the mixture stirred 15 min further. A solution of aldehyde (+)-18 (6.96 g, 18.3 mmol) in THF (50 mL) was introduced via cannula (10 mL rinse), and the reaction mixture was stirred at −23° C. for 10 min, warmed to room temperature, stirred for 3 h, and then quenched with MeOH (10 mL). Following concentration and filtration through a silica column (50% ethyl acetate/ hexane), the filtrate was washed with saturated aqueous Na$_2$S$_2$O$_3$, brine (300 mL each), dried over MgSO$_4$, filtered and concentrated. Flash chromatography (5% ethyl acetate/hexane) furnished B (6:1 Z/E, 3.94 g, 41% yield) as a colorless oil.

An analytical sample of (−)-B was obtained by reversed-phase HPLC (gradient elution, 90% CH$_3$CN/H$_2$O→100% CH$_3$CN): [α]$^{23}_D$ −23° ©0.30, CHCl$_3$); IR (CHCl$_3$) 3000 (m), 2960 (s), 2930 (s), 2880 (m), 2855 (s), 1610 (m), 1588 (w), 1510 (s), 1463 (m), 1453 (m), 1428 (m), 1405 (w), 1390 (m), 1377 (m), 1360 (m), 1303 (m), 1250 (s), 1180 (m), 1172 (m), 1080 (s, br), 1033 (s), 1002 (m), 948 (m), 935 (m), 922 (m), 833 (s), 803 (m), 760 (m, br), 720 (m), 658 (m) cm$^{−1}$; $^1$H NMR (500 MHZ, CDCl$_3$) d 7.25 (d, J=8.6 Hz, 2 H), 6.87 (d, J=8.7 Hz, 2 H), 5.28 (apparent dd, J=8.9, 1.4 Hz, 1 H), 4.41 (ABq, J$_{AB}$=7.0 Hz, Δδ$_{AB}$=10.2 Hz, 2 H), 3.80 (s, 3 H), 3.60 (apparent t, J=5.3 Hz, 1 H), 3.51 (dd, J=9.1, 5.1 Hz, 1 H), 3.23 (dd, J=9.0, 8.0 Hz, 1 H), 2.54–2.47 (m, 1 H), 2.44 (d, J=1.4 Hz, 3 H), 2.00–1.92 (m, 1 H), 1.00 (d, J=6.9 Hz, 3 H), 0.95 (d, J=6.7 Hz, 3 H), 0.89 (s, 9 H), 0.02 (s, 3 H), 0.01 (s, 3 H); $^{13}$C NMR (125 MHZ, CDCl$_3$) d 159.1, 139.6, 131.0, 129.1, 113.7, 98.9, 76.5, 72.6, 72.5, 55.3, 44.5, 38.7, 33.5, 26.1, 18.4, 14.7, 14.5, −3.95, −3.99; high resolution mass spectrum (FAB, NBA) m/z 541.1626 [(M+Na)$^+$; calcd for C$_{23}$H$_{39}$O$_3$ISiNa: 541.1611].

EXAMPLE 34

Olefin (−)-39

ZnCl$_2$ (1.32 g, 9.69 mmol) was dried at 160° C. under vacuum overnight and then treated with a solution of (−)-A (5.25 g, 9.59 mmol) in dry Et$_2$O (50 mL) via a cannula (2×25 mL rinse). The mixture was stirred at room temperature until most of the ZnCl$_2$ dissolved and cooled to −78° C. t-BuLi (1.7 M in pentane, 17.0 mL) was added over 30 min, and the resultant solution was stirred 15 min further, warmed to room temperature, and stirred for 1 h. The solution was added by cannula to a mixture of B (3.21 g, 6.19 mmol; 6:1 Z/E) and Pd(PPh$_3$)$_4$ (364.0 mg, 0.315 mmol). The mixture was covered with aluminum foil, stirred overnight, and then diluted with ethyl acetate (100 mL), washed with brine (2×100 mL), dried over MgSO$_4$, filtered and concentrated. Flash chromatography (5% ethyl acetate/hexane) gave (−)-39 (3.32 g, 66% yield) as a white semisolid: [α]$^{23}_D$ −28.6° ©1.53, CHCl$_3$); IR (CHCl$_3$) 3010 (m), 2970 (s), 2940 (s), 2865 (s), 1620 (m), 1590 (w), 1520 (s), 1465 (s), 1445 (m), 1390 (m), 1380 (m), 1360 (m), 1305 (m), 1250 (s), 1175 (m), 1115 (s), 1080 (s), 1040 (s), 970 (m), 940 (w), 860 (m), 835 (s) cm$^{−1}$; $^1$H NMR (500 MHZ, CDCl$_3$) d 7.36 (d, J=8.7 Hz, 2 H), 7.22 (d, J=8.6 Hz, 2 H), 6.86 (d, J=9.0 Hz, 2 H), 6.84 (d, J=8.9 Hz, 2 H), 5.37 (s, 1 H), 5.00 (d, J=10.2 Hz, 1 H), 4.36 (ABq, J$_{AB}$=11.6 Hz, Δδ$_{AB}$=17.4 Hz, 2 H), 4.08 (dd, J=11.2, 4.7 Hz, 1 H), 3.78 (s, 3 H), 3.77 (s, 3 H), 3.61 (dd, J=7.1, 1.8 Hz, 1 H), 3.51 (dd, J=9.9, 1.7 Hz, 1 H), 3.47 (apparent t, J=11.0 Hz, 1 H), 3.46 (dd, J=9.1, 5.0 Hz, 1 H), 3.38 (dd, J=6.0, 4.8 Hz, 1 H), 3.19 (apparent t, J=8.8 Hz, 1 H), 2.51 (ddq, J=10.1, 6.5, 6.5 Hz, 1 H), 2.32 (apparent t, J=12.2 Hz, 1 H), 2.08–2.02 (m, 1 H), 1.99–1.93 (m, 2 H), 1.88 (dqd, J=7.1, 7.1, 1.8 Hz, 1 H), 1.67 (br d, J=11.1 Hz, 1 H), 1.55 (d, J=0.5 Hz, 3 H), 1.01 (d, J=7.1 Hz, 3 H), 0.94 (d, J=6.9 Hz, 3 H), 0.90 (s, 9 H), 0.89 (d, J=6.7 Hz, 3 H), 0.87 (s, 9 H), 0.74 (d, J=6.3 Hz, 3 H), 0.73 (d, J=6.4 Hz, 3 H), 0.03 (s, 3 H), 0.013 (s, 3 H), 0.008 (s, 3 H), 0.003 (s, 3 H); $^{13}$C NMR (125 MHZ, CDCl$_3$) d 159.8, 159.0, 132.0, 131.5, 131.2, 131.1, 129.0, 127.3, 113.7, 113.5, 101.1, 83.4, 78.49, 78.46, 73.3, 72.6, 72.5, 55.3, 38.8, 38.2, 37.5, 35.6, 33.7, 30.8, 26.27, 26.25, 23.1, 18.42, 18.40, 17.0, 14.6, 12.6, 12.1, 10.9, −3.5, −3.7, −3.8, −3.9; high resolution mass spectrum (FAB, NBA) m/z 835.5315 [(M+Na)$^+$; calcd for C$_{47}$H$_{80}$O$_7$Si$_2$Na: 835.5341].

Anal. Calcd for C$_{47}$H$_{80}$O$_7$Si$_2$: C, 69.41; H, 9.91. Found: C, 69.52; H, 10.10.

EXAMPLE 35

Alcohol (−)-40

A solution of olefin (−)-39 (2.65 g, 3.26 mmol) in CH$_2$Cl$_2$ (32 mL) was cooled to 0° C. and treated with H$_2$O (1.50 mL) and DDQ (774 mg, 3.41 mmol)O. After 4 h, the mixture was diluted with CH$_2$Cl$_2$ (20 mL), dried over MgSO$_4$, and filtered through a silica column (50% ethyl acetate/hexane). Following concentration, the residue was dissolved in EtOH (50 mL) and treated with NaBH$_4$ (500 mg, excess) at room temperature to reduce the contaminated p-methoxybenzyl aldehyde. After 0.5 h, the mixture was quenched with saturated aqueous NH$_4$Cl (50 mL) at 0° C. then concentrated. The residue was partitioned between CH$_2$Cl$_2$ (200 mL) and water (100 mL). The organic phase was washed with water (100 mL), dried over MgSO$_4$, filtered and concentrated. Flash chromatography (10% ethyl acetate/hexane) provided (−)-40 (2.06 g, 91% yield) as a white solid. mp 99–100° C.; [α]$^{23}_D$ −25.4° ©1.35, CHCl$_3$); IR (CHCl$_3$) 3520 (w), 3010 (m), 2960 (s), 2940 (s), 2880 (m), 2860 (m), 1620 (m), 1593 (w), 1520 (m), 1565 (m), 1390 (m), 1360 (m), 1255 (s), 1175 (m), 1165 (m), 1117 (m), 1075 (s), 1037 (s), 1025 (s), 1005 (m), 982 (m), 965 (m), 930 (w), 835 (s), 800 (m), 705 (w), 675 (w), 660 (w) cm$^{−1}$; $^1$H NMR (500 MHZ, CDCl$_3$) d 7.36 (d, J=8.7 Hz, 2 H), 6.86 (d, J=8.8 Hz, 2 H), 5.37 (s, 1 H), 5.01 (d, J=10.1 Hz, 1 H), 4.09 (dd, J=11.2, 4.7 Hz, 1 H), 3.79 (s, 3 H), 3.65 (dd, J=10.4, 4.7 Hz, 1 H), 3.63 (dd, J=7.0, 1.8 Hz, 1 H), 3.54–3.50 (m, 1 H), 3.51 (dd, J=10.0, 2.0 Hz, 1 H), 3.47 (apparent t, J=11.2 Hz, 1 H), 3.41 (dd, J=6.6, 4.0 Hz, 1 H), 2.59 (ddq, J=13.2, 6.7, 6.7 Hz, 1 H), 2.33 (apparent t, J=12.2 Hz, 1 H), 2.24 (apparent t, J=5.5 Hz, 1 H), 2.09–1.95 (m, 2 H), 1.89 (dqd, J=7.0, 7.0, 1.7 Hz, 1 H), 1.84–1.77 (m, 1 H), 1. 72 (br d J=11.0 Hz, 1 H), 1.58 (d, J=0.8 Hz, 3 H), 1.01 (d, J=7.1 Hz, 3 H), 0.98 (d, J=7.1 Hz, 3 H), 0.94 (d, J=6.7 Hz, 3 H), 0.910 (s, 9 H), 0.905 (s, 9 H), 0.75 (d, J=7.1 Hz, 3 H), 0.74 (d, J=7.1 Hz, 3 H), 0.09 (s, 3 H), 0.07 (s, 3 H), 0.05 (s, 3 H), 0.01 (s, 3 H); $^{13}$C NMR (125 MHZ, CDCl$_3$) d 159.8, 133.0, 131.5, 130.5, 127.3, 113.4, 101.0, 83.3, 81.6, 78.4, 73.3, 65.4, 55.3, 38.5, 38.2, 37.6, 37.0, 33.7, 30.8, 26.17, 26.16, 23.2, 18.4, 18.3, 17.4, 15.7, 12.6, 12.1, 10.9, −3.57, −3.61, −3.66, −3.9; high resolution mass spectrum (CI, NH$_3$) m/z 693.4918 [(M+H)$^+$; calcd for C$_{39}$H$_{73}$O$_6$Si$_2$: 693.4945].

Anal. Calcd for C$_{39}$H$_{72}$O$_6$Si$_2$: C, 67.58; H, 10.47. Found: C, 67.30; H, 10.54.

EXAMPLE 36

Phosphonium Salt (−)-49

A solution of alcohol (−)-40 (402.8 mg, 0.577 mmol) in PhH/Et$_2$O (1:2, 45 mL) was treated with PPh$_3$ (532 mg, 2.03 mmol) and imidazole (158 mg, 2.32 mmol). After the imidazole dissolved, I$_2$ (437 mg, 1.72 mmol) was added under vigorous stirring. The mixture was stirred 2 h and then treated with NEt$_3$ (2 mL). The resultant yellow suspension was diluted with CH$_2$Cl$_2$ (50 mL) and washed with saturated aqueous Na$_2$S$_2$O$_3$ (100 mL), saturated aqueous NaHCO$_3$ (100 mL), and brine (2×100 mL). The organic phase was dried over MgSO$_4$, filtered and concentrated. Filtration through a short silica column (NEt$_3$/ethyl acetate/hexane, 2:10:90) removed triphenylphosphine oxide, affording the impure iodide 42. Preparative TLC (500 mm silica gel plate, 4% acetone/hexane) furnished an analytical sample as an unstable white solid: $^1$H NMR (500 MHZ, CDCl$_3$) d 7.35 (d, J=8.8 Hz, 2 H), 6.85 (d, J=8.7 Hz, 2 H), 5.37 (s, 1 H), 5.02 (d, J=10.2 Hz, 1 H), 4.08 (dd, J=11.2, 4.7 Hz, 1 H), 3.78 (s, 3 H), 3.62 (dd, J=7.0, 1.8 Hz, 1 H), 3.51 (dd, J=9.9, 1.7 Hz, 1 H), 3.47 (apparent t, J=11.1 Hz, 1 H), 3.37 (dd, J=6.3, 4.3 Hz, 1 H), 3.32 (dd, J=9.6, 4.5 Hz, 1 H), 2.99 (dd, J=9.5, 8.8 Hz, 1 H), 2.50 (ddq, J=10.2, 6.5, 6.5 Hz, 1 H), 2.31 (apparent t, J=12.2 Hz, 1 H), 2.08–1.95 (m, 2 H), 1.88 (dqd, J=7.1, 7.1, 1.7 Hz, 1 H), 1.85–1.78 (m, 1 H), 1.74 (br d, J=11.7 Hz, 1 H), 1.57 (apparent s, 3 H), 1.01 (apparent d, J=7.0 Hz, 6 H), 0.91–0.89 (m, 3 H), 0.90 (s, 9 H), 0.89 (s, 9 H), 0.74 (d, J=6.8 Hz, 3 H), 0.73 (d, J=6.7 Hz, 3 H), 0.06 (s, 3 H), 0.05 (s, 3 H), 0.01 (s, 3 H), −0.02 (s, 3 H); $^{13}$C NMR (125 MHZ, CDCl$_3$/1% pyridine-d$_5$, 20 mg sample) d 159.8, 132.9, 131.5, 130.4, 127.3, 113.5, 101.1, 83.3, 79.6, 78.5, 73.3, 55.3, 41.4, 38.3, 37.6, 36.0, 33.7, 30.8, 26.20, 26.17, 23.2, 18.4, 17.7, 17.3, 13.5, 12.6, 12.2, 10.9, −3.5, −3.6, −4.0; high resolution mass spectrum (FAB, NBA) m/z 803.3935 [(M+H)+; calcd for C$_{39}$H$_{72}$O$_5$ISi$_2$: 803.3963].

The very sensitive impure iodide (obtained by filtration through silica) was quickly mixed with I-Pr$_2$NEt (300 µL, 1.72 mmol) and PPh$_3$ (2.47 g, 9.42 mmol). The mixture was heated at 80° C. for 24 h, then cooled to room temperature and extracted with hexane (2×30 mL). The residue was purified by flash chromatography (2% MeOH/CHCl$_3$) furnishing (−)-49 (224.9 mg, 37% yield from (−)-39) as a pale yellow foam. The hexane extract was concentrated and purified by flash chromatography (2% ethyl acetate/hexane) affording a mixture of cyclization products (200 mg). Further purification by normal phase HPLC (1.5% ethyl acetate/hexane) provided (−)-50 as the major cyclization product.

Wittig reagent (−)-49: $[\alpha]^{23}_D$ −25.30° © 1.48, CHCl$_3$); IR (CHCl$_3$) 2960 (s), 2930 (s), 2860 (m), 1615 (m), 1590 (w), 1515 (m), 1485 (w), 1460 (m), 1440 (m), 1385 (m), 1360 (m), 1300 (m), 1250 (s), 1215 (m, br), 1180 (m), 1110 (s), 1080 (m), 1025 (m), 1005 (m), 965 (m), 945 (w), 860 (m), 830 (s), 732 (m), 725 (m), 710 (m), 680 (m), 653 (m) cm$^{-1}$; $^1$H NMR (500 MHZ, CDCl$_3$; concentration dependent) d 7.82–7.76 (m, 15 H), 7.35 (d, J=8.8 Hz, 2 H), 6.84 (d, J=8.8 Hz, 2 H), 5.35 (s, 1 H), 5.30 (d, J=10.5 Hz, 1 H), 4.07 (dd, J=11.2, 4.7 Hz, 1 H), 3.77 (s, 3 H), 3.73–3.67 (m, 2 H), 3.56 (dd, J=7.0, 1.8 Hz, 1 H), 3.48 (dd, J=9.8, 1.7 Hz, 1 H), 3.46 (apparent t, J=11.1 Hz, 1 H), 3.31 (ddd, J=15.6, 11.2, 11.2 Hz, 1 H), 2.49 (ddq, J=10.5, 6.4, 6.4 Hz, 1 H), 2.25 (apparent t, J=12.1 Hz, 1 H), 2.10–1.92 (m, 3 H), 1.85 (dqd, J=7.1, 7.1, 1.8 Hz, 1 H), 1.57–1.52 (m, 1 H), 1.56 (s, 3 H), 0.98 (d, J=7.1 Hz, 3 H), 0.89 (d, J=6.6 Hz, 3 H), 0.852 (s, 9 H), 0.849 (s, 9 H), 0.72–0.71 (m, 3 H), 0.71 (d, J=6.6 Hz, 3 H), 0.69 (d, J=6.9 Hz, 3 H), 0.10 (s, 3 H), −0.02 (s, 3 H), −0.03 (s, 3 H), −0.07 (s, 3 H); $^{13}$C NMR (125 MHZ, CDCl$_3$) d 159.8, 135.2 (J$_{CP}$=2.6 Hz), 133.5 (J$_{CP}$=10.0 Hz), 132.9, 131.4, 130.6 (J$_{CP}$=12.6 Hz), 130.3, 127.3, 118.4 (J$_{CP}$=85.5 Hz), 113.4, 101.0, 83.2, 80.1 (J$_{CP}$=14.0 Hz), 78.3, 73.2, 55.3, 38.1, 37.4, 36.0, 33.7 (J$_{CP}$=4.4 Hz), 33.6, 30.7, 26.1, 25.5 (J$_{CP}$=49.7 Hz), 22.9, 18.33, 18.29, 17.2, 17.1, 12.5, 12.1, 10.9, −3.2, −3.6, −3.7, −4.0; high resolution mass spectrum (FAB, NBA) m/z 937.5708 [(M-I)+; calcd for C$_{57}$H$_{86}$O$_5$PSi$_2$: 937.5751].

Olefin (−)50: white solid; mp 80–82° C.; $[\alpha]^{23}_D$ −18° © 0.48, CHCl$_3$); IR (CHCl$_3$) 2955 (s), 2920 (s), 2880 (m), 2850 (s), 1640 (w), 1613 (m), 1588 (w), 1517 (m), 1460 (m), 1387 (m), 1360 (m),1300 (m), 1250 (s), 1178 (m), 1170 (m), 1160 (m), 1115 (m), 1080 (m), 1023 (s), 1000 (m), 980 (m), 960 (m), 930 (w), 887 (m), 855 (m), 830 (m), 715 (m) cm$^{-1}$; $^1$H NMR (500 MHZ, C$_6$D$_6$) d 7.62 (d, J=8.7 Hz, 2 H), 6.83 (d, J=8.7 Hz, 2 H), 5.46 (s, 1 H), 5.00 (s, 1 H), 4.95 (s, 1 H), 3.93 (dd, J=11.1, 4.7 Hz, 1 H), 3.89 (dd, J=7.2, 1.5 Hz, 1 H), 3.55 (dd, J=9.9, 1.9 Hz, 1 H), 3.51 (apparent t, J=5.9 Hz, 1 H), 3.27 (s, 3 H), 3.22 (apparent t, J=11.0 Hz, 1 H), 2.32 (dd, J=13.6, 3.5 Hz, 1 H), 2.27–2.20 (m, 1 H), 2.16 (dd, J=13.7, 9.5 Hz, 1 H), 2.07–1.92 (m, 4 H), 1.87–1.80 (m, 1 H), 1.50–1.42 (m, 1 H), 1.18 (d, J=7.1 Hz, 3 H), 1.10 (d, J=6.6 Hz, 3 H), 1.06 (d, J=6.6 Hz, 3 H), 1.04 (s, 9 H), 1.02 (d, J=7.0 Hz, 3 H), 1.00 (s, 9 H), 0.41 (d, J=6.7 Hz, 3 H), 0.13 (s, 3 H), 0.09 (s, 3 H), 0.08 (s, 3 H), 0.06 (s, 3 H); $^{13}$C NMR (125 MHZ, CDCl$_3$) d 159.8 (q), 150.7 (q), 131.5 (q), 127.3, 113.4, 108.3 (CH$_2$), 101.0, 83.2, 81.9, 78.1, 73.3 (CH$_2$), 55.2, 49.9, 44.9, 41.4 (CH$_2$), 39.0 (CH$_2$), 38.3, 36.6, 33.4, 30.8, 26.3, 25.9, 18.5 (q), 18.2 (q), 17.8, 15.5, 12.9, 12.1, 11.0, −3.4, −3.7, −4.6, −4.7; high resolution mass spectrum (FAB, NBA) m/z 697.4642 [(M+Na)+; calcd for C$_{39}$H$_{70}$O$_5$Si$_2$Na: 697.4659].

EXAMPLE 37

Model Olefin (+)-43

NaHMDS (0.6 M in PhMe, 9.46 mL, 5.68 mmol) was added over 10 min to a suspension of (CH$_3$)$_2$CHP$^+$Ph$_3$ I$^-$ (2.52 g, 5.83 mmol) in PhMe (20 mL) at room temperature. After 15 min, the mixture was cooled to −78° C., and aldehyde (+)-18 (1.46 g, 3.84 mmol) in PhMe (15 mL) was introduced via a cannula (15 mL rinse). After 20 min at −78° C. and 30 min at room temperature, the reaction was quenched with MeOH (1.0 mL). The solution was separated, and the oil residue was extracted with hexane (3×30 mL). The combined organic solutions were then concentrated and, and flash chromatography (2% ethyl acetate/hexane) provided (+)-43 (1.44 g, 92% yield) as a colorless oil: $[\alpha]^{23}_D$ +8.07° © 2.57, CHCl$_3$); IR (CHCl$_3$) 2960 (s), 2925 (s), 2880 (s), 2855 (s), 1610 (m), 1585 (m), 1510 (s), 1460 (s), 1375 (m), 1360 (m), 1300 (m), 1245 (m), 1172 (m), 1085 (s, br), 1035 (s), 1003 (m), 970 (m), 950 (m), 935 (m), 862 (s), 835 (s) cm$^{-1}$; $^1$H NMR (500 MHZ, CDCl$_3$) d 7.23 (d, J=9.0 Hz, 2 H), 6.85 (d, J=8.6 Hz, 2 H), 4.92 (d-quintet, J=9.7, 1.4 Hz, 1 H), 4.37 (apparent s, 2 H), 3.78 (s, 3 H), 3.49 (dd, J=9.2, 4.9 Hz, 1 H), 3.39 (dd, J=6.3, 4.5 Hz, 1 H), 3.19 (dd, J=9.0, 8.4 Hz, 1 H), 2.49 (ddq, J=9.6, 6.7, 6.7 Hz, 1 H), 2.00–1.92 (m, 1 H), 1.63 (d, J=1.2 Hz, 3 H), 1.55 (d, J=1.3 Hz, 3 H), 0.945 (d, J=7.0 Hz, 3 H), 0.874 (d, J=6.7 Hz, 3 H), 0.873 (s, 9 H), 0.01 (apparent s, 6 H); $^{13}$C NMR (125 MHZ, CDCl$_3$) 159.0, 131.1, 129.7, 129.4, 129.1, 113.7, 78.6, 72.6, 55.3, 38.5, 36.0, 26.2, 25.8, 18.4, 17.9, 17.0, 14.8, −3.88, −3.95; high resolution mass spectrum (CI, NH$_3$) m/z 407.2984 [(M+H)+; calcd for C$_{24}$H$_{43}$O$_3$Si: 407.2981].

EXAMPLE 38

Alcohol (+) -44

A mixture of olefin (+)-43 (387.6 mg, 0.954 mmol) in CH$_2$Cl$_2$ (10 mL) was treated with H$_2$O (500 µL) and DDQ (320 mg, 1.41 mmol). After 30 min at room temperature, the mixture was filtered through a short silica plug (50% ethyl acetate/hexane) and concentrated. Flash chromatography (3% ethyl acetate/hexane) provided (+)-43 (273.1 mg, 99% yield) as a colorless oil: $[\alpha]^{23}_D$ +17.5° © 2.80, CHCl$_3$); IR (CHCl$_3$) 3620 (w), 3500 (m, br), 2955 (s), 2925 (s), 2880 (s), 2860 (s), 1460 (s), 1405 (m), 1375 (m), 1360 (m), 1337 (m), 1252 (s), 1070 (s), 1050 (s), 1015 (s), 1002 (m), 978 (m), 933 (m), 832 (s) cm$^{-1}$; $^1$H NMR (500 MHZ, CDCl$_3$) d 4.92 (apparent d quintet, J=9.7, 1.4 Hz, 1 H), 3.66 (ddd, J=11.0, 4.4, 4.4 Hz, 1 H), 3.52 (ddd, J=11.0, 5.5, 5.5 Hz, 1 H), 3.42 (dd, J=6.8, 4.0 Hz, 1 H), 2.57 (ddq, J=9.6, 6.8, 6.8 Hz, 1 H), 2.45 (apparent t, J=5.2 Hz, 1 H), 1.85–1.78 (m, 1 H), 1.65 (d, J=1.3 Hz, 3 H), 1.59 (d, J=1.3 Hz, 3 H), 0.98 (d, J=7.1 Hz, 3 H), 0.92 (d, J=6.8 Hz, 3 H), 0.90 (s, 9 H), 0.08 (s, 3 H), 0.05 (s, 3 H); $^{13}$C NMR (125 MHZ, CDCl$_3$) d 130.7, 128.5, 81.7, 65.5, 38.1, 37.4, 26.2, 25.8, 18.3, 17.9, 17.4, 15.9, −3.7, −3.9; high resolution mass spectrum (CI, NH$_3$) m/z 287.2418 [(M+H)$^+$; calcd for C$_{16}$H$_{35}$O$_2$Si: 287.2406].

EXAMPLE 39

Wittig reagent (+)-46

Iodine (1.08 g, 4.24 mmol) was added to a solution of alcohol (+)-44 (810 mg, 2.83 mmol), PPh$_3$ (1.11 g, 4.24 mmol) and imidazole (289 mg, 4.24 mmol) in benzene/ether (1:2, 21 mL) under vigorous stirring at room temperature. After 40 min, the mixture was diluted with ether (100 mL), washed with saturated Na$_2$S$_2$O$_3$ (50 mL), brine (100 mL), dried over MgSO$_4$, filtered and concentrated. Flash chromatography (hexane) provided a mixture of 45/47/48 (1.06 g, 97% yield, 18:1:1) as a colorless oil; This material was then treated with I-Pr$_2$NEt (928 μL, 5.33 mmol) and PPh$_3$ (7.01 g, 26.7 mmol) then heated at 80° C. for 13 h. The mixture was extracted with hexane (3×100 mL). The residue was purified by flash chromatography (2% MeOH/CHCl$_3$) providing Wittig reagent (+)-48 (207.1 mg, 38% yield from (+)-46) as a pale yellow foam. The hexane extract was concentrated and purified by flash chromatography (hexane) affording a mixture of two cyclization products (380 mg) and further purification by preparative TLC (hexane) afforded (−)-49 and (−)-50.

Wittig reagent (+)-46:

$[\alpha]^{23}_D$ +4.8° © 1.23, CHCl$_3$); IR CHCl$_3$) 2940 (s), 2860 (m), 1588 (w), 1482 (w), 1468 (m), 1460 (m), 1440 (s), 1380 (m), 1360 (w), 1310 (w), 1253 (m), 1230 (m), 1210 (m), 1110 (s), 1080 (m), 1050 (m), 1018 (m), 1000 (m), 995 (m), 860 (m), 832 (s), 800 (m), 708 (m), 680 (m), 652 (m) cm$^{-1}$; $^1$H NMR (500 MHZ, CDCl$_3$; concentration dependent) d 7.81–7.67 (m, 15 H), 4.92 (d, J=9.7 Hz, 1 H), 3.50 (apparent t, J=5.3 Hz, 1 H), 3.38 (ddd, J=14.9, 14.9, 1.5 Hz, 1 H), 3.25 (ddd, J=15.6, 11.1, 11.1 Hz, 1 H), 2.42 (ddq, J=9.7, 6.6, 6.6 Hz, 1 H), 2.10–2.00 (m, 1 H), 1.53 (s, 3 H), 1.43 (s, 3 H), 0.83 (s, 9 H), 0.81 (d, J=6.7 Hz, 3 H), 0.75 (d, J=6.8 Hz, 3 H), 0.03 (s, 3 H), −0.02 (s, 3 H); $^{13}$C NMR (125 MHZ, CDCl$_3$) d, 135.3 (J$_{cp}$=2.8 Hz), 133.3 (J$_{cp}$=9.9 Hz), 131.0, 130.6 (J$_{cp}$=12.4 Hz), 128.0, 118.2 (J$_{cp}$=85.6 Hz), 80.4 (J$_{cP}$=13.3 Hz), 36.0, 33.0 (J$_{cp}$=4.0 Hz), 26.1, 25.6, 25.1 (J$_{cp}$=50.8 Hz), 18.3, 18.1, 17.9, 16.4, −3.3, −4.0; high resolution mass spectrum (FAB, NBA) m/z 531.3221 [(M-I)$^+$; calcd for C$_{34}$H$_{48}$OPSi: 531.3213].

Olefin (−)-47:

(Colorless oil; $[\alpha]^{23}_D$ −14° © 0.36, CHCl$_3$); IR (CHCl$_3$) 2960 (s), 2930 (s), 2860 (s), 1470 (m), 1460, 1370 (m), 1360 (m), 1250 (m), 1206 (w), 1165 (m), 1140 (m), 1070 (s), 1020 (s), 1000 (m), 932 (w), 908 (w), 897 (w), 853 (m), 830 (s) cm$^{-1}$; $^1$H NMR (500 MHZ, CDCl$_3$) d 3.63 (d, br, J=3.6 Hz, 1 H), 2.50 (apparent q, J=7.3 Hz, 1 H), 2.28 (ddd, J=15.5, 7.7, 0.8 Hz, 1 H), 2.13–2.03 (m, 1 H), 1.99–1.91 (m, 1 H), 1.60 (apparent br s, 3 H), 1.57 (apparent d, J=0.8 Hz, 1 H) 0.94 (d, J=6.7 Hz, 3 H), 0.91 (d, J=7.4 Hz, 3 H), 0.85 (s, 9 H), 0.01 (apparent s, 6 H); $^{13}$C NMR (125 MHZ, CDCl$_3$) d 138.9 (q), 122.0 (q), 82.9, 46.1, 36.4, 35.8 (CH$_2$), 25.9, 21.2, 20.4, 18.3 (q), 18.0, 14.3, −4.6, −4.8; high resolution mass spectrum (CI, NH$_3$) m/z 269.2310 [(M+H)$^+$; calcd for C$_{16}$H$_{33}$OSi: 269.2300].

Olefin (−)-48:

Colorless oil; $[\alpha]^{23}_D$ −3.8° © 0.24, CHCl$_3$); IR (CHCl$_3$) 2953 (s), 2925 (s), 2880 (m), 2855 (m), 1638 (w), 1470 (m), 1460 (m), 1385 (w), 1373 (m), 1360 (w), 1250 (m), 1135 (m), 1117 (m), 1100 (m), 1075 (m), 1028 (m), 1000 (m), 932 (w), 865 (m), 830 (s) cm$^{-1}$; $^1$H NMR (500 MHZ, C$_6$D$_6$) d 4.84–4.83 (m, 1 H), 4.79–4.77 (m, 1 H), 3.46 (apparent t, J=5.3 Hz, 1 H), 1.94–1.88 (m, 1 H), 1.87–1.78 (m, 2 H), 1.73 (ddd, J=12.4, 7.3, 7.3 Hz, 1 H), 1.66 (apparent dd, J=1.3, 0.8 Hz, 3 H), 1.45 (ddd, J=12.2, 10.3, 8.7 Hz, 1 H), 1.00 (d, J=6.9 Hz, 3 H), 0.99 (s, 9 H), 0.96 (d, J=6.7 Hz, 3 H), 0.06 (s, 3 H), 0.05 (s, 3 H); $^{13}$C NMR (125 MHZ, C$_6$D$_6$) d 147.4 (q), 110.3 (CH$_2$), 82.3, 53.1, 45.4, 37.5 (CH$_2$), 37.3, 26.1, 19.3, 18.4 (q), 18.0, 15.6, −4.4, −4.5; high resolution mass spectrum (CI, NH$_3$) m/z 269.2315 [(M+H)$^+$; calcd for C$_{16}$H$_{33}$OSi: 269.2300].

EXAMPLE 40

Alcohol (+)-51

A solution of olefin (+)-44 (70.9 mg, 0.28 mmol) in EtOH/EtOAc (1:8, 4.5 mL) was treated with Pd/C (10% wet, E101 NE/W, 15.2 mg) under H$_2$ atmosphere for 18 h. The mixture was then filtered through a short silica pipet and concentrated. Flash chromatography (5% ethyl acetate/hexane) provided (+)-51 (70.8 mg, 100% yield) as a colorless oil. $[\alpha]^{23}_D$ +28° © 0.15, CHCl$_3$); IR (CHCl$_3$) 3680 (w), 3620 (w), 3500 (w, br), 3010 (m), 2960 (s), 2935 (s), 2900 (m), 2885 (m), 2860 (m), 1522 (w), 1510 (w), 1470 (m), 1426 (m), 1420 (m), 1412 (m), 1387 (m), 1370 (m), 1255 (m), 1205 (m), 1070 (m), 1030 (m), 1013 (m), 1002 (m), 980 (m), 925 (m), 833 (s), 720 (m), 665 (m), 658 (m) cm$^{-1}$; $^1$H NMR (500 MHZ, CDCl$_3$) d 3.60–3.56 (m, 2 H), 3.46 (dd, J=5.5, 3.8 Hz, 1 H), 2.46 (br s, 1 H), 1.89–1.81 (m, 1 H), 1.74–1.66 (m, 1 H), 1.64–1.56 (m, 1 H), 1.21 (ddd, J=13.3, 8.9, 4.6 Hz, 1 H), 1.09 (ddd, J=13.7, 9.6, 5.3 Hz, 1 H), 0.94 (d, J=7.0 Hz, 3 H), 0.90 (s, 9 H), 0.88 (d, J=6.6 Hz, 3 H), 0.86 (d, J=6.9 Hz, 3 H), 0.83 (d, J=6.6 Hz, 3 H), 0.095 (s, 3 H), 0.07 (s, 3 H); $^{13}$C NMR (125 MHZ, CDCl$_3$) d 81.3, 66.3, 42.5, 37.8, 35.7, 26.1, 25.4, 23.8, 21.8, 16.4, 15.1, −3.9, −4.1; high resolution mass spectrum (CI, NH$_3$) m/z 289.2565 [(M+H)$^+$; calcd for C$_{16}$H$_{37}$O$_2$Si: 289.2562].

EXAMPLE 41

Iodide (+)-52

A solution of alcohol (+)-51 (150 mg, 0.520 mmol), PPh$_3$ (205 mg, 0.780 mmol) and imidazole (53 mg, 0.780 mmol) in benzene/ether (1:2; 6.0 mL) was treated with iodine (198 mg, 0.780 mmol) under vigorous stirring at room temperature. After 40 min, the mixture was diluted with ether (100 mL), washed with saturated Na$_2$S$_2$O$_3$ (50 mL), brine (100 mL), dried over MgSO$_4$, filtered and concentrated. Flash chromatography (hexane) provided (+)-51 (195 mg, 94% yield) as a colorless oil: $[\alpha]^{23}_D$ +24.2° © 2.21, CHCl$_3$); IR (CHCl$_3$) 2960 (s), 2935 (s), 2900 (m), 2860 (s), 1470 (m), 1463 (m), 1425 (w), 1405 (w), 1382 (m), 1368 (m), 1360 (m), 1290 (w), 1255 (s), 1190 (m), 1170 (m), 1082 (s), 1065 (m), 1028 (m), 1003 (m), 970 (w), 932 (w), 832 (s) cm$^{-1}$; $^1$H NMR (500 MHZ, CDCl$_3$) d 3.41 (dd, J=9.6, 3.7 Hz, 1 H), 3.38 (dd, J=6.3, 2.6 Hz, 1 H), 3.10 (dd, J=9.6, 7.5 Hz, 1 H), 1.72–1.56 (m, 3 H), 1.17 (ddd, J=13.4, 8.3, 5.4 Hz, 1 H), 1.09 (ddd, J=13.3, 5.9, 2.1 Hz, 1 H), 0.99 (d, J=6.8 Hz, 3 H), 0.89 (s, 9 H), 0.88 (d, J=6.6 Hz, 3 H), 0.84 (d, J=6.6 Hz, 3 H), 0.81 (d, J=6.8 Hz, 3 H), 0.09 (s, 3 H), 0.06 (s, 3 H); $^{13}$C NMR (125 MHZ, CDCl$_3$) d 79.1, 43.7, 39.8, 33.8, 26.2, 25.3, 23.5, 22.0, 18.7, 18.5, 15.9, 14.4, −3.65, −3.71; high resolution mass spectrum (CI, NH$_3$) m/z 399.1572 [(M+H)$^+$; calcd for C$_{16}$H$_{36}$OISi: 399.1580].

EXAMPLE 42

Wittig Reagent (+)-53

A mixture of Iodide (+)-52 (195 mg, 0.489 mmol) and benzene (100 mL) was treated with I-Pr$_2$NEt (85 μL, 0.488 mmol) and PPh$_3$ (1.28 g, 4.88 mmol), then heated at 70° C. for 24 h. The mixture was extracted with hexane (3×20 mL). The residue was purified by flash chromatography (3% MeOH/CHCl$_3$) furnishing (+)-53 (303 mg, 94% yield) as a white foam; [α]$^{23}_D$ +3.3° © 2.14, CHCl$_3$); IR (CHCl$_3$) 2950 (s), 2930 (s), 2855 (m), 1588 (w), 1482 (w), 1463 (m), 1438 (s), 1385 (m), 1365 (w), 1253 (m), 1225 (m), 1207 (m), 1110 (s), 1080 (m), 1032 (m), 1000 (m), 832 (s), 804 (m), 708 (m), 680 (m), 653 (m) cm$^{-1}$; $^1$H NMR (500 MHZ, CDCl$_3$) d 7.83–7.67 (m, 15 H), 3.70 (ddd, J=15.6, 11.0, 11.0 Hz, 1 H), 3.52 (dd, J=7.6, 1.7 Hz, 1 H), 3.45 (apparent t, J=15.4 Hz, 1 H), 2.08–1.97 (m, 1 H), 1.70–1.62 (m, 1 H), 1.51 (9 lines, J=6.5 Hz, 1 H), 1.09–0.97 (m, 2 H), 0.850 (s, 9 H), 0.79 (d, J=6.7 Hz, 3 H), 0.77 (d, J=7.9 Hz, 3 H), 0.74 (d, J=6.5 Hz, 3 H), 0.68 (d, J=6.8 Hz, 3 H), 0.12 (s, 3 H), 0.11 (s, 3 H); $^{13}$C NMR (125 MHZ, CDCl$_3$) d 135.2 (J$_{cp}$=2.7 Hz), 133.6 (J$_{cp}$=9.9 Hz), 130.6 (J$_{cp}$=12.4 Hz), 118.5 (J$_{cp}$=85.5 Hz), 80.1 (J$_{cp}$=12.9 Hz), 43.5, 33.6, 32.6 (J$_{cp}$=3.7 Hz), 26.2, 25.3 (J$_{cp}$=51.1 Hz), 25.0, 23.4, 21.7, 18.6, 18.5, 13.7, –2.7, –3.8; high resolution mass spectrum (FAB,NBA) m/z 533.3369 [(M-I)$^+$; calcd for C$_{34}$H$_{50}$OPSi: 533.3357].

EXAMPLE 43

Olefin (–)-54

Phosphonium salt (–)-49 was dried azeotropically with anhydrous benzene and heated at 50° C. under vacuum for 3 h before use. A solution of (–)-49 (97.7 mg, 0.0917 mmol) in THF (700 μL) was cooled to –78° C. and treated with NaHMDS (1.0 M in THF, 85.5 μL, 0.0855 mmol). The mixture was stirred for 20 min at 0° C., recooled to –78° C. and aldehyde C (28.0 mg, 0.0570 mmol) in THF (300 μL) was added. After 10 min at –78° C. and 2 h at room temperature, the mixture was quenched with saturated aqueous NH$_4$Cl (1.0 mL) and extracted with ether (30 mL). The ether solution was washed with water, brine (30 mL each), dried over MgSO$_4$, filtered and concentrated. Flash chromatography (2% ethyl acetate/hexane) provided (–)-56 (50.0 mg, 76% yield) as a colorless oil: [α]$^{23}_D$ –44.9° © 2.09, CHCl$_3$); IR (CHCl$_3$) 2960 (s), 2930 (s), 2855 (s), 1615 (t), 1587 (w), 1517 (m), 1463 (s), 1380 (m), 1360 (m), 1320 (m), 1300 (m), 1250 (s), 1170 (m), 1160 (m), 1120–1000 (s, br), 990 (m), 965 (m), 935 (m), 900 (m), 835 (s), 807 (m), 670 (m) cm$^-$; $^1$H NMR (500 MHZ, CDCl$_3$) d 7.35 (d, J=8.7 Hz, 2 H), 6.85 (d, J=8.8 Hz, 2 H), 5.37 (s, 1 H), 5.27 (dd, J=11.2, 7.8 Hz, 1 H), 5.19 (apparent t, J=10.9 Hz, 1 H), 5.08 (d, J=10.1 Hz, 1 H), 5.06 (d, J=2.2 Hz, 1 H), 4.68 (apparent t, J=9.1 Hz, 1 H), 4.08 (dd, J=11.2, 4.7 Hz, 1 H), 3.78 (s, 3 H), 3.68 (apparent t, J=10.1 Hz, 1 H), 3.61 (dd, J=7.1, 1.7 Hz, 1 H), 3.53 (apparent t, J=2.6 Hz, 1 H), 3.50 (dd, J=9.9, 1.6 Hz, 1 H), 3.46 (apparent t, J=11.1 Hz, 1 H), 3.25 (apparent t, J=5.3 Hz, 1 H), 2.71–2.58 (m, 1 H), 2.68 (dq, J=12.8, 7.4 Hz, 1 H), 2.62 (dq, J=12.8, 7.4 Hz, 1 H), 2.50 (m, 1 H), 2.30 (apparent t, J=12.2 Hz, 1 H), 2.08–2.01 (m, 1 H), 1.98–1.90 (m, 1 H), 1.88 (dqd, J=7.1, 7.1, 1.7 Hz, 1 H), 1.82 (apparent qt, J=7.1, 2.6 Hz, 1 H), 1.65 (br d, J=12.4 Hz, 1 H), 1.62–1.57 (m, 2 H), 1.56 (d, J=0.4 Hz, 3 H), 1.38 (ddd, J=13.6, 10.7, 1.5 Hz, 1 H), 1.29–1.22 (apparent t, J=7.4 Hz, 3 H), 1.00 (d, J=7.1 Hz, 3 H), 0.94 (d, J=7.3 Hz, 3 H), 0.930 (d, J=6.9 Hz, 3 H), 0.925 (d, J=7.1 Hz, 3 H), 0.90 (s, 18 H), 0.89 (s, 9 H), 0.86 (s, 9 H), 0.74 (apparent d, J=6.6 Hz, 6 H), 0.73 (d, J=6.1 Hz, 3 H), 0.05 (s, 3 H), 0.04 (s, 3 H), 0.03 (s, 3 H), 0.019 (s, 3 H), 0.017 (s, 3 H), 0.013 (s, 3 H), 0.009 (s, 3 H), 0.00 (s, 3 H); $^{13}$C NMR (125 MHZ, CDCl$_3$) d 159.8, 134.4, 131.9, 131.8, 131.5, 131.4, 127.3, 113.4, 101.0, 83.4, 80.9, 80.4, 78.5, 76.7, 76.5, 74.2, 73.3, 65.5, 55.2, 42.5, 41.9, 38.2, 37.5, 37.1, 35.4, 34.4, 33.8, 26.3, 26.2, 26.0, 25.9, 25.1, 23.2, 18.5, 18.4, 18.12, 18.08, 17.0, 16.6, 15.6, 14.4, 12.7, 12.1, 11.6, 10.9, –2.7, –3.5, –3.66, –3.69, –4.2, –4.5, –4.9, –5.0; high resolution mass spectrum (FAB, NBA) m/z 1171.7799 [(M+Na)$^+$; calcd for C$_{63}$H$_{120}$O$_8$SSi$_4$Na: 1171.7781].

EXAMPLE 44

Hydroxy Diene (–)-55

A solution of the olefin (–)-54 (49.8 mg, 0.0434 mmol) in CH$_2$Cl$_2$ (4.4 mL) was cooled to –78° C. and DIBAL (1.0 M in toluene, 430 μL, 0.430 mmol) was added over 5 min. After 10 min at –78° C. and 30 min at 0° C., the reaction was quenched with saturated aqueous Rochelle's salt (500 μL). The mixture was diluted with ether (60 mL), washed with saturated aqueous Rochelle salt, brine (30 mL each), dried over MgSO$_4$, filtered and concentrated. Flash chromatography (5% ethyl acetate/hexane) furnished (–)-57 (38.0 mg, 88% yield) as a colorless oil: [α]$^{23}_D$ –32° © 1.90, CHCl$_3$); IR (CHCl$_3$) 3500 (w, br), 2960 (s), 2935 (s), 2900 (m), 2885 (m), 2860 (s), 1610 (m), 1585 (w), 1510 (m), 1470 (m), 1460 (m), 1400 (m), 1375 (m), 1360 (m), 1300 (m), 1250 (s), 1170 (m), 1095 (m), 1080 (m), 1047 (s), 1000 (m), 960 (m), 950 (m), 933 (m), 835 (s), 805 (m), 665 (m) cm$^{-1}$; $^1$H NMR (500 MHZ, CDCl$_3$) d 7.24 (d, J=8.6 Hz, 2 H), 6.85 (d, J=8.6 Hz, 2 H), 5.27 (dd, J=11.4, 7.8 Hz, 1 H), 5.20 (apparent t, J=10.3 Hz, 1 H), 5.10 (d, J=10.0 Hz, 1 H), 5.05 (d, J=2.2 Hz, 1 H), 4.68 (apparent t, J=9.2 Hz, 1 H), 4.49 (ABq, J$_{AB}$=10.4 Hz, Δδ$_{AB}$=23.4 Hz, 2 H), 3.78 (s, 3 H), 3.73 (ddd, J=10.7, 4.0, 4.0 Hz, 1 H), 3.68 (apparent t, J=10.4 Hz, 1 H), 3.57 (ddd, J=10.6, 5.1, 5.1 Hz, 1 H), 3.53 (dd, J=5.4, 3.4 Hz, 1 H), 3.50 (apparent t, J=5.2 Hz, 1 H), 3.35 (apparent t, J=5.5 Hz, 1 H), 3.26 (apparent t, J=5.2 Hz, 1 H), 2.68 (dq, J=12.8, 7.4 Hz, 1 H), 2.61 (dq, J=12.8, 7.5 Hz, 1 H), 2.71–2.58 (m, 2 H), 2.51–2.44 (m, 1 H), 2.22 (apparent t, J=12.4 Hz, 1 H), 1.99–1.86 (m, 3 H), 1.81 (apparent qt, J=7.1, 2.6 Hz, 1 H), 1.72 (br d, J=12.7 Hz, 1 H), 1.62–1.57 (m, 1 H), 1.61 (s, 3 H), 1.56–1.48 (m, 1 H), 1.38 (ddd, J=13.5, 12.3, 1.4 Hz, 1 H), 1.27 (apparent t, J=7.4 Hz, 3 H), 1.03 (d, J=6.9 Hz, 3 H), 1.02 (d, J=6.8 Hz, 3 H), 0.95–0.92 (m, 9 H), 0.93 (s, 9 H), 0.90 (s, 9 H), 0.89 (s, 9 H), 0.86 (s, 9 H), 0.74 (d, J=8.0 Hz, 3 H), 0.73 (d, J=7.0 Hz, 3 H), 0.08 (s, 6 H), 0.05 (s, 3 H), 0.024 (s, 3 H), 0.020 (s, 3 H), 0.012 (s, 3 H), 0.009 (s, 3 H), 0.006 (s, 3 H); $^{13}$C NMR (125 MHZ, CDCl$_3$) d 159.4, 134.4, 132.3, 131.7, 130.9, 130.4, 129.3, 114.0, 86.3, 80.9, 80.4, 77.6, 76.5, 75.3, 74.2, 65.6, 65.5, 55.3, 42.6, 41.9, 40.0, 37.6, 37.0, 36.8, 35.9, 35.2, 34.5, 26.30, 26.27, 25.9, 25.8, 25.1, 23.2, 18.53, 18.47, 18.13, 18.07, 17.1, 16.6, 15.7, 15.6, 14.4, 13.6, 11.6, 11.4, –2.8, –3.2, –3.4, –3.6, –4.2, –4.5, –4.9; high resolution mass spectrum (FAB, NBA) m/z 1173.7859 [(M+Na)$^+$; calcd for C$_{63}$H$_{122}$O$_8$SSi$_4$Na: 1173.7835].

EXAMPLE 45

Aldehyde (–)-56

A solution of alcohol (–)-55 (13.8 mg, 0.0120 mmol) and Et$_3$N (42 μL, 0.30 mmol) in CH$_2$Cl$_2$ (200 μL) was cooled to 0° C. and treated with SO$_3$.pyridine (40 mg, 0.251 mmol) in DMSO (600 μL). After 45 min at 0° C., the mixture was diluted with ethyl acetate (30 mL), washed with aqueous NaHSO$_4$ (1.0 M, 30 mL), brine (2×30 mL), dried over MgSO$_4$, filtered and concentrated. Pipette flash chromatography (3% ethyl acetate/hexane) afforded (–)-56 (13.2 mg, 96% yield) as a colorless oil: [α]$^{23}_D$ –32.1° © 1.40, CHCl$_3$); IR (CHCl$_3$) 2960 (s), 2935 (s), 2880 (m), 1720 (m), 1610 (m), 1512 (m), 1470 (m), 1460 (m), 1387 (m), 1380 (m), 1360 (m), 1340 (m), 1320 (m), 1300 (m), 1250 (s), 1110 (s), 1098 (s), 1080 (s), 1048 (s), 1002 (m), 988 (m), 965 (m), 950 (m), 935 (m), 835 (s) cm$^{-1}$; $^1$H NMR (500 MHZ, CDCl$_3$) d 9.78 (d, J=2.5 Hz, 1 H), 7.20 (d, J=8.6 Hz, 2 H), 6.85 (d, J=8.7 Hz, 2 H), 5.27 (dd, J=11.1, 7.8 Hz, 1 H), 5.19 (apparent t, J=10.4 Hz, 1 H), 5.10 (d, J=10.0 Hz, 1 H), 5.05 (d, J=2.1 Hz, 1 H), 4.67 (apparent t, J=8.9 Hz, 1 H), 4.45 (apparent s, 2 H), 3.78 (s, 3 H), 3.68 (apparent t, J=10.2 Hz, 1 H), 3.58–3.56 (m, 2 H), 3.51 (apparent t, J=2.6 Hz, 1 H), 3.25 (apparent t, J=5.2 Hz, 1 H), 2.73 (dqd, J=7.1, 6.0, 2.6 Hz, 1 H), 2.70–2.57 (m, 3 H), 2.51–2.44 (m, 1 H), 2.23 (apparent t, J=12.4 Hz, 1 H), 1.98–1.85 (m, 2 H), 1.81 (apparent qt, J=7.1, 2.6 Hz, 1 H), 1.67 (br d, J=13.0 Hz, 1 H), 1.60 (s, 3 H), 1.62–1.50 (m, 2H), 1.37 (ddd, J=13.8, 10.4, 1.5 Hz, 1 H), 1.26 (apparent t, J=7.4 Hz, 3 H), 1.10 (d, J=7.0 Hz, 3 H), 1.02 (d, J=7.0 Hz, 3 H), 0.938 (d, J=7.1 Hz, 3 H), 0.932 (d, J=7.8 Hz, 3 H), 0.919 (s, 9 H), 0.918 (d, J=6.6 Hz, 3 H), 0.90 (s, 9 H), 0.88 (s, 9 H), 0.86 (s, 9 H), 0.732 (d, J=6.7 Hz, 3 H), 0.726 (d, J=6.8 Hz, 3 H), 0.07 (s, 3 H), 0.053 (s, 3 H), 0.047 (s, 3 H), 0.02 (s, 6 H), 0.009 (s, 3 H), 0.005 (s, 6 H); $^{13}$C NMR (125 MHZ, CDCl$_3$) d 204.6, 159.3, 134.4, 132.3, 131.8, 130.8, 130.3, 129.1, 128.3, 113.8, 82.6, 80.9, 80.4, 76.5, 74.5, 74.2, 65.5, 55.3, 49.5, 42.5, 41.9, 40.3, 37.1, 36.8, 35.4, 34.9, 34.4, 26.3, 26.2, 25.9, 25.8, 25.1, 23.2, 18.49, 18.45, 18.12, 18.07, 17.0, 16.6, 15.6, 14.4, 13.3, 12.1, 11.6, 11.4, −2.8, −3.3, −3.4, −3.7, −4.2, −4.5, −4.9, −5.0; high resolution mass spectrum (FAB, NBA) m/z 1171.7670 [(M+Na)$^+$; calcd for C$_{63}$H$_{120}$O$_8$SSiNa: 1171.7676].

EXAMPLE 46

Tetraene (−) -57

A solution of Ph$_2$PCH$_2$CH=CH$_2$ (40 μL, 0.19 mmol) in THF (1.0 mL) was cooled to −78° C. and t-BuLi (1.7 M in pentane, 72.0 μL, 0.122 mmol) was added. The mixture was stirred at 0° C. for 30 min, recooled to −78° C. and treated with Ti(OiPr)$_4$ (45 μL, 0.15 mmol). After 30 min, a cold (−78° C.) solution of the aldehyde (−)-56 (30.2 mg, 0.0262 mmol) in THF (1.0 mL) was introduced via cannula, and the resultant mixture was stirred for 10 min at −78° C. and 1 h at 0° C. MeI (20 μL, 0.32 mmol) was then added, and the reaction was maintained at 0° C. for 30 min, warmed to room temperature, protected from light with aluminum foil, and stirred overnight. The reaction mixture was diluted with ether (30 mL), washed with aqueous NaHSO$_4$ (1.0 M), brine (30 mL each), dried over MgSO$_4$, filtered and concentrated. Flash chromatography (2% ethyl acetate/hexane) gave a 16:1 mixture of Z/E isomers (20.0 mg, 70% yield) as an oil. Pipette flash chromatography (20% benzene/hexane) furnished the Z-olefin (−)-57 as a colorless oil: [α]$^{23}_D$ −57.2° © 2.56, CHCl$_3$); IR (CHCl$_3$) 3015 (m), 2960 (s), 2940 (s), 2900 (m), 2885 (m), 2860 (s), 1613 (w), 1515 (m), 1475 (m), 1465 (m), 1390 (w), 1380 (w), 1360 (w), 1250 (s), 1110 (m), 1100 (m), 1080 (m), 1050 (s), 1003 (m), 963 (w), 950 (w), 835 (s), 800 (m), 790 (m), 770 (m), 700 (w), 690 (w), 670 (w), 655 (w) cm$^{-1}$; $^1$H NMR (500 MHZ, CDCl$_3$) d 7.25 (d, J=8.2 Hz, 2 H), 6.84 (d, J=8.7 Hz, 2 H), 6.57 (dddd, J=16.8, 11.0, 11.0, 0.7 Hz, 1 H), 6.00 (apparent t, J=11.1 Hz, 1 H), 5.55 (apparent t, J=10.5 Hz, 1 H), 5.26 (dd, J=11.2, 7.8 Hz, 1 H), 5.20–5.16 (m, 2 H), 5.09 (d, J=10.1 Hz, 1 H), 5.05 (d, J=2.2 Hz, 1 H), 5.03 (d, J=10.0 Hz, 1 H), 4.67 (apparent t, J=9.1 Hz, 1 H), 4.49 (ABq, J$_{AB}$=10.6 Hz, Δδ$_{AB}$=41.3 Hz, 2 H), 3.78 (s, 3 H), 3.68 (apparent t, J=10.2 Hz, 1 H), 3.52 (apparent t, J=2.6 Hz, 1 H), 3.43 (dd, J=4.8, 3.9 Hz, 1 H), 3.24–3.21 (m, 2 H), 3.01–2.94 (m, 1 H), 2.67 (dq, J=12.8, 7.4 Hz, 1 H), 2.61 (dq, J=12.8, 7.5 Hz, 1 H), 2.71–2.57 (m, 1 H), 2.46–2.39 (m, 1 H), 2.00 (apparent t, J=12.4 Hz, 1 H), 1.83–1.73 (m, 3 H), 1.64 (br d, J=14.0 Hz, 1 H), 1.62–1.52 (m, 2 H), 1.55 (d, J=0.5 Hz, 3 H), 1.36 (ddd, J=13.7, 10.8, 1.5 Hz, 1 H), 1.26 (d, J=7.4 Hz, 3 H), 1.25 (d, J=7.4 Hz, 3 H), 1.08 (d, J=6.8 Hz, 3 H), 0.98 (d, J=6.8 Hz, 3 H), 0.94 (d, J=7.1 Hz, 3 H), 0.93 (s, 9 H), 0.90 (s, 9 H), 0.89 (s, 9 H), 0.89–0.86 (m, 3 H), 0.86 (S, 9 H), 0.73 (d, J=6.8 Hz, 3 H), 0.70 (d, J=6.7 Hz, 3 H), 0.08 (s, 6 H), 0.05 (s, 3 H), 0.02 (s, 3 H), 0.013 (s, 3 H), 0.010 (s, 6 H), −0.02 (s, 3 H); $^{13}$C NMR (125 MHZ, CDCl$_3$) d 159.1, 134.5, 134.3, 132.2, 131.9, 131.8, 131.2, 129.13, 129.07, 117.6, 113.7, 84.6, 80.9, 80.5, 76.5, 75.0, 74.2, 65.5, 55.3, 42.5, 41.9, 40.2, 37.2, 36.1, 35.4, 35.3, 34.5, 29.7, 26.3, 26.0, 25.9, 25.1, 23.1, 18.7, 18.6, 18.5, 18.14, 18.09, 17.0, 16.8, 15.6, 14.8, 14.4, 11.6, 10.6, −2.8, −3.2, −3.3, −3.6, −4.2, −4.5, −4.90, −4.93; high resolution mass spectrum (FAB, NBA) m/z 1195.8001 [(M+Na)$^+$; calcd for C$_{66}$H$_{124}$O$_7$SSi$_4$Na: 1195.8042].

EXAMPLE 47

Lactone (−)-58

A solution of diene (−)-57 (7.0 mg, 0.00597 mmol) in THF/CH$_3$CN (2:1, 1.50 mL) was treated with pH 7.0 phosphate buffer (500 μL) and HgCl$_2$ (215 mg). The suspension was stirred at room temperature for 40 min, diluted with ether (30 mL), washed with brine (2×30 mL), dried over MgSO$_4$, filtered and concentrated. Pipette flash chromatography (5% ethyl acetate/hexane) provided a mixture of lactols as a colorless oil which was further treated with DMSO (1.0 mL) and Ac$_2$O (200 mL) at room temperature for 2 days. The mixture was diluted with ether (30 mL), washed with saturated NaHCO$_3$ (30 mL), brine (30 mL), dried over MgSO$_4$, filtered and concentrated. Pipette flash chromatography (2% ethyl acetate/hexane) provided (−)-58 (5.5 mg, 82% yield from (−)-57) as a colorless oil: [α]$^{23}_D$ −31.6 © 0.23, CHCl$_3$); IR (CHCl$_3$) 3015 (m), 2960 (s), 2930 (s), 2880 (m), 2855 (m), 1725 (m), 1610 (w), 1510 (w), 1460 (m),1385 (m), 1373 (m), 1360 (m), 1300 (w), 1250 (s), 1230 (m), 1200 (m), 1170 (m), 1120 (m), 1097 (m), 1060 (m), 1045 (s), 1020 (m), 1003 (m), 980 (w), 955 (w), 930 (w), 905 (w), 867 (m), 835 (s), 800 (m), 695 (m), 670 (m), 660 (m) cm$^{-1}$; $^1$H NMR (500 MHZ, CDCl$_3$) d 7.25 (d, J=9.0 Hz, 2 H), 6.84 (d, J=8.7 Hz, 2 H), 6.57 (ddd, J=16.7, 10.6, 10.6 Hz, 1 H), 6.00 (apparent t, J=11.0 Hz, 1 H), 5.55 (apparent t, J=10.5 Hz, 1 H), 5.26 (dd, J=11.1, 7.9 Hz, 1 H), 5.19 (dd, J 15.4, 1.4 Hz, 1 H), 5.18 (apparent t J=10.1 Hz, 1 H), 5.10 (d, J=10.2 Hz, 1 H), 5.01 (d, J=10.0 Hz, 1 H), 4.75 (apparent t, J=9.2 Hz, 1 H), 4.50 (ddd, J=10.5, 1.3, 1.3 Hz, 1 H), 4.50 (ABq, J$_{AB}$=10.6 Hz, Δδ$_{AB}$=42.6 Hz, 2 H), 3.78 (s, 3 H), 3.60 (apparent t, J=2.4 Hz, 1 H), 3.42 (dd, J=5.1, 3.7 Hz, 1 H), 3.23 (dd, J=7.5, 3.7 Hz, 1 H), 3.20 (apparent t, J=5.4 Hz, 1 H), 3.01–2.94 (m, 1 H), 2.60 (qd, J=7.7, 2.6 Hz, 1 H), 2.62–2.55 (m, 1 H), 2.45–2.38 (m, 1 H), 1.98 (apparent t, J=12.3 Hz, 1 H), 1.84–1.67 (m, 3 H), 1.63 (br d, J 13.2 Hz, 1H), 1.52 (s, 3 H), 1.55–1.48 (m, 1 H), 1.20 (d, J=7.6 Hz, 3 H), 1.09 (d, J=6.8 Hz, 3 H), 0.98 (d, J=6.8 Hz, 3 H), 0.93 (apparent d, J=6.7 Hz, 6 H), 0.93 (s, 9 H), 0.89 (s, 9 H), 0.86 (s, 9 H), 0.85 (s, 9 H), 0.84 (d, J=6.8 Hz, 3 H), 0.69 (d, J=6.7 Hz, 3 H), 0.085 (s, 3 H), 0.079 (s, 3 H), 0.051 (s, 3 H), 0.046 (s, 3 H), 0.042 (s, 3 H), 0.029 (s, 3 H), 0.028 (s, 3 H), −0.02 (s, 3 H); $^{13}$C NMR (125 MHZ, CDCl$_3$) d 173.2, 159.1, 134.4, 133.4, 132.4, 132.2, 131.9., 131.3, 131.2, 129.11, 129.09, 117.6, 113.7, 84.6, 80.5, 76.9, 75.0, 74.9, 64.6, 55.3, 44.1, 42.7, 40.1, 37.5, 36.0, 35.44, 35.37, 35.2, 34.2, 26.31, 26.28, 25.9, 25.7, 23.0, 18.7, 18.6, 18.4, 18.1, 18.0, 17.1, 16.5, 16.4, 14.9, 14.1, 10.5, −3.0, −3.2, −3.3, −4.3, −4.4, −4.5, −4.8, −4.9; high resolution mass spectrum (FAB, NBA) m/z 1149.7836 [(M+Na)$^+$; Calcd for C$_{64}$H$_{118}$O$_8$Si$_4$Na: 1149.7802].

EXAMPLE 48

Alcohol (−) -59

A solution of (−)-58 (4.0 mg, 0.00355 mmol) in $CH_2Cl_2$ (500 μL) was treated with $H_2O$ (50 μL) and DDQ (3.0 mg, 0.0132 mmol) at 0° C. After 1 h, the mixture was diluted with ethyl acetate (30 mL), washed with brine (3×30 mL), dried over $MgSO_4$, filtered and concentrated. Pipette flash chromatography (2% ethyl acetate/hexane) provided (−)-59 (3.4 mg, 95% yield) as a colorless oil: $[α]^{23}_D$ −20° © 0.34, $CHCl_3$); IR (film, $CHCl_3$ on NaCl plate) 3500 (w, br), 2960 (s), 2930 (s), 2890 (s), 2855 (s), 1740 (m), 1460 (m), 1405 (m), 1380 (m), 1360 (s), 1253 (m), 1220 (m), 1120 (s), 1093 (s), 1075 (s), 1045 (s), 1022 (s), 1002 (m), 980 (m), 933 (m), 902 (m), 833 (s), 808 (m), 770 (s), 663 (m) cm$^{-1}$; $^1$H NMR (500 MHZ, $CDCl_3$) d 6.61 (ddd, J=16.8, 10.9, 10.9 Hz, 1 H), 6.13 (apparent t, J=11.0 Hz, 1 H), 5.32 (apparent t, J=10.5 Hz, 1 H), 5.28 (dd, J=11.1, 7.9 Hz, 1 H), 5.24–5.21 (m, 1 H), 5.19 (apparent t, J=10.3 Hz, 1 H), 5.14 (d, J=10.2 Hz, 1 H), 5.06 (d, J=10.0 Hz, 1 H), 4.76 (apparent t, J=9.3 Hz, 1 H), 4.50 (apparent t, J=9.9 Hz, 1 H), 3.62 (apparent t, J=2.4 Hz, 1 H), 3.60 (dd, J=5.5, 3.4 Hz, 1 H), 3.32 (br d, J=5.3 Hz, 1 H), 3.24 (apparent t, J=5.1 Hz, 1 H), 2.79 (ddq, J=9.9, 6.7, 6.7 Hz, 1 H), 2.60 (qd, J=7.6, 2.7 Hz, 1 H), 2.63–2.57 (m, 1 H), 2.50–2.45 (m, 1 H), 2.16 (apparent t, J=12.3 Hz, 1 H), 1.90–1.77 (m, 3 H), 1.75–1.69 (m, 2 H), 1.57 (s, 3 H), 1.60–1.50 (m, 1 H), 1.20 (d, J=7.6 Hz, 3 H), 0.96 (d, J=6.8 Hz, 3 H), 0.95 (d, J=6.6 Hz, 3 H), 0.95–0.93 (m, 6 H), 0.91 (s, 9 H), 0.89 (s, 9 H), 0.89–0.84 (m, 3 H), 0.87 (s, 9 H), 0.85 (s, 9 H), 0.73 (d, J=6.8 Hz, 3 H), 0.07 (apparent s, 6 H), 0.052 (s, 3 H), 0.051 (s, 3 H), 0.04 (apparent s, 6 H), 0.03 (s, 3 H), −0.01 (s, 3 H); $^{13}$C NMR (125 MHZ, $CDCl_3$) d 173.3, 134.7, 133.5, 132.5, 132.1, 132.0, 131.5, 131.0, 118.4, 80.5, 78.8, 76.4, 74.9, 64.7, 44.1, 42.7, 38.0, 37.4, 36.3, 36.1, 35.2, 35.1, 34.2, 26.3, 26.2, 25.9, 25.7, 23.2, 18.5, 18.1, 18.0, 17.3, 17.2, 16.4, 16.1, 14.1, 13.7, 9.4, −3.0, −3.3, −3.6, −4.34, −4.36, −4.5, −4.8; high resolution mass spectrum (FAB, NBA) m/z 1029.7273 [(M+Na)$^+$; calcd for $C_{56}H_{110}O_7Si_4Na$: 1029.7226].

EXAMPLE 49

Carbamate (−)-60

A solution of alcohol (−)-59 (2.2 mg, 0.00219 mmol) in $CH_2Cl_2$ (500 μL) was treated with $Cl_3CON=C=O$ (20 μL, 0.168 mmol) at room temperature. After 30 min, the mixture was diluted with regular $CH_2Cl_2$ (2.0 mL) and treated with neutral $Al_2O_3$ (500 mg). The mixture was stirred at room temperature for 2 h, filtered through a short silica plug, and concentrated. Pipette flash chromatography (10% ethyl acetate/hexane) provided (−)-60 (1.9 mg, 83% yield) as a colorless oil: $[α]^{23}_D$ −37° © 0.19, $CHCl_3$); IR (film, $CHCl_3$ on NaCl plate) 3510 (m), 3360 (m, br), 3180 (m), 2960 (s), 2930 (s), 2880 (s), 2855 (s), 1730 (s, br), 1596 (m), 1460 (s), 1385 (s), 1362 (s), 1325 (m), 1255 (m), 1220 (m), 1100 (s), 1043 (s), 983 (m), 937 (m), 904 (m), 832 (s), 770 (s), 663 (m) cm$^{-1}$; $^1$H NMR (500 MHZ, $CDCl_3$) d 6.58 (dddd, J=16.8, 10.6, 10.6, 0.7 Hz, 1 H), 6.01 (apparent t, J=11.0 Hz, 1 H), 5.36 (apparent t, J=10.4 Hz, 1 H), 5.27 (dd, J=11.1, 7.9 Hz, 1 H), 5.22–5.16 (m, 2 H), 5.12 (d, J=10.1 Hz, 1 H), 5.03 (d, J=10.0 Hz, 1 H), 4.76 (apparent t, J=9.2 Hz, 1 H), 4.71 (apparent t, J=6.1 Hz, 1 H), 4.50 (ddd, J=10.5, 10.5, 1.3 Hz, 1 H), 4.44 (br s, 2 H), 3.62 (apparent t, J=2.4 Hz, 1 H), 3.42 (apparent t, J=4.5 Hz, 1 H), 3.22 (apparent t, J=5.3 Hz, 1 H), 2.98 (ddq, J=10.1, 6.6, 6.6 Hz, 1 H), 2.60 (qd, J=7.6, 2.7 Hz, 1 H), 2.63–2.55 (m, 1 H), 2.48–2.41 (m, 1 H), 2.09 (apparent t, J=12.4 Hz, 1 H), 1.93–1.88 (m, 1 H), 1.87–1.77 (m, 2 H), 1.71 (ddd, J=14.1, 10.8, 1.6 Hz, 1 H), 1.67 (br d, J=13.7 Hz, 1 H), 1.56 (apparent s, 3 H), 1.55–1.50 (m, 1 H), 1.21 (d, J=7.6 Hz, 3 H), 0.98 (d, J=6.8 Hz, 3 H), 0.95 (d, J=7.0 Hz, 3 H), 0.94 (d, J=7.5 Hz, 3 H), 0.918 (d, J=6.8 Hz, 3 H), 0.915 (s, 9 H), 0.89 (s, 9 H), 0.86 (s, 9 H), 0.853 (d, J=6.4 Hz, 3 H), 0.847 (s, 9 H), 0.70 (d, J=6.8 Hz, 3 H), 0.09 (s, 3 H), 0.07 (s, 3 H), 0.053 (s, 3 H), 0.051 (s, 3 H), 0.040 (s, 3 H), 0.037 (s, 3 H), 0.03 (s, 3 H), −0.02 (s, 3 H); $^{13}$C NMR (125 MHZ, $CDCl_3$) d 173.3, 156.9, 133.6, 133.5, 132.4, 132.1, 131.9, 131.4, 129.8, 118.0, 80.5, 78.9, 74.9, 64.6, 44.2, 42.7, 37.8, 37.4, 36.0, 35.3, 35.2, 34.5, 34.2, 26.3, 26.2, 25.9, 25.7, 23.0, 18.5, 18.4, 18.1, 18.0, 17.5, 17.1, 16.44, 16.38, 14.1, 13.7, 10.1, −3.0, −3.4, −3.6, −4.4, −4.5, −4.8; high resolution mass spectrum (FAB, NBA) m/z 1072.7264 [(M+Na)$^+$; calcd for $C_{57}H_{111}NO_8Si_4Na$: 1072.7283].

EXAMPLE 50

Discodermolide [(−)-1]

A solution of olefin (−)-60 (5.8 mg, 5.5 mmol) in 48% HF—$CH_3CN$ (1:9, 1.0 mL) was stirred at room temperature for 12 h, then quenched with saturated aqueous $NaHCO_3$ (5.0 mL). The mixture was extracted with ethyl acetate (3×10 mL). The combined organic extracts were washed with brine (5.0 mL), dried over $MgSO_4$, filtered and concentrated. Pipette flash chromatography (gradient elution, 1:30 to 1:6 MeOH/$CHCl_3$) provided (−)-1 (2.0 mg, 60% yield) as a white amorphous solid: $[α]^{23}_D$ −16° © 0.03, MeOH); IR ($CHCl_3$) 3690 (w), 3620 (w), 3540 (w), 3430 (w), 3020 (s), 2975 (m), 2935 (m), 1740 (m), 1590 (w), 1540 (w), 1520 (w), 1467 (w), 1430 (w), 1385 (m), 1330 (w), 1233 (s), 1210 (s), 1100 (w), 1045 (m), 1033 (m), 975 (w), 930 (m), 910 (w), 793 (m), 777 (m), 765 (m), 750 (m), 705 (m), 687 (m), 670 (m), 660 (m), 625 (w) cm$^{-1}$; $^1$H NMR (500 MHZ, $CDCl_3$) d 6.60 (dddd, J=16.8, 8.4, 8.4, 0.8 Hz, 1 H), 6.02 (apparent t, J=11.1 Hz, 1 H), 5.51 (dd, J=11.2, 7.9 Hz, 1 H), 5.42 (ddd, J=10.6, 10.6, 0.6 Hz, 1 H), 5.34 (apparent t, J=10.4 Hz, 1 H), 5.20 (dd, J=16.9, 1.9 Hz, 1 H), 5.16 (d, J=10.0 Hz, 1 H), 5.11 (d, J=10.1 Hz, 1 H), 4.77–4.69 (m, 1 H), 4.70 (dd, J=7.3, 4.2 Hz, 1 H), 4.60 (ddd, J=10.0, 10.0, 2.4 Hz, 1 H), 4.56 (br s, 2 H), 3.73 (m, 1 H), 3.28 (m, 1 H), 3.18 (dd, J=6.8, 4.8 Hz, 1 H), 2.98 (ddq, J=10.1, 6.9, 6.9 Hz, 1 H), 2.78 (ddq, J=9.8, 6.8, 6.8 Hz, 1 H), 2.66 (qd, J=7.3, 4.6 Hz, 1 H), 2.60–2.55 (m, 1 H), 2.10–1.80 (m, 10 H), 1.69 (ddd, J=14.4, 10.3, 3.1 Hz, 1 H), 1.64 (d, J=1.3 Hz, 3 H), 1.30 (d, J=7.4 Hz, 3 H), 1.06 (d, J=6.9 Hz, 3 H), 1.00 (d, J=6.8 Hz, 3 H), 0.99 (d, J=6.7 Hz, 3 H), 0.97 (d, J=6.8 Hz, 3 H), 0.94 (d, J=6.8 Hz, 3 H), 0.82 (d, J=6.3 Hz, 3 H); $^{13}$C NMR (125 MHZ, $CDCl_3$) d 173.6, 157.0, 134.4, 133.7, 133.4, 132.9, 132.2, 129.9, 129.8, 117.9, 79.1, 78.9, 77.9, 75.7, 73.2, 64.4, 43.1, 41.0, 37.4, 36.1, 36.0, 35.8, 35.3, 34.8, 33.1, 23.3, 18.4, 17.4, 15.6, 15.5, 13.7, 12.5, 9.0; high resolution mass spectrum (FAB, NBA) m/z 616.3840 [(M+Na)$^+$; calcd for $C_{33}H_{55}NO_8Na$: 616.3826].

EXAMPLE 51

Figure 16:
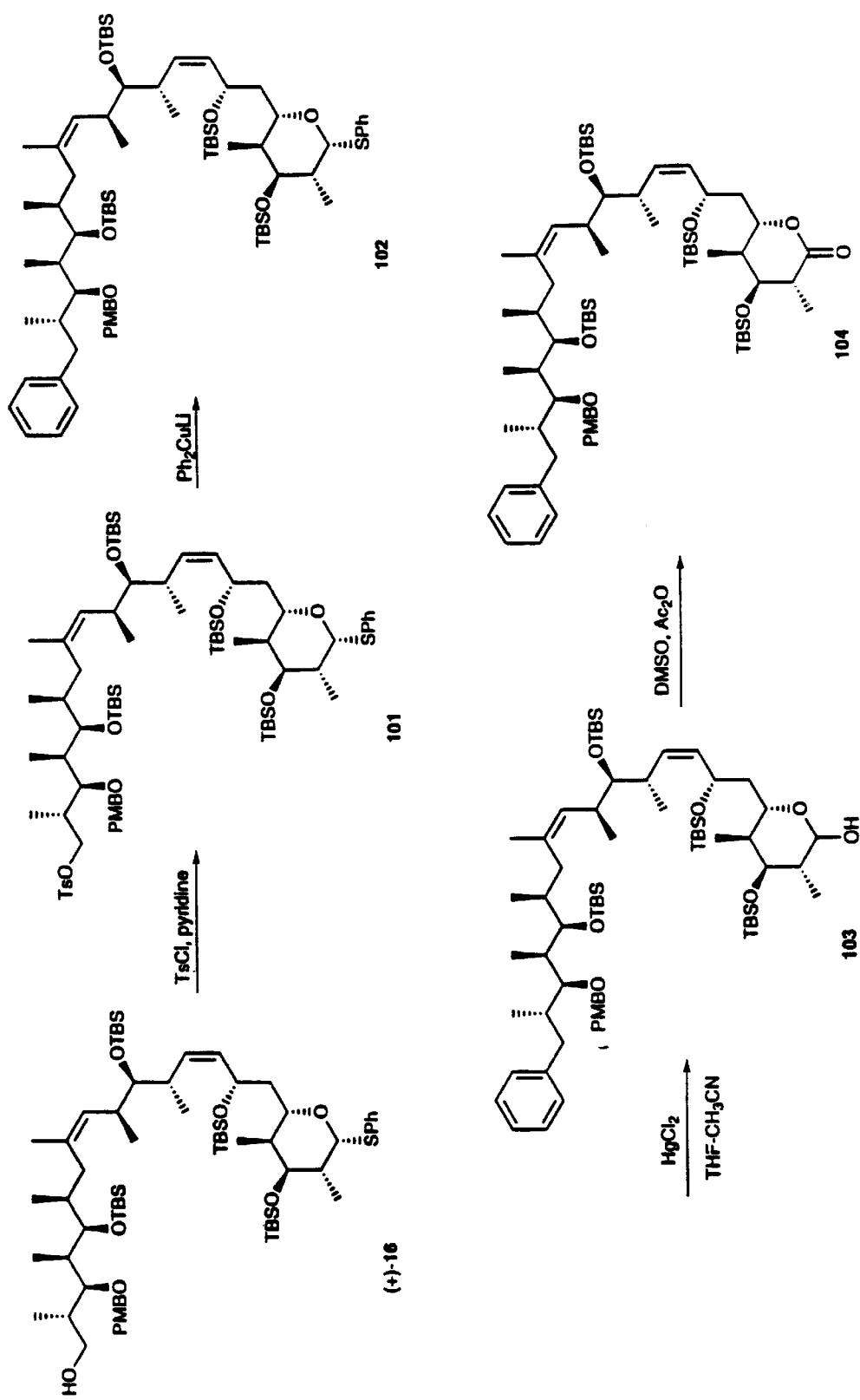
FIG. 16 shows a synthetic scheme for compound 104.
Figure 17:
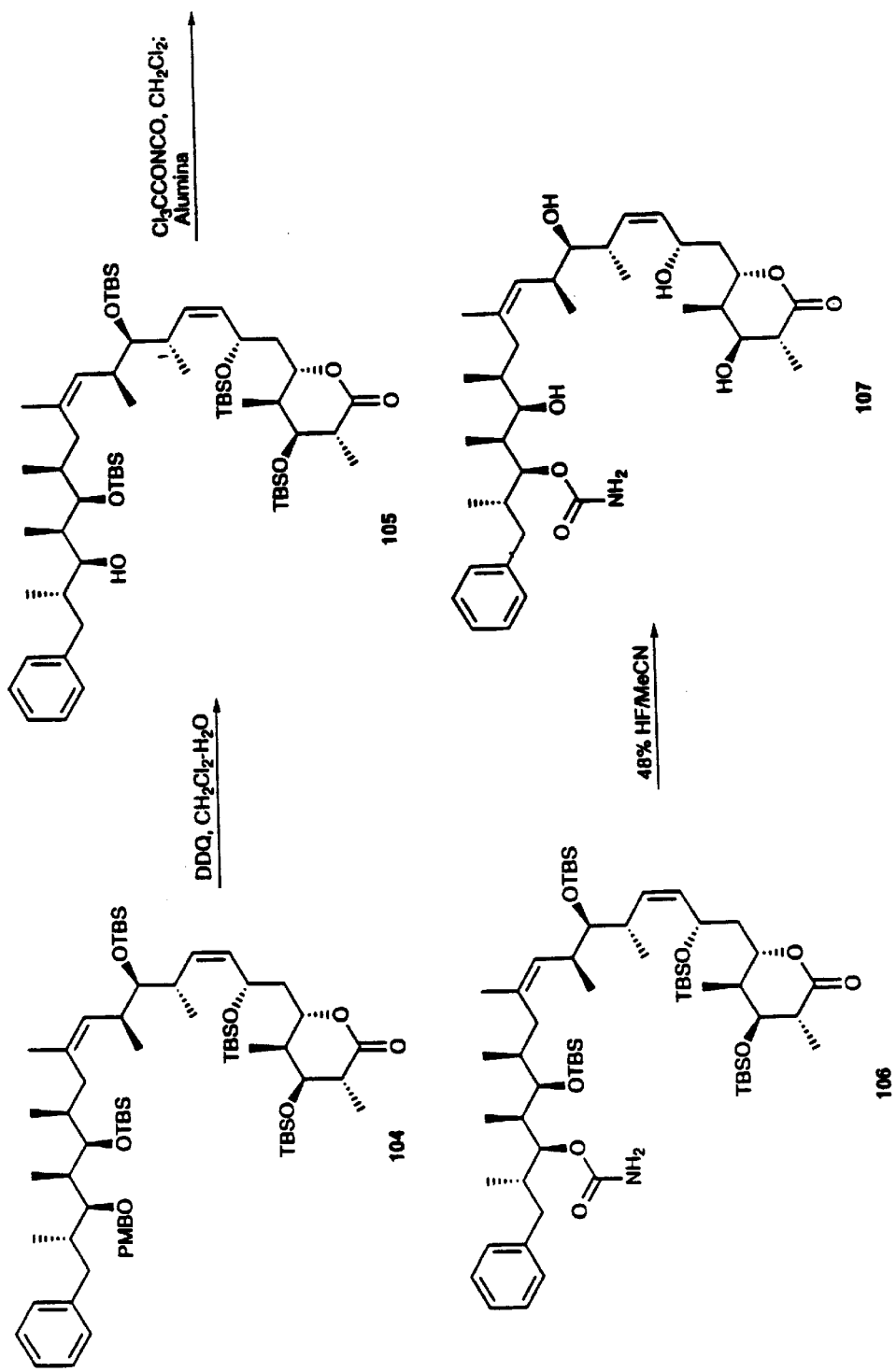
FIG. 17 shows a synthetic scheme for compound 107.
Figure 18:
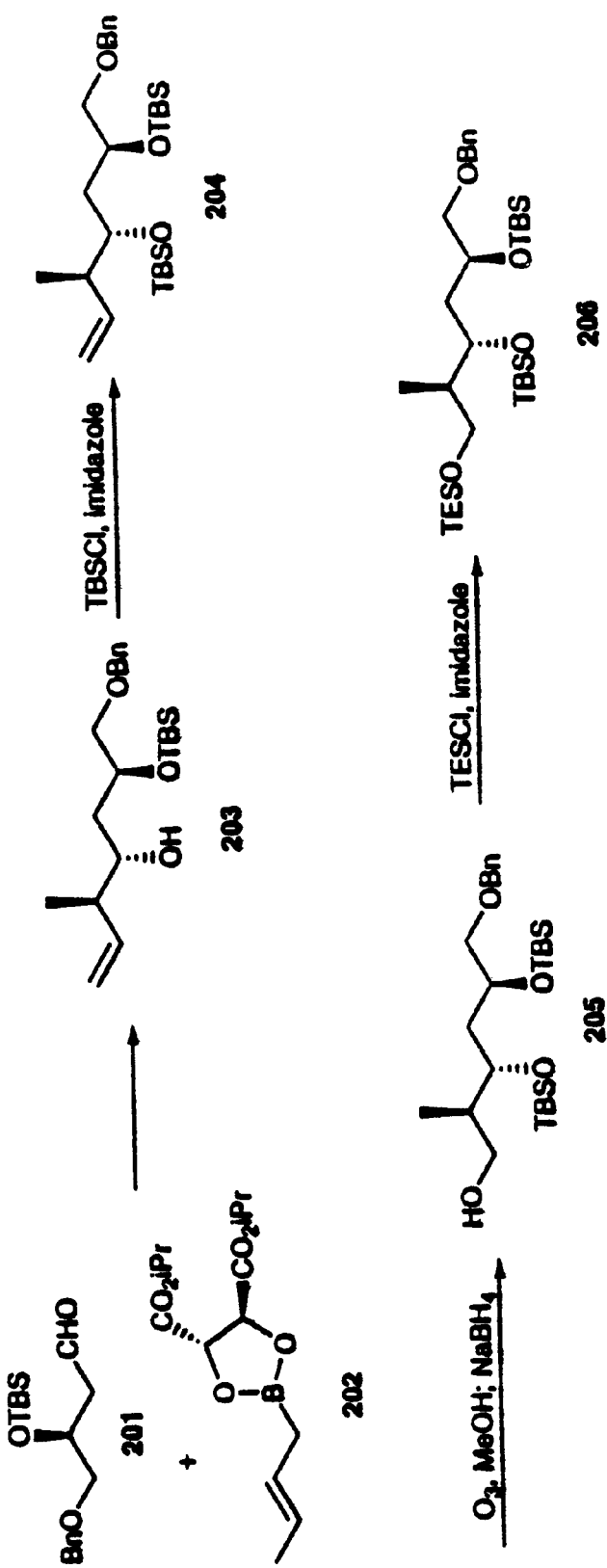
FIG. 18 shows a synthetic scheme for compound 206.
Figure 19:
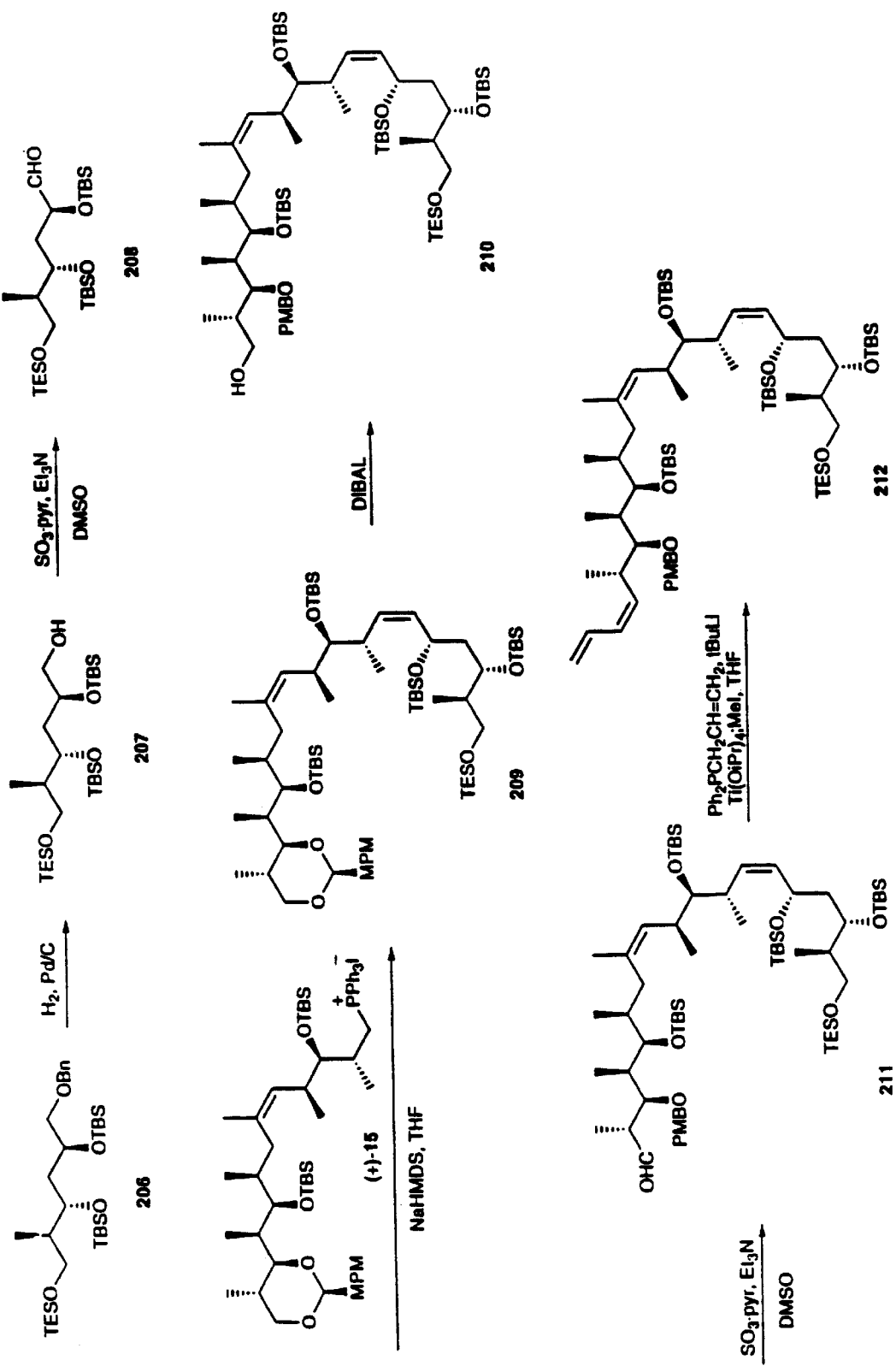
FIG. 19 shows a synthetic scheme for compound 212.
Figure 20:
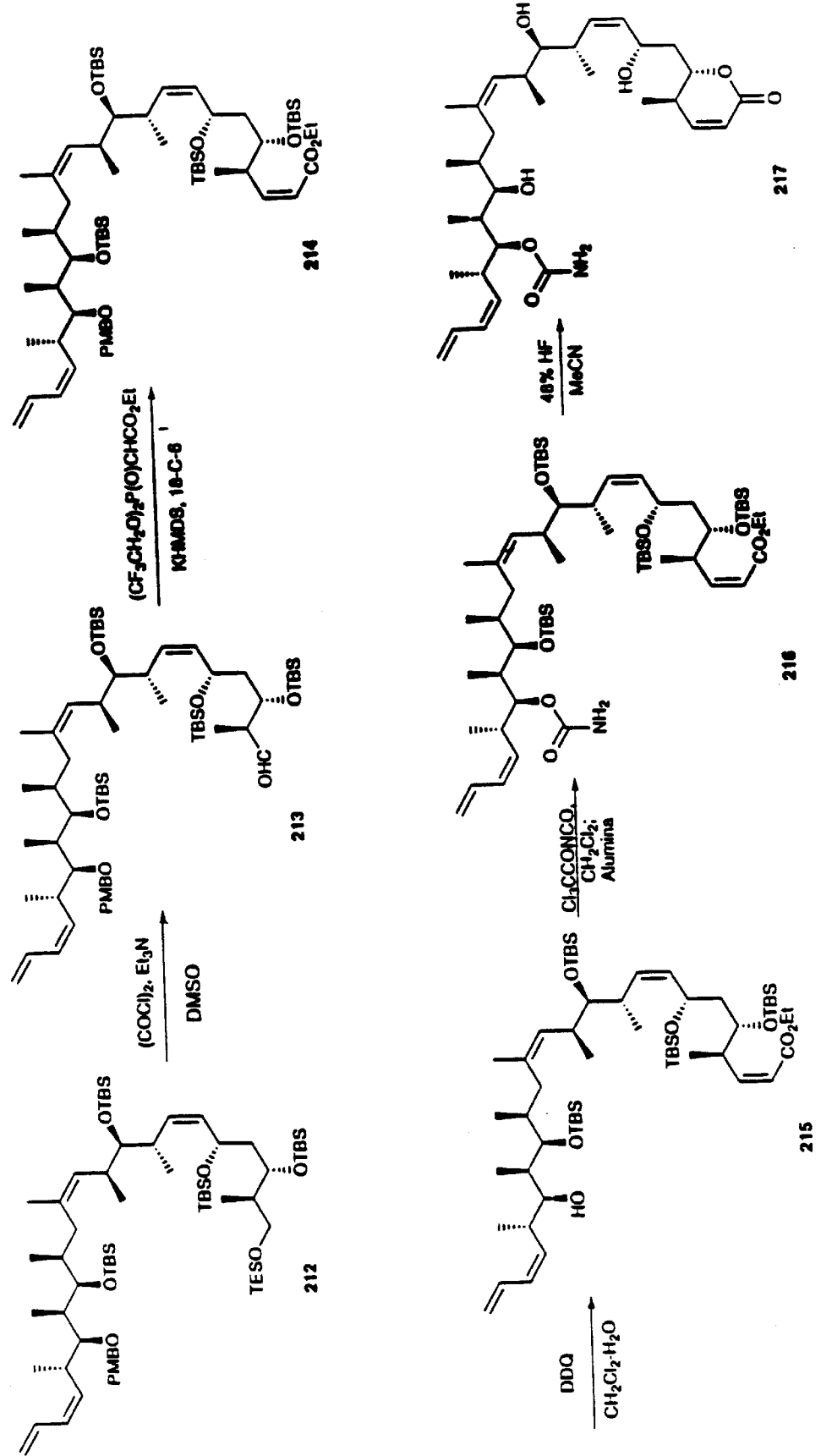
FIG. 20 shows a synthetic scheme for compound 217.

FIGS. 16 and 17

A. Tosylate 101

A solution of diene 16 (see, Smith, et al., *J. Am. Chem. Soc.* 1995, 117, 12011) (1.15 g, 1.0 mmol) in anhydrous pyridine (10 mL) at 0° C. is treated with p-toluenesulfonyl chloride (286 mg, 1.5 mmol). The mixture is allowed to warm to room temperature for 4–6 h. The pyridine is removed in vacuo and the residue is purified by flash chromatography to afford tosylate 101.

B. Arene 102

Phenyllithium (2.7 mL, 1.8 M in cyclohexane-ether (70:30)) is added dropwise to a solution of copper (I) iodide (460 mg, 2.4 mmol) in anhydrous diethyl ether (5 mL) at 0° C. To the resultant mixture is added a solution of tosylate 101 (780 mg, 0.6 mmol) in ether (5 mL) and the resultant mixture is warmed to room temperature with stirring. After 4 h, saturated aqueous ammonium chloride (20 mL) is added. The layers are separated and the aqueous layer is extracted with ethyl acetate. The combined organics are dried over magnesium sulfate and concentrated in vacuo. The residue is purified by flash chromatography to afford 102.

C. Lactol 103.

To a solution of 102 (120 mg, 0.1 mmol) in tetrahydrofuran-acetonitrile (15 mL, 2:1) is added phosphate buffer (pH 7, 5 mL) and mercury (II) chloride (272 mg, 1.0 mmol). The resultant mixture is stirred 1 h at room temperature. The reaction mixture is diluted with ether (100 mL) and washed with saturated aqueous brine (2×50 mL), dried over magnesium sulfate and concentrated in vacuo. The residue is purified by flash chromatography to afford 103 as a mixture of α and β anomers.

D. Lactone 104.

To a solution of 103 (84 mg, 0.070 mmol) in dimethyl sulfoxide (10 mL) is added acetic anhydride (2 mL). After 2 days at room temperature, the mixture is diluted with ether (100 mL) and washed with saturated aqueous sodium bicarbonate (50 mL), saturated aqueous brine (50 mL), dried over magnesium sulfate and concentrated in vacuo. The residue is purified by flash chromatography to afford 104.

E. Alcohol 105.

To a solution of 104 (56 mg, 0.050 mmol) in dichloromethane (3 mL) at 0° C. is added water (50 mL) and 2,3-dichloro-5,6-dicyano-1,4-benzoquinone (52 mg, 0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 105.

F. Carbamate 106.

To a solution of 105 (10 mg, 0.010 mmol) in dichloromethane (2 mL) is added trichloroacetyl isocyanate (0.12 mL, 1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 106.

G. Tetrol 107.

A solution of 106 (10 mg, 0.0096 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 107.

EXAMPLE 52

FIGS. 18–20

A. Alcohol 203.

To a slurry of powdered 4-Å molecular sieves (2.0 g) in 100 mL of anhydrous toluene is added boronate 202 (see, Roush, et al., *J. Am. Chem. Soc.* 1990, 112, 6348) (170 mL, 1.0 M in toluene). The resultant solution is stirred 10 min at room temperature and then cooled to −78° C. A solution of aldehyde 201 (see, Solladie, et al., *Tetrahedron Lett.* 1987, 28, 797) (113 mmol) in toluene (100 mL) is added over a 2 h period, after which the reaction is maintained at −78° C. for 10 h. Excess ethanolic sodium borohydride (ca. 0.75 g/10 mL) is added and the reaction mixture is warmed to 0° C. Aqueous 1 N sodium hydroxide (300 mL) is added and the mixture is stirred vigorously for 2 h. The layers are separated and the aqueous layer is extracted with ether (5×300 mL). The combined organics are dried over potassium carbonate and concentrated in vacuo. The residue is purified by flash chromatography to afford 203.

B. Bis-silyl ether 204

A solution of 203 (75 mmol) in dimethylformamide (150 mL) is cooled to 0° C. and treated with imidazole (150 mmol) and tert-butyldimethylsilyl chloride (100 mmol). The resultant solution is warmed to room temperature. After 12 h, the reaction mixture is poured into 1500 mL of water and extracted with ether (3×200 mL). The ethereal extracts are washed with water (2×50 mL) and saturated aqueous brine (50 mL), dried over magnesium sulfate and concentrated in vacuo. The residue is purified by flash chromatography to afford 204.

C. Alcohol 205.

A solution of 204 (20 mmol) in 500 mL of methanol is cooled to −78° C. and treated with a stream of ozone and oxygen until the colorless solution is converted into a steel blue one. The crude reaction mixture is cautiously quenched with sodium borohydride (100 mmol) and the resultant solution is warmed to room temperature. After 3 h, the excess sodium borohydride is destroyed by the cautious addition of water. The methanol is removed in vacuo and the residue is partitioned between saturated aqueous ammonium chloride (200 mL) and ethyl acetate (200 mL). The layers are separated and the aqueous layer is further extracted with ethyl acetate (2×100 mL). The combined organics are dried over anhydrous magnesium sulfate and concentrated in vacuo. The residue is purified by flash chromatography to afford 205.

D. Triethylsilyl ether 206.

A solution of 205 (15 mmol) in dimethylformamide (30 mL) is cooled to 0° C. and treated with imidazole (30 mmol) and triethylsilyl chloride (20 mmol). The resultant solution is warmed to room temperature. After 12 h, the reaction mixture is poured into 300 mL of water and extracted with ether (3×40 mL). The ethereal extracts are washed with water (2×25 mL) and saturated aqueous brine (25 mL), dried over magnesium sulfate and concentrated in vacuo. The residue is purified by flash chromatography to afford 206.

E. Alcohol 207.

To a solution of 206 (6 mmol) in ethyl acetate-ethanol (8:1, 90 mL) is added palladium on carbon (10% wet, 500 mg). The mixture is stirred under hydrogen atmosphere for 3–6 h, then filtered and concentrated in vacuo. The residue is purified by flash chromatography to afford 207.

F. Aldehyde 208.

To a −10° C. solution of 207 (13 mmol) and triethylamine (50 mmol) in dichloromethane (26 mL) is added a solution of sulfur trioxide-pyridine (39 mmol) in dimethyl sulfoxide (50 mL). The mixture is stirred 1 h at room temperature and diluted with ether (150 mL). The organic phase is washed with aqueous sodium bisulfate (1 M, 100 mL), saturated aqueous brine (4×100 mL), dried over magnesium sulfate, and concentrated in vacuo. The residue is purified by flash chromatography to afford 208.

G. Wittig product 209.

Phosphonium salt 15 (see, Smith, et al., *J. Am. Chem. Soc.* 1995, 117, 12011) (0.2 mmol) is dissolved in anhydrous tetrahydrofuran (2 mL) and chilled to 0° C. A solution of sodium bis(trimethylsilyl)amide (0.2 mmol, 1.0 M in tetrahydrofuran) is added and the reaction mixture is stirred 30 min at 0° C. After cooling to −78° C., a solution of aldehyde 208 (0.1 mmol) in tetrahydrofuran (2 mL) is added and the mixture is stirred 10 min at −78° C. and 2 h at room temperature. Saturated aqueous ammonium chloride (2 mL) is added and the resultant mixture is extracted with ether (3×20 mL). The ethereal layer is washed with water (2×25 mL) and saturated aqueous brine (25 mL), dried over magnesium sulfate and concentrated in vacuo. The residue is purified by flash chromatography to afford 209.

H. Hydroxy diene 210.

A −78° C. solution of 209 (0.05 mmol) in $CH_2Cl_2$ (5 mL) is treated with diisobutylaluminum hydride (0.5 mL, 1.0 M in toluene). The resultant solution is stirred 10 min at −78° C. and 30 min at 0° C. The reaction is quenched with a saturated solution of sodium potassium tartrate (50 mL) and the mixture is diluted with ether (60 mL). The organic layer is separated, dried over magnesium sulfate, and concentrated in vacuo. The residue is purified by flash chromatography to afford 210.

I. Aldehyde 211.

To a −10° C. solution of 207 (1.3 mmol) and triethylamine (5.0 mmol) in dichloromethane (3 mL) is added a solution of sulfur trioxide-pyridine (3.9 mmol) in dimethyl sulfoxide (5 mL). The mixture is stirred 1 h at room temperature and diluted with ether (15 mL). The organic phase is washed with aqueous sodium bisulfate (1 M, 10 mL), saturated aqueous brine (4×10 mL), dried over magnesium sulfate, and concentrated in vacuo. The residue is purified by flash chromatography to afford 211.

J. Tetraene 212.

A solution of diphenylallylphosphine (0.08 mL, 0.38 mmol) in tetrahydrofuran (2 mL) is cooled to −78° C. and tert-butyllithium (0.14 mL, 1.7 M in pentane) is added. The mixture is warmed to 0° C. for 30 min, then recooled to −78° C. and treated with titanium (IV) isopropoxide (0.30 mmol). After 30 min, aldehyde 211 (0.30 mmol) is introduced as a solution in tetrahydrofuran (2 mL). The resultant solution is stirred at −78° C. for 15 min and at 0° C. for 1 h. Methyl iodide (0.64 mmol) is added, and the reaction is warmed to room temperature for 12 h. The reaction mixture is diluted with ether (60 mL), washed with aqueous sodium bisulfate (30 mL, 1.0 M), saturated aqueous brine (30 mL), and is dried over magnesium sulfate and concentrated in vacuo. The residue is purified by flash chromatography to afford 212.

K. Aldehyde 213.

Oxalyl chloride (1.5 mmol) is added dropwise to a −78° C. solution of dimethyl sulfoxide (3 mmol) in dichloromethane (4 mL). After 15 min, a −78° C. solution of 212 (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 213.

L. Ester 214.

To a −78° C. solution of $(F_3CCH_2O)_2POCH_2CO_2Et$ (2 mmol) and 18-crown-6 (2.4 mmol) in tetrahydrofuran (5 mL) is added potassium bis(trimethylsilyl)amide (2 mmol) in tetrahydrofuran (2 mL). The resultant solution is stirred 10 min at −78° C. and then treated with aldehyde 213 (1.2 mmol) in 4 mL of tetrahydrofuran. The reaction mixture is warmed to 0° C. for 6–8 h and then quenched with saturated aqueous ammonium chloride (10 mL). The aqueous layer is separated and extracted with hexane (2×25 mL). The combined organics are dried over magnesium sulfate and concentrated in vacuo. The residue is purified by flash chromatography to afford 214.

M. Alcohol 215.

To a solution of 214 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 215.

N. Carbamate 216.

To a solution of 215 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 216.

O. Triol 217.

A solution of 216 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 217.

EXAMPLE 53

Figure 21:
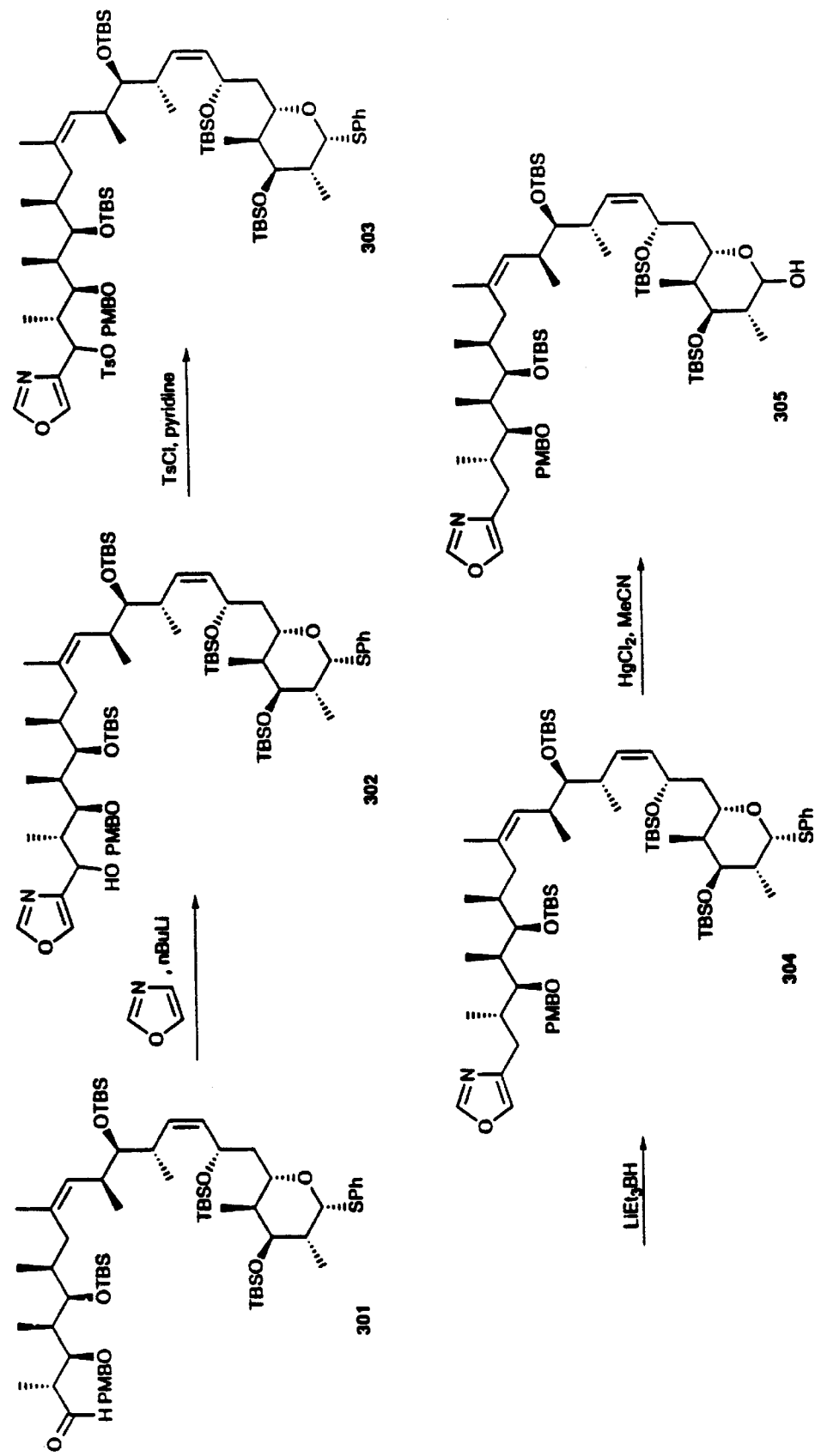
FIG. 21 shows a synthetic scheme for compound 305.
Figure 22:
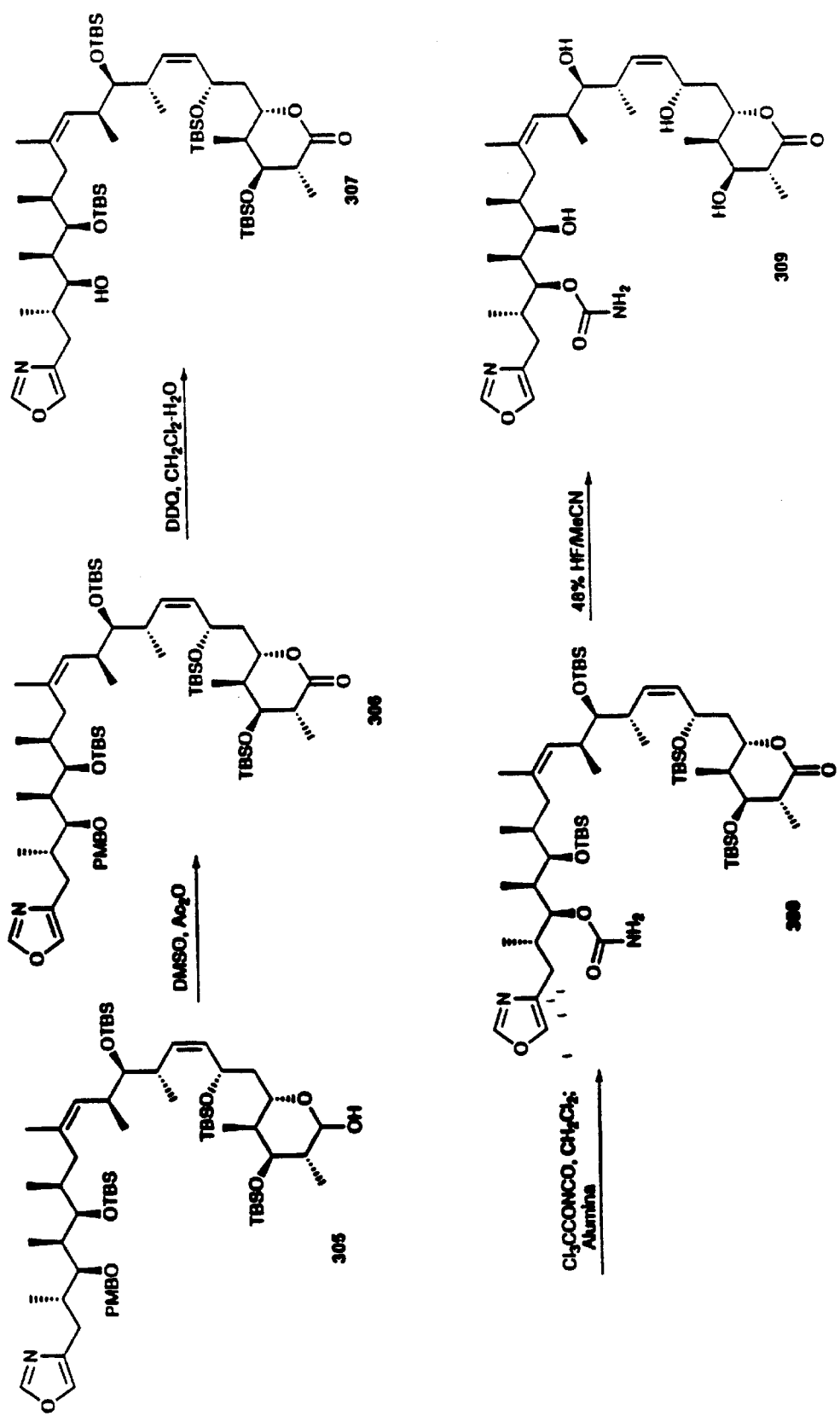
FIG. 22 shows a synthetic scheme for compound 309.

FIGS. 21 and 22

A. Hydroxy-oxazole 302.

A solution of oxazole (3 mmol) in tetrahydrofuran (15 mL) is cooled to −78° C. and treated with n-BuLi (3 mmol) in hexane. (see, Hodges, et al., *J. Org. Chem.* 1991, 56, 449). After 30 min at −78° C., previously prepared (see, Smith, et al., *J. Am. Chem. Soc.* 1995, 117, 12011) aldehyde 301 (2 mmol) is added in tetrahydrofuran (10 mL) and the reaction mixture is gradually allowed to warm to room temperature. After 18–24 h, the reaction is quenched by addition of saturated aqueous ammonium chloride (25 mL). The aqueous layer is separated and extracted with ether (3×25 mL). The combined organics are dried over magnesium sulfate and concentrated in vacuo. The residue is purified by flash chromatography to afford 302.

B. Tosylate 303.

A solution of 302 (1.0 mmol) in anhydrous pyridine (10 mL) at 0° C. is treated with p-toluenesulfonyl chloride (286 mg, 1.5 mmol). The mixture is allowed to warm to room temperature for 4–6 h. The pyridine is removed in vacuo and the residue is purified by flash chromatography to afford tosylate 303.

C. Reduction product 304.

To a 0° C. solution of tosylate 303 (0.5 mmol) in tetrahydrofuran (2 mL) is added lithium triethylborohydride (2 mmol) as a solution in tetrahydrofuran (1.0 M). The resultant solution is warmed to room temperature for 2–4 h and then quenched with water (1 mL) and diluted with ether (25 mL). The ethereal layer is washed with saturated aqueous brine (2×10 mL), dried over magnesium sulfate, and concentrated in vacuo. The residue is purified by flash chromatography to afford 304.

D. Lactol 305.

To a solution of 304 (0.1 mmol) in tetrahydrofuran-acetonitrile (15 mL, 2:1) is added phosphate buffer (pH 7, 5 mL) and mercury (II) chloride (1.0 mol). The resultant mixture is stirred 1 h at room temperature. The reaction mixture is diluted with ether (100 mL) and washed with saturated aqueous brine (2×50 mL), dried over magnesium sulfate and concentrated in vacuo. The residue is purified by flash chromatography to afford 305 as a mixture of α and β anomers.

E. Lactone 306.

To a solution of 305 (0.070 mmol) in dimethyl sulfoxide (10 mL) is added acetic anhydride (2 mL). After 2 days at room temperature, the mixture is diluted with ether (100 mL) and washed with saturated aqueous sodium bicarbonate (50 mL), saturated aqueous brine (50 mL), dried over magnesium sulfate and concentrated in vacuo. The residue is purified by flash chromatography to afford 306.

F. Alcohol 307.

To a solution of 306 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 307.

G. Carbamate 308.

To a solution of 307 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 308.

H. Tetrol 309.

A solution of 308 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 309.

EXAMPLE 54

Figure 23:
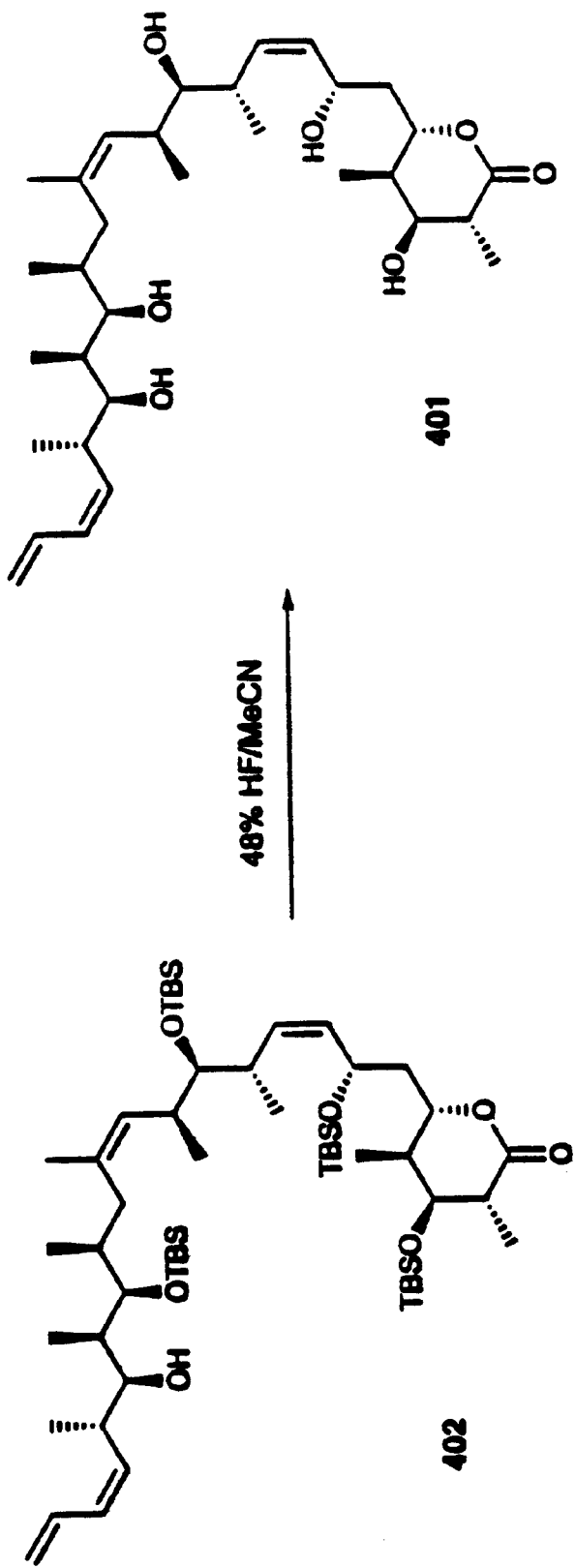
FIG. 23 shows a synthetic scheme for compound 401.
Figure 24:
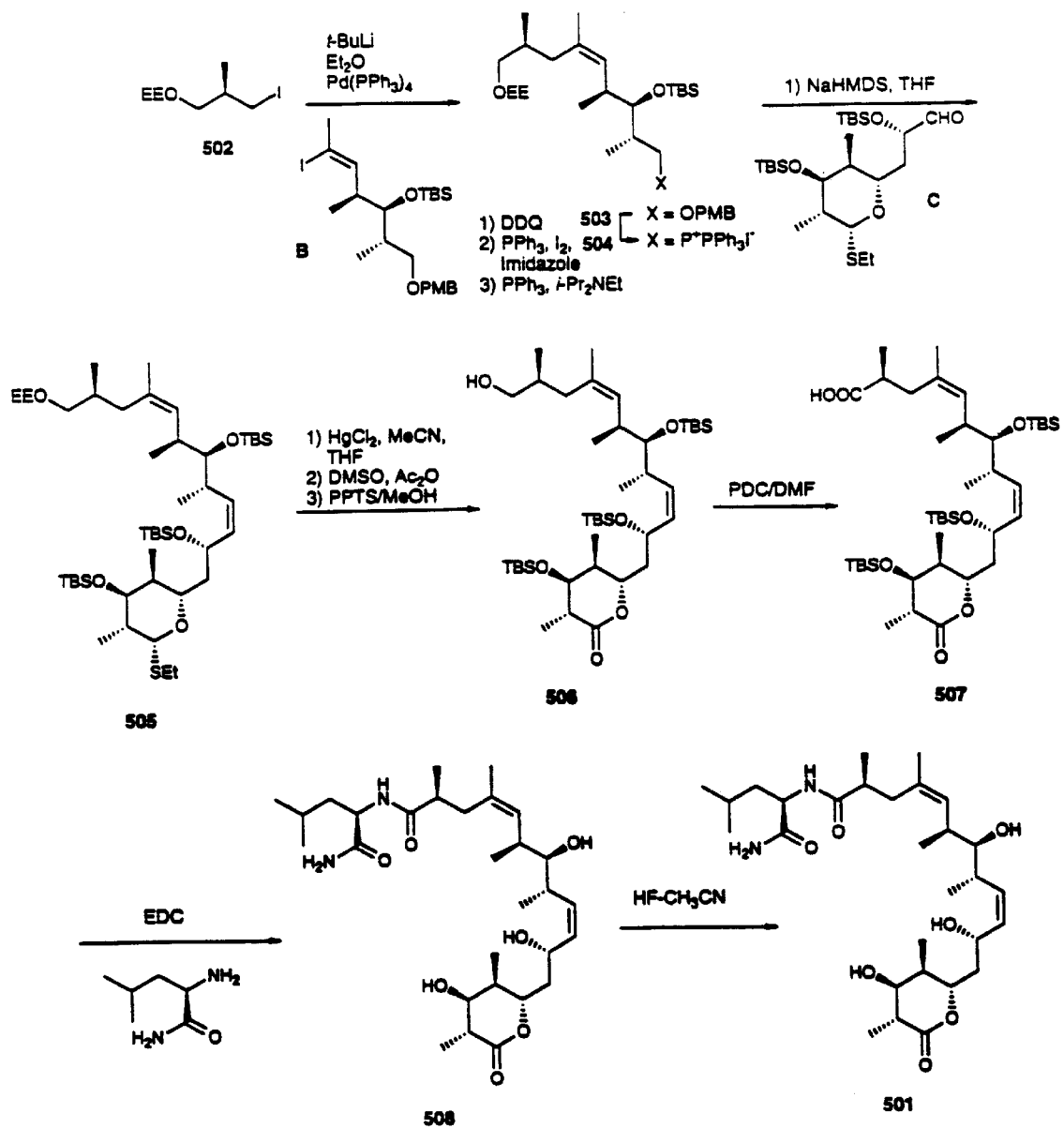
FIG. 24 shows a synthetic scheme for compound 501.
Figure 25:
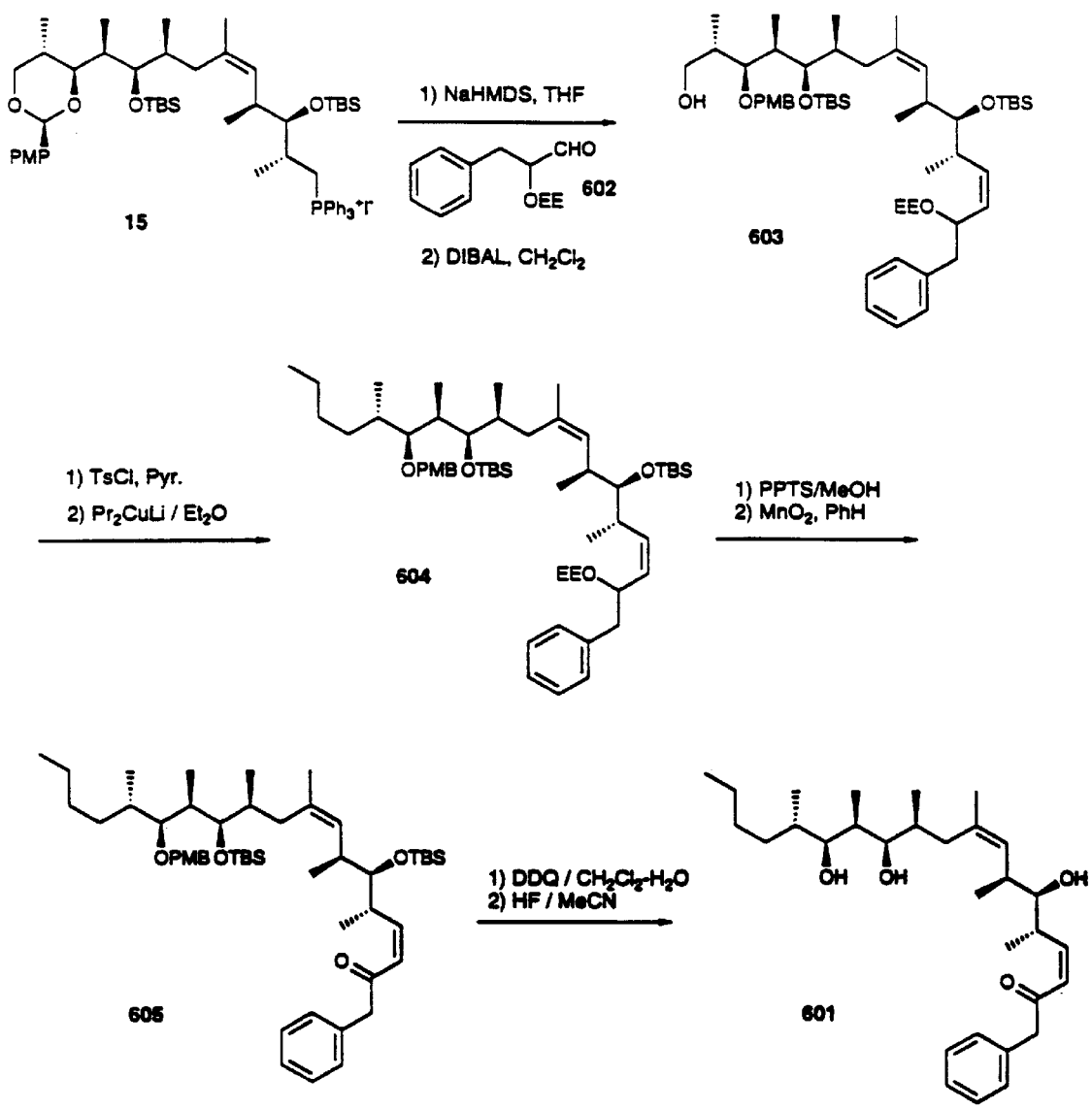
FIG. 25 shows a synthetic scheme for compound 601.
Figure 26:
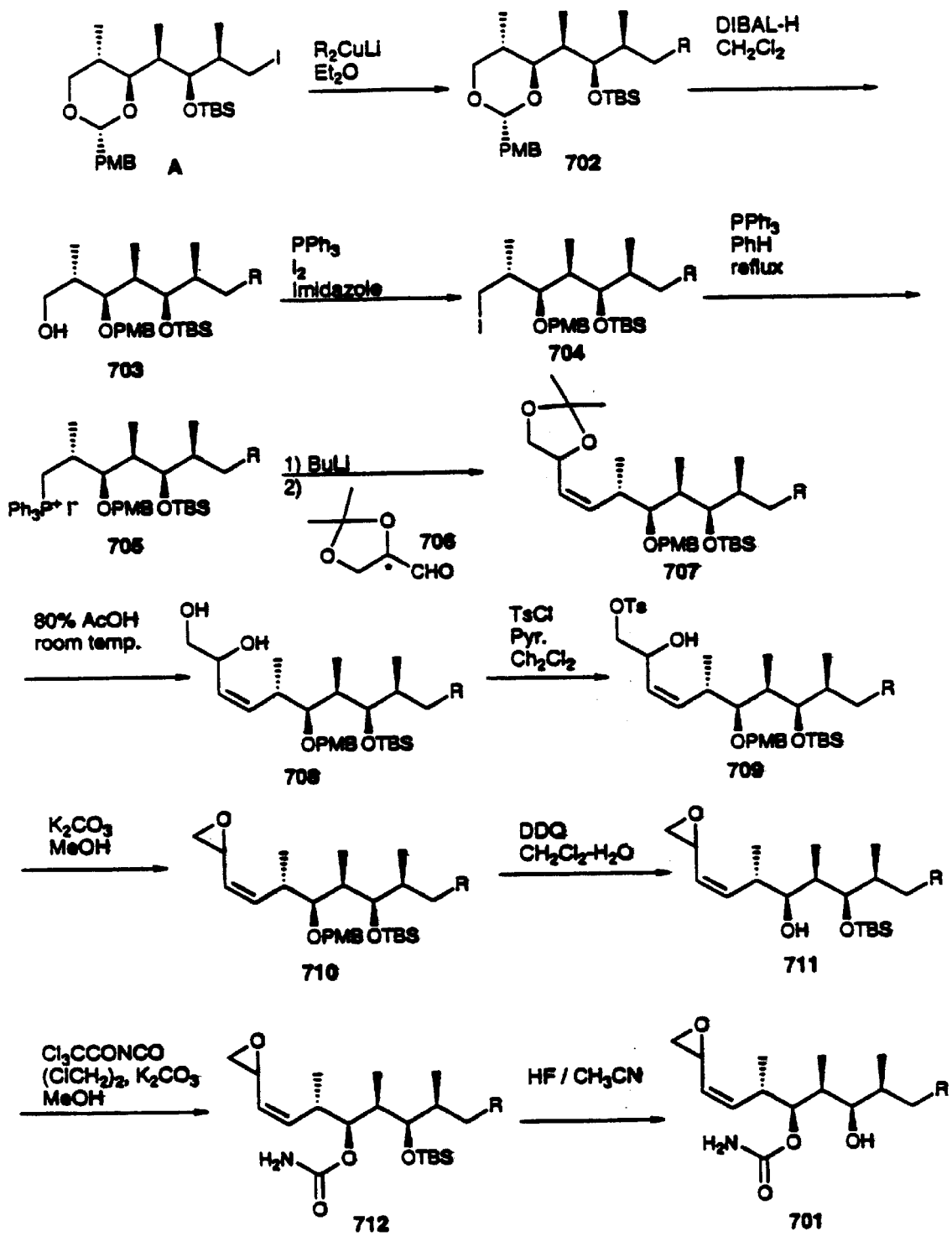
FIG. 26 shows a synthetic scheme for compound 701 R=alkyl).

As shown in FIG. 23, a solution of 402 (10.5 mg, 10.4 mmol) in 48% HF—CH$_3$CN (1:9, 1.0 mL) is stirred at room temperature for 12 hr. The reaction is quenched by saturated NaHCO$_3$ (5.0 mL). The mixture is extracted with ethyl acetate (3×10 mL). The combined organic phase is then washed with brine (5.0 mL), dried over MgSO$_4$, concentrated in vacuo. The residue is purified by flash chromatography to afford 401.

EXAMPLE 55

FIG. 24

A. PMB-ether 503

ZnCl$_2$(1.32 g, 9.69 mmol) is dried at 160° C. under vacuum overnight and then treated with a solution of iodide 502 (2.46 g, 9.59 mmol) in dry Et$_2$O (50 mL). The mixture is stirred at room temperature until most of the ZnCl$_2$ is dissolved and then cooled to −78° C. t-BuLi (1.7M in pentane, 17.0 mL) is added over 30 min, and the resultant solution is stirred an additional 15 min, warmed to room temperature, and stirred for 1 hr. The solution is added by cannula to a mixture of iodoolefin B (see, Smith, et al., *J. Am. Chem. Soc.* 1995, 117, 12011) (3.21 g, 6.19 mmol) and Pd(PPh$_3$)$_4$ (364.2 mg, 0.315 mmol). The mixture is covered with aluminum foil, stirred overnight, and then diluted with ethyl acetate (100 mL), washed with brine (2×100 mL), dried over MgSO$_4$, filtered and concentrated in vacuo. The residue is purified by flash chromatography to afford 503.

B. Phosphonium salt 504

A solution of alcohol 503 (1.70 g, 3.26 mmol) in CH$_2$Cl$_2$ (28 mL) is cooled to 0° C. and treated with water (1.3 mL) and 2,3-dichloro-5,6-dicyano-1,4-benzoquinone (774 mg, 3.41 mmol). The mixture is stirred at 0° C. for 5 hr, diluted with CH$_2$Cl$_2$ (20 mL), dried over MgSO$_4$, and filtered through a column of silica gel. Following concentration in vacuo, the residue is dissolved in ethanol (50 mL) at room temperature, and excess sodium borohydride is added. After 30 min, the reaction is cooled to 0° C., quenched with saturated aqueous NH$_4$Cl (50 mL), and concentrated. The residue is then dissolved in CH$_2$Cl$_2$(90 mL), and the solution is washed with water, dried over MgSO$_4$, filtered and concentrated in vacuo. The residue is purified by flash chromatography to afford an alcohol A solution of this alcohol (400 mg, 1.0 mmol) in dry benzene/ether (1:2, 50 mL) is treated with triphenylphosphine (923 mg, 3.6 mmol) and imidazole (273 mg, 4.0 mmol). After all of the imidazole dissolved, iodine (761 mg, 3.0 mmol) is added with vigorous stirring of the reaction mixture. The mixture is stirred 2 h further and then treated with triethylamine (4 mL). The resultant solution is diluted with CH$_2$Cl$_2$ (50 mL) and washed with saturated aqueous Na$_2$S$_2$O$_3$(100 mL), saturated aqueous NaHCO$_3$ (100 mL), and brine (2×100 mL). The organic phase is dried over MgSO$_4$, filtered and concentrated in vacuo. Filtration though silica gel to remove triphenylphosphine oxide, affords an iodide. The iodide was mixed with diisopropylethylamine (0.6 mL, 3.44 mmol) and triphenylphosphine (4.94 g, 18.8 mmol). The mixture is heated at 80° C. for 24 hr, cooled to room temperature, and washed with hexane (2×50 mL). The product is isolated by flash chromatography to afford 504.

C. Coupled product 505.

Phosphonium salt 504 (386 mg, 0.5 mmol) is dried azeotropically with dry benzene and heated at 50° C. under vacuum for 3 hr before use. It is then dissolved in tetrahydrofuran (3.0 mL). Sodium bis(trimethylsilyl)amide (1.0 M in tetrahydrofuran, 0.48 mL, 0.48 mmol) is added at −78° C., and the mixture is stirred for 25 min and then recooled to −78° C. A solution of aldehyde C (see, Smith, et al., *J. Am. Chem. Soc.* 1995, 117, 12011) (147 mg, 0.30 mmol) in tetrahydrofuran (1.5 mL) is added, and the mixture is stirred for 10 min at −78° C., and 2 hr at room temperature. The reaction is quenched with saturated aqueous NH$_4$Cl (4.0 mL), the resultant mixture is extracted with ether (120 mL), and the ether layer is washed with water (100 mL) and brine(100 mL3), dried over MgSO$_4$, filtered and concentrated in vacuo. Flash chromatography provides olefin 505.

D. Lactone 506.

To a solution of 505 (200 mg, 0.23 mmol) in tetrahydrofuran-acetonitrile (10 mL, 2:1) is added a phosphate buffer solution (pH=7.0, 3.3 mL), and HgCl$_2$(1.3 g). The suspension is stirred at room temperature for 40 min, then diluted with ether (150 mL), washed with brine (2×70 mL), dried over MgSO$_4$, and concentrated in vacuo. Flash chromatography provides a mixture of lactols as α/β anomers. This material is used directly in the next oxidation: Under argon, to a solution of lactols in dimethylsulfoxide (5.0 mL) is added acetic anhydride (1.0 mL). After 2 days at room temperature, the mixture is diluted with ether (150 mL), washed with saturated NaHCO$_3$ (150 mL), brine(150 mL), dried over MgSO$_4$, and concentrated in vacuo. Flash chromatography affords a lactone. A solution of the lactone (160 mg, 0.20 mmol) in methanol (4 mL) is treated with pyridinium p-toluenesulfonate (10 mg) and stirred at 40° C. for 30 min. The mixture is diluted with ether (80 mL) and washed successively with saturated aqueous NaHCO$_3$ solution (90 mL) and brine (40 mL), and then dried over MgSO$_4$. The organic solution is concentrated in vacuo, and the residue is passed through a column of silica gel to provide alcohol 506.

E. Acid 507.

To a solution of alcohol 506 (140 mg, 0.19 mmol) in dimethylformamide (5.0 ml), is added pyridinium dichromate (210 mg, 0.55 mmol). The reaction mixture is stirred at room temperature for 5 hr, and diluted with water (120 mL). The mixture is extracted with ether (3×15 mL). The organic solutions are combined and washed with brine (40 ml), and dried over MgSO$_4$. Then it is concentrated in vacuo to give a residue, which is purified by flash chromatography to afford carboxylic acid 507.

F. Amino-amide 508.

To a solution of 507 (60.0 mg, 78.1 mmol) and D-leucine hydrochloride (26.0 mg, 0.16 mmol) in CH$_2$Cl$_2$ (3 mL) is added 1-(3-dimethylaminopropyl)-3-ethylcarbodiimide hydrochloride (EDC, 23 mg, 0.12 mmol) and 1-hydroxybenzotriazole (21.0 mg, 0.14 mmol), followed by diisopropylamine (40 mL, 0.23 mmol). The mixture is stirred at room temperature overnight before addition of 5% KHSO$_4$ solution. The resulting mixture is extracted with ethyl acetate (30 mL). The organic layer is washed with brine (20 mL) and dried over MgSO$_4$, and then concentrated in vacuo. The residue is purified by column chromatography to afford 508.

G. Analog 501.

A solution of 508 (52 mg, 59 mmol) in 48% acetonitrile (1:9, 1.0 mL) is stirred at room temperature for 12 hr. The reaction is quenched by saturated NaHCO$_3$ (5.0 mL). The mixture is extracted with ethyl acetate (3×10 mL). The combined organic phase is then washed with brine (5.0 mL), dried over MgSO$_4$, and concentrated in vacuo. Flash chromatography provides 501.

EXAMPLE 56

FIG. 25

A. Diene 603.

Phosphonium salt 15 (98.0 mg, 0.092 mmol) is dried azeotropically with dry benzene and heated at 50° C. under vacuum for 3 hr before use. It is then dissolved in tetrahydrofuran (0.7 mL). Sodium bis(trimethylsilyl)amide (1.0 M in tetrahydrofuran, 86 mL, 0.0855 mmol) is added at −78° C., and the mixture is stirred for 20 min and then recooled to −78° C. A solution of aldehyde 602 (13 mg, 60 mmol) in tetrahydrofuran (300 mL) is added, and the mixture is stirred for 10 min at −78° C., and 2 hr at room temperature. The reaction is quenched with saturated aqueous NH$_4$Cl (1.0 mL). The resultant mixture is extracted with ether (30 mL), and the ether layer is washed with water (30 mL) and brine (30 mL), dried over MgSO$_4$, filtered and concentrated in vacuo. Flash chromatography provides the coupled product.

A solution of the olefin (39 mg, 44 mmol) in CH$_2$Cl$_2$ is cooled to −78° C., diisobutylaluminum hydride (1.0 M in toluene, 440 mL, 0.40 mmol) is added dropwise over 5 min, and the resultant solution is stirred for 10 min at −78° C. and 30 min at 0° C. The reaction is quenched with a saturated solution of Rochelle's salt, and the mixture is diluted with ether (60 mL), washed with Rochelle solution, and brine(30 mL each), dried over MgSO$_4$, filtered and concentrated in vacuo. Flash chromatography provides alcohol 603.

B. Alkane 604.

To a solution of alcohol 603 (82 mg, 0.93 mmol) in pyridine (1.5 mL) at 0° C. is added p-toluenesulfonyl chloride(26.6 mg, 0.14 mmol) with stirring. After 3 hr, the reaction mixture is concentrated in vacuo. The residue is purified by column chromatography to give a tosylate. To a solution of this tosylate (94 mg, 0.91 mmol) in ether (5 mL) is added lithium diisopropylcuprate (Pr$_2$CuLi) (ca. 0.5 M in ether, 10 mL, excess. The resultant solution is stirred for 8 hr and then quenched with saturated aqueous solution of NH$_4$Cl (50 mL). Stirring is continued for an additional 2 h. The organic phase is separated and washed with NH$_4$Cl solution (20 mL), dried over MgSO$_4$, and concentrated in vacuo. Flash chromatography provides 604.

C. Enone 605.

A solution of 604 (75 mg, 83 mmol) in methanol (2 mL) is treated with pyridinium p-toluenesulfonate (ca.4 mg) and stirred at 40° C. for 30 min. The mixture is diluted with ether (20 mL) and washed successively with saturated aqueous NaHCO$_3$ solution (25 mL) and brine (10 mL), and then dried over MgSO$_4$. The organic solution is concentrated in vacuo, and the residue is passed through a column of silica gel to provide an alcohol. To a solution of the alcohol (62.0 mg, 68.2 mmol) in benzene (2.0 mL) is added manganese (IV) oxide (100 mg, 1.15 mmol). After stirring for 8 h at room temperature, the reaction mixture is filtered through a pad of celite. The filtrate is concentrated in vacuo. Flash chromatography of the residue affords α,β-unsaturated ketone 605.

D. Triol 606.

A solution of the α,β-unsaturated ketone 605 (45 mg, 56 mmol) in CH$_2$Cl$_2$ (2 mL) is cooled to 0° C. and treated with water (0.1 mL) and 2, 3-dichloro-5, 6-dicyano-1, 4-benzoquinone (15 mg, 66 mmol). The mixture is stirred at 0° C. for 5 hr, diluted with CH$_2$Cl$_2$ (15 mL), dried over MgSO$_4$, and filtered through a column of silica gel. Following concentration in vacuo, the residue is used for next step without further purification. A solution of the crude alcohol in 48% HF-acetonitrile (1:9, 1.0 mL) is stirred at room temperature for 12 hr. The reaction is quenched by saturated NaHCO$_3$ (5.0 mL). The mixture is extracted with ethyl acetate(3×10 mL). The combined organic phase is then washed with brine (5.0 mL), dried over MgSO$_4$, concentrated in vacuo. The residue is purified by flash chromatography to afford 601.

EXAMPLE 57

FIG. 26

A. Alkane 702

To a solution of iodide A (300 mg, 0.54 mmol) in ether (5 mL) is added lithium dibutylcuprate (Bu$_2$CuLi) (ca. 0.5 M in ether, 5.4 mL, excess) at −25° C. The resultant solution is stirred for 8 hr and then quenched with saturated aqueous NH$_4$Cl (50 mL). Stirring is continued for another 2 hr and the organic phase is separated. The organic solution is washed with $NH_4Cl$ solution (20 mL) and dried over $MgSO_4$, and concentrated in vacuo. Flash chromatography provides 702.

B. Alcohol 703.

A solution of 702 (240 mg, 0.50 mmol) in $CH_2Cl_2$ (6.0 mL) is cooled to −78° C. Diisobutylaluminum hydride (1.0 M in toluene, 1.50 mL, 1.50 mmol) is added dropwise over 5 min, and the resultant solution is stirred for 10 min at −78° C. and 30 min at 0° C. The reaction is quenched with a saturated solution of Rochelle's salt, and the mixture is diluted with ether (60 mL), washed with Rochelle solution, and brine (30 mL each), dried over $MgSO_4$, filtered and concentrated in vacuo. Flash chromatography provides alcohol 703.

C. Iodide 704

A solution of alcohol 703 (210 mg, 0.44 mmol) in dry benzene/ether (1:2, 5 mL) is treated with triphenylphosphine (420 mg, 1.6 mmol) and imidazole (123 mg, 1.8 mmol). After all of the imidazole dissolved, iodine (335 mg, 1.32 mmol) is added with vigorous stirring. The mixture is stirred for 2 h and then treated with triethylamine (1.8 mL). The resultant solution is diluted with $CH_2Cl_2$ (22 mL) and washed with saturated aqueous $Na_2S_2O_3$ (40 mL), saturated aqueous $NaHCO_3$ (40 mL), and brine (2×40 mL). The organic phase is dried over $MgSO_4$, filtered and concentrated in vacuo. The residue is purified by flash chromatography to afford iodide 704.

D. Phosphonium salt 705.

The iodide 704 is mixed with triphenylphosphine (2.17 g, 8.27 mmol) and the mixture is heated at 80° C. for 24 hr, cooled to room temperature, and washed with hexane (2×20 mL). Flash chromatography provides phosphonium salt 705.

E. Alkene 707.

A solution of 705 (260 mg, 0.30 mmol) in tetrahydrofuran (6.0 mL) is cooled to −10° C. and a solution of n-butyl lithium (1.0 M in hexane, 0.29 mL, 0.29 mmol) is introduced dropwise over 5 min. The resultant solution is stirred for 50 min at room temperature and then the mixture is recooled to −78° C. and aldehyde 706 (39 mg, 0.3 mmol) is added a solution in tetrahydrofuran (1.5 mL). The mixture is stirred for 10 min at −78° C., and 1 hr at 0° C. The reaction is quenched with saturated aqueous $NH_4Cl$ (1.0 mL) and the resultant mixture is extracted with ether (30 mL). The ether layer is washed with water (30 mL) and brine (30 mL), dried over $MgSO_4$, filtered and concentrated in vacuo. The residue is purified by flash chromatography to afford olefin 707 (149 mg, 85% yield).

F. Diol 708.

Acetonide 707 (147 mg, 0.25 mmol) is dissolved in 80% aqueous acetic acid (2.5 mL) at room temperature. The reaction mixture is stirred for 4 hr at room temperature and then diluted with water (20 mL). The mixture is extracted with ethyl acetate(2×5 mL). The combined organic layers are washed with saturated $NaHCO_3$ solution, and brine (10 mL each), and then dried over $MgSO_4$. The organic solution is concentrated in vacuo, and the residue is flash chromatographed over silica gel to afford diol 708.

G. Tosylate 709.

To a solution of diol 708 (134 mg, 0.25 mmol) in pyridine (2 mL) is added p-toluenesulfonyl chloride( 52 mg, 0.27 mmol). After 3 hr, the reaction mixture is diluted with ether (30 mL), and washed with ice cold 1 M hydrochloric acid (60 mL), saturated $NaHCO_3$ solution (20 mL), and brine (20 mL) and then concentrated in vacuo. The residue is purified by column chromatography to give a monotosylate 709.

H. Epoxide 710.

A solution of tosylate 709 (145 mg, 0.21 mmol) in methanol (3.0 mL) is added potassium carbonate (10 mg) at room temperature. The mixture is stirred for 20 min, and then diluted with water (60 mL) and extracted with ethyl acetate (2×20 mL). The combined organic layers are washed with brine and concentrated in vacuo. Flash chromatography provides epoxide 710.

I. Alcohol 711.

To a solution of 710 (41 mg, 79 mmol) in $CH_2Cl_2$ (3.0 mL) at 0° C. is added water (0.15 mL) and 2, 3-dichloro-5,6-dicyano-1, 4-benzoquinone (60 mg, 0.26 mmol). The mixture is stirred at 0° C. for 5 hr, diluted with $CH_2Cl_2$ (15 mL), dried over $MgSO_4$, and filtered through a column of silica gel. Following concentration in vacuo, the crude 711 is used without further purification.

J. Carbamate 712.

To a solution of 711 (8.7 mg, 22 mmol) in $CH_2Cl_2$ (1.0 mL) is added trichloroacetyl isocyanate (0.20 mL, 1.7 mmol) at room temperature. After 30 min, the mixture is diluted with $CH_2Cl_2$(20 mL), and some neutral $Al_2O_3$ (500 mg) is added. The mixture is then stirred at room temperature for 2 hr, then filtered though a short column of silica gel, and concentrated in vacuo. The residue is purified by flash chromatography to afford 712.

K. Hydroxy-urethane 701.

A solution of 712 (6.0 mg, 14 mmol) in 48% HF-acetonitrile (1:9, 1.0 mL) is stirred at room temperature for 12 hr. The reaction is quenched by saturated $NaHCO_3$ (5.0 mL). The mixture is extracted with ethyl acetate (3×10 mL). The combined organic phase is then washed with brine (5.0 mL), dried over $MgSO_4$, and concentrated in vacuo. The residue is purified by flash chromatography afford 701.

EXAMPLE 58

Figure 27:
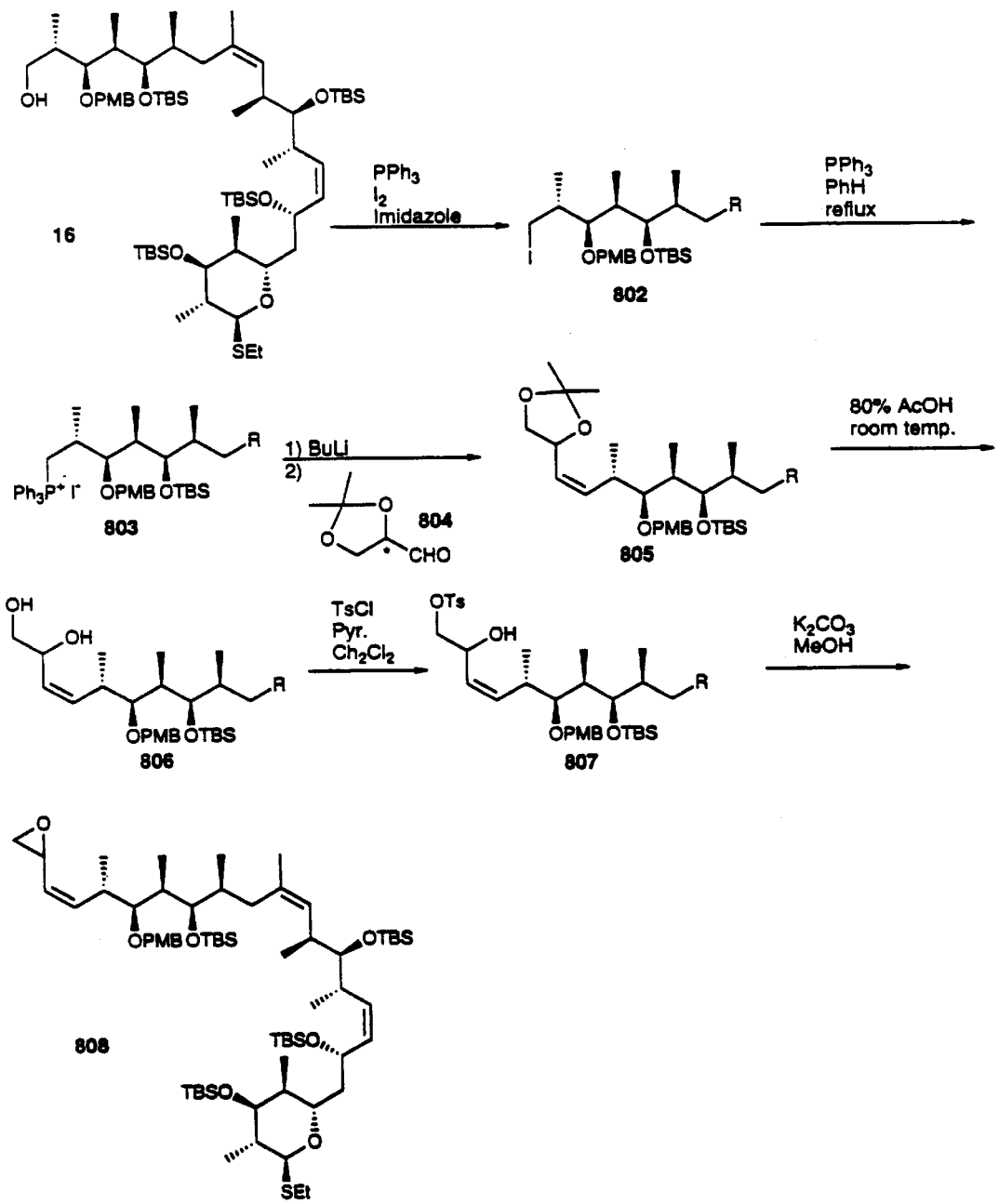
FIG. 27 shows a synthetic scheme for compound 808.
Figure 28:
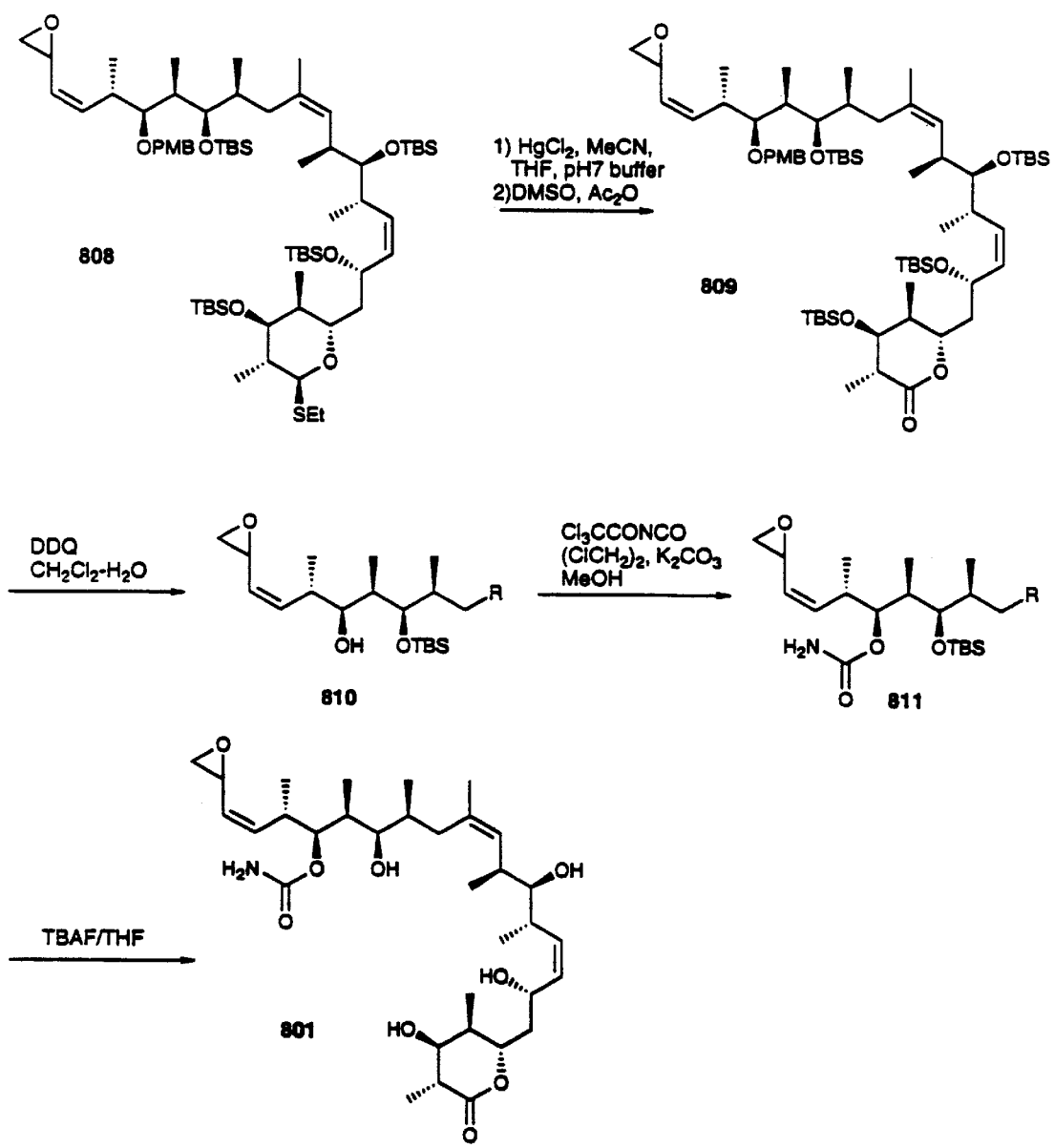
FIG. 28 shows a synthetic scheme for compound 801.
Figure 29:
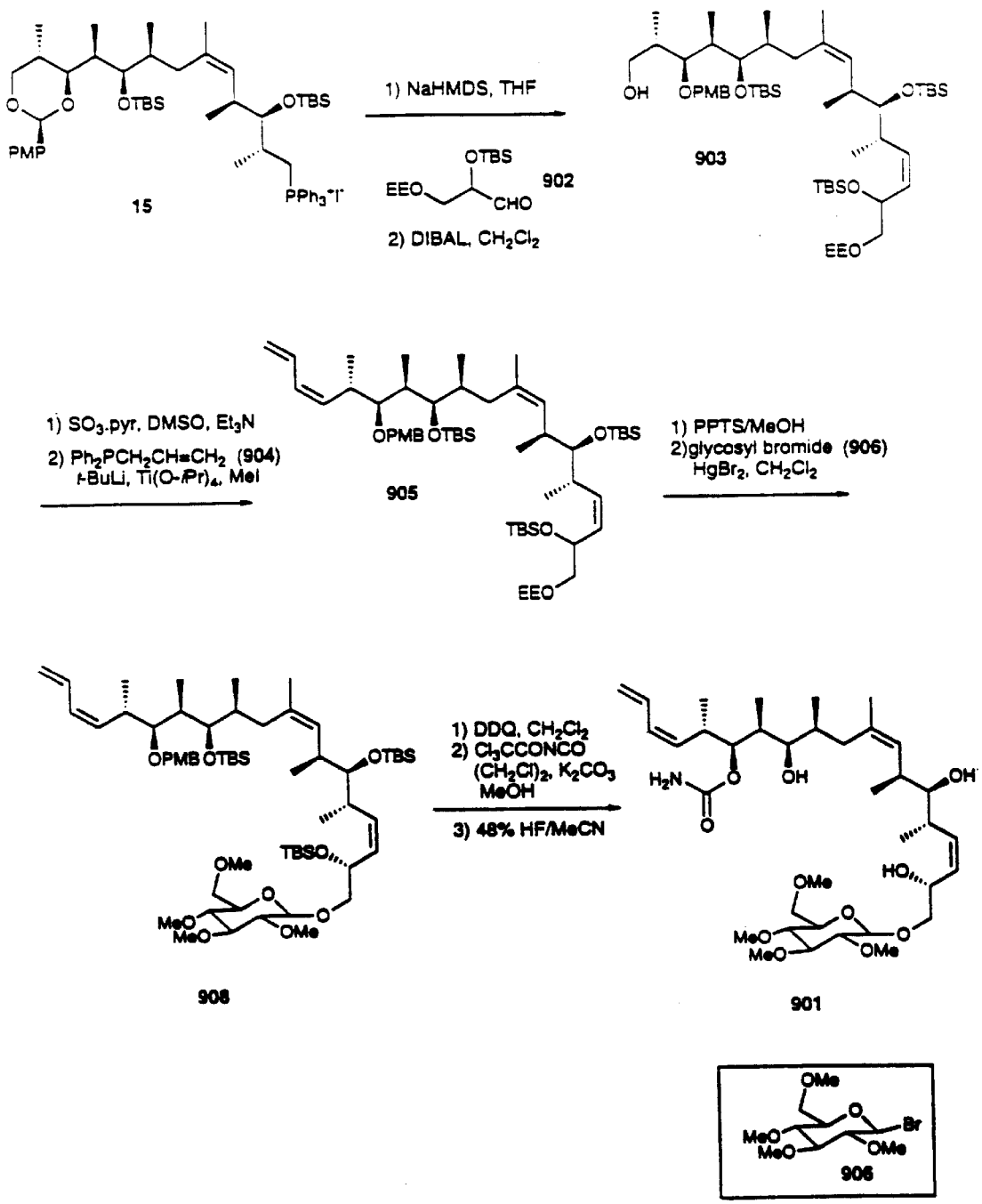
FIG. 29 shows a synthetic scheme for compound 901.

FIGS. 27 and 28

A. Iodide 802.

A solution of alcohol 16 (see, Smith, et al., *J. Am. Chem. Soc.* 1995, 117, 12011) (410 mg, 0.360 mmol) in dry benzene/ether (1:2, 10 mL) is treated with triphenylphosphine (378 mg, 1.44 mmol) and imidazole (111 mg, 1.62 mmol). After complete dissolution of the imidazole, iodine (301 mg, 1.19 mmol) is added with vigorous stirring. The reaction mixture is stirred 2 h and then treated with triethylamine (1.7 mL). The resultant solution is diluted with $CH_2Cl_2$ (30 mL) and washed with saturated aqueous $Na_2S_2O_3$ (40 mL), saturated aqueous $NaHCO_3$ (40 mL), and brine (2×40 mL). The organic phase is dried over $MgSO_4$, filtered and concentrated in vacuo. Purification of the residue by flash chromatography affords iodide 802.

B. Phosphonium salt 803.

To a solution of iodide 802 (410 mg, 0.325 mmol) in benzene (20 mL) is added triphenylphosphine(1.00 g, 3.81 mmol). The mixture is heated at 80° C. for 24 hr, cooled to room temperature, and concentrated in vacuo. The residue is washed with hexane (2×20 mL). Flash chromatography affords phosphonium salt 803.

C. Alkene 805

A solution of 803 (460 mg, 0.30 mmol) in tetrahydrofuran (9.0 mL) is cooled to −10° C. A solution of n-butyl lithium (1.0 M in hexane, 0.29 mL, 0.29 mmol) is added dropwise over 5 min, and the resultant solution is stirred for 50 min at room temperature. Then the mixture is recooled to −78° C. and a solution of aldehyde 804 (39 mg, 0.3 mmol) in tetrahydrofuran (1.5 mL) is added. The mixture is stirred for 10 min at −78° C., and 1 hr at 0° C. The reaction is quenched with saturated aqueous $NH_4Cl$ (20 mL), the resultant mixture is extracted with ether (40 mL), and the ether layer is washed with water (30 mL) and brine (30 mL), dried over $MgSO_4$, filtered and concentrated in vacuo. Flash chromatography of the residue affords 805.

D. Diol 806

Acetonide 805 (280 mg, 0.22 mmol) is dissolved in 80% aqueous acetic acid (3.5 mL) at room temperature. The reaction mixture is stirred for 4 hr at room temperature and then diluted with water (40 mL). The mixture is extracted with ethyl acetate (2×10 mL). The combined organic layers are washed with saturated $NaHCO_3$ solution, and brine (10 mL each), and then dried over $MgSO_4$. The organic solution is concentrated in vacuo, and the residue is flash chromatographed over silica gel to afford diol 806.

E. Tosylate 807.

To a solution of diol 806 (235 mg, 0.19 mmol) in pyridine (2 mL) at 0° C. is added p-toluenesulfonyl chloride (45 mg, 0.23 mmol). After 3 hr, the reaction mixture is diluted with ether (30 mL), and washed with ice cold 1 M hydrochloric acid (30 mL), saturated $NaHCO_3$ solution (20 mL), and brine (20 mL) and then concentrated in vacuo. The residue is purified by column chromatography to give a monotosylate 807.

F. Epoxide 808.

To a solution of tosylate 807 (187 mg, 0.21 mmol) in methanol (3.0 mL) is added potassium carbonate (10 mg) at room temperature. The mixture is stirred for 20 min, and then diluted with water (60 mL) and extracted with ethyl acetate (2×20 mL). The combined organic layers were washed with brine and concentrated in vacuo. Flash chromatography provides epoxide 808.

G. Lactone 809.

To a solution of 808 (110 mg, 93 mmol) in tetrahydrofuran-acetonitrile (10 mL, 2:1) is added a phosphate buffer solution (pH=7.0, 3.5 mL), and $HgCl_2$ (2.3 g). The suspension is stirred at room temperature for 40 min, then diluted with ether (30 mL), washed with brine (2×30 mL), dried over $MgSO_4$, and concentrated in vacuo. Flash chromatography affords the lactol as an α/β anomeric mixture. This material is used directly in the next oxidation: Under argon atmosphere, a solution of the lactols in dimethylsulfoxide (3.0 mL) is treated with acetic anhydride (0.60 mL). After 2 days at room temperature, the mixture is diluted with ether (50 mL), washed with saturated $NaHCO_3$ (30 mL), brine (30 mL), dried over $MgSO_4$, and concentrated in vacuo. Flash chromatography provides 809.

H. Alcohol 810.

To a solution of 809 (90 mg, 79 mmol) in $CH_2Cl_2$ (3.0 mL) at 0° C. is added water (0.15 mL) and 2, 3-dichloro-5, 6-dicyano-1, 4-benzoquinone(60 mg, 0.26 mmol). The mixture is stirred at 0° C. for 5 hr. diluted with $CH_2Cl_2$ (15 mL), dried over $MgSO_4$, and filtered through a column of silica gel. Following concentration in vacuo, the crude 810 is used in the next reaction without further purification.

I. Carbamate 811

To a solution of 810 (22 mg, 22 mmol) in $CH_2Cl_2$ (1.0 mL) is added trichloroacetyl isocyanate (0.20 mL, 1.7 mmol) at room temperature. After 30 min, the mixture is diluted with $CH_2Cl_2$(20 mL), and some neutral $Al_2O_3$ (500 mg) is added. The mixture is then stirred at room temperature for 2hr, then filtered though a short column of silica gel and concentrated in vacuo. Flash chromatography affords 811.

J. Epoxide analog 812.

A solution of 811 (15 mg, 14 mmol) in tetrahydrofuran (1.0 mL) is cooled to 0° C., and treated with a 1.0 M solution of tetrabutylammonium fluoride in tetrahydrofuran (0.14 mL, 0.14 mmol). The reaction mixture is stirred for 2 hr, and diluted with water (20 mL). The mixture is extracted with ethyl acetate (3×10 mL). The combined organic phase is then washed with brine (10 mL), dried over $MgSO_4$, concentrated in vacuo. Flash chromatography affords 801.

EXAMPLE 59

FIG. 29

A. Alcohol 903.

Phosphonium salt 15 (98.0 mg, 0.092 mmol) is dried azeotropically with dry benzene and heated at 50° C. under vacuum for 3 hr before use. It is then dissolved in tetrahydrofuran (0.7 mL). Sodium bis(trimethylsilyl)amide (1.0 M in tetrahydrofuran, 86 mL, 0.0855 mmol) is added at −78° C., and the mixture is stirred for 20 min and then recooled to −78° C. A solution of aldehyde 902 (60 mmol) in tetrahydrofuran (300 mL) is added, and the mixture is stirred for 10 min at −78° C., and 2 hr at room temperature. The reaction is quenched with saturated aqueous $NH_4Cl$ (1.0 mL). The resultant mixture is extracted with ether (30 mL), and the ether layer is washed with water (30 mL) and brine (30 mL), dried over $MgSO_4$, filtered and concentrated in vacuo. Flash chromatography provides an olefin. A solution of the olefin (44 mmol) in $CH_2Cl_2$ is cooled to −78° C. Diisobutylaluminum hydride (1.0 M in toluene, 440 mL, 0.40 mmol) is added dropwise over 5 min, and the resultant solution is stirred for 10 min at −78° C. and 30 min at 0° C. The reaction is quenched with a saturated solution of Rochelle's salt, and the mixture is diluted with ether (60 mL), washed with Rochelle solution, and brine (30 mL each), dried over $MgSO_4$, filtered and concentrated in vacuo. Flash chromatography provides alcohol 903.

B. Diene 905.

A solution of 903 (0.012 mmol) and $Et_3N$ (42 mL, 0.30 mmol) in $CH_2Cl_2$ (2.0 mL) is cooled to 0° C. and a solution of $SO_3$-pyridine complex (40 mg, 0.251 mmol) in dimethylsulfoxide (0.6 mL) is added. The mixture is stirred at 0° C. for 45 min and then diluted with ethyl acetate (30 mL), washed with aqueous $NaHSO_4$ (1.0 M, 30 mL) and brine (2×30 mL), dried over $MgSO_4$, and concentrated in vacuo. Flash chromatography affords an aldehyde. A solution of allyldiphenylphosphine 904 (0.19 mmol) in tetrahydrofuran (1.0 mL) is cooled to −78° C. and t-butyl lithium (1.7 M in pentane, 0.122 mmol) is added. The mixture is stirred at 0° C. for 30 min, recooled to −78° C. and treated titanium tetra-I-propoxide (0.15 mmol). After 30 min, a cold (−78° C.) solution of the aldehyde (0.26 nmol) in tetrahydrofuran (1.0 mL) is introduced via cannula, and the mixture is stirred 10 min further at −78° C. and at 0° C. for 1 hr. Iodomethane (0.32 mmol) is added, and the reaction is maintained at 0° C. for 30 min, warmed to room temperature, protected from light, and stirred overnight. The reaction mixture is diluted with ether (30 mL), washed with 1.0 M aqueous $NaHSO_4$ and brine (30 mL each), dried over $MgSO_4$, concentrated in vacuo. Flash chromatography affords diene 905.

C. Glycoside 908.

A solution of 905 (83 mmol) in methanol (2 mL) is treated with pyridinium p-toluenesulfonate (ca.4 mg) and stirred at 40° C. for 30 min. The mixture is diluted with ether (20 mL) and washed successively with saturated aqueous $NaHCO_3$ solution (25 mL) and brine (10 mL), and then dried over MgSO$_4$. The organic solution is concentrated in vacuo, and the residue is passed through a column of silica gel to give an alcohol.

To a solution of glycosyl bromide 906 (75 mmol) in CH$_2$Cl$_2$(2.0 ml) is added HgBr$_2$ (7 mmol) and powdered molecular sieves (4 Å, 50 mg) and stirred for 60 min at room temperature. The mixture is then cooled to 0° C., and the alcohol (74 mmol) prepared above is added in CH$_2$Cl$_2$ (0.7 mL). The resultant mixture is stirred 6 hr at 0° C. and then warmed to room temperature and diluted with CH$_2$Cl$_2$ (10 mL), and filtered through a pad of celite. The filtrate is washed with aqueous KI solution, and dried over MgSO$_4$. The organic solution is concentrated in vacuo, and the residue is passed through a column of silica gel to give an anomeric mixture of glycosides 908.

D. Triol 901.

To a solution of 908 (79 mmol) in CH$_2$Cl$_2$ (3.0 mL) at 0° C. is added water (0.15 mL) and 2, 3-dichloro-5, 6-dicyano-1, 4-benzoquinone (60 mg, 0.26 mmol). The mixture is stirred at 0° C. for 5 hr, diluted with CH$_2$Cl$_2$ (15 mL), dried over MgSO$_4$, and filtered through a column of silica gel. Following concentration in vacuo, the crude alcohol is used for next step without further purification. To a solution of the alcohol (22 mmol) in CH$_2$Cl$_2$ (1.0 mL) is added trichloroacetyl isocyanate (0.20 mL, 1.7 mmol) at room temperature. After 30 min, the mixture is diluted with CH$_2$Cl$_2$(20 mL), and some neutral Al$_2$O$_3$ (500 mg) is added. The mixture is then stirred at room temperature for 2 hr, then filtered though a short column of silica gel, and concentrated in vacuo. Flash chromatography affords a carbamate. A solution of the carbamate (14 mmol) in 48% HF-acetonitrile (1:9, 1.0 mL) is stirred at room temperature for 12 hr. The reaction is quenched by saturated NaHCO$_3$ (5.0 mL). The mixture is extracted with ethyl acetate (3×10 mL). The combined organic phase is then washed with brine(5.0 mL), dried over MgSO$_4$, concentrated in vacuo. Flash chromatography affords 901.

EXAMPLE 60

FIG. 30

A. Olefin 1001

A solution of model phosphonium salt (0.0917 mmol) in THF (700 mL) is cooled to −78° C. and treated with NaHMDS (1.0 M in THF, 85.5 mL, 0.0855 mmol). The mixture is stirred for 20 min at 0° C., recooled to −78° C. and aldehyde C (0.0570 mmol) in THF (300 mL) is added. After 10 min at −78° C. and 2 h at room temperature, the mixture is quenched with saturated aqueous NH$_4$Cl (1.0 mL) and extracted with ether (30 mL). The ether solution is washed with water, brine (30 mL each), dried over MgSO$_4$, filtered and concentrated. Flash chromatography provides olefin 1001.

B. Lactone 1002

A solution of olefin 1001 (0.00597 mmol) in THF/CH$_3$CN (2:1, 1.50 mL) is treated with pH 7.0 phosphate buffer (500 mL) and HgCl$_2$ (215 mg). The suspension is stirred at room temperature for 40 min, diluted with ether (30 mL), washed with brine (2×30 mL), dried over MgSO$_4$, filtered and concentrated. Pipette flash chromatography (5% ethyl acetate/hexane) provides a mixture of lactols as a colorless oil which is further treated with DMSO (1.0 mL) and Ac$_2$O (200 mL) at room temperature for 2 days. The mixture is diluted with ether (30 mL), washed with saturated NaHCO$_3$ (30 mL), brine (30 mL), dried over MgSO$_4$, filtered and concentrated. Flash chromatography provides lactone 1002.

C. Model Compound 1003

A solution of olefin 1002 (5.5 mmol) in 48% HF—CH$_3$CN (1:9, 1.0 mL) is stirred at room temperature for 12 h, then quenched with saturated aqueous NaHCO$_3$ (5.0 mL). The mixture is extracted with ethyl acetate (3×10 mL). The combined organic extracts are washed with brine (5.0 mL), dried over MgSO$_4$, filtered and concentrated. Pipette flash chromatography (gradient elution, 1:30 to 1:6 MeOH/CHCl3) provides 1003.

EXAMPLE 61

Figure 32:
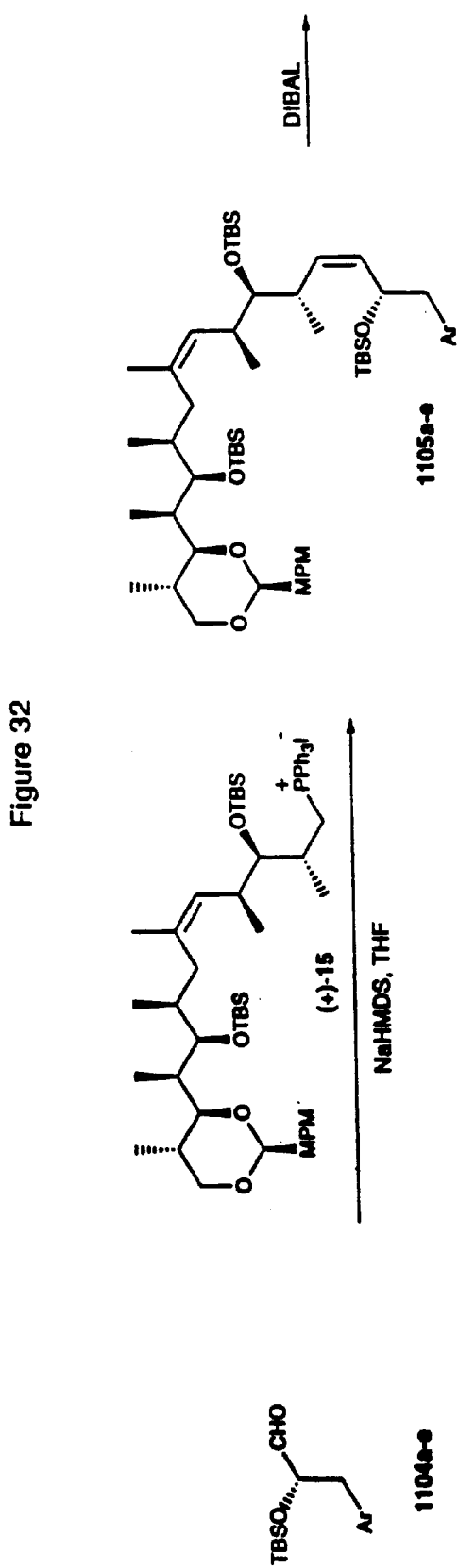
FIG. 32 shows a synthetic scheme for compound 1111.
Figure 32A:
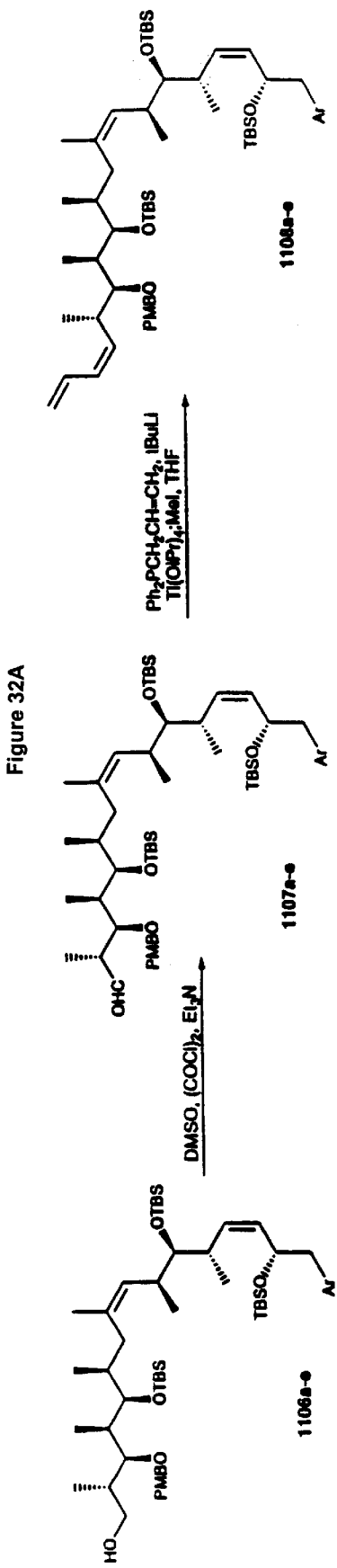
Figure 32B:
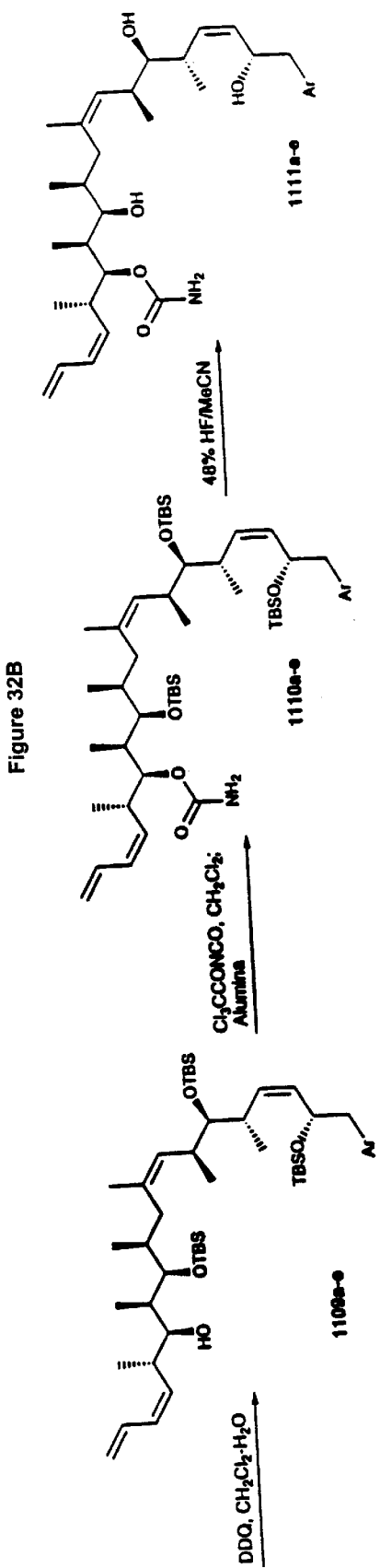
Figure 34:
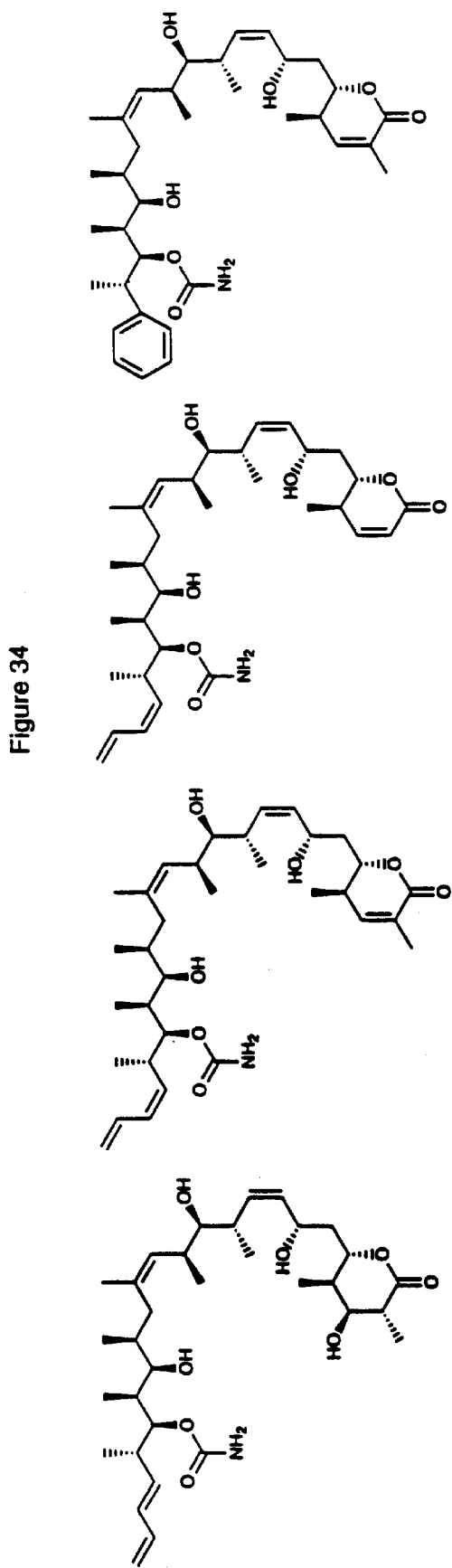
Figure 36:
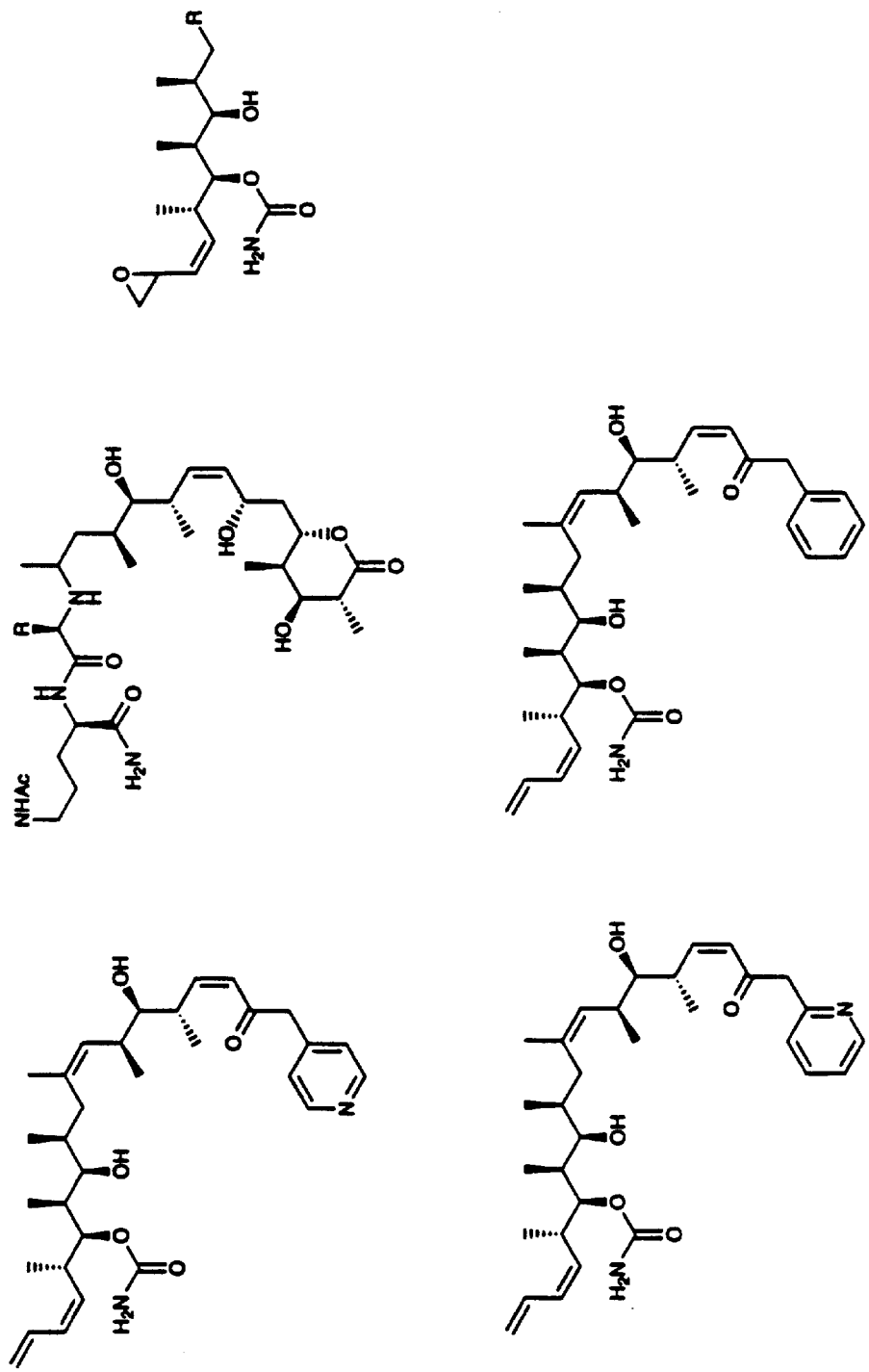

FIGS. 31 and 32

I. General Procedure For Synthesis Of Hydroxy Aldehydes 1104

A. TBS ether 1102a

A solution of bromide 1101a (see, Jacquesy, et al., *Tetrahedron* 1981, 37, 747) (20 mmol) in ether (40 mL) is added slowly to a −78° C. solution of tert-butyllitium (40 mmol, 1.7 M in pentane). After 1 h at −78° C., the cold solution is transferred to a suspension of copper (I) iodide (10 mmol) in ether at 0° C. After an additional 30 min at 0° C., a solution of benzyl (S)-(+)-glycidyl ether (9 mmol) in ether (20 mL) is added and the reaction is allowed to warm to room temperature. After 18–24 h, the reaction is quenched by the addition of tert-butyldimethylsilyl triflate (10 mmol). The reaction mixture is poured into saturated aqueous sodium bicarbonate (100 mL). The aqueous layer is separated and extracted with ether (2×50 mL). The combined organics are washed with saturated aqueous brine (50 mL), dried over magnesium sulfate and concentrated in vacuo. The residue is purified by flash chromatography to afford 1102a.

B. Alcohol 1103a.

To a solution of 1102a (6 mmol) in ethyl acetate-ethanol (8:1, 90 mL) is added palladium on carbon (10% wet, 500 mg). The mixture is stirred under hydrogen atmosphere for 3–6 h, then filtered and concentrated in vacuo. The residue is purified by flash chromatography to afford 1103a.

C. Aldehyde 1104a.

Oxalyl chloride (1.5 mmol) is added dropwise to a −78° C. solution of dimethyl sulfoxide (3 mmol) in dichloromethane (4 mL). After 15 min, a −78° C. solution of 1103a (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 1104a.

II. General Procedure For The Conversion Of 1104 To Arene Analog 1111

A. Diene 1105.

Phosphonium salt 15 (see, Smith, et al., *J. Am. Chem. Soc.* 1995, 117, 12011) (0.2 mmol) is dissolved in anhydrous tetrahydrofuran (2 mL) and chilled to 0° C. A solution of sodium bis(trimethylsilyl)amide (0.2 mmol, 1.0 M in tetrahydrofuran) is added and the reaction mixture is stirred 30 min at 0° C. After cooling to −78° C., a solution of aldehyde 1104 (0.1 mmol) in tetrahydrofuran (2 mL) is added and the mixture is stirred 10 min at −78° C. and 2 h at room temperature. Saturated aqueous ammonium chloride (2 mL) is added and the resultant mixture is extracted with ether (3×20 mL). The ethereal layer is washed with water (2×25 mL) and saturated aqueous brine (25 mL), dried over magnesium sulfate and concentrated in vacuo. The residue is purified by flash chromatography to afford 1105.

B. Hydroxy diene 1106.

A −78° C. solution of 1105 (0.05 mmol) in $CH_2Cl_2$ (5 mL) is treated with diisobutylaluminum hydride (0.5 mL, 1.0 M in toluene). The resultant solution is stirred 10 min at −78° C. and 30 min at 0° C. The reaction is quenched with a saturated solution of sodium potassium tartrate (50 mL) and the mixture is diluted with ether (60 mL). The organic layer is separated, dried over magnesium sulfate, and concentrated in vacuo. The residue is purified by flash chromatography to afford 1106.

C. Aldehyde 1107.

Oxalyl chloride (1.5 mmol) is added dropwise to a −78° C. solution of dimethyl sulfoxide (3 mmol) in dichloromethane (4 mL). After 15 min, a −78° C. solution of 1106 (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 1107.

D. Tetraene 1108.

A solution of diphenylallylphosphine (0.08 mL, 0.38 mmol) in tetrahydrofuran (2 mL) is cooled to −78° C. and tert-butyllithium (0.14 mL, 1.7 M in pentane) is added. The mixture is warmed to 0° C. for 30 min, then recooled to −78° C. and treated with titanium (IV) isopropoxide (0.30 mmol). After 30 min, aldehyde 1107 (0.30 mmol) is introduced as a solution in tetrahydrofuran (2 mL). The resultant solution is stirred at −78° C. for 15 min and at 0° C. for 1 h. Methyl iodide (0.64 mmol) is added, and the reaction is warmed to room temperature for 12 h. The reaction mixture is diluted with ether (60 mL), washed with aqueous sodium bisulfate (30 mL, 1.0 M), saturated aqueous brine (30 mL), and is dried over magnesium sulfate and concentrated in vacuo. The residue is purified by flash chromatography to afford 1108.

E. Alcohol 1109.

To a solution of 1108 (0.050 mmol) in dichloromethane (3 mL) at 0° C. is added water (50 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford 1109.

F. Carbamate 1110.

To a solution of 1109 (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford 1110.

G. Arene analog 1111.

A solution of 1110 (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 1111.

EXAMPLE 62

Synthesis of Aldehyde 67

Enone (64).

To a −78° C. solution of aldehyde 27 (1.94 g, 6.13 mmol prepared from commercially available methyl (S)-(+)-3-hydroxy-2-methyl propionate generally according to Smith, et. al., *J. Am. Chem. Soc.* 1995, 117, 12011) in $CH_2Cl_2$ (50 mL) was added (dropwise over 3 min) a −78° C. solution of $TiCl_4$ (0.68 mL, 6.18 mmol) in $CH_2Cl_2$ (6 mL). The resultant solution was stirred an additional 3 min at −78° C. 4-Methyl-2-trimethylsiloxy-1,3-pentadiene (1.89 g, 11.1 mmol, see Paterson, *Tetrahedron Lett.* 1979, 1519) was added dropwise over 2 min and the reaction mixture was further stirred at −78° C. for 2 h. A solution comprised of pH 8 phosphate buffer (100 mL) and saturated aqueous bicarbonate (50 mL) was added and the biphasic solution was warmed to ambient temperature, diluted with water (100 mL), and extracted with $CH_2Cl_2$ (2×100 mL). The combined extracts were washed with saturated brine (75 mL), dried ($MgSO_4$) and concentrated. The residual oil was diluted with $CH_2Cl_2$/hexanes (1:1, 30 mL), cooled to 0° C. and treated with trichloroacetic acid (1.54 g, 9.42 mmol). After 5 h, the reaction mixture was diluted with hexanes (75 mL) and washed with water (2×50 mL), pH 8 phosphate buffer (50 mL) and saturated brine (50 mL) and was dried ($MgSO_4$) and concentrated in vacuo. Flash chromatography (hexanes/$CH_2Cl_2$/ethyl acetate, 12:4:1) afforded 64 (1.21 g, 56%) as a colorless oil: $[\alpha]_D^{23}$ −10.6° © 0.88, $CHCl_3$); $^1H$ NMR (500 MHZ, $CDCl_3$) d 6.09 (m, 1 H), 4.78 (ddd, J=10.0, 6.6, 4.3 Hz, 1 H), 3.65 (t, J=2.8 Hz, 1 H), 2.72 (dd, J=15.8, 4.3 Hz, 1 H), 2.66 (dd, J=15.8, 6.7 Hz, 1 H), 2.62 (qd, J=7.6, 3.2 Hz, 1 H), 2.13 (d, J=1.1 Hz, 3 H), 2.07 (dqd, J=10.0, 6.8, 2.4 Hz, 1 H), 1.87 (d, J=1.2 Hz, 3 H), 1.25 (d, J=7.6 Hz, 3 H), 0.97 (d, J=6.8 Hz, 3 H), 0.87 (s, 9 H), 0.05 (s, 3 H), 0.04 (s, 3 H); $^{13}C$ NMR (125 MHZ, $CDCl_3$) d 196.9, 173.6, 156.8, 124.1, 77.8, 74.3, 47.0, 43.9, 33.6, 27.7, 25.7, 20.9, 18.0, 16.1, 13.8, −4.5, −4.7.

Alcohol (65).

A solution of enone 64 (109 mg, 0.307 mmol) in toluene (8 mL) was cooled to −95° C. and treated with K-Selectride (1.0 M in THF, 0.35 mL). After 2 h, glacial acetic acid (0.015 mL) was added and the resultant solution was warmed to ambient temperature and treated with pH 7 aqueous phosphate buffer solution (10 mL) and 30% aqueous hydrogen peroxide (0.5 mL). After 2 h, the aqueous layer was extracted with $CH_2Cl_2$ (4×20 mL) and the combined organics were dried ($MgSO_4$) and concentrated. Flash chromatography (15% ethyl acetate/hexanes) afforded 65 (70 mg, 64%) as a colorless oil: $^1H$ NMR (500 MHZ, $CDCl_3$) d 5.21 (apparent dt, J=8.6, 1.3 Hz, 1 H), 4.75 (br t, J=9.1 Hz, 1 H), 4.60 (td, J=9.9, 2.3 Hz, 1 H), 3.67 (t, J=3.0 Hz, 1 H), 2.66 (qd, J=7.5, 3.4 Hz, 1 H), 1.90 (dqd, 9.7, 6.8, 2.6 Hz, 1 H), 1.83 (ddd, J=14.5, 9.9, 2.4 Hz, 1 H), 1.71 (d, J=1.1 Hz, 3 H), 1.70 (d, J=1.2 Hz, 3 H), 1.65 (br s, 1 H), 1.60 (ddd, J=14.5, 10.1, 2.9 Hz, 1 H), 1.26 (d, J=7.6 Hz, 3 H), 0.99 (d, J=6.7 Hz, 3 H),0.89 (s, 9 H), 0.08 (s, 3 H), 0.07 (s, 3 H); $^{13}C$ NMR (125 MHZ, $CDCl_3$) d 174.0, 134.8, 127.7, 77.8, 74.2, 64.1, 43.7, 41.5, 34.6, 25.7, 25.6, 18.2, 17.9, 16.0, 13.7, −4.6, −4.8.

Silyl Ether (66).

A solution of alcohol 65 (493 mg, 1.38 mmol) and imidazole (306 mg, 4.49 mmol) in DMF (6 mL) was cooled to 0° C. and treated with tert-butyldimethylsilyl chloride (386 mg, 2.56 mmol). The resultant solution was stirred 12 h at ambient temperature, diluted with ether (75 mL), washed with water (2×15 mL) and saturated brine (15 mL), dried over MgSO$_4$, and concentrated in vacuo. Flash chromatography (5% ethyl acetate/hexanes) afforded 66 (615 mg, 95%) as a colorless oil: $^1$H NMR (500 MHZ, CDCl$_3$) d 5.11 (apparent dt, J=8.6, 1.3 Hz, 1 H), 4.71 (ddd, 10.4, 8.7, 2.2 Hz, 1 H), 5.55 (td, J 10.4, 1.7 Hz, 1 H), 3.65 (t, J=2.7 Hz, 1 H), 2.63 (qd, J=7.6, 3.0 Hz, 1 H), 1.83 (dqd, 10.0, 6.8, 2.5 Hz, 1 H), 1.74 (ddd, J=14.2, 10.5, 1.8 Hz, 1 H), 1.68 (d, J=1.1 Hz, 3 H), 1.65 (d, J=1.2 Hz, 3 H), 1.44 (ddd, J=14.2, 10.6, 2.3 Hz, 1 H), 1.26 (d, J=7.6 Hz, 3 H), 0.98 (d, J=6.7 Hz, 3 H), 0.89 (s, 9 H), 0.85 (s, 9 H), 0.07 (s, 3 H), 0.06 (s, 3 H), 0.05 (s, 3 H), 0.01 (s, 3 H);

Aldehyde (67).

A solution of olefin 66 (615 mg, 1.30 mmol) in CH$_2$Cl$_2$ (20 mL) was cooled to −78° C. and treated with a stream of ozone and oxygen until the colorless solution became steel-blue in appearance. The reaction mixture was purged with a stream of air for 10 min, followed by the cautious addition of triphenylphosphine (375 mg, 1.42 mmol). The cooling bath was removed and the solution was stirred at ambient temperature for 1 h, concentrated, and chromatographed (20% ethyl acetate/hexanes) to afford 67 (486 mg, 84%) as a colorless oil that solidified upon standing at 0° C. $^1$H NMR (500 MHZ, CDCl$_3$) d 9.67 (br s, 1 H), 4.52 (td, J=10.5, 2.1 Hz, 1 H), 4.46 (dd, J=10.5, 3.5 Hz, 1 H), 3.67 (t, J=2.3 Hz, 1 H), 2.66 (qd, J=7.6, 2.6 Hz, 1 H), 1.95–1.84 (m, 3 H), 1.77 (ddd, J=14.1, 10.5, 2.1 Hz, 1 H), 1.27 (d, J=7.6 Hz, 3 H), 0.99 (d, J=6.7 Hz, 3 H), 0.92 (s, 9 H), 0.89 (s, 9 H), 0.13 (s, 3 H), 0.11 (s, 3 H), 0.08 (s, 3 H), 0.07 (s, 3 H); $^{13}$C NMR (125 MHZ, CDCl$_3$) d 203.2, 173.1, 76.0, 74.7, 73.7, 44.2, 36.2, 34.1, 25.72, 25.66, 18.1, 17.9, 16.5, 14.0, −4.55, −4.63, −4.9, −5.2.

EXAMPLE 63

Synthesis of Phosphonium Salt (49) Employing Ultrahigh Pressure

Iodine (132 mg, 0.52 mmol) was added in one portion to a vigorously stirred solution of alcohol 40 (122 mg, 0.176 mmol, prepared from commercially available methyl (S)-(+)-3-hydroxy-2-methyl propionate generally according to Smith, et. al., *J. Am. Chem. Soc.* 1995, 117, 12011), PPh$_3$ (172 mg, 0.656 mmol) and imidazole (42 mg, 0.62 mmol) in benzene/ether (1:2, 1.5 mL) at 0° C. The resultant solution was stirred 1 h at 0° C. and 1 h at ambient temperature. The mixture was diluted with ether (10 mL), washed with saturated aqueous sodium metabisulfite (5 mL) and brine (10 mL), dried over MgSO$_4$, filtered and concentrated. Flash chromatography afforded a colorless oil (147 mg, 100 % yield). This material was combined with diisopropylethylamine (0.016 mL, 0.091 mmol), triphenylphosphine (152 mg, 0.58 mmol) and benzene/toluene (7:3, 1.0 mL) in a plastic syringe and subjected to a pressure of 12.8 Kbar. After 6 days, the reaction mixture was concentrated and chromatographed (10% MeCN/CHCl$_3$) to provide 49 [138 mg, 74% yield from 40] as a pale yellow foam: $^1$H NMR (500 MHZ, CDCl$_3$; concentration-dependent) d 7.82–7.76 (m, 15 H), 7.35 (d, J=8.8 Hz, 2 H), 6.84 (d, J=8.8 Hz, 2 H), 5.35 (s, 1 H), 5.30 (d, J=10.5 Hz, 1 H), 4.07 (dd, J=11.2, 4.7 Hz, 1 H), 3.77 (s, 3 H), 3.73–3.67 (m, 2 H), 3.56 (dd, J=7.0, 1.8 Hz, 1 H), 3.48 (dd, J=9.8, 1.7 Hz, 1 H), 3.46 (apparent t, J=11.1 Hz, 1 H), 3.31 (ddd, J=15.6, 11.2, 11.2 Hz, 1 H), 2.49 (ddq, J=10.5, 6.4, 6.4 Hz, 1 H), 2.25 (apparent t, J=12.1 Hz, 1 H), 2.10–1.92 (m, 3 H), 1.85 (dqd, J=7.1, 7.1, 1.8 Hz, 1 H), 1.57–1.52 (m, 1 H), 1.56 (s, 3 H), 0.98 (d, J=7.1 Hz, 3 H), 0.89 (d, J=6.6 Hz, 3 H), 0.852 (s, 9 H), 0.849 (s, 9 H), 0.72–0.71 (m, 3 H), 0.71 (d, J=6.6 Hz, 3 H), 0.69 (d, J=6.9 Hz, 3 H), 0.10 (s, 3 H), −0.02 (s, 3 H), −0.03 (s, 3 H), −0.07 (s, 3 H); $^{13}$C NMR (125 MHZ, CDCl$_3$) d 159.8, 135.2 (d, J$_{CP}$=2.6 Hz), 133.5 (d, J$_{CP}$=10.0 Hz), 132.9, 131.4, 130.6 (d, J$_{CP}$=12.6 Hz), 130.3, 127.3, 118.4 (d, J$_{CP}$=85.5 Hz), 113.4, 101.0, 83.2, 80.1 (d, J$_{CP}$=14.0 Hz), 78.3, 73.2, 55.3, 38.1, 37.4, 36.0, 33.7 (d, J$_{CP}$=4.4 Hz), 33.6, 30.7, 26.1, 25.5 (d, J$_{CP}$=49.7 Hz), 22.9, 18.33, 18.29, 17.2, 17.1, 12.5, 12.1, 10.9, −3.2, −3.6, −3.7, −4.0; high resolution mass spectrum (FAB, NBA) m/z 937.5708 [(M-I)$^+$; calcd for C$_{57}$H$_{86}$O$_5$PSi$_2$: 937.5751].

EXAMPLE 64

Synthesis of Diene (76)

Phosphonium salt 49 (166 mg, 0.156 mmol), was heated to 50° C. under vacuum (0.1 torr) for 18 h, dissolved in 0.8 mL of toluene, and cooled to 0° C. The resultant solution was treated with potassium bis(trimethylsilyl)amide (0.5 M in toluene, 0.32 mL), was stirred 20 min at 0° C. and 20 min at ambient temperature and re-chilled to −78° C. To this reaction mixture was transferred via cannula a solution of aldehyde 67 (58 mg, 0.13 mmol) in toluene (0.3 mL+2×0.2 mL rinse). The resultant solution was allowed to slowly warm to −20° C. during 1 h. A solution of pH 7 phosphate buffer was added and the biphasic solution was warmed to ambient temperature and extracted with CH$_2$Cl$_2$ (4×20 mL). The combined organics were dried (MgSO$_4$), concentrated, and chromatographed (10% ethyl acetate/hexanes) to afford 76 (83 mg, 57%) as a colorless oil that solidified upon standing: [α]$_D^{23}$ +32.1° © 0.68, CHCl$_3$); $^1$H NMR (500 MHZ, CDCl$_3$) d 6.97 (br d, J=8.7 Hz, 2 H), 6.87 (br d, J=8.7 Hz, 2 H), 5.34 (s, 1 H), 5.29 (dd, J=11.1, 7.8 Hz, 1 H), 5.19 (t, J=10.6 Hz, 1 H), 5.07 (d, J=10.0 Hz, 1 H), 4.78 (br t, J=9.1 Hz, 1 H), 4.52 (br t, J=10.0 Hz, 1 H), 4.10 (dd, J=11.1, 4.6 Hz, 1 H), 3.80 (s, 3 H), 3.64 (m, 2 H), 3.54–3.46 (m, 2 H), 3.25 (t, J=5.3 Hz, 1 H), 2.65–2.57 (m, 2 H), 2.51 (m, 1 H), 2.31 (t, J=12.2 Hz, 1 H), 2.06 (m, 1 H), 1.96 (m, 1 H), 1.90 (dqd, J=7.1, 7.0, 1.5 Hz, 1 H), 1.78 (ddd, J=10.3, 6.6, 2.1 Hz, 1 H), 1.72 (ddd, J=14.0, 11.0, 1.5 Hz, 1 H), 1.67 (br d, J=11.6 Hz, 1 H), 1.56 (m, 1 H), 1.55 (s, 3 H), 1.20 (d, J=7.6 Hz, 3 H), 1.02 (d, J=7.1 Hz, 3 H), 0.92 (s, 9 H), 0.91 (s, 9 H), 0.90 (d, J=7.0 Hz, 3 H), 0.96 (d, J=6.8 Hz, 3 H), 0.95 (d, J=6.7 Hz, 3 H), 0.89 (s, 9 H), 0.87 (s, 9 H), 0.75 (d, J=6.9 Hz, 3 H), 0.74 (d, J=6.7 Hz, 3 H), 0.073 (s, 3 H), 0.071 (s, 3 H), 0.06 (s, 6 H), 0.05 (s, 6 H), 0.01 (s, 3 H), 0.00 (s, 3 H); $^{13}$C NMR (125 MHZ, CDCl$_3$) d 173.2, 159.8, 133.6, 132.4, 131.9, 131.5, 131.4, 127.3, 113.4, 101.0, 83.4, 80.4, 78.4, 76.9, 74.9, 73.3, 64.7, 55.2, 44.1, 42.7, 38.0, 37.4, 35.2, 34.2, 34.0, 30.8, 26.3, 26.2, 25.9, 25.7, 23.2, 18.43, 18.39, 18.1, 17.9, 17.1, 16.4, 16.2, 14.0, 12.8, 12.1, 10.8, −2.9, −3.5, −3.8, −4.37, −4.41, −4.5, −4.87, −4.88. Recrystallization from hexanes afforded fine needles: mp 117–119° C.

EXAMPLE 65

Synthesis of Aldehyde (77)

A solution of acetal 76 (20 mg, 0.018 mmol) in CH$_2$Cl$_2$ (2 mL) was cooled to −78° C. and diisobutylaluminum hydride (1.0 M in toluene, 0.18 mL, 0.18 mmol) was added over 5 min. After an additional 10 min at −78° C. and 30 min at 0° C., the reaction was quenched with saturated aqueous potassium sodium tartrate (0.5 mL). The mixture was then diluted with ether (20 mL), washed with saturated aqueous potassium sodium tartrate and brine (10 mL each), dried over MgSO$_4$, filtered and concentrated. Flash chromatography (10% ethyl acetate/hexanes) provided an epimeric mixture of hydroxy-lactols (14.7 mg, 74% yield) as a colorless oil. The mixture of lactols (14.7 mg, 0.0133 mmol) in CH$_2$Cl$_2$ (2 mL) was cooled to 0° C. and treated with pyridinium dichromate (26 mg, 0.069 mmol). The reaction mixture was stirred 12 h at ambient temperature, diluted with ethyl acetate (10 mL), filtered (Celite) and concentrated. Flash chromatography (10% ethyl acetate/hexanes) afforded 77 (12.4 mg, 62% from 76) as a colorless oil: $^1$H NMR (500 MHZ, CDCl$_3$) d 9.80 (d, J=2.4 Hz, 1 H), 7.22 (br d, J=8.6 Hz, 2 H), 6.86 (br d, J=8.6 Hz, 2 H), 5.30 (dd, J=11.1, 7.9 Hz, 1 H), 5.20 (dd, J=10.9, 10.1 Hz, 1 H), 5.11 (d, J=10.0 Hz, 1 H), 4.79 (apparent t, J=9.2 Hz, 1 H), 4.52 (br t, J=9.6 Hz, 1 H), 4.47 (s, 2 H), 3.80 (s, 3 H), 3.62 (t, J=2.5 Hz, 1 H), 3.59 (m, 2 H), 3.26 (t, J=5.3 Hz, 1 H), 2.75 (m, 1 H), 2.62 (m, 2 H), 2.50 (m, 1 H), 2.24 (t, J=12.4 Hz, 1 H), 1.99–1.88 (m, 2 H), 1.83–1.65 (m, 3 H), 1.59 (s, 3 H), 1.58 (m, 1 H), 1.21 (d, J=7.6 Hz, 3 H), 1.13 (d, J=7.0 Hz, 3 H), 1.04 (d, J=7.0 Hz, 3 H), 0.96 (d, J=6.8 Hz, 3 H), 0.95 (d, J=6.9 Hz, 3 H), 0.94 (s, 9H), 0.91 (s, 9 H), 0.89 (d, J=6.9 Hz, 3 H), 0.88 (s, 9 H), 0.87 (s, 9 H), 0.75 (d, J=6.8 Hz, 3 H), 0.09 (s, 3 H), 0.08 (s, 3 H), 0.07 (s, 3 H), 0.06 (s, 6 H), 0.05 (s, 6 H), 0.01 (s, 3 H); $^{13}$C NMR (125 MHZ, CDCl$_3$) d 204.5, 173.2, 159.3, 133.5, 132.5, 132.3, 130.8, 130.3, 129.1, 113.8, 82.6, 80.4, 76.9, 74.9, 74.4, 64.6, 55.3, 49.5, 44.1, 42.7, 40.3, 37.4, 36.8, 35.2, 35.0, 34.2, 26.3, 26.2, 25.9, 25.7, 23.1, 18.5, 18.4, 18.1, 17.9, 17.1, 16.4, 16.2, 14.1, 13.4, 12.2, 11.4, −3.0, −3.3, −3.4, −4.3, −4.4, −4.5, −4.9.

EXAMPLE 66

Synthesis of Tetraene (58)

Method A.

A solution of allyldiphenylphosphine (0.0035 mL, 0.0162 mmol) in anhydrous THF was cooled to −78° C. and t-BuLi (1.7 M in pentane, 0.010 mL, 0.017 mmol) was added. The mixture was stirred at 0° C. for 30 min, recooled to −78° C. and treated Ti(OiPr)$_4$ (0.005 mL, 0.017 mmol). After 30 min, a cold (−78° C.) solution of the aldehyde 77 (3.5 mg, 0.0032 mmol) in THF (0.25 mL+0.25 mL rinse) was introduced via cannula, and the mixture was stirred 10 min further at −78° C. and at 0° C. for 30 min. Methyl Iodide (0.0025 mL, 0.04 mmol) was then added, and the reaction was warmed to room temperature and stirred overnight. The reaction mixture was diluted with ether (10 mL), washed with 1.0 M aqueous NaHSO$_4$ and brine (5 mL each), dried over MgSO$_4$, filtered and concentrated in vacuo. Flash chromatography (2% ethyl acetate/hexane) gave a 1.2:1 mixture of Z/E isomers (2.1 mg, 58%) as an oil. Pipette flash chromatography on 10% silver nitrate-silica gel (5% ether/hexanes) furnished the Z-olefin 58 as a colorless oil: $^1$H NMR (500 MHZ, CDCl$_3$) d 7.25 (d, J=8.2 Hz, 2 H), 6.84 (d, J=8.7 Hz, 2 H), 6.57 (dddd, J=16.8, 11.0, 11.0, 0.7 Hz, 1 H), 6.00 (apparent t, J=11.1 Hz, 1 H), 5.55 (apparent t, J=10.5 Hz, 1 H), 5.26 (dd, J=11.2, 7.8 Hz, 1 H), 5.20–5.16 (m, 2 H), 5.09 (d, J=10.1 Hz, 1 H), 5. 05 (d, J=2.2 Hz, 1 H), 5.03 (d, J=10.0 Hz, 1 H), 4.67 (apparent t, J=9.1 Hz, 1 H), 4.49 (AB$_q$, J=10.6 Hz, Δv$_{AB}$=41.3 Hz, 2 H), 3.78 (s, 3 H), 3.68 (apparent t, J=10.2 Hz, 1 H), 3.52 (apparent t, J=2.6 Hz, 1 H), 3.43 (dd, J=4.8, 3.9 Hz, 1 H), 3.24–3.21 (m, 2 H), 3.01–2.94 (m, 1 H), 2.67 (dq, J=12.8, 7.4 Hz, 1 H), 2.61 (dq, J=12.8, 7.5 Hz, 1 H), 2.71–2.57 (m, 1 H), 2.46–2.39 (m, 1 H), 2.00 (apparent t, J=12.4 Hz, 1 H), 1.83–1.73 (m, 3 H), 1.64 (br d, J=14.0 Hz, 1 H), 1.62–1.52 (m, 2 H), 1.55 (d, J=0.5 Hz, 3 H), 1.36 (ddd, J=13.7, 10.8, 1.5 Hz, 1 H), 1.26 (d, J=7.4 Hz, 3 H), 1.25 (d, J=7.4 Hz, 3 H), 1.08 (d, J=6.8 Hz, 3 H), 0.98 (d, J=6.8 Hz, 3 H), 0.94 (d, J=7.1 Hz, 3 H), 0.93 (s, 9 H), 0.90 (s, 9 H), 0.89 (s, 9 H), 0.89–0.86 (m, 3 H), 0.86 (s, 9 H), 0.73 (d, J=6.8 Hz, 3 H), 0.70 (d, J=6.7 Hz, 3 H), 0.08 (s, 6 H), 0.05 (s, 3 H), 0.02 (s, 3 H), 0.013 (s, 3 H), 0.010 (S, 6 H), −0.02 (s, 3 H); $^{13}$C NMR (125 MHZ, CDCl$_3$) d 159.1, 134.5, 134.3, 132.2, 131.9, 131.8, 131.2, 129.13, 129.07, 117.6, 113.7, 84.6, 80.9, 80.5, 76.5, 75.0, 74.2, 65.5, 55.3, 42.5, 41.9, 40.2, 37.2, 36.1, 35.4, 35.3, 34.5, 29.7, 26.3, 26.0, 25.9, 25.1, 23.1, 18.7, 18.6, 18.5, 18.14, 18.09, 17.0, 16.8, 15.6, 14.8, 14.4, 11.6, 10.6, −2.8, −3.2, −3.3, −3.6, −4.2, −4.5, −4.90, −4.93; high resolution mass spectrum (FAB, NBA) m/z 1195.8001 [(M+Na)$^+$; calcd for C$_{66}$H$_{124}$O$_7$SSi$_4$Na: 1195.8042].

Method B.

A vigorously stirred suspension of chromium(III) chloride (7.8 mg, 0.048 mmol) in anhydrous THF (0.6 mL) was cooled to 0° C. and treated with lithium aluminum hydride (1.0 M in ether, 0.022 mL, 0.022 mmol). The resultant solution was stirred 20 min at room temperature and re-cooled to 0° C. Aldehyde 77 (3.9 mg, 0.035 mmol) was added in THF (0.4 mL). After 10 min, a mixture of 3-bromo-1-trimethylsilyl-1-propene and 3-bromo-3-trimethlsilyl-1-propene (3:1, 0.002 mL, 0.01 mmol, see, Hodgson, et. al., Tetrahedron Lett. 1992, 33, 4761) was added. The reaction mixture was stirred at ambient temperature for 12 h and then diluted with hexanes-ethyl acetate (9:1), washed with water, saturated aqueous sodium bicarbonate and brine, dried over MgSO$_4$ and concentrated. Flash chromatography afforded a 2.8:1 mixture of hydroxy silanes (3.8 mg, 89%). The mixture was dissolved in THF (0.6 mL), cooled to 0° C. and treated with potassium bis(trimethylsilyl)amide (0.5 M in toluene, 0.068 mL, 0.34 mmol). After 15 min, trichloroacetic acid (5 mg, 0.03 mmol) was added and the reaction mixture was diluted with hexanes and washed with water and brine. The combined aqueous washings were further extracted with hexanes. The combine organics were dried over MgSO$_4$ and concentrated in vacuo. Flash Chromatography afforded (2.6 mg, 65% yield for 2 steps) of tetraene 58 as a colorless oil.

Method C.

Phosphonium salt 75 (120 mg, 0.11 mmol) was heated to 50° C. under vacuum (0.1 torr) for 18 h and dissolved in 0.4 mL of anhydrous toluene. The resultant solution was cooled to 0° C. and was treated with potassium bis(trimethylsilyl) amide (0.5 M in toluene, 0.23 mL, 0.115 mmol). The resultant solution was stirred 20 min at 0° C. and 20 min at ambient temperature before being chilled to −78° C. Aldehyde 67(46 mg, 0.10 mmol) was added in toluene (0.4 mL) and the reaction mixture was allowed to warm to 0° C. during 2.5 h. The reaction was partitioned between hexanes (10 mL) and pH 7 phosphate buffer solution(10 ml). The aqueous layer was extracted with CH$_2$Cl$_2$ (4×15 mL) and the combined organics were dried over MgSO$_4$ and concentrated. Flash chromatography afforded tetraene 58 (49 mg, 42% yield).

EXAMPLE 67

Synthesis of Alcohol (71)

A solution of (+)-39 (106 mg, 0.13 mmol, prepared from commercially available methyl (S)-(+)-3-hydroxy-2-methyl propionate generally as described by Smith, et. al., J. Am. Chem. Soc. 1995, 117, 12011)) in CH$_2$Cl$_2$ was cooled to 0°

C. and treated with neat diisobutylaluminum hydride (0.15 mL, 0.84 mmol). After 1 h, a solution of saturated aqueous potassium sodium tartrate (10 mL) was added (dropwise until cessation of hydrogen evolution) and the resultant biphasic mixture was stirred 4 h at ambient temperature. The aqueous layer was extracted with $CH_2Cl_2$ (3×10 mL) and the combined organics were dried over $MgSO_4$ and concentrated in vacuo. Flash chromatography (15% ethyl acetate/hexanes) afforded alcohol 71 (88 mg, 83%) as a colorless oil: $^1H$ NMR (500 MHZ, $CDCl_3$) d 7.26–7.20 (m, 4 H), 6.87–6.82 (m, 4 H), 5.03 (br d, J=10.2 Hz, 1 H), 4.50 ($AB_q$, J=10.5 Hz, Dv=12.1 Hz, 2 H), 4.37 ($AB_q$, J=11.6 Hz, Dv=14.2 Hz, 2 H), 3.78 (s, 3 H), 3.77 (s, 3 H), 3.74 (m, 1 H), 3.57 (quintet, J=10.5 Hz, 1 H), 3.51 (dd, J=5.1, 3.7 Hz, 1 H), 3.47 (dd, J=9.1, 4.9 Hz, 1 H), 3.38 (dd, J=6.0, 4.6 Hz, 1 H), 3.35 (t, J=5.5 Hz, 1 H), 3.20 (t, dd, J=8.9, 8.6 Hz, 1 H), 2.68 (br t, J=5.5 Hz, 1 H), 2.51 (m, 1 H), 2.22 (br t, J=12.4 Hz, 1 H), 2.00–1.84 (m, 4 H), 1.74 (br d, J=12.5 Hz, 1 H), 1.58 (d, J=0.9 Hz, 3 H), 1.04 (d, J=7.3 Hz, 3 H), 1.02 (d, J=7.2 Hz, 3 H), 0.93 (d, J=7.0 Hz, 3 H), 0.92 (s, 9 H), 0.88 (d, J=6.9 Hz, 3 H), 0.87 (s, 9 H), 0.07 (s, 3 H), 0.06 (s, 3 H), 0.02 (s, 3 H), 0.1 (s, 3 H); $^{13}C$ NMR (125 MHZ, $CDCl_3$) d 159.4, 159.0, 131.64, 131.60, 131.0, 130.4, 129.3, 129.0, 113.9, 113.7, 86.2, 78.4, 77.5, 75.2, 72.7, 72.6, 65.4, 55.3, 39.9, 38.7, 37.5, 36.7, 35.7, 35.2, 26.2, 26.1, 23.1, 18.5, 18.4, 17.0, 15.7, 14.6, 13.7, 11.4, −3.3, −3.4, −3.9.

EXAMPLE 68

Synthesis of Aldehyde (72)

A solution of alcohol 71(88 mg, 0.108 mmol) and triethylamine (0.075 mL, 0.54 mmol) in $CH_2Cl_2$ (2 mL) and dimethylsulfoxide (1 mL) was treated with sulfur trioxide-pyridine (55 mg, 0.34 mmol). After 90 min, the mixture was diluted with ether (30 mL), washed with water (10 mL), aqueous $NaHSO_4$ (0.1 M, 10 mL) and brine (10 mL), dried over $MgSO_4$, filtered and concentrated. Flash chromatography (5% ethyl acetate/hexanes) afforded 72 (84 mg, 96% yield) as a colorless oil: $^1H$ NMR (500 MHZ, $CDCl_3$) d 9.79 (d, J=2.4 Hz, 1 H), 7.24–7.18 (m, 4 H), 6.87–6.82 (m, 4 H), 5.03 (br d, J=10.2 Hz, 1 H), 4.46 ($AB_q$, J=10.8 Hz, Dv=7.1 Hz, 2 H), 4.37 ($AB_q$, J=11.6 Hz, Dv=14.0 Hz, 2 H), 3.78 (s, 3 H), 3.77 (s, 3 H), 3.57 (m, 2 H), 3.47 (dd, J=9.1, 5.0 Hz, 1 H), 3.39 (dd, J=5.9, 4.7 Hz, 1 H), 3.21 (t, J=8.7 Hz, 1 H), 2.73 (m, 1 H), 2.51 (m, 1 H), 2.25 (t, J=12.4 Hz, 1 H), 1.99–1.86 (m, 3 H), 1.70 (br d, J=12.4 Hz, 1 H), 1.58 (s, 3 H), 1.12 (d, J=7.0 Hz, 3 H), 1.03 (d, J=7.0 Hz, 3 H), 0.93 (d, J=7.0 Hz, 3 H), 0.92 (s, 9 H), 0.88 (d, J=6.9 Hz, 3 H), 0.87 (s, 9 H), 0.74 (d, J=6.8 Hz, 3 H), 0.07 (s, 3 H), 0.06 (s, 3 H), 0.02 (s, 3 H), 0.01 (s, 3 H); $^{13}C$ NMR (125 MHZ, $CDCl_3$) d 204.5, 159.3, 159.0, 131.7, 131.5, 131.0, 130.3, 129.1, 129.0, 113.8, 113.7, 82.6, 78.4, 77.2, 74.4, 72.7, 72.5, 55.25, 55.24, 49.5, 40.3, 38.7, 36.7, 35.7, 35.0, 26.2, 26.1, 23.1, 18.5, 18.4, 17.0, 14.6, 13.4, 12.2, 11.4, −3.3, −3.4, −3.89, −3.91.

EXAMPLE 69

Synthesis of Triene (73)

A solution lithium aluminum hydride (1.0 M in ether, 0.022 mL, 0.022 mmol).was added dropwise to a vigorously stirred suspension of chromium(III) chloride (40 mg, 0.25 mmol) in anhydrous THF (2 mL) at 0° C. The resultant solution was stirred 45 min at room temperature and re-cooled to 0° C. Aldehyde 72 (50 mg, 0.061 mmol) was added in THF (3 mL) via cannula. After 10 min, a mixture of 3-bromo-1-trimethylsilyl-1-propene and 3-bromo-3-trimethlsilyl-1-propene (3:1, 0.025 mL, 0.13 mmol) was added. The reaction mixture was further stirred 30 min at 0° C. and at ambient temperature for 12 h. Methanol (1 mL) and aqueous potassium hydroxide solution (6 M, 2 mL) were added and the resultant solution was stirred 1 h. at ambient temperature. The aqueous layer was extracted with hexanes (3×15 mL). The combined organics were washed with brine, dried over $MgSO_4$ and concentrated. Flash chromatography provided triene 73 (47 mg, 92%) as a single geometric isomer: $^1H$ NMR (500 MHZ, $CDCl_3$) d 7.27–7.20 (m, 4 H), 6.87–6.82 (m, 4 H), 6.57 (dt, J=16.8, 10.4 Hz, 1 H), 6.00 (t, J=11.0 Hz, 1 H), 5.55 (t, J=10.5 Hz, 1 H), 5.18 (dd, J 16.8, 1.6 Hz, 1 H), 5.09 (d, J 10.1 Hz, 1 H), 4.96 (d, J=10.2 Hz, 1 H), 4.50 ($AB_q$, J=10.6 Hz, Dv=43.6 Hz, 2 H), 4.36 ($AB_q$, J=11.6 Hz, Dv=16.9 Hz, 2 H), 3.78 (s, 3 H), 3.77 (s, 3 H), 3.44 (m, 2 H), 3.36 (dd, J=6.4, 4.4 Hz, 1 H), 3.24 (dd, J=7.4, 3.7 Hz, 1 H), 3.19 (t, J=8.8 Hz, 1 H), 2.98 (m, 1 H), 2.44 (m, 1 H), 2.03 (t, J=12.4 Hz, 1 H), 1.95 (m, 1 H), 1.84–1.72 (m, 2 H), 1.65 (br d, J=11.4 Hz, 1 H), 1.52 (s, 3 H), 1.09 (d, J=6.8 Hz, 3 H), 0.99 (d, J=6.9 Hz, 3 H), 0.93 (s, 9 H), 0.91 (d, J=7.0 Hz, 3 H), 0.87 (s, 9 H), 0.85 (d, J=6.6 Hz, 3 H), 0.70 (d, J=6.7 Hz, 3 H), 0.09 (s, 3 H), 0.08 (s, 3 H), 0.01 (s, 6 H); $^{13}C$ NMR (125 MHZ, $CDCl_3$) d 159.1, 159.0, 134.5, 132.2, 131.8, 131.2, 131.1, 129.1, 129.0, 117.6, 113.7, 84.6, 78.4, 77.2, 75.0, 72.7, 72.5, 55.3, 40.1, 38.9, 36.1, 35.5, 35.4, 26.3, 26.1, 23.0, 18.7, 18.6, 18.4, 17.2, 14.7, 14.4, 10.6, −3.2, −3.3, −3.89, −3.92.

EXAMPLE 70

Synthesis of Alcohol (74)

Method A:

Bis-ether 73 is dissolved in a mixture of $CH_2Cl_2$ and water (19:1) and cooled to 0° C. 2,3-Dichloro-5,6-dicyano-1,4-benzoquinone (1 eq) is added and the resultant solution is stirred 2 h at 0° C. The reaction mixture is diluted with hexanes and washed with aqueous sodium hydroxide solution, dried over $MgSO_4$ and concentrated. Flash chromatography affords 74.

Method B:

A solution of 73 and ethanethiol in $CH_2Cl_2$ is cooled to −78° C. and treated with a Lewis acid (e.g. magnesium bromide, borontrifluoride etherate, tin(IV) chloride, titanium (IV) chloride, etc.). The resultant solution is allowed to slowly warm until reaction ensues. The reaction is then quenched with aqueous sodium hydroxide solution, washed with water and brine, dried over $MgSO_4$, concentrated and chromatographed to afford 74: $^1H$ NMR (500 MHZ, $CDCl_3$) d 7.27 (br d, J=8.6 Hz, 2 H), 6.87 (br d, J=8.6 Hz, 2 H), 6.60 (dt, J=16.8, 10.5 Hz, 1 H), 6.04 (t, J=11.0 Hz, 1 H), 5.57 (t, J=10.5 Hz, 1 H), 5.55 (dd, J=16.8, 1.8 Hz, 1 H), 5.12 (d, J=10.3 Hz, 1 H), 4.97 (d, J=10.2 Hz, 1 H), 4.51 ($AB_{quartet}$, J=10.6 Hz, Dv=47.6 Hz, 2 H), 3.80 (s, 3 H), 3.66 (dt, J=10.9, 4.3 Hz, 1 H), 3.50 (m, 1 H), 3.44 (dd, J=4.8, 4.0 Hz, 1 H), 3.39 (dd, 6.9, 3.8 Hz, 1 H), 3.25 (dd, J=7.4, 3.7 Hz, 1 H), 3.00 (m, 1 H), 2.54 (m, 1 H), 2.31 (br t, J=5.5 Hz, OH), 2.05 (t, J=12.4 Hz, 1 H), 1.85–1.73 (m, 3 H), 1.67 (br d, J=13.4 Hz, 1 H), 1,56 (s, 3 H), 1.11 (d, J=6.8 Hz, 3 H), 1.00 (d, J=7.0 Hz, 3 H), 0.99 (d, J=7.0 Hz, 3 H), 0.95 (s, 9 H), 0.92 (s, 9 H), 0.91 (d, =6.6 Hz, 3 H), 0.72 (d, J=6.7 Hz, 3 H), 0.10 (s, 9 H), 0.07 (s, 3 H).

EXAMPLE 71

Synthesis of Phosphonium Salt (75)

Iodine (127 mg, 0.50 mmol) was added in one portion to a vigorously stirred solution of alcohol 74 (120 mg, 0.167 mmol), triphenylphosphine (156 mg, 0.595 mmol), and imidazole (40 mg, 0.59 mmol) in benzene/ether (1:1) at −10° C. The resultant solution was stirred 30 min at −10° C. and 30 min at ambient temperature, was diluted with 30 mL hexanes and was washed with water (2×10 mL), saturated aqueous sodium metabisulfite (10 mL), saturated aqueous sodium bicarbonate (10 mL) and saturated brine (10 mL), dried over $MgSO_4$ and concentrated. Flash chromatography (2% ether/hexanes) provided a colorless oil. The oil was combined with diisopropylethylamine (0.015 mL, 0.086 mmol), triphenylphosphine (199 mg, 0.758 mmol), and benzene/toluene (7:3, 1.0 mL) in a plastic syringe and was subjected to a pressure of 12.8 Kbar. After 16 days, the reaction mixture was concentrated and chromatographed (10% acetonitrile/chloroform) to afford phosphonium salt 75 (126 mg, 76% for two steps) as a pale yellow film: $^1$H NMR (500 MHZ, $CDCl_3$) d 8.84–7.65 (m, 15 H), 7.27 (br d, J=8.6 Hz, 2 H), 6.87 (br d, J=8.6 Hz, 2 H), 6.54 (dt, J=16.8, 10.5 Hz, 1 H), 5,89 (t, J=11.0 Hz, 1 H), 5.51 (t, J=10.5 Hz, 1 H), 5.30 (d, J=10.5 Hz, 1 H), 5.21 (d, J=16.8, 1 H), 5.08 (d, J=10.2 Hz, 1 H), 4.51 ($AB_q$, J=10.4 Hz, Dv=55.6 Hz, 2 H), 3.78 (s, 3 H), 3.76–3.68 (m, 2 H), 3.42 (dd, J=5.4, 3.1 Hz, 1 H), 3.25–3.17 (m, 2 H), 2.97 (m, 1 H), 2.41 (m, 1 H), 2.06 (m, 1 H), 1.95 (t, J=12.3 Hz, 1 H), 1.77–1.72 (m, 2 H), 1.58 (br d, J=11.9 Hz, 1 H), 1.53 (s, 3 H), 1.10 (d, J=6.8 Hz, 3 H), 0.96 (d, J=6.8 Hz, 3 H), 0.91 (s, 9 H), 0.89 (d, J=7.0 Hz, 3 H), 0.86 (s, 9 H), 0.69 (d, J=6.9 Hz, 3 H), 0.66 (d, J=6.7 Hz, 3 H), 0.09 (s, 3 H), 0.08 (s, 3 H), 0.04 (s, 3 H), −0.05 (s, 3 H).

EXAMPLE 72

Synthesis of Alcohol (+)-59

At 0° C., a solution of PMB ether (+)-58 (4.0 mg, 3.55 mmol) in $CH_2Cl_2$ (0.5 mL) was treated with $H_2O$ (50 mL) and DDQ (3.0 mg, 13.2 mmol). The mixture was stirred for 1 h and then diluted with ethyl acetate (30 mL), washed with brine (3×30 mL), dried over $MgSO_4$, filtered and concentrated. Pipette flash chromatography (2% ethyl acetate/hexanes) provided 59 (3.4 mg, 95% yield) as a colorless oil: $^1$H NMR (500 MHZ, $CDCl_3$) d 6.61 (ddd, J=16.8, 10.9, 10.9 Hz, 1 H), 6.13 (apparent t, J=11.0 Hz, 1 H), 5.32 (apparent t, J=10.5 Hz, 1 H), 5.28 (dd, J=11.1, 7.9 Hz, 1 H), 5.24–5.21 (m, 1 H), 5.19 (apparent t, J=10.3 Hz, 1 H), 5.14 (d, J=10.2 Hz, 1 H), 5.06 (d, J=10.0 Hz, 1 H), 4.76 (apparent t, J=9.3 Hz, 1 H), 4.50 (apparent t, J=9.9 Hz, 1 H), 3.62 (apparent t, J=2.4 Hz, 1 H), 3.60 (dd, J=5.5, 3.4 Hz, 1 H), 3.32 (br d, J=5.3 Hz, 1 H), 3.24 (apparent t, J=5.1 Hz, 1 H), 2.79 (ddq, J=9.9, 6.7, 6.7 Hz, 1 H), 2.60 (qd, J=7.6, 2.7 Hz, 1 H), 2.63–2.57 (m, 1 H), 2.50–2.45 (m, 1 H), 2.16 (apparent t, J=12.3 Hz, 1 H), 1.90–1.77 (m, 3 H), 1.75–1.69 (m, 2 H), 1.57 (s, 3 H), 1.60–1.50 (m, 1 H), 1.20 (d, J=7.6 Hz, 3 H), 0.96 (d, J=6.8 Hz, 3 H), 0.95 (d, J=6.6 Hz, 3 H), 0.95–0.93 (m, 6 H), 0.91 (s, 9 H), 0.89 (s, 9 H), 0.89–0.84 (m, 3 H), 0.87 (s, 9 H), 0.85 (s, 9 H), 0.73 (d, J=6.8 Hz, 3 H), 0.07 (apparent s, 6 H), 0.052 (s, 3 H), 0.051 (s, 3 H), 0.04 (apparent s, 6 H), 0.03 (s, 3 H), −0.01 (s, 3 H); $^{13}$C NMR (125 MHZ, $CDCl_3$) d 173.3, 134.7, 133.5, 132.5, 132.1, 132.0, 131.5, 131.0, 118.4, 80.5, 78.8, 76.4, 74.9, 64.7, 44.1, 42.7, 38.0, 37.4, 36.3, 36.1, 35.2, 35.1, 34.2, 26.3, 26.2, 25.9, 25.7, 23.2, 18.5, 18.1, 18.0, 17.3, 17.2, 16.4, 16.1, 14.1, 13.7, 9.4, −3.0, −3.3, −3.6, −4.34, −4.36, −4.5, −4.8; high resolution mass spectrum (FAB, NBA) m/z 1029.7273 [(M+Na)$^+$; calcd for $C_{56}H_{110}O_7Si_4Na$: 1029.7226].

EXAMPLE 73

Synthesis of Carbamate (+)-60

A solution of alcohol 59 (2.2 mg, 2.19 mmol) in $CH_2Cl_2$ (0.5 mL) was treated with trichloroacetyl isocyanate (20 mL, 0.17 mmol) at room temperature for 30 min. $CH_2Cl_2$ (2.0 mL) and neutral alumina (500 mg) were then added and the mixture was stirred at room temperature for 2 h, filtered through a short plug of silica, and concentrated. Pipette flash chromatography (10% ethyl acetate/hexane) furnished 60 (1.9 mg, 83% yield) as a colorless oil: IR (film, NaCl) 3510 (m), 3360 (m, br), 3180 (m), 2960 (s), 2930 (s), 2880 (s), 2855 (s), 1730 (s, br), 1596 (m), 1460 (s), 1385 (s), 1362 (s), 1325 (m), 1255 (s), 1220 (m), 1100 (s), 1043 (s), 983 (m), 937 (m), 904 (m), 832 (s), 770 (s), 663 (m) $cm^{-1}$; $^1$H NMR (500 MHZ, $CDCl_3$) d 6.58 (dddd, J=16.8, 10.6, 10.6, 0.7 Hz, 1 H), 6.01 (apparent t, J=11.0 Hz, 1 H), 5.36 (apparent t, J=10.4 Hz, 1 H), 5.27 (dd, J=11.1, 7.9 Hz, 1 H), 5.22–5.16 (m, 2 H), 5.12 (d, J=10.1 Hz, 1 H), 5.03 (d, J=10.0 Hz, 1 H), 4.76 (apparent t, J=9.2 Hz, 1 H), 4.71 (apparent t, J=6.1 Hz, 1 H), 4.50 (ddd, J=10.5, 10.5, 1.3 Hz, 1 H), 4.44 (br s, 2 H), 3.62 (apparent t, J=2.4 Hz, 1 H), 3.42 (apparent t, J=4.5 Hz, 1 H), 3.22 (apparent t, J=5.3 Hz, 1 H), 2.98 (ddq, J=10.1, 6.6, 6.6 Hz, 1 H), 2.60 (qd, J=7.6, 2.7 Hz, 1 H), 2.63–2.55 (m, 1 H), 2.48–2.41 (m, 1 H), 2.09 (apparent t, J=12.4 Hz, 1 H), 1.93–1.88 (m, 1 H), 1.87–1.77 (m, 2 H), 1.71 (ddd, J=14.1, 10.8, 1.6 Hz, 1 H), 1.67 (br d, J=13.7 Hz, 1 H), 1.56 (apparent s, 3 H), 1.55–1.50 (m, 1 H), 1.21 (d, J=7.6 Hz, 3 H), 0.98 (d, J=6.8 Hz, 3 H), 0.95 (d, J=7.0 Hz, 3 H), 0.94 (d, J=7.5 Hz, 3 H), 0.918 (d, J=6.8 Hz, 3 H), 0.915 (s, 9 H), 0.89 (s, 9 H), 0.86 (s, 9 H), 0.853 (d, J=6.4 Hz, 3 H), 0.847 (s, 9 H), 0.70 (d, J=6.8 Hz, 3 H), 0.09 (s, 3 H), 0.07 (s, 3 H), 0.053 (s, 3 H), 0.051 (s, 3 H), 0.040 (s, 3 H), 0.037 (s, 3 H), 0.03 (s, 3 H), −0.02 (s, 3 H); $^{13}$C. NMR (125 MHZ, $CDCl_3$) d 173.3, 156.9, 133.6, 133.5, 132.4, 132.1, 131.9, 131.4, 129.8, 118.0, 80.5, 78.9, 74.9, 64.6, 44.2, 42.7, 37.8, 37.4, 36.0, 35.3, 35.2, 34.5, 34.2, 26.3, 26.2, 25.9, 25.7, 23.0, 18.5, 18.4, 18.1, 18.0, 17.5, 17.1, 16.44, 16.38, 14.1, 13.7, 10.1, −3.0, −3.4, −3.6, −4.4, −4.5, −4.8; high resolution mass spectrum (FAB, NBA) m/z 1072.7264 [(M+Na)$^+$; calcd for $C_{57}H_{111}NO_8Si_4Na$: 1072.7283 ].

EXAMPLE 74

Synthesis of (+)-Discodermolide

Tetrasilyl derivative (+)-60 (5.8 mg, 5.5 mmol) was dissolved in 48% HF—$CH_3CN$ (1:9, 1.0 mL) at room temperature. After 12 h, the reaction mixture was quenched with saturated aqueous $NaHCO_3$ (5 mL) and extracted with ethyl acetate (3×10 mL). The combined extracts were washed with brine (5 mL), dried over $MgSO_4$, filtered and concentrated. Pipette flash chromatography (gradient elution; 1:30 ->1:6 MeOH/$CHCl_3$) gave (+)-1 (2.0 mg, 60% yield) as a white amorphous solid: $[\alpha]_D^{23}$ +15° © 0.033, MeOH); IR ($CHCl_3$) 3690 (w), 3620 (w), 3540 (w), 3430 (w), 3020 (s), 2975 (m), 2935 (m), 1740 (m), 1590 (w), 1540 (w), 1520 (w), 1467 (w), 1430 (w), 1385 (m), 1330 (w), 1233 (s), 1210 (s), 1100 (w), 1045 (m), 1033 (m), 975 (w), 930 (m), 910 (w), 793 (m), 777 (m), 765 (m), 750 (m), 705 (m), 687 (m), 670 (m), 660 (m), 625 (w) $cm^{-1}$; $^1$H NMR (500 MHZ, $CDCl_3$) d 6.60 (dddd, J=16.8, 8.4, 8.4, 0.8 Hz, 1 H), 6.02 (apparent t, J=11.1 Hz, 1 H), 5.51 (dd, J=11.2, 7.9 Hz, 1 H), 5.42 (ddd, J=10.6, 10.6, 0.6 Hz, 1 H), 5.34 (apparent t, J=10.4 Hz, 1 H), 5.20 (dd, J=16.9, 1.9 Hz, 1 H), 5.16 (d, J=10.0 Hz, 1 H), 5.11 (d, J=10.1 Hz, 1 H), 4.77–4.69 (m, 1 H), 4.70 (dd, J=7.3, 4.2 Hz, 1 H), 4.60 (ddd, J=10.0, 10.0, 2.4 Hz, 1 H), 4.56 (br s, 2 H), 3.73 (m, 1 H), 3.28 (m, 1 H), 3.18 (dd, J=6.8, 4.8 Hz, 1 H), 2.98 (ddq, J=10.1, 6.9, 6.9 Hz, 1 H), 2.78 (ddq, J=9.8, 6.8, 6. 8Hz, 1 H), 2.66 (qd, J=7.3, 4.6 Hz, 1 H), 2.60–2.55 (m, 1 H), 2.10–1.80 (m, 10 H), 1.69 (ddd, J=14.4, 10.3, 3.1 Hz, 1 H), 1.64 (d, J=1.3 Hz, 3 H), 1.30 (d, J=7.4 Hz, 3 H), 1.06 (d, J=6.9 Hz, 3 H), 1.00

(d, J=6.8 Hz, 3 H), 0.99 (d, J=6.7 Hz, 3 H), 0.97 (d, J=6.8 Hz, 3 H), 0.94 (d, J=6.8 Hz, 3 H), 0.82 (d, J=6.3 Hz, 3 H); $^{13}$C NMR (125 MHZ, CDCl$_3$) d 173.6, 157.0, 134.4, 133.7, 133.4, 132.9, 132.2, 129.9, 129.8, 117.9, 79.1, 78.9, 77.1, 75.7, 73.2, 64.4, 43.1, 41.0, 37.4, 36.1, 36.0, 35.8, 35.3, 34.8, 33.1, 23.3, 18.4, 17.4, 15.6, 15.5, 13.7, 12.5, 9.0; high resolution mass spectrum (FAB, NBA) m/z 616.3840 [(M+Na)$^+$; calcd for C$_{33}$H$_{55}$NO$_8$Na: 616.3826].

EXAMPLE 75

I. General Procedure For Synthesis Of Siloxy Aldehydes (85)

Figure 41:
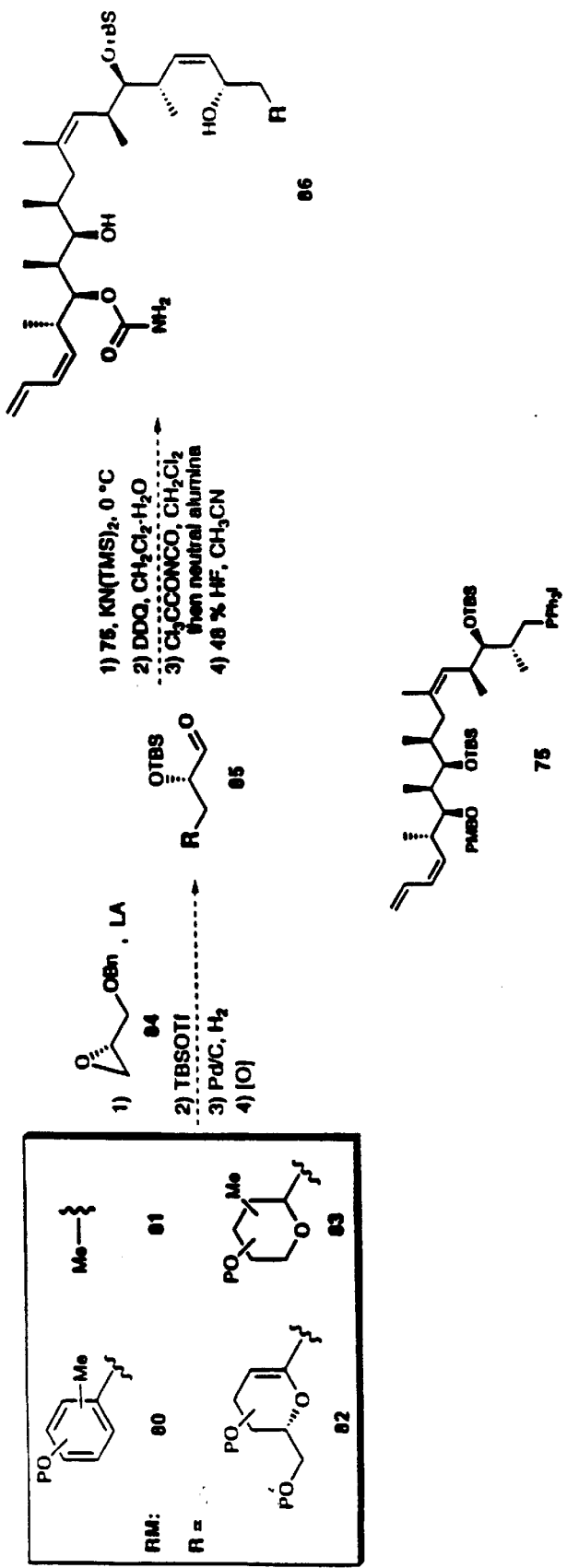
FIG. 41 shows a synthetic scheme for compound 86.

A. A solution of organolithium (M=Li, FIG. 41)) of type 80–83 (20 mmol) in ether (40 mL) is added slowly to a 0° C. solution of benzyl (S)-(+)-glycidyl ether (9 mmol) in ether (20 mL). The reaction is allowed to warm to room temperature. After 18–24 h, the reaction mixture is quenched by the addition of tert-butyldimethylsilyl triflate (10 mmol) and poured into saturated aqueous sodium bicarbonate (100 mL). The aqueous layer is separated and extracted with ether (2×50 mL). The combined organics are washed with saturated aqueous brine (50 mL), dried over magnesium sulfate and concentrated in vacuo. The residue is purified by flash chromatography to afford an alpha-siloxy benzyl ether.

B. To a solution of the above benzyl ether (6 mmol) in ethyl acetate-ethanol (8:1, 90 mL) is added palladium on carbon (10% wet, 500 mg). The mixture is stirred under hydrogen atmosphere for 3–6 h, then filtered and concentrated in vacuo. The residue is purified by flash chromatography to afford an alcohol.

C. Aldehyde 85.

Oxalyl chloride (1.5 mmol) is added dropwise to a −78° C. solution of dimethyl sulfoxide (3 mmol) in dichloromethane (4 mL). After 15 min, a −78° C. solution of the alcohol prepared in part B (1 mmol) in dichloromethane (2 mL) is added via canula. After an additional 15 min, diisopropylethylamine (4.5 mmol) is added and the reaction is gradually warmed to room temperature over 1 h and quenched with aqueous sodium bisulfate. The mixture is diluted with ether (50 mL) and is washed with water (2×30 mL), saturated aqueous brine (2×30 mL), is dried over magnesium sulfate and concentrated in vacuo. The residue is purified by flash chromatography to afford 85.

II. General Procedure For The Conversion Of (85) To Tetraene (86)

D. Phosphonium salt 75 (0.2 mmol) is dissolved in anhydrous tetrahydrofuran (2 mL) and chilled to 0° C. A solution of potassium bis(trimethylsilyl)amide (0.2 mmol, 0.5 M in tetrahydrofuran) is added and the reaction mixture is stirred 30 min at 0° C. After cooling to −78° C., a solution of aldehyde 85 (0.1 mmol) in tetrahydrofuran (2 mL) is added and the mixture is stirred 10 min at −78° C. and 2 h at room temperature. Saturated aqueous ammonium chloride (2 mL) is added and the resultant mixture is extracted with ether (3×20 mL). The ethereal layer is washed with water (2×25 mL) and saturated aqueous brine (25 mL), dried over magnesium sulfate and concentrated in vacuo. The residue is purified by flash chromatography to afford a tetraene.

E. To a solution of the tetraene prepared in part D (0.050 mmol) in dichloromethane (3 mL) at 0° C. is added water (0.050 mL) and 2,3-dichloro-5,6-dicyano-1,4-benzoquinone (0.018 mmol). After 1 h, the reaction mixture is diluted with ethyl acetate (50 mL), washed with saturated aqueous brine (3×25 mL), dried over magnesium sulfate and concentrated in vacuo. The residue is purified by flash chromatography to afford an alcohol.

F. To a solution of the alcohol prepared in part E (0.010 mmol) in dichloromethane (2 mL) is added trichloroacetyl isocyanate (1.00 mmol). After 30 min, the reaction mixture is diluted with dichloromethane (4 mL) and neutral alumina (1 g) is added. The resultant suspension is stirred an additional 4 h. The reaction mixture is filtered and the concentrated filtrate is chromatographed on silica gel to afford a carbamate.

G. Analog 86.

A solution of the carbamate prepared in part F (0.010 mmol) in 48% hydrofluoric acid-acetonitrile (1:9, 2 mL) is stirred at ambient temperature. After 12 h, saturated aqueous sodium bicarbonate (25 mL) is added and the mixture is extracted with ethyl acetate (3×20 mL). The combined organics are dried over magnesium sulfate and concentrated in vacuo. The residue is purified by flash chromatography to afford 86.

Aldol (−) -5:

PMB protection: p-Methoxybenzyl alcohol (200 g, 1.45 mol) was added to a suspension of NaH (60% in mineral oil; 5.82 g, 0.146 mol) in anhydrous ether (450 mL) over 1 h at room temperature. The mixture was stirred 1 h further and cooled to 0° C. Trichloroacetonitrile (158 mL, 1.58 mol) was then introduced over 80 min. After 1.5 h the solution was concentrated with the water bath temperature maintained below 40° C. The residue was treated with a mixture of pentane (1.5 L) and MeOH (5.6 mL), stirred at room temperature for 30 min, and filtered through a short Celite column. Concentration gave the trichloroimidate (370.9 g) as a yellow oil which was used without further purification.

A solution of Roush's ester (+)-6 (129.0 g, 1.09 mol) in CH$_2$Cl$_2$/cyclohexane (1:2, 1.5 L) was cooled to 0° C. and treated with crude trichloroimidate (370.9 g) and PPTS (13.69 g, 55.0 mmol) over 0.5 h. After 3 h, the mixture was warmed to room temperature, stirred for 40 h, and concentrated. Suction filtration through a short silica plug (5×6" sintered glass funnel; 20% ethyl acetate/hexanes) afforded the corresponding PMB ether (234.2 g) as a pale yellow oil which was divided into two portions for the next reaction.

Reduction:

A solution of the above PMB ether(116.1 g) in anhydrous THF (800 mL) was cooled to 0° C. and added via cannula to a solution of LiAlH$_4$ (0.67 M in THF, 800 mL, 0.536 mol) over 1 h (150 mL THF rinse), warmed gradually to room temperature, and stirred for 1 h. The reaction mixture was cooled to 0° C. and quenched via dropewise addition of H$_2$O (20 mL), 15% NaOH (20 mL), then H$_2$O (60 mL). The resultant mixture was then treated with MgSO$_4$ (10 g), filtered (100 mL Et$_2$O rinse), and concentrated, furnishing a red oil (91.0 g). The remaining 118.1 g was processed using the same protocol to yield an additional 94 g, yielding a total of 185 g of the corresponding alcohol(+)-8, which was divided into three portions for the next two reactions.

Swern:

A solution of DMSO (72.1 mL, 1.02 mol) in CH$_2$Cl$_2$ (1.5 L) was cooled to −78° C. and oxalyl chloride (44.3 mL, 0.51 mmol) was added over 30 min (internal temp <−65° C.). After an additional 30 min, a solution of the above alcohol (71.2 g, 0.338 mol) in CH$_2$Cl$_2$ (100 mL) was added dropwise via cannula down the side of the flask over 30 min (20-mL rinse). The resultant mixture was stirred 45 min further at −78° C., then i-Pr$_2$NEt (345 mL, 2.03 mol) was added over 45 min. The mixture was stirred 30 min further at −78° C. then slowly warmed to 0° C. (internal temp) via removal of the external cooling bath. The reaction was quenched via addition to a vigourously stirred aqueous NaHSO$_4$ solution (1.0 M, 2.0 L). The layers were separated, the aqueous phase extracted (3×Et$_2$O). The combined organic layers were concentrated (30° C. water bath), diluted with ether (1000 mL), washed with aqueous NaHSO$_4$ (3×), water (1×), saturated aqueous NaHCO$_3$ (1×), and brine (1×). The combined organic layers were dried over MgSO$_4$, filtered and concentrated to give the corresponding aldehyde (70.5 g, ca. 100%) as a colorless oil.

Evans Aldol Reaction:

A solution of oxazolidinone 61 (90.7 g, 389 mmol) in degassed CH$_2$Cl$_2$ (972 mL, 4 Å MS dried, argon sparged) was cooled to −55° C. (internal temp) and n-Bu$_2$BOTf (1.0 M in CH$_2$Cl$_2$, 403 mL) was introduced over 0.5 h, followed by addition of NEt$_3$ (61.3 mL, 440 mmol) over 20 min. The mixture was warmed to 0° C. (internal temp), stirred for 10 min, and cooled to −70° C. A degassed solution of above aldehyde (70.5 g, 0.338 mmol) in CH$_2$Cl$_2$ (200 mL) was then added via a cannula down the side of the flask over 1 h (20 mL rinse). After an additional 1.0 h at −78° C., the reaction was warmed to −8° C., stirred for 1 h, then quenched with pH 7 potassium phosphate monobasic-sodium hydoxide buffer (0.05 M, 220 mL). A solution of 30% H$_2$O$_2$ in MeOH (1:2, 700 mL) was added to the vigorously stirred reaction mixture at such a rate as to maintain an internal temp <8° C. (60 min, −10° C. cooling bath). The reaction was stirred 10 h at room temperature, and concentrated to ca. 1000 mL. The residue was dissolved in 1500 mL of 10:1 Et$_2$O/CH$_2$Cl$_2$, and the resulting layers were separated. The aqueous layer was extracted (3×10:1 Et$_2$O/CH$_2$Cl$_2$), and the combined organic layers were washed with saturated aqueous NaHCO$_3$ (1000 mL), water (1000 mL) and saturated brine (2×500 mL). The organic layer was dried over MgSO$_4$, filtered and concentrated to ca. 400 mL (3× using a 2000 mL rb). The resulting white solid was filtered and dried overnight to give analytically pure 62 (83.8g, 56%). The combined mother liquors were concentrated and recrystallized from Et$_2$O to give an additional 10.0 g (7.0%, total yield of 63%) of 62. The remaining 120 g of precursor alcohol was processed through the above two steps to give an additional 155.4 of 62 for a total of 249.2 g (52% yield over 4 steps). X-ray quality crystals were grown by recrystallization from ether-hexanes: mp 111.5–113.0° C.; [α]$^{23}_D$ +34.3°; IR (CHCl$_3$) 3600–3400 (br), 1780, 1705 cm$^{-1}$; $^1$H NMR (500 MHz, CDCl$_3$) 67 7.42–7.33 (m, 3 H), 7.28–7.21 (m, 4 H), 6.85 (m, 2 H), 5.59 (d, J=6.9 Hz, 1 H), 4.72 (quintet, J=6.6 Hz, 1 H), 4.43 (s, 2 H), 3.92 (qd, J=6.8, 3.4 Hz, 1 H), 3.88 (dd, J=8.2, 3.4 Hz, 1 H), 3.76 (s, 3 H), 3.69 (br s, OH), 3.55 (m, 2 H), 1.95 (m, 1 H), 1.20 (d, J=6.9 Hz, 3 H), 0.95 (d, J=7.0 Hz, 3 H), 0.88 (d, J=6.6 Hz, 3 H); $^{13}$C NMR (125 MHz, CDCl$_3$) δ 175.9, 159.3, 152.8, 133.3, 129.8, 129.4, 128.77, 128.7, 125.6, 113.8, 78.9, 75.6, 74.7, 73.2, 55.2, 55.1, 40.9, 36.0, 14.3, 13.6, 9.6; high resolution mass spectrum (CI) m/z 441.2133, [(M)+, calcd for C$_{25}$H$_{31}$NO$_6$Na: 441,2151]. Anal. Calcd for C$_{25}$H$_{31}$NO$_6$: C, 68.01; H, 7.08; N: 3.17. Found: C, 68.29; H, 7.17; N, 3.16.

Common Precursor (−)-5:

At 0° C., a suspension of N,O-dimethylhydroxylamine hydrochloride (50.8 g, 521 mmol) in THF (380 mL) was cautiously treated with AlMe$_3$ (2.0 M in hexane, 256 mL, 512 mmol) over 30 min. The resultant solution was stirred 30 min at 0° C. and 90 min at ambient temperature, and then cooled to −20° C. A solution of oxazolidinone 62 (76.7 g, 174 mmol) in THF (380 mL) was introduced over 60 min via a cannula (20-mL rinse). After an additional 90 min at −20°

C., the solution was poured slowly into a solution of aqueous HCl (1.0 N, 1.0 L) and CH$_2$Cl$_2$ (1.0 L) and stirred vigorously at 0° C. for 90 min. The aqueous phase was extracted with CH$_2$Cl$_2$ (3 X1L) and the combined organic solutions were washed with water (2×500 mL) and saturated brine (500 mL), dried over MgSO$_4$, filtered and concentrated. The crude material was dissolved in a minimal amount of ether. An equal volume of hexanes was added, and the resultant solution was refrigerated (4° C.) overnite. Filtration of the crystals afforded (4R, 5S)-4-methyl-5-phenyl-2-oxazolidinone (30.68 g, 100%). Concentration of the residual liquid and flash chromatography (20% acetone/hexanes) afforded (−)-5 (55.5 g, 98% yield) as a colorless oil; [α]$^{23}_D$ −−3.6° (c 1.67, CHCl$_3$); IR (CHCl$_3$) 3470, 1680 cm$^{-1}$; $^1$H NMR (500 MHz, CDCl$_3$) δ 7.25 (d, J=8.6 Hz, 2 H), 6.86 (d, J=8.7 Hz, 2 H), 4.44 (ABq, J$_{AB}$=11.6 Hz, Δ$_{AB}$=17.1 Hz, 2 H), 3.95 (d, J=2.8 Hz, 1 H), 3.79 (s, 3 H), 3.70 (ddd, J=8.2, 3.2, 3.2 Hz, 1 H), 3.66 (s, 3 H), 3.62 (dd, J=9.0, 4.0 Hz, 1 H), 3.53 (dd, J=9.1, 5.9 Hz, 1 H), 3.17 (s, 3 H), 3.04 (m, 1 H), 1.91–1.84 (m, 1 H), 1.17 (d, J=7.0 Hz, 3 H), 0.98 (d, J=6.9 Hz, 3 H); $^{13}$C NMR (125 MHz, CDCl$_3$) δ 178.0, 159.0, 130.6, 129.1, 113.7, 113.6, 73.8, 72.8, 72.6, 61.3, 55.1, 36.5, 36.0, 14.2, 10.4; high resolution mass spectrum (CI, NH$_3$) m/z 326.1962 [(M+H)$^+$; calcd for C$_{17}$H$_{28}$NO$_5$: 326.1967].

Anal. Calcd for C$_{17}$H$_{27}$NO$_5$: C, 62.74; H, 8.36. Found: C, 62.74; H, 8.24.

FRAGMENT A:

PMP Acetal (+)-11:

At −10° C., a vigorously stirred solution of common precursor (−)-5 (21.55 g, 66.2 mmol) and powdered 4 Å molecular sieves (25 g) in CH$_2$Cl$_2$ (500 mL) was treated with DDQ (17.80 g, 78.4 mmol). The resultant mixture was warmed to 0° C. over 90 min and filtered through a pad of Celite (CH$_2$Cl$_2$, 500 mL). The filtrate was washed with aqueous NaOH (1 N, 200 mL), concentrated to ca. ⅒ volume, diluted with hexanes (400 mL), washed with aqueous NaOH (2×100 mL) and saturated brine (2×200 mL), dried over MgSO., filtered and concentrated to afford a pale yellow-colored solid. Crystallization from hexanes-ether afforded (+)-6 as colorless needles (15.90 g). Flash chromatography (25% ethyl acetate/hexanes) of the mother liquor provided an additional 2.50 g of (+)-11 (86% total yield): mp 92.0–93.5° C.; [α]$^{23}_D$ +36.4° (c 0.73, CHCl$_3$); IR (CHCl$_3$) 3010, 1663, 1620 cm$^{-1}$; $^1$H NMR (500 MHz, CDCl$_3$) δ 7.41 (d, J=8.8 Hz, 2 H), 6.87 (d, J=8.8 Hz, 2 H), 5.46 (s, 1 H), 4.04 (dd, J=11.3, 4.7 Hz, 1 H), 3.82 (dd, J=9.8, 6.5 Hz, 1 H), 3.79 (s, 3 H), 3.71 (s, 3 H), 3.51 (apparent t, J=11.2 Hz, 1 H), 3.19 (s, 3 H), 3.21–3.14 (m, 1 H), 1.98–1.92 (m, 1 H), 1.27 (d, J=7.0 Hz, 3 H), 0.75 (d, J=6.8 Hz, 3 H); $^{13}$C NMR (125 MHz, CDCl$_3$) δ 175.8, 159.8, 131.2, 127.2, 113.5, 100.7, 82.8, 72.8, 61.3, 55.3, 39.0, 33.8, 32.6, 13.1, 12.4; high resolution mass spectrum (CI, NH$_3$) m/z 323.1736 [M+; calcd for C$_{17}$H$_{25}$NO$_5$: 323.1732]. Anal. Calcd for C$_{17}$H$_{25}$NO$_5$: C, 63.14; H, 7.79. Found: C, 63.18; H, 7.74.

Aldehyde (+)-12.

A solution of amide (+)-11 (16.4 g, 50.7 mmol) in THF (100 mL) was added via cannula over 15 min to a −60° C. solution of LiAlH$_4$ (3.09 g, 81.4 mmol) in THF (400 mL). The resultant solution was stirred 2 h at −60° C., warmed 0° C., stirred 60 min, and quenched via dropwise addition of glacial acetic acid (15.0 mL, 254 mmol), over 45 min. Saturated aqueous sodium potassium tartrate (500 mL) was added, and the resultant solution was vigorously stirred at ambient temperature. After 1 h, the reaction mixture was diluted with hexanes (500 miL), and the organic layer was separated and concentrated to ca. ½ volume in vacuo. The aqueous layer was extracted with $CH_2Cl_2$ (2×250 mL), and the comibined organic layers were washed with water (200 mL), saturated brine (2×200 mL), and saturated $NaHCO_3$ (200 mL). The organic solution was dried ($MgSO_4$), filtered, and concentrated to give (+)-11 as a white slurry (14.4 g) that was used without further purification. An analytical sample was obtained by recrystallization from ether: mp 68–71° C.; $[\alpha]^{23}{}_D$ +16.2° (c 1.02, $CHCl_3$); IR ($CHCl_3$) 1735, 1725 $cm^{-1}$; $^1H$ NMR (500 MHz, $CDCl_3$) δ 9.74 (apparent s, 1 H), 7.32 (d, J=8.8 Hz, 2 H), 6.84 (d, J=8.7 Hz, 2 H), 5.46 (s, 1 H), 4.13 (dd, J=11.5, 4.8 Hz, 1 H), 4.05 (dd, J=10.4, 2.6 Hz, 1 H), 3.77 (s, 3 H), 3.56 (apparent t, J=11.1 Hz, 1 H), 2.56 (qd, J=7.1, 2.6 Hz, 1 H), 2.15–2.03 (m, 1 H), 1.23 (d, J=7.1 Hz, 3 H), 0.80 (d, J=6.7 Hz, 3 H); $^{13}C$ NMR (125 MHz, $CDCl_3$) δ 204.0, 159.9, 130.7, 127.2, 113.5, 100.9, 81.6, 72.8, 55.2, 47.4, 30.3, 11.9, 7.1; high resolution mass spectrum (CI, $NH_3$) m/z 265.1432 [(M+H)$^+$; calcd for $C_{15}H_{21}O_4$: 265.1439]. Anal. Calcd for $C_{15}H_{20}O_4$: C, 68.16; H, 7.63. Found: C, 67.84; H, 7.50.

Aldol (−)-13.

A solution of oxazolidinone (−)-9 (17.8 9, 76.2 mmol) in $CH_2Cl_2$ (100 mL) was cooled to 0° C. and n-$BU_2BOTf$ (1.0 M in $CH_2Cl_2$, 70.85 mL) was added over 0.5 h, followed by addition of $NEt_3$ (12.9 mL, 92.7 mmol) over 20 min. The mixture was stirred at 0° C. for 1 h and cooled to −78° C. A solution of aldehyde (+)-12 (14.4 g) in $CH_2Cl_2$ (20 mL) was added over 10 min, and the mixture was stirred 20 min further at −78° C., warmed to 0° C. and stirred for 1 h. The reaction was quenched with pH 7 potassium phosphate monobasic-sodium hydroxide buffer (0.05 M, 100 mL) and MeOH (300 mL) and cautiously treated with 30% $H_2O_2$ in MeOH (100 mL) at 0° C. with stirring. After 1 h, saturated aqueous $Na_2S_2O_3$ (100 mL) was added. Following concentration and extraction with ethyl acetate (3×250 mL), the combined extracts were washed with saturated aqueous $Na_2S_2O_3$, aqueous 10% $NaHCO_3$, brine (200 mL each), dried ($MgSO_4$), filtered and concentrated. Flash chromatography (10% ethyl acetate/hexanes) provided (−)-13 (20.9 g, 77%, two steps) as a white solid: mp 98–100° C.; $[\alpha]^{23}{}_D$ −13.5° (c 1.19, $CHCl_3$); IR ($CHCl_3$) 3690, 3520 (br),1790, 1695 $cm^{-1}$; $^1H$ NMR (500 MHz, $CDCl_3$) δ 7.35 (d, J=8.7 Hz, 2 H), 7.31 (d, J=7.6 Hz, 2 H), 7.27 (d, J=7.2 Hz, 1 H), 7.19 (d, J=7.7 Hz, 2 H), 6.84 (d, J=8.7 Hz, 2 H), 5.45 (s, 1 H), 4.67–4.62 (m, 1 H), 4.14 (apparent d, J=5.3 Hz, 2 H), 4.08 (dd, J=11.4, 4.8 Hz, 1 H), 4.07 (apparent t, J=4.1 Hz, 1 H), 4.04–3.99 (m, 1 H), 3.76 (s, 3 H), 3.61 (dd, J=9.9, 2.2 Hz, 1 H), 3.51 (apparent t, J=11.1 Hz, 1 H), 3.33 (d, J=1.3 Hz, 1 H), 3.21 (dd, J=13.4, 3.4 Hz, 1 H), 2.76 (dd, J=13.4, 9.4 Hz, 1 H), 2.12–2.06 (m, 1 H), 1.92–1.86 (m, 1 H), 1.31 (d, J=6.9 Hz, 3 H), 1.07 (d, J=7.0 Hz, 3 H), 0.74 (d, J=6.7 Hz, 3 H); $^{13}C$ NMR (125 MHz, $CDCl_3$) δ 177.1, 160.0, 152.7, 135.0, 131.0, 129.4, 128.9, 127.40, 127.39, 113.6, 101.2, 85.8, 74.5, 73.0, 66.0, 55.2, 54.9, 39.8, 37.7, 35.7, 30.4, 12.8, 11.7, 7.8; high resolution mass spectrum (CI, $NH_3$) m/z 497.2410 [M$^+$; calcd for $C_{28}H_{35}NO_7$: 497.2413]. Anal. Calcd for $C_{28}H_{35}NO_7$: C, 67.58; H, 7.09. Found: C, 67.42; H, 7.02.

TBS Ether (−)-14:

A solution of alcohol (−)-13 (26.3 g, 52.9 mmol) and 2,6-lutidine (11.1 mL, 95.3 mmol) in $CH_2Cl_2$ (150 mL) was cooled to −20° C. and TBSOTf (20.5 mL, 79.3 mmol) was added over 30 min. After an additional 2 h at 0° C., the mixture was diluted with ether (300 mL), washed with aqueous $NaHSO_4$ (1.0 M) and brine (200 mL each), dried over $MgSO_4$, filtered and concentrated. Flash chromatography (gradient elution, 5 10% Å ethyl acetate/hexanes) afforded (−)-13 (32.4 9, 100% yield) as a colorless oil: $[\alpha]^{23}{}_D$ −20.3° (c 1.32, $CHCl_3$); IR ($CHCl_3$) 1788, 1705 $cm^{-1}$; $^1H$ NMR (500 MHz, $CDCl_3$) δ 7.38 (d, J=8.7 Hz, 2 H), 7.30–7.12 (m, 5 H), 6.82 (d, J=8.7 Hz, 2 H), 5.44 (s, 1 H), 4.30 (ddt, J=13.4, 7.3, 5.1, 1 H), 4.11 (dd, J=7.1, 4.0 Hz, 1 H), 4.02 (dd, J=11.2, 4.7 Hz, 1 H), 3.97 (dq, J=7.0, 7.0 Hz, 1 H), 3.80 (dd, J=8.9, 2.3 Hz, 1 H), 3.740 (apparent t, J=4.9 Hz, 1 H), 3.738 (s, 3 H), 3.48 (apparent t, J=11.1 Hz, 1 H), 3.27 (apparent t, J=8.2 Hz, 1 H), 3.15 (dd, J=13.4, 3.2 Hz, 1 H), 2.59 (dd, J=13.4, 9.8 Hz, 1 H), 2.05 (apparent qd, J=7.4, 4.2 Hz, 1 H), 2.02–1.94 (m, 1 H), 1.19 (d, J=6.9 Hz, 3 H), 1.04 (d, J=7.5 Hz, 3 H), 0.92 (s, 9 H), 0.73 (d, J=6.7 Hz, 3 H), 0.05 (s, 3 H), 0.04 (s, 3 H); $^{13}C$ NMR (125 MHz, $CDCl_3$) δ 175.6, 159.9, 152.4, 135.5, 132.0, 129.4, 128.8, 127.8, 127.2, 113.4, 100.7, 80.7, 74.6, 73.1, 65.3, 55.3, 55.2, 41.4, 40.9, 37.4, 30.6, 26.0, 18.1, 15.0, 12.7, 11.5, −4.0, −4.6; high resolution mass spectrum (CI, $NH_3$) m/z 612.3340 [(M+H)$^+$; calcd for $C_{34}H_{50}NO_7Si$: 612.3356]. Anal. Calcd for $C_{34}H_{49}NO_7Si$: C, 66.74; H, 8.07. Found: C, 66.69; H, 7.98.

Alcohol (+)-15

At −30° C., a solution of imide (−)-14 (32.0 g, 52.3 mmol) in THF (600 mL) was treated with EtOH (6.14 mL, 105 mmol). $LiBH_4$ (2.0 M in THF, 52.3 mL, 105 mmol) was then added over 15 min. After an additional 1 h at 0° C. and 12 h at room temperature, the mixture was diluted with ether (1.0 L), quenched carefully with aqueous NaOH (1.0 N, 200 mL), and stirred at room temperature for 2 h. The layers were separated, and the organic phase was washed with brine (500 mL), dried over $Na_2SO_4$, filtered and concentrated. Flash chromatography (20% ethyl acetate/hexanes) provided (+)-15 (18.7 g, 81% yield) as a colorless oil that solidified upon standing. An analytical sample was obtained by recrystallization from hexane: mp 65.0–67.0° C.; $[\alpha]^{23}{}_D$ or $[\alpha]_D{}^{23}$=+36.4° (c 1.57, $CHCl_3$); IR ($CHCl_3$) 3630, 3480 (br) $cm^{-1}$; $^1H$ NMR (500 MHz, $CDCl_3$) δ 7.36 (d, J=8.7 Hz, 2 H), 6.85 (d, J=8.8 Hz, 2 H), 5.38 (s, 1 H), 4.08 (dd, J=11.2, 4.7 Hz, 1 H), 3.84 (dd, J=6.7, 1.9 Hz, 1 H), 3.77 (s, 3 H), 3.53 (dd, J=9.9, 1.8 Hz, 1 H), 3.55–3.52 (m, 1 H), 3.47 (apparent t, J=11.1 Hz, 1 H), 3.44 (dd, J=10.3, 6.2 Hz, 1 H), 2.08–1.97 (m, 2 H), 1.94 (dqd, J=7.1, 7.1, 1.7 Hz, 1 H), 1.76 (br s, 1 H), 1.02 (d, J=7.1, 3 H), 0.88 (s, 9 H), 0.84 (d, J=6.9 Hz, 3 H), 0.73 (d, J=6.7 Hz, 3 H), 0.03 (s, 3 H), 0.00 (s, 3 H); $^{13}C$ NMR (125 MHz, $CDCl_3$) δ 159.8, 131.4, 127.3, 113.5, 101.0, 82.9, 74.3, 73.3, 66.3, 55.2, 38.7, 37.8, 30.7, 26.1, 18.3, 12.2, 11.1, 10.7, −4.0, −4.2; high resolution mass spectrum (CI, $NH_3$) m/z 439.2889 [(M+H)$^+$; calcd for $C_{24}H_{43}O_5Si$: 439.2879]. Anal. Calcd for $C_{24}H_{42}O_5Si$: C, 65.71; H, 9.65. Found: C, 65.51; H 9.54.

Iodide (+)-A.

A vigorously stirred solution of alcohol (+)-15 (4.70 g, 10.7 mmol), triphenylphosphine (4.21 g, 16.1 mmol) and imidazole (1.09 g, 16.1 mmol) in benzene/ether (1:2, 75 mL) was treated with iodine (4.08 g, 16.1 mmol). After 1 h, the mixture was diluted with ether (200 mL), washed with saturated $Na_2S_2O_3$ and brine (100 mL each), dried over $MgSO_4$, filtered and concentrated. Flash chromatography (2% ethyl acetate/hexanes) furnished (+)-A (5.56 g, 95% yield) as a colorless oil that solidified on standing. Recrystallization from ethanol afforded colorless needles: mp 43–44° C.; $[\alpha]^{23}{}_D$ +51.3° (c 1.22, EtOH); $^1H$ NMR (500 MHz, $CDCl_3$) δ 7.39 (d, J=8.7 Hz, 2 H), 6.86 (d, J=8.8 Hz, 2 H), 5.40 (s, 1 H), 4.09 (dd, J=11.2, 4.7 Hz, 1 H), 3.85 (dd, J=7.1, 1.9 Hz, 1 H), 3.79 (s, 3 H), 3.48 (dd, J=8.2, 1.5 Hz, 1 H), 3.47 (apparent t, J=11.1 Hz, 1 H), 3.18–3.12 (m, 2 H), 2.11–2.00 (m, 2 H), 1.84 (dqd, J=7.1, 7.1, 1.6 Hz, 1 H), 1.02 (d, J=7.1 Hz, 3 H), 0.98 (d, J=6.7 Hz, 3 H), 0.89 (s, 9 H), 0.72 (d, J=6.7 Hz, 3 H), 0.06 (s, 3 H), 0.04 (s, 3 H); $^{13}$C NMR (125 MHz, CDCl$_3$) δ 159.8, 131.4, 127.4, 113.4, 100.9, 82.4, 75.5, 73.2, 55.3, 39.6, 38.7, 30.7, 26.2, 18.4, 14.7, 14.5, 12.2, 10.7, −3.7, −3.8; high resolution mass spectrum (Cl, NH$_3$) m/z 548.1833 [M$^+$; calcd for C$_{24}$H$_{41}$IO$_4$Si: 548.1819]. Anal. Calcd for C$_{24}$H$_{41}$O$_4$ISi: C, 52.55; H, 7.53. Found: C, 52.77; H, 7.68.

FRAGMENT B:

TBS Ether (−)-17:

A solution of common precursor (−)-5 (48.0 g, 148 mmol) and 2,6-lutidine (30.1 mL, 258 mmol) in CH$_2$Cl$_2$ (370 mL) was cooled to −20° C. (1:1 acetone/water) and tert-butyldimethylsilyl trifluoromethanesulfonate (38.6 mL, 168 mmol) was added over 20 min. The mixture was stirred for 1.5 h, diluted with cold Et$_2$O (800 mL, 0° C.), poured into 300 mL of 1 M NaHSO$_4$, and the resulting layers were separated. The aqueous layer was extracted (3×Et$_2$O), and the combined organic layers were washed with aqueous 1.0 M NaHSO$_4$ (4×), water, saturated NaHCO$_3$ (2×), and brine. The organic layer was dried over MgSO$_4$, filtered and concentrated to yield (−)-17 (65.1 g, 100%, purity >95% by $^1$H NMR) as a clear, colorless oil. An analytical sample was prepared via flash chromatography (10% ethyl acetate/hexanes): [α]$^{23}_D$ −9.5° (c 1.84, CHCl$_3$); IR (CHCl$_3$) 1658 cm$^{−1}$; $^1$H NMR (500 MHz, CDCl$_3$) δ 7.21 (d, J=8.7 Hz, 2 H), 6.83 (d, J=8.7, 2 H), 4.36 (ABq, J$_{AB}$=11.6 Hz, Δ$_{AB}$=17.3 Hz, 2 H), 3.92 (dd, J=8.2, 3.0 Hz, 1 H), 3.77 (s, 3 H), 3.55 (s, 3 H), 3.54 (dd, J=9.2, 2.5 Hz, 1 H), 3.13 (dd, J=9.2, 7.8 Hz, 1 H), 3.09 (s, 3 H), 3.15–3.09 (m, 1 H), 1.92–1.87 (m, 1 H), 1.09 (d, J=7.0 Hz, 3 H), 0.98 (d, J=7.0 Hz, 3 H), 0.88 (s, 9 H), 0.04 (apparent s, 6 H); $^{13}$C NMR (125 MHz, CDCl$_3$) δ 176.8, 159.1, 130.9, 129.2, 113.7, 76.0, 72.7, 71.9, 61.1, 55.2, 39.3, 38.9, 26.1, 18.4, 15.3, 15.0, −3.87, −3.93; high resolution mass spectrum (CI, NH$_3$) m/z 440.2823 [(M+H)$^+$; calcd for C$_{23}$H$_{42}$NO$_5$Si: 440.2832]. Anal. Calcd for C$_{23}$H$_{41}$NO$_5$Si: C, 62.83; H, 9.40. Found: C, 63.05; H, 9.32.

Aldehyde (−)-18:

At −78° C., a solution of amide (−)-17 (9.19 g, 20.9 mmol) in THF (750 mL, dried over 4 Å MS) was treated with DIBAL-H (1.0 M in hexane, 115.0 mL) via dropwise addition down the sides of the flask (30 min addition time). The reaction was stirred for an additional 3 h and quenched with MeOH (8 mL). The −78° C. reaction mixture was poured into saturated aqueous Rochelle's salt (1000 mL) and diluted with Et$_2$O (1500 mL)). After stirring at rt for 30 min, the mixture was poured into a separatory funnel and virourously shaken to break up the emulsion. The layers were separated, and the combined organic layers were washed with saturated aqueous Rochelle's salt, water, saturated NaHCO$_3$, and brine (2×300 mL each). The organic layer was dried over MgSO$_4$, filtered and concentrated to give (−)-18 (31 g, 100%) as a clear, colorless oil, which was taken on to the next step without further purification. An analytical sample was obtained via flash chromatography (10% ethyl acetate/hexanes): [α]$^{23}_D$ −22.9° (c 1.50, CHCl$_3$); IR (CHCl$_3$) 1730 cm$^{−1}$; $^1$H NMR (500 MHz, CDCl$_3$) δ 9.67 (d, J=0.9 Hz, 1 H), 7.22 (d, J=8.7 Hz, 2 H), 6.86 (d, J=8.7 Hz, 2 H), 4.37 (ABq, J$_{AB}$=11.6 Hz, Dn$_{AB}$=23.6 Hz, 2 H), 4.18 (dd, J=6.1, 3.7 Hz, 1 H), 3.78 (s, 3 H), 3.41 (dd, J=9.2, 5.7 Hz, 1 H), 3.31 (dd, J=9.2, 6.0 Hz, 1 H), 2.47 (qdd, J=7.1, 3.7, 0.9 Hz, 1 H), 2.03–1.95 (m, 1 H), 1.08 (d, J=7.0 Hz, 3 H), 0.94 (d, J=7.0 Hz, 3 H), 0.84 (s, 9 H), 0.04 (s, 3 H), −0.03 (s, 3 H); $^{13}$C NMR (125 MHz, CDCl$_3$) δ 204.8, 159.2, 130.5, 129.2, 113.8, 72.7, 72.4, 71.7, 55.3, 50.0, 38.3, 25.9, 18.2, 14.3, 8.4, −4.1, −4.4; high resolution mass spectrum (FAB, NBA) m/z 403.2304 [(M+Na)$^+$; calcd for C$_{21}$H$_{36}$O$_4$SiNa: 403.2280].

Fragment B (+)-3:

At −23° C., a suspension of EtPh$_3$PI (68.7g, 164 mmol, dried at 70° C./0.2 Torr for 2 h) in THF (600 mL, dried over 4 Å MS, sparged with argon) was treated with n-BuLi (2.5 M in hexane, 64.0 mL, 160.1 mmol) over 30 min to form a dark red solution. After an additional 10 min, the red ylide solution was added over 40 min via cannula to a cooled (−78° C.) solution of I$_2$ (41.7 g, 164.2 mmol) in THF (1400 mL, solution prepared by adding I$_2$ to degassed THF at rt and vigorously stirring for 40 min before cooling) such that the internal temperature does not exceed −70° C. The resultant yellow slurry was stirred at −75° C. (internal) for 5 min and warmed to −23° C. (internal). NaHMDS (1.0 M in THF, 147 mL) was added via cannula over 30 min, and the resulting orange suspension was stirred 15 min further and cooled to −33° C. (internal). A solution of crude aldehyde (−)-13 (31.2 g, 82.1 mmol) in THF (200 mL) was introduced via cannula over 15 min, and the reaction mixture was stirred at −30° C. for an additional 45 min, warmed to 7° C. over 1 h, and quenched with MeOH (20 mL). Following concentration and suction filtration through a 6×8" silica plug (100% Et$_2$O, 2000 mL suction filtration sintered glass frit), the filtrate was washed with saturated aqueous Na$_2$S$_2$O$_3$ and brine, dried over MgSO$_4$, filtered and concentrated. Flash chromatography (15% CHCl/hexanes; then gradient elution 1% ethyl acetate/hexanes 32% ethyl acetate/hexanes) furnished (+)-3 (19.6 g, 46% yield for two steps, 9:1 Z/E) as a clear, colorless oil). An analytical sample of the Z isomer was obtained by reversed-phase HPLC (gradient elution; 90% CH$_3$CN/H$_2$O Å 100% CH$_3$CN): colorless oil; [α]$^{23}_D$ +23° (c 0.30, CHCl$_3$); $^1$H NMR (500 MHz, CDCl$_3$) d 7.25 (d, J=8.6 Hz, 2 H), 6.87 (d, J=8.7 Hz, 2 H), 5.28 (apparent dd, J=8.9, 1.4 Hz, 1 H), 4.41 (ABq, J$_{AB}$=7.0 Hz, Dn$_{AB}$=10.2 Hz, 2 H), 3.80 (s, 3 H), 3.60 (apparent t, J=5.3 Hz, 1 H), 3.51 (dd, J=9.1, 5.1 Hz, 1 H), 3.23 (dd, J=9.0, 8.0 Hz, 1 H), 2.54–2.47 (m, 1 H), 2.44 (d, J=1.4 Hz, 3 H), 2.00–1.92 (m, 1 H), 1.00 (d, J=6.9 Hz, 3 H), 0.95 (d, J=6.7 Hz, 3 H), 0.89 (s, 9 H), 0.02 (s, 3 H), 0.01 (s, 3 H); $^{13}$C NMR (125 MHz, CDCl$_3$) d 159.1, 139.6, 131.0, 129.1, 113.7, 98.9, 76.5, 72.6, 72.5, 55.3, 44.5, 38.7, 33.5, 26.1, 18.4, 14.7, 14.5, −3.95, −3.99; high resolution mass spectrum (FAB, NBA) m/z 541.1626 [(M+Na)$^+$; calcd for C$_{23}$H$_{39}$IO$_3$SiNa: 541.1611].

FRAGMENT C:

Aldehyde (−)-27:

A mixture of PMB ether (−)-5 (4.27 g, 9.71 mmol), Pearlman's catalyst (20% Pd(OH)$_2$/C, 1.60 g) and EtOH (120 mL) was stirred for 9 h under H$_2$ (balloon) at room temperature, filtered and concentrated. The resulting alcohol (−)-13 (3.84 g, containing p-methoxyanisole) was used without further purification. At 0° C., a solution of crude alcohol(3.84 g) and Et$_3$N (6.4 mL, 46 mmol) in CH$_2$Cl$_2$ (24 mL) and DMSO (48 mL) was treated with SO$_3$.pyridine (5.7 g, 36 mmol). After 90 min, the mixture was diluted with ether (150 mL), washed with H$_2$O (100 mL), aqueous NaHSO$_4$ (1.0 M, 100 mL), H$_2$O (100 mL) and brine (100 mL), dried over MgSO$_4$, and concentrated. Flash chromatography (20% ethyl acetate/hexanes) afforded (−)-27 (2.88 g, 93% yield) as a colorless oil that solidified on standing at 0° C. Recrystallization (hexanes) afforded colorless plates: mp 45–46° C.; [α]$^{23}_D$ −65.0° (c 1.38, CHCl$_3$); IR (CHCl$_3$) 1750, 1720 cm$^{−1}$; $^1$H NMR (500 MHz, CDCl$_3$) δ 9.68 (d, J=1.6 Hz, 1 H), 4.22 (dd, J=8.9, 2.6 Hz, 1 H), 3.68 (s, 3 H), 3.10 (apparent s, 4 H), 2.46 (qdd, J=7.1, 2.6, 1.5 Hz, 1 H), 1.16 (d, J=6.9 Hz, 3 H), 1.10 (d, J=7.0 Hz, 3 H), 0.88 (s, 9 H), 0.092 (s, 3 H), 0.088 (s, 3 H); $^{13}$C NMR (125 MHz, CDCl$_3$) δ 203.2, 175.6, 75.1, 61.5, 52.1, 39.6, 32.1, 25.9, 18.2, 15.4, 10.2, −4.07, −4.11; high resolution mass spectrum (CI, NH$_3$) m/z 318.2096 [(M+H)$^+$; calcd for C$_{15}$H$_{32}$NO$_4$Si: 318.2100].

Enone (−)-64:

To a −78° C. solution of diisopropylamine (14.24 mL, 104.1 mmol) in THF (77 mL) was added n-BuLi (2.5M in hexanes, 43 mL, 107.6 mmol). The mixture was slowly warmed to −30° C. over 30 min, stirred at 0° C. for 15 min, then cooled to −78° C. Neat mesityl oxide was then added (7.94 mL, 69.4 mmol), stirred for 5 min, followed by dropwise addition of trimethylsilylchloride (15.51 mL, 122.19 mmol). The mixture was stirred 5 min, quenched with 15 mL saturated NaHCO$_3$ solution, and diluted with 50 mL pentane. The mixture was washed (H$_2$O), separated, and the aqueous layer was extracted with pentane (2×30 mL). The combined organic extracts were dried (MgSO$_4$), filtered, and concentrated. Distillation (70° C. @ 30 Torr) provided 7.55 g (15:1 mixture)of 63 as a clear oil.

To a −78° C. solution of aldehyde (−)-27 (7.15 g, 22.5 mmol) in CH$_2$Cl$_2$ (50 mL) was added (dropwise over 20 min) TiCl$_4$ (1M in CH$_2$Cl$_2$, 22.7 mL, 22.7 mmol). The resultant solution was stirred 10 min at −78° C., then neat 63 (4.67 g, 27.4 mmol) was added dropwise over 2 min (rinse 2×5mL) and the reaction mixture was further stirred at −78° C. for 2 h. The solution was next poured into a solution comprised of pH 8 phosphate buffer (130 mL) and saturated aqueous NaHCO$_3$ solution (66 mL) and stirred for 10 min. The aqueous layer was seperated and extracted with CH$_2$Cl$_2$ (2×250 mL). The combined organic layers were washed (H$_2$O, 250 mL), diluted (hexanes, 200 mL) and treated with 1 ml of trifluoroacetic acid. The solution was stirred 10 min at ambient temperature, dried (MgSO$_4$), filtered, and concentrated. Flash chromatography (gradient elution, 1–10% EtOAc/hexanes) afforded (−)-64 (5.72 g, 72%) as a white solid: mp 53–55° C.; [α]$^{23}_D$ −10.60 (c 0.88, CHCl$_3$); IR (CHCl$_3$) 1728, 1719, 1695 cm$^{-1}$; $^1$H NMR (500 MHz, CDCl$_3$) δ 6.09 (m, 1 H), 4.78 (ddd, J=10.0, 6.6, 4.3 Hz, 1 H), 3.65 (t, J=2.8 Hz, 1 H), 2.72 (dd, J=15.8, 4.3 Hz, 1 H), 2.66 (dd, J=15.8, 6.7 Hz, 1 H), 2.62 (qd, J=7.6, 3.2 Hz, 1 H), 2.13 (d, J=1.1 Hz, 3 H), 2.07 (dqd, J=10.0, 6.8, 2.4 Hz, 1 H), 1.87 (d, J=1.2 Hz, 3 H), 1.25 (d, J=7.6 Hz, 3 H), 0.97 (d, J=6.8 Hz, 3 H), 0.87 (s, 9 H), 0.05 (s, 3 H), 0.04 (s, 3 H); $^{13}$C NMR (125 MHz, CDCl$_3$) δ 196.9, 173.6, 156.8, 124.1, 77.8, 74.3, 47.0, 43.9, 33.6, 27.7, 25.7, 20.9, 18.0, 16.1, 13.8, −4.5, −4.7; high resolution mass spectrum (ES) m/z 377.2127 [(M+Na)$^+$; calcd for C$_{19}$H$_{34}$O$_4$SiNa: 377.2124]

Alcohol (−)-65:

A solution of enone (−)-64 (6.0 g, 16.9 mmol) in toluene (170 mL) was cooled to −78° C. and treated with K-Selectride, (1.0 M in THF, 19.5 mL, 19.5 mmol). After 3 h, the mixture was added to a solution containing pH 7.0 buffer (100 mL), H$_2$O$_2$ (10 mL, 10% in MeOH), and glacial AcOH (2 mL). The resulting solution was stirred for 45 min at ambient temperature. The aqueous layer was extracted with CH$_2$Cl$_2$ (4×200 mL) and the combined organics were dried (MgSO$_4$), filtered, and concentrated.

Flash chromatography (15% ethyl acetate/hexanes, 1% AcOH) afforded (−)-65 (3.09 g, 51%) as a colorless oil that solidified on standing. Recrystallization (hexanes) afforded colorless needles: mp 77.5–78.5° C.; [α]$^{23}_D$ −21.1° (c 2.02, CHCl$_3$); IR (CHCl$_3$) 3620, 3400–3600 (br), 1725 cm$^{-1}$; $^1$H NMR (500 MHz, CDCl$_3$) δ 5.21 (apparent dt, J=8.6, 1.3 Hz, 1 H), 4.75 (br t, J=9.1 Hz, 1 H), 4.60 (td, J=9.9, 2.3 Hz, 1 H), 3.67 (t, J=3.0 Hz, 1 H), 2.66 (qd, J=7.5, 3.4 Hz, 1 H), 1.90 (dqd, 9.7, 6.8, 2.6 Hz, 1 H), 1.83 (ddd, J=14.5, 9.9, 2.4 Hz, 1 H), 1.71 (d, J=1.1 Hz, 3 H), 1.70 (d, J=1.2 Hz, 3 H), 1.65 (br s, 1 H), 1.60 (ddd, J=14.5, 10.1, 2.9 Hz, 1 H), 1.26 (d, J=7.6 Hz, 3 H), 0.99 (d, J=6.7 Hz, 3 H),0.89 (s, 9 H), 0.08 (s, 3 H), 0.07 (s, 3 H); $^{13}$C NMR (125 MHz, CDCl$_3$) δ 174.0, 134.8, 127.7, 77.8, 74.2, 64.1, 43.7, 41.5, 34.6, 25.7, 25.6, 18.2, 17.9, 16.0, 13.7, −4.6, −4.8. Anal. Calcd for C$_{19}$H$_{36}$O$_4$Si: C, 64.00; H, 10.18. Found: C, 63.92; H, 10.43.

TBS Ether (−)-66:

A solution of alcohol (−)-65 (3.09 g, 8.67 mmol) and imidazole (1.92 g, 28.2 mmol) in DMF (44 mL) was cooled to 0° C. and treated with tert-butyldimethylsilyl chloride (2.41 mg, 16.0 mmol). The resultant solution was stirred 12 h at ambient temperature, diluted with ether (75 mL), washed with H$_2$O (2×100 mL) and saturated brine (100 mL), dried over MgSO$_4$, and concentrated. Flash chromatography (5% ethyl acetate/hexanes) afforded (−)-19 (3.55 g, 87%) as a colorless oil: [α]$^{23}_D$ −20.6° (c 0.80, CHCl$_3$); IR (CHCl$_3$) 1718 cm$^{-1}$; $^1$H NMR (500 MHz, CDCl$_3$) δ 5.11 (apparent dt, J=8.6, 1.3 Hz, 1 H), 4.71 (ddd, 10.4, 8.7, 2.2 Hz, 1 H), 5.55 (td, J=10.4, 1.7 Hz, 1 H), 3.65 (t, J=2.7 Hz, 1 H), 2.63 (qd, J=7.6, 3.0 Hz, 1 H), 1.83 (dqd, 10.0, 6.8, 2.5 Hz, 1 H), 1.74 (ddd, J=14.2, 10.5, 1.8 Hz, 1 H), 1.68 (d, J=1.1 Hz, 3 H), 1.65 (d, J=1.2 Hz, 3 H), 1.44 (ddd, J=14.2, 10.6, 2.3 Hz, 1 H), 1.26 (d, J=7.6 Hz, 3 H), 0.98 (d, J=6.7 Hz, 3 H), 0.89 (s, 9 H), 0.85 (s, 9 H), 0.07 (s, 3 H), 0.06 (s, 3 H), 0.05 (s, 3 H), 0.01 (s, 3 H); $^{13}$C NMR (125 MHz, CDCl$_3$) d 173.9, 131.6, 129.1, 77.4, 74.6, 65.2, 44.0, 42.8, 34.4, 25.9, 25.7, 25.6, 18.3, 18.1, 18.0, 16.4, 14.0, −4.3, −4.5, −4.8, −4.9; high resolution mass spectrum (EI) m/z 469.3156 [(M−H)$^+$; calcd for C$_{25}$H$_{50}$O$_4$Si$_2$: 469.3156]

Fragment (−)-C:

A solution of olefin (−)-66 (570 mg, 1.20 mmol) in CH$_2$Cl$_2$ (20 mL) was cooled to −78° C. and treated with a stream of ozone and oxygen until the colorless solution became steel-blue in appearance. The reaction mixture was purged with a stream of argon for 40 min, followed by the cautious addition of triphenylphosphine (349 mg, 1.3 mmol). The cooling bath was removed, and the solution was stirred at ambient temperature for 1 h, concentrated, and chromatographed (20% ethyl acetate/hexanes) to afford (−)-67 (508 mg, 94%) as a colorless oil that solidified upon standing at 5° C. Recrystallization from hexanes afforded an analytical sample: mp 58–60° C.; [α]$^{23}_D$ −55.5° (c 1.46, CHCl$_3$); IR (CHCl$_3$) 1730 (br) cm$^{-1}$; $^1$H NMR (500 MHz, CDCl$_3$) δ 9.67 (br s, 1 H), 4.52 (td, J=10.5, 2.1 Hz, 1 H), 4.46 (dd, J=10.5, 3.5 Hz, 1 H), 3.67 (t, J=2.3 Hz, 1 H), 2.66 (qd, J=7.6, 2.6 Hz, 1 H), 1.95–1.84 (m, 3 H), 1.77 (ddd, J=14.1, 10.5, 2.1 Hz, 1 H), 1.27 (d, J=7.6 Hz, 3 H), 0.99 (d, J=6.7 Hz, 3 H), 0.92 (s, 9 H), 0.89 (s, 9 H), 0.13 (s, 3 H), 0.11 (s, 3 H), 0.08 (s, 3 H), 0.07 (s, 3 H); $^{13}$C NMR (125 MHz, CDCl$_3$) δ 203.2, 173.1, 76.0, 74.7, 73.7, 44.2, 36.2, 34.1, 25.72, 25.66, 18.1, 17.9, 16.5, 14.0, −4.55, −4.63, −4.9, −5.2; high resolution mass spectrum (CI) m/z 445.2793 [(M+H)$^+$; calcd for C$_{22}$H$_{45}$O$_5$Si$_2$: 445.2806]

(+)-39 (Modified Negeshi Coupling):

A 1.0 M solution of anhydrous ZnCl$_2$ (20 mL, 19.93 mmol) was added via syringe to a solution of alkyl iodide (+)-A (10.93 g, 19.93 mmol) in dry Et$_2$O (80 mL), and the resulting solution was degassed (2 freeze-pump thaw cycles). The solution was cooled to −78° C., and t-BuLi (1.7 M in pentane, 35.2.0 mL, 59.8 mmol) was added via cannula over 12 min. The resultant solution was stirred 5 min further, evacuated and purged (1×0.1 Torr). The −78° C. bath was removed, and the reaction was stirred at ambient temperature for 1 h. The resulting cloudy suspension was transfered by cannula into a mixture of vinyl iodide (+)-B (8.98 g, 17.3 mmol; 9:1 Z/E) and Pd(PPh$_3$)$_4$ (1.0 g, 0.87 mmol). The reaction mixture was covered with aluminum foil, stirred overnight, and quenched via slow addition of the reaction mixture to water (200 mL). The mixture was diluted with $Et_2O$, and the layers were separated. The water layer was extracted (3×$Et_2O$) and the combined organic layers were washed [saturated aqueous $NaHCO_3$, brine), dried ($MgSO_4$), filtered and concentrated. Flash chromatography (gradient elution; 2% EtOAc/hexanes ᴋ 5% or to EtOAc/hexanes] gave a white wax that was recrystrallized from 75 mL of ethanol to afford (+)-39 [9.3 g (two crops), 66% yield; 73% based on purity of vinyl iodide] as white needles: mp 81.0–81.5° C.; $[\alpha]^{23}_D$ +28.6° (c 1.12, $CHCl_3$); $^1H$ NMR (500 MHz, $CDCl_3$) d 7.36 (d, J=8.7 Hz, 2 H), 7.22 (d, J=8.6 Hz, 2 H), 6.86 (d, J=9.0 Hz, 2 H), 6.84 (d, J=8.9 Hz, 2 H), 5.37 (s, 1 H), 5.00 (d, J=10.2 Hz, 1 H), 4.36 (ABq, $J_{AB}$=11.6 Hz, $Dn_{AB}$=17.4 Hz, 2 H), 4.08 (dd, J=11.2, 4.7 Hz, 1 H), 3.78 (s, 3 H), 3.77 (s, 3 H), 3.61 (dd, J=7.1, 1.8 Hz, 1 H), 3.51 (dd, J=9.9, 1.7 Hz, 1 H), 3.47 (apparent t, J=11.0 Hz, 1 H), 3.46 (dd, J=9.1, 5.0 Hz, 1 H), 3.38 (dd, J=6.0, 4.8 Hz, 1 H), 3.19 (apparent t, J=8.8 Hz, 1 H), 2.51 (ddq, J=10.1, 6.5, 6.5 Hz, 1 H), 2.32 (apparent t, J=12.2 Hz, 1 H), 2.08–2.02 (m, 1 H), 1.99–1.93 (m, 2 H), 1.88 (dqd, J=7.1, 7.1, 1.8 Hz, 1 H), 1.67 (br d, J=11.1 Hz, 1 H), 1.55 (d, J=0.5 Hz, 3 H), 1.01 (d, J=7.1 Hz, 3 H), 0.94 (d, J=6.9 Hz, 3 H), 0.90 (s, 9 H), 0.89 (d, J=6.7 Hz, 3 H), 0.87 (s, 9 H), 0.74 (d, J=6.3 Hz, 3 H), 0.73 (d, J=6.4 Hz, 3 H), 0.03 (s, 3 H), 0.013 (s, 3 H), 0.008 (s, 3 H), 0.003 (s, 3 H); $^{13}C$ NMR (125 MHz, $CDCl_3$) δ 159.8, 159.0, 132.0, 131.5, 131.2, 131.1, 129.0, 127.3, 113.7, 113.5, 101.1, 83.4, 78.49, 78.46, 73.3, 72.6, 72.5, 55.3, 38.8, 38.2, 37.5, 35.6, 33.7, 30.8, 26.27, 26.25, 23.1, 18.42, 18.40, 17.0, 14.6, 12.6, 12.1, 10.9, −3.5, −3.7, −3.8, −3.9; high resolution mass spectrum (FAB, NBA) m/z 835.5315 [(M+Na)$^+$; calcd for $C_{47}H_{80}O_7Si_2Na$: 835.5341]. Anal. Calcd for $C_{47}H_{80}O_7Si_2$: C, 69.41; H, 9.91. Found: C, 69.52; H, 10.10.

Alcohol (+)-40 (Chemselective Hydrolysis of PMB Ether):

At 0° C., a solution of PMB ether (+)-39 (10.6 g, 12.95 mmol) in $CH_2Cl_2$ (124 mL) was treated with $H_2O$ (6 mL) and DDQ (3.18 g, 13.99 mmol) and stirred for 3 h. The mixture was quenched with 20 mL saturated $NaHCO_3$, washed with $H_2O$ (4×) and seperated. The aqueous layer was then extracted with $CH_2Cl_2$ (2×). The combined organic extracts were then dried ($MgSO_4$), filtered and concentrated from hexanes to provide an amorphous white solid. Recrystallization (250 mL EtOH) provided (+)-40 (7.31 g) as white needles. The mother liquors were then treated with $NaBH_4$ (200 mg), and the reaction mixture concentrated, diluted with $CH_2Cl_2$, washed with aqueous saturated ammonium chloride and brine. The organic layer was dried over $NaSO_4$, decanted, concentrated and chromatographed (5% EtOAc/hexanes) to provided an additional 560 mg of (+)-40 as a white solid (7.87 g total, 88%): mp 99–100° C.; $[\alpha]^{23}_D$ +26.5° (c 0.95, $CHCl_3$); IR ($CHCl_3$) 3520 cm$^{-1}$; $^1H$ NMR (500 MHz, $CDCl_3$) δ 7.36 (d, J=8.7 Hz, 2 H), 6.86 (d, J=8.8 Hz, 2 H), 5.37 (s, 1 H), 5.01 (d, J=10.1 Hz, 1 H), 4.09 (dd, J=11.2, 4.7 Hz, 1 H), 3.79 (s, 3 H), 3.65 (dd, J=10.4, 4.7 Hz, 1 H), 3.63 (dd, J=7.0, 1.8 Hz, 1 H), 3.54–3.50 (m, 1 H), 3.51 (dd, J 10.0, 2.0 Hz, 1 H), 3.47 (apparent t, J=11.2 Hz, 1 H), 3.41 (dd, J=6.6, 4.0 Hz, 1 H), 2.59 (ddq, J=13.2, 6.7, 6.7 Hz, 1 H), 2.33 (apparent t, J=12.2 Hz, 1 H), 2.24 (apparent t, J=5.5 Hz, 1 H), 2.09–1.95 (m, 2 H), 1.89 (dqd, J=7.0, 7.0, 1.7 Hz, 1 H), 1.84–1.77 (m, 1 H), 1.72 (br d, J=11.0 Hz, 1 H), 1.58 (d, J=0.8 Hz, 3 H), 1.01 (d, J=7.1 Hz, 3 H), 0.98 (d, J=7.1 Hz, 3 H), 0.94 (d, J=6.7 Hz, 3 H), 0.910 (s, 9 H), 0.905 (s, 9 H), 0.75 (d, J=7.1 Hz, 3 H), 0.74 (d, J=7.1 Hz, 3 H), 0.09 (s, 3 H), 0.07 (s, 3 H), 0.05 (s, 3 H), 0.01 (s, 3 H); $^{13}C$ NMR (125 MHz, $CDCl_3$) δ 159.8, 133.0, 131.5, 130.5, 127.3, 113.4, 101.0, 83.3, 81.6, 78.4, 73.3, 65.4, 55.3, 38.5, 38.2, 37.6, 37.0, 33.7, 30.8, 26.17, 26.16, 23.2, 18.4, 18.3, 17.4, 15.7, 12.6, 12.1, 10.9, −3.57, −3.61, −3.66, −3.9; high resolution mass spectrum (CI, $NH_3$) m/z 693.4918 [(M+H)$^+$; calcd for $C_{39}H_{73}O_6Si_2$: 693.4945]. Anal. Calcd for $C_{39}H_{72}O_6Si_2$: C, 67.58; H, 10.47. Found: C, 67.20; H, 10.39.

Trityl protected anisylidene acetal (+)-87:

To a solution of alcohol (+)-40 (8.16 g, 11.8 mmol) in pyridine (118 mL) were added trityl chloride (6.90 g, 24.8 mmol) and DMAP (3.02 g, 24.8 mmol). The mixture was then refluxed for 18 h, cooled to ambient temperature, and added to a solution of 1M citric acid (500 mL). The mixture was extracted with $CH_2Cl_2$ (3×100 mL), washed with 1 M citric acid (2×100 mL) $H_2O$ (100 mL) and saturated $NaHCO_3$ solution (100 mL). The organic solution was separated, dried ($NaSO_4$), filtered, and concentrated in vacuo. Flash chromatography (5% EtOAc/hexanes) provided (+)-87 (10.38 g, 94%) as a white foam: $[\alpha]^{23}_D$ +16.7° (c 0.30, $CHCl_3$); IR ($CHCl_3$) 2980, 2880, 1620, 1255 cm$^{-1}$; $^1H$ NMR (500 MHz, $C_6D_6$) δ 7.62 (d, J=8.69 Hz, 2 H), 7.60 (d, J=8.09 Hz, 6 H), 7.15 (dd, J=8.8, 6.6 Hz, 6 H), 7.04 (apparent t, J=7.4 Hz, 3 H), 6.84 (d, J=8.7, 2 H), 5.43 (s, 1 H), 5.06 (d, J=9.9 Hz, 1 H), 3.95 (dd, J=4.6, 11.0, 1 H), 3.77 (d, J=7.1 Hz, 1 H), 3.53 (m, 3 H), 3.48 (dd, J=5.2, 8.6, 1 H), 3.24 (s, 3 H), 3.00 (apparent t, J=8.9 Hz, 1 H), 2.72 (m, 1 H), 2.49 (apparent t, J=12.3 Hz, 1 H) 2.41 (m, 1 H), 2.19 (m, 1 H), 1.98 (m, 1 H), 1.92 (m, 2 H), 1.75 (apparent d, J=12.1 Hz, 1 H), 1.61 (s, 3 H), 1.23 (d, J=6.8 Hz, 3 H), 1.16 (d, J=7.0 Hz, 3 H), 1.14 (d, J=6.7 Hz, 3 H), 1.04 (s, 9 H), 0.98 (d, J=6.8 Hz, 3 H), 0.95 (s, 9 H), 0.42 (d, J=6.6 Hz, 3 H), 0.01 (s, 3 H), 0.08 (s, 3 H), 0.07 (s, 3 H), 0.03 (s, 3 H); $^{13}C$ NMR (125 MHz, $C_6D_6$) δ 160.4, 145.2, 132.4, 129.2, 128.3, 128.0, 127.9, 127.1, 113.8, 101.8, 86.9, 83.5, 79.1 (2), 73.3, 66.6, 54.7, 40.7, 38.7, 37.9, 36.3, 33.9, 31.0, 26.5, 26.4, 23.2, 18.7, 18.5, 18.3, 14.5, 12.9, 11.9, 11.3, −3.3, −3.5, −3.6, −3.8; high resolution mass spectrum (FAB, NBA) m/z 959.6040 [(M+Na)$^+$; calcd for $C_{58}H_{86}O_6Si_2Na$: 959.6017].

Trityl protected alcohol (−)-88:

To a 0° C. solution of trityl ether (+)-87 (10.38 g, 11.1 mmol) in $CH_2Cl_2$ (111 mL) was added DIBAL-H (1M in Toluene, 33.3 mL, 33.3 mmol). The resulting solution was stirred for 4.5 h, quenched via dropwise addition of pH 7.0 buffer (20 mL), then diluted with $CH_2Cl_2$ (100 mnL). The mixture was then added to 100 mL of saturated sodium potassium tartrate solution, extracted with $CH_2Cl_2$ (4×100 mL), and separated. The organic layer was washed with $H_2O$ (400 mL), dried ($MgSO_4$), filtered, and concentrated. Flash chromatography (20% EtOAc/hexanes) provided (−)-88 (9.5 g, 91%) as a white foam: $[\alpha]^{23}_D$ −30° (c 0.05, $CHCl_3$); IR ($CHCl_3$) 3500, 2940, 1640, 1035 cm$^{-1}$; $^1H$ NMR (500 MHz, $CDCl_3$) δ 7.42 (dd, J=7.9, 1.4 Hz, 6 H), 7.26 (m, 8 H), 7.18 (m, 3 H), 6.87 (d, J=8.6 Hz, 2 H), 4.85 (d, J=10.2 Hz, 1 H), 4.52 (d, J=10.5 Hz, 1 H), 4.49 (d, J=10.5 Hz, 1 H), 3.78 (s, 3 H), 3.73 (ddd, J=11.0, 5.2, 3.5 Hz), 3.57 (ddd, J=11.0, 5.5, 5.5 Hz, 1 H), 3.47 (dd, J=5.4, 3.4 Hz, 1 H), 3.38 (dd, J=6.3, 4.4 Hz, 1 H), 3.35 (apparent t, J=5.5 Hz, 1 H), 3.17 (dd, J=8.8, 5.4 Hz, 1 H), 2.74 (aqpparent t, J=8.8 Hz, 1 H) 2.42 (m, 1 H), 2.12 (m, 2 H), 1.93 (m, 2 H), 1.84 (m, 1 H), 1.48 (apparent d, J=11.0 Hz, 1 H), 1.40 (s, 3 H), 1.38 (m, 1 H), 1.03 (d, J=7.0 Hz, 3 H), 1.01 (d, J=6.9 Hz, 3 H), 0.96 (d, J=6.9 Hz, 3 H) 0.93 (s, 9 H), 0.86 (J=6.6 Hz, 3 H), 0.82 (s, 9 H), 0.70 (d, J=6.7 Hz, 3 H), 0.07 (s, 3 H), 0.02 (s, 3 H), −0.01 (s, 3 H), −0.08 (s, 3 H); $^{13}C$ NMR (125 MHz, $CDCl_3$) δ 159.4, 144.6, 131.4, 131.0, 130.4, 129.3, 128.8, 127.6, 126.7, 114.0, 86.3, 86.2, 78.2, 77.5, 75.2, 66.4, 65.5, 55.3, 40.2, 40.0, 37.5, 36.6, 35.7, 35.0, 26.2, 26.0, 22.9, 18.5, 18.2, 17.6, 15.6, 13.7, 13.5, 11.4, −3.4 (2), −3.9, −4.1; high resolution mass spectrum (FAB, NBA) m/z 957.5844 [(M−2H+Na)$^+$; calcd for $C_{58}H_{86}O_6Si_2Na$: 957.5861].

Trityl Protected Triene 90:

To a 0° C. solution of alcohol (−)-88 (2.65 g, 2.83 mmol) in $CH_2Cl_2$ (28 mL) were added Dess-Martin periodinane (1.31 g, 3.1 mmol) and $NaHCO_3$ (615 mg, 8.48 mmol). The resulting solution was stirred for 2.5 h and quenched with saturated $NaS_2O_3$ solution (15 mL) and saturated $NaHCO_3$ solution (15 mL). The mixture was then extracted with $Et_2O$ (3×) and separated. The organic solution was then washed with $H_2O$, dried ($MgSO_4$), filtered, and concentrated. The resulting white foam (2.54 g) was used without further purification [89]: IR ($CHCl_3$) 2960, 2850, 1720, 1250 cm$^{-1}$; $^1$H NMR (500 MHz, $CDCl_3$) δ 9.87 (d, J=2.5 Hz, 1 H), 7.54 (d, J=7.5 Hz, 6 H), 7.17 (d, J=8.5 Hz, 2 H), 7.10 (m, 6 H), 6.99 (apparent t, 7.3 Hz, 3 H), 6.74 (d, J=8.6 Hz, 2 H), 4.99 (d, J=10.2 Hz, 1 H), 4.39 (d, J=10.8 Hz, 1 H), 4.34 (d, J=10.8 Hz, 1 H), 3.56 (dd, J=2.8, 5.8 Hz, 1 H), 3.53 (dd, J=5.3, 5.2 Hz, 1 H), 3.50 (dd, J=6.6, 4.3 Hz, 1 H), 3.41 (dd, J=8.6, 5.4 Hz, 1 H), 3.24 (s, 3 H), 2.96 (apparent t, J=8.9 Hz), 2.65 (m, 1 H), 2.51 (m, 1 H), 2.33 (apparent t, J=12.4 Hz, 1 H), 1.95 (m, 1 H), 1.89 (m, 1 H), 1.64 (apparent d, J=12.1 Hz, 1 H), 1.48 (s, 3 H), 1.18 (d, J=6.9 Hz, 3 H), 1.07 (d, J=4.2, 3 H), 1.05 (d, J=4.6 Hz, 3 H), 0.97 (s, 9 H), 0.96 (s, 9 H), 0.88 (d, J=7.0 Hz, 3 H), 0.83 (d, J=6.7 Hz, 3 H), 0.05 (s, 3 H), 0.03 (s, 3 H), 0.026 (s, 3 H), 0.01 (s, 3 H); $^{13}$C NMR (125 MHz, $CDCl_3$) δ 204.4, 159.3, 144.6, 131.6, 131.5, 130.7, 129.5, 129.1 (3), 128.7, 128.0 (3), 127.1, 113.8, 86.3, 82.5, 78.2, 77.3, 74.4, 66.4, 55.2, 49.5, 40.3, 40.2, 36.6, 35.7, 34.7, 36.2 (3), 26.0 (3), 22.9, 18.5, 18.2, 17.6, 13.7, 13.2, 12.1, 11.4, −3.4 (2), −3.9, −4.1; high resolution mass spectrum (FAB, NBA) m/z 957.5861 [(M+Na)$^+$; calcd for $C_{58}H_{86}O_6Si_2Na$: 957.5963].

To a −78° C. solution of allyldiphenylphosphine (1.17 mL, 5.43 mmol) in THF (17 mL, degassed) was added 3.2 mL of t-butyllithium (1.7M in pentane, 5.43 mmol) and stirred for 5 min. The solution was then immersed into a 0° C. bath, stirred for 30 min and cooled to −78° C. The solution was treated with Ti(i-OPr)$_4$ (1.61 mL, 5.43 mmol) and stirred for 30 min. A precooled (−78° C.) solution of aldehyde 89(2.54 g, 2.72 mmol) in THF (10 mL) was added via cannula (rinse 1×2 mL) and stirred for 1 h, then warmed to 0° C. Iodomethane (1.69 mL, 27.2 mmol) was added and the solution was warmed to ambient temperature and stirred for 16 h. The solution was quenched with pH 7.0 buffer (20 mL) and extracted with $CH_2Cl_2$ (3×) and $Et_2O$ (3×). The combined organic layers were washed with saturated brine solution, dried ($MgSO_4$), filtered, and concentrated. Flash chromatography (2% EtOAc/hexanes) provided 90 (1.69 g, 62%, 2 steps, 8:1 mixture of diastereomers) as a white foam: IR ($CHCl_3$) 3060, 2940, 1600, 1450 cm$^{-1}$; $^1$H NMR (500 MHz, $CDCl_3$, major dastereomer) d 7.41 (d, J=7.2 Hz, 6 H), 7.26 (m, 8 H), 7.18 (apparent t, J=7.25 Hz, 3 H), 6.86 (d, J=8.57, 2 H), 6.56 (ddd, J=16.8, 10.7, 10.7 Hz, 1 H), 5.96 (apparent t, J=11.0 Hz, 1 H), 5.52 (apparent t, J=10.5 Hz, 1 H), 5.16 (d, J=16.8 Hz, 1 H), 5.07 (d, J=10.2 Hz, 1 H), 4.77 (d, J=10.1 Hz, 1 H), 4.76 (d, J=10.4 Hz, 1 H), 4.55 (d, J=10.4 Hz, 1 H), 3.80 (s, 3 H), 3.37 (dd, J=9.4, 4.5 Hz, 1 H), 3.35 (dd, J=6.6, 4.3 Hz, 1 H), 3.23 (dd, J=7.2, 3.7 Hz, 1 H), 3.13 (dd, J=8.7, 5.5 Hz, 1 H), 2.97 (m, 1 H), 2.73 (apparent t, J=8.9 Hz, 1 H), 2.35 (m, 1 H), 2.10 (m, 1 H), 1.90 (apparent t, J=12.4 Hz, 1 H), 1.74 (m, 1 H), 1.69 (m, 1 H); $^{13}$C NMR (125 MHz, $CDCl_3$, major diastereomer) δ 159.1, 144.7, 134.5, 132.2, 131.7, 131.3, 130.6, 129.2, 129.1, 128.8, 127.6, 126.8, 117.6, 113.7, 86.3, 84.6, 78.2, 75.0, 66.5, 55.3, 40.5, 40.1, 35.9, 35.5, 35.4, 35.2, 26.3, 26.0, 22.8, 18.6, 18.2, 17.7, 14.7, 14.1, 13.5, 10.5, −3.15, −3.35, −3.97, −4.12; high resolution mass spectrum (FAB, NBA) m/z 981.6225 [(M+Na)$^+$; calcd for $C_{61}H_{90}O_5Si_2Na$: 981.6224].

Triene Alcohol 74:

Anhydrous MeOH (151 mL) was added to a cold (0° C.) solution of chlorocatecholborane (2.31 g, 14.5 mmol) in 4.5 mL of $CH_2Cl_2$ (3.2 M), and the resulting solution was added in 0.6 mL (1.94 mmol) aliquots at 10 min intervals to a 0.07 M solution of trityl ether 90 (1.86 g, 1.94 mmol, 8:1 dr) at 0° until TLC (20% EtOAc/hexanes) indicated ca. 90% reaction completion (total of 2.4 mL of rgt solution, 7.74 mmol), at which point the reaction was quenched via dropewise addition of 20 mL of saturated $NaHCO_3$. The resulting mixture was stirred for 15 min, diluted with 40 mL $Et_2O$, stirred an additional 30 min, and the layers were separated. The aqueous layer was extracted (3×$Et_2O$), and the resulting organic layers were combined, washed (water and saturated brine solution), dried ($MgSO_4$), filtered, added to 10 g of $SiO_2$ and concentrated. Flash chromatography (gradient elution; 5% EtOAc/hexanes to 10% EtOAc/hexanes; 2nd column: 100% $CH_2Cl_2$; then 20% EtoAc/hexanes) provided 74 (1.20 g, 86%, 8:1 dr) as a white foam and starting ether 90 (247 mg, 13%; 99% based on recovered starting material). $[α]^{23}{}_D$ +32° (c 0.70, $CHCl_3$; 12:1 dr); IR ($CHCl_3$) 3500, 2950, 1620, 1250 cm$^{-1}$; $^1$H NMR (500 MHz, $CDCl_3$, major diastereomer) δ 7.27 (d, J=8.6 Hz, 2 H), 6.87 (d, J=8.6 Hz, 2 H), 6.61 (ddd, J=16.8, 10.6, 10.6, 1 H), 6.05 (apparent t, J=11.0 Hz, 1 H), 5.58 (apparent t, J=10.6 Hz, 1 H), 5.23 (d, J=16.8 Hz, 1 H), 5.12 (d, J=10.3 Hz, 1 H), 4.98 (d, J=10.2 Hz, 1 H), 4.57 (d, J=10.6 Hz, 1 H), 4.45 (d, J=10.5 Hz, 1 H), 3.80 (s, 3 H), 3.66 (ddd, J=10.8, 4.8, 4.5, 1 H), 3.51 (ddd, J=11.0, 5.7, 5.6 Hz, 1 H), 3.45 (dd, J=4.7, 3.9 Hz, 1 H), 3.40 (dd, J=6.9, 3.8 Hz, 1 H), 0.26 (dd, J=7.3, 3.7 Hz, 1 H), 3.0 (m, 1 H), 2.56 (m, 1 H), 2.29 (apparent t, J=5.52 Hz, 1 H), 2.06 (apparent t, J=12.4 Hz, 1 H), 1.81 (m, 3 H), 1.65 (apparent d, J=11.2 Hz, 1 H), 1.59 (s, 3 H), 1.11 (d, J=6.8 Hz, 3 H), 1.01 (d, J=7.0 Hz, 3 H), 0.99 (d, J=7.2 Hz, 3 H), 0.95 (s, 9 H), 0.92 (m, 12 H), 0.72 (d, J=6.7 Hz, 3 H), 0.11 (s 9 H), 0.08 (s, 3 H), ; $^{13}$C NMR (125 MHz, $CDCl_3$, major diastereomer) δ 159.1, 134.5, 132.8, 132.3, 131.2, 130.5, 129.2, 129.0, 117.5, 113.7, 84.6, 81.7, 77.1, 75.0, 65.3, 55.3, 40.1, 38.5, 36.8, 36.1, 35.4, 35.3, 26.7, 26.3, 26.2, 23.0, 18.7, 18.6, 18.3, 17.6, 15.8, 14.6, 10.6, −3.2, −3.4, −3.6, −3.9; high resolution mass spectrum (FAB, NBA) m/z 739.5129 [(M+Na)$^+$; calcd for $C_{42}H_{76}O_5Si_2Na$: 739.5156].

Phosphonium Salt 75:

A solution of iodine (1.07 g, 4.24 mmol) in 10 mL of $Et_2O$ was added dropwise to a vigorously stirred solution of alcohol (+)-74 (1.41 g, 1.97 mmol; 8:1 mix of cis/trans diene isomers), $PPh_3$ (1.37 g, 5.22 mmol) and imidazole (342 mg, 5.02 mmol) in benzene/ether (1:1, 40 mL) at 0° C. The resultant cannary yellow suspension was stirred 30 min at 0° C. and poured into 150 mL of 1:1 water/hexanes. The layers were separated and the aqueous layer was extracted with hexanes. The combined organic layers were washed with saturated aqueous sodium metabisulfite (2×50 mL), water (1×50 mL) and brine (100 mL). The clear, colorless organic layer was dried over $MgSO_4$, filtered and concentrated. The resulting white slurry was loaded onto a plug of $SiO_2$ with a minimal amount of $CH_2Cl_2$ and rapidly eluted off the column (0.05% $Et_3N$/2% $Et_2O$/hexanes) to afford the corresponding iodide as colorless oil (8:1 ds mixture of diene isomers; contaminated with ca. 20% $PPh_4$) which was taken on to the next step without further purification: $^1$H NMR (500 MHz, $C_6D_6$, major diene isomer) δ 7.51 (m, 6 H), 7.43 (d, J=8.6 Hz, 2 H), 7.18 (m, 9 H), 6.97 (d, J=8.6 Hz, 2 H), 6.84 (ddd, J=16.8, 10.8, 10.8 Hz, 1 H), 6.23 (apparent t, J=10.8 Hz, 1 H), 5.84 (apparent t, J=10.5 Hz, 1 H), 5.33 (dd, J=16.8, 1.9 Hz, 1 H), 5.27 (d, J=10.4, 1 H), 5.23 (d, J=10.2 Hz), 4.74 (d, J=10.7 Hz, 1 H), 4.66 (d, J=10.7 Hz, 1 H), 3.76 (apparent t, J=4.4 Hz, 1 H), 3.58 (dd, J=6.6, 4.0 Hz, 1 H), 3.48 (m, 2 H), 3.46 (s, 3 H), 3.24 (m, 1 H), 3.17 (dd, J=9.6, 8.0 Hz, 1 H), 2.80 (m, 1 H), 2.44 (apparent t, J=12.3 Hz, 1 H), 2.17 (m, 1 H), 2.10 (m, 1 H), 2.02 (m, 1 H), 1.78 (s, 3 H), 1.38 (d, J=6.9 Hz, 3 H), 1.27 (d, J=6.8 Hz, 3 H), 1.20 (s, 9 H), 1.18 (m, 6 H), 1.10 (s, 9 H), 1.06 (d, J=6.7 Hz, 3 H), 0.33 (s, 3 H), 0.31 (s, 3 H), 0.24 ( s, 3 H), 0.23 ( s, 3 H).

To a solution of above Iodide in benzene/toluene (7:3, 5.0 mL) was added diisopropylethylamine (0.2 mL, 1.14 mmol) and triphenylphosphine (2.5 g, 9.53 mmol). The resulting solution was loaded into a 20 mL polyethylene syringe and capped in such a way as to eliminate any trapped air (3×1.0 mL rinse of 7:3 benzene/toluene solution). The syringe was loaded into a high pressure apparatus and subjected to a pressure of 12.8 Kbar. After 14 days, the reaction mixture was concentrated and chromatographed (gradient elution, 20% EtOAc/hexanes to 50% EtOAc/hexanes, then 20% MeCN/CH$_2$Cl$_2$) to provide 75 as a light yellow solid [1.68 g, 78% yield from alcohol 46; 8:1 dr]: $[\alpha]^{23}_D$ +22° (c 1.0,CHCl$_3$); IR (CHCl$_3$) 2940, 1610, 1580, 1250 cm$^{-1}$; $^1$H NMR (500 MHz, CDCl$_3$, Major isomer) δ 7.75 (m, 15 H) 7.27 (d, J=8.6 Hz, 2 H) 6.86 (d, J=8.6 Hz, 2 H), 6.54 (ddd, J=16.8, 10.6, 10.6 Hz, 1 H), 5.89 (apparent t, J=11.0 Hz, 1 H), 5.50 (apparent t, J=10.5 Hz, 1 H),5.30 (d, J=10.6 Hz, 1 H), 5.12 (d, J=16.8 Hz, 1 H), 5.08 (d, J=10.2 Hz, 1 H), 4.56 (d, J=10.4 Hz, 1 H),4.45 (d, J=10.4 Hz, 1 H), 3.78 (s, 3 H), 3.70 (m, 1 H), 3.69 (dd, J=6.7, 4.6 Hz, 1 H), 3.42 (dd, J=5.3, 3.1 Hz, 1 H), 3.23 (dd, J=7.9, 3.2 Hz, 1 H), 3.19 (m, 1 H), 2.97 (m, 1 H), 2.41 (m, 1 H), 2.03 (m, 1 H), 1.94 (apparent t, J=12.2 Hz, 1 H), 1.84 (m, 2 H), 1.57 (m, 1 H), 1.54 (s, 3 H), 1.10 (d, J=6.8 Hz, 3 H), 0.96 (d, J=6.8 Hz, 3 H), ) 0.89 (m, 21 H), 0.69 (d, J=6.9 Hz, 3 H), 0.66 (d, J=6.7 Hz, 3 H), 0.095 (s, 3 H), 0.08 (s, 3 H), 0.04 (s, 3 H), −0.05 (s, 3 H); $^{13}$C NMR (125 MHz, CDCl$_3$) δ 159.1, 135.3, 135.2, 134.2, 133.5, 133.4, 132.5, 132.3, 131.0, 130.9, 130.7, 130.6, 130.4, 129.1, 128.8, 128.2, 118.6, 118.0, 117.6, 113.7, 84.6, 80.0, 79.9, 76.8, 75.1, 55.3, 39.8, 35.8, 35.5, 35.3, 35.2, 26.2, 26.1 (2), 26.0, 22.6, 18.6, 18.5, 18.2, 17.4, 16.9, 15.0, 10.5, −3.3, −3.4 (2), −4.0; high resolution mass spectrum (FAB, NBA) m/z 961.6134[(M-I)$^+$; calcd for C$_{60}$H$_{90}$O$_4$PSi$_2$: 961.6115].

Tetraene 58 (Wittig Coupling):

Phosphonium salt 75 (1.20 g, 1.10 mmol; 8:1 ratio of diene isomers), was azeotropically dried with benzene (3×1.5 mL) using a double manifold and further dried by heating to 50° C. under vacuum (0.2 torr) for 12 h. The salt was dissolved in 6 mL of freshly distilled THF, sparged with argon for 15 min, and cooled to −20° C. The resultant solution was treated with sodium bis(trimethylsilyl)amide (1.0 M in THF, 1.04 mL), stirred 15 min, warmed to 0° C., stirred 30 min, and re-chilled to −24° C. To this orange/red solution was transferred via cannula a degassed solution of aldehyde (−)-67 (508 mg, 1.14 mmol) in THF (3 mL+1×0.5 mL rinse) over 7 min. The orange solution was allowed to slowly warm to −8° C. over 3.25 h. The resulting light yellow solution was quenched with saturated NH$_4$Cl, diluted with Et$_2$O and H$_2$O. The layers were separated, and the aqueous layer was extracted (3×Et$_2$O). The combined organic layers were dried (Na$_2$SO$_4$), concentrated, and chromatographed (gradient elution; 2% EtOAc/hexanes or 50% to EtOAc/hexanes; then 40% CH$_3$CN/CH$_2$Cl$_2$) to afford cis isomer 58 (767 mg, 65%; white foam, 8:1 ratio of diene isomers), transi isomer 58 (50 mg, 4%; clear oil; 8:1 ratio of diene isomers), and phosphonium salt 75 (399 mg, 33%; 8:1 ratio of diene isomers). [enant-(+)-58 $[\alpha]^{23}_D$ −32° (c 0.23, CHCl$_3$)]; IR (CHCl$_3$) 1725 cm$^{-1}$; $^1$H NMR (500 MHz, CDCl$_3$, major diene isomer) δ 7.25 (d, J=9.0 Hz, 2 H), 6.84 (d, J=8.7 Hz, 2 H), 6.57 (ddd, J=16.7, 10.6, 10.6 Hz, 1 H), 6.00 (apparent t, J=11.0 Hz, 1 H), 5.55 (apparent t, J=10.5 Hz, 1 H), 5.26 (dd, J=11.1, 7.9 Hz, 1 H), 5.19 (dd, J=15.4, 1.4 Hz, 1 H), 5.18 (apparent t J=10.1 Hz, 1 H), 5.10 (d, J=10.2 Hz, 1 H), 5.01 (d, J=10.0 Hz, 1 H), 4.75 (apparent t, J=9.2 Hz, 1 H), 4.50 (ddd, J=10.5, 1.3, 1.3 Hz, 1 H), 4.50 (ABq, J$_{AB}$=10.6 Hz, Δ$_{AB}$=42.6 Hz, 2 H), 3.78 (s, 3 H), 3.60 (apparent t, J=2.4 Hz, 1 H), 3.42 (dd, J=5.1, 3.7 Hz, 1 H), 3.23 (dd, J=7.5, 3.7 Hz, 1 H), 3.20 (apparent t, J=5.4 Hz, 1 H), 3.01–2.94 (m, 1 H), 2.60 (qd, J=7.7, 2.6 Hz, 1 H), 2.62–2.55 (m, 1 H), 2.45–2.38 (m, 1 H), 1.98 (apparent t, J=12.3 Hz, 1 H), 1.84–1.67 (m, 3 H), 1.63 (br d, J=13.2 Hz, 1 H), 1.52 (s, 3 H), 1.55–1.48 (m, 1 H), 1.20 (d, J=7.6 Hz, 3 H), 1.09 (d, J=6.8 Hz, 3 H), 0.98 (d, J=6.8 Hz, 3 H), 0.93 (apparent d, J=6.7 Hz, 6 H), 0.93 (s, 9 H), 0.89 (s, 9 H), 0.86 (s, 9 H), 0.85 (s, 9 H), 0.84 (d, J=6.8 Hz, 3 H), 0.69 (d, J=6.7 Hz, 3 H), 0.085 (s, 3 H), 0.079 (s, 3 H), 0.051 (s, 3 H), 0.046 (s, 3 H), 0.042 (s, 3 H), 0.029 (s, 3 H), 0.028 (s, 3 H), −0.02 (s, 3 H); $^{13}$C NMR (125 MHz, CDCl$_3$) δ 173.2, 159.1, 134.4, 133.4, 132.4, 132.2, 131.9, 131.3, 131.2, 129.11, 129.09, 117.6, 113.7, 84.6, 80.5, 76.9, 75.0, 74.9, 64.6, 55.3, 44.1, 42.7, 40.1, 37.5, 36.0, 35.44, 35.37, 35.2, 34.2, 26.31, 26.28, 25.9, 25.7, 23.0, 18.7, 18.6, 18.4, 18.1, 18.0, 17.1, 16.5, 16.4, 14.9, 14.1, 10.5, −3.0, −3.2, −3.3, −4.3, −4.4, −4.5, −4.8, −4.9; high resolution mass spectrum (FAB, NBA) m/z 1149.7836 [(M+Na)$^+$; calcd for C$_{64}$H$_{118}$O$_8$Si$_4$Na: 1149.7802].

Alcohol (+)-59:

At 0° C., a solution of PMB ether 58 (1.12 g, 0.993 mol, 8:1 mixture of cis/trans diene isomers) in CH$_2$Cl$_2$ (10 mL) was treated with H$_2$O (0.5 mL) and DDQ (270 mg, 1.19 mmol). The mixture was stirred for 10 min at 0° C., warmed to rt and stirred an additional 5 min. The mixture was quenched with 50 mL saturated NaHCO$_3$, diluted with CH$_2$C$_{12}$ (300 mL), and washed with H$_2$O (500 mL) and saturated brine solution (500 mL). The combined organic layers were dried (MgSO$_4$), filtered and concentrated. Flash chromatography (gradient elution; 4%EtOAc to 20% EtOAc/hexanes) provided (+)-59 (822 mg, 82%) as a white foam: [enant-(+)-33 $[\alpha]^{23}_D$ −20° (c 0.34, CHCl$_3$)]; IR (film, NaCl) 3500 (br), 1740 cm$^-$; $^1$H NMR (500 MHz, CDCl$_3$) δ 6.61 (ddd, J=16.8, 10.9, 10.9 Hz, 1 H), 6.13 (apparent t, J=11.0 Hz, 1 H), 5.32 (apparent t, J=10.5 Hz, 1 H), 5.28 (dd, J=11.1, 7.9 Hz, 1 H), 5.24–5.21 (m, 1 H), 5.19 (apparent t, J=10.3 Hz, 1 H), 5.14 (d, J=10.2 Hz, 1 H), 5.06 (d, J=10.0 Hz, 1 H), 4.76 (apparent t, J=9.3 Hz, 1 H), 4.50 (apparent t, J=9.9 Hz, 1 H), 3.62 (apparent t, J=2.4 Hz, 1 H), 3.60 (dd, J=5.5, 3.4 Hz, 1 H), 3.32 (br d, J=5.3 Hz, 1 H), 3.24 (apparent t, J=5.1 Hz, 1 H), 2.79 (ddq, J=9.9, 6.7, 6.7 Hz, 1 H), 2.60 (qd, J=7.6, 2.7 Hz, 1 H), 2.63–2.57 (m, 1 H), 2.50–2.45 (m, 1 H), 2.16 (apparent t, J=12.3 Hz, 1 H), 1.90–1.77 (m, 3 H), 1.75–1.69 (m, 2 H), 1.57 (s, 3 H), 1.60–1.50 (m, 1 H), 1.20 (d, J=7.6 Hz, 3 H), 0.96 (d, J=6.8 Hz, 3 H), 0.95 (d, J=6.6 Hz, 3 H), 0.95–0.93 (m, 6 H), 0.91 (s, 9 H), 0.89 (s, 9 H), 0.89–0.84 (m, 3 H), 0.87 (s, 9 H), 0.85 (s, 9 H), 0.73 (d, J=6.8 Hz, 3 H), 0.07 (apparent s, 6 H), 0.052 (s, 3 H), 0.051 (s, 3 H), 0.04 (apparent s, 6 H), 0.03 (s, 3 H), −0.01 (s, 3 H); $^{13}$C NMR (125 MHz, CDCl$_3$) d 173.3, 134.7, 133.5, 132.5, 132.1, 132.0, 131.5, 131.0, 118.4, 80.5, 78.8, 76.4, 74.9, 64.7, 44.1, 42.7, 38.0, 37.4, 36.3, 36.1, 35.2, 35.1, 34.2, 26.3, 26.2, 25.9, 25.7, 23.2, 18.5, 18.1, 18.0, 17.3, 17.2, 16.4, 16.1, 14.1, 13.7, 9.4, −3.0, −3.3, −3.6, −4.34, −4.36, −4.5, −4.8; high resolution mass spectrum (FAB, NBA) m/z 1029.7273 [(M+Na)$^+$; calcd for $C_{56}H_{110}O_7Si_4Na$: 1029.7226; DDQ Adduct 32: $[\alpha]^{23}{}_D$ +47° (c 1.2, $CHCl_3$)]; IR ($CHCl_9$) 3225, 2900, 1710, 1580, 1070 cm$^{-1}$; $^1H$ NMR (500 MHz, $C_6D_6$, 1:1 mixture of C21 diastereomers) δ 5.60 (m, 2 H), 5.26 (m, 2 H), 5.15 (m, 2 H) 4.75 (apparent t, J=10.5 Hz, 1 H), 4.43 (dd, J=11.6, 1.0 Hz, 1 H), 3.47 (m, 2 H), 3.04 (2, 1 H), 2.92 (m, 1 H), 2.80 (m, 1 H), 2.73 (m, 1 H), 2.66 (m, 1 H), 2.44 (apparent d, J=9.6 Hz, 1 H), 2.25 (m, 2 H), 2.12 (dd, J=17.1, 5.4 Hz, 1 H), 1.86 (m, 7 H), 1.76 (m, 1 H), 1.70 (apparent t, J=12.6 Hz, 1 H), 1.24 (d, J=6.8 Hz, 3 H), 1.21 (d, J=6.6 Hz, 3 H), 1.15 (d, J=7.6 Hz, 3 H), 1.13 (s, 9 H), 1.08 (s, 9 H), 1.06 (s, 9 H), 1.01 (d, J=6.7 Hz, 3 H), 0.94 (s, 9 H), 0.94 (s, 9 H), 0.90 (d, J=6.6 Hz, 3 H), 0.84 (d, J=6.8 Hz, 3 H), 0.40 (d, J=6.6 Hz, 3 H), 0.34 (s, 3 H), 0.30 (s, 3 H), 0.27 (s, 3 H), 0.26 (s, 3 H), 0.21 (s, 6 H), −0.01 (s, 3 H), −0.04 (s, 3 H); high resolution mass spectrum (FAB, NBA) m/z 1255.6598 [(M+Na)$^+$; calcd for $C_{64}H_{110}Cl_2N_2O_9Si_4Na$: 1255.6563].

Carbamate (−)-60.

A solution of alcohol (+)-59 (822 mg, 0.816 tmol) in $CH_2Cl_2$ (8.2 mL) was treated with $Cl_3CCON{=}C{=}O$ (980 mL, 0.979 mmol) at room temperature for 30 min. Solution was loaded directly onto neutral $Al_2O_3$ (1.5×4" plug). After 4 h, the material was flushed from the $Al_2O_3$ (EtOAc, 500 mL), concentrated, and purified by flash chromatography (10% ethyl acetate/hexanes) providing 786 mg (+)-60 (92%) as a white foam: [enant (+)-60 $[\alpha]^{23}{}_D$ −37° (c 0.19, $CHCl_3$)]; IR (film, NaCl) 3510, 3360 (br), 3180, 1730 (br) cm$^{-1}$; $^1H$ NMR (500 MHz, $CDCl_3$) d 6.58 (dddd, J=16.8, 10.6, 10.6, 0.7 Hz, 1 H), 6.01 (apparent t, J=11.0 Hz, 1 H), 5.36 (apparent t, J=10.4 Hz, 1 H), 5.27 (dd, J=11.1, 7.9 Hz, 1 H), 5.22–5.16 (m, 2 H), 5.12 (d, J=10.1 Hz, 1 H), 5.03 (d, J=10.0 Hz, 1 H), 4.76 (apparent t, J=9.2 Hz, 1 H), 4.71 (apparent t, J=6.1 Hz, 1 H), 4.50 (ddd, J=10.5, 10.5, 1.3 Hz, 1 H), 4.44 (br s, 2 H), 3.62 (apparent t, J=2.4 Hz, 1 H), 3.42 (apparent t, J=4.5 Hz, 1 H), 3.22 (apparent t, J=5.3 Hz, 1 H), 2.98 (ddq, J=10.1, 6.6, 6.6 Hz, 1 H), 2.60 (qd, J=7.6, 2.7 Hz, 1 H), 2.63–2.55 (m, 1 H), 2.48–2.41 (m, 1 H), 2.09 (apparent t, J=12.4 Hz, 1 H), 1.93–1.88 (m, 1 H), 1.87–1.77 (m, 2 H), 1.71 (ddd, J=14.1, 10.8, 1.6 Hz, 1 H), 1.67 (br d, J=13.7 Hz, 1 H), 1.56 (apparent s, 3 H), 1.55–1.50 (m, 1 H), 1.21 (d, J=7.6 Hz, 3 H), 0.98 (d, J=6.8 Hz, 3 H), 0.95 (d, J=7.0 Hz, 3 H), 0.94 (d, J=7.5 Hz, 3 H), 0.918 (d, J=6.8 Hz, 3 H), 0.915 (s, 9 H), 0.89 (s, 9 H), 0.86 (s, 9 H), 0.853 (d, J=6.4 Hz, 3 H), 0.847 (s, 9 H), 0.70 (d, J=6.8 Hz, 3 H), 0.09 (s, 3 H), 0.07 (s, 3 H), 0.053 (s, 3 H), 0.051 (s, 3 H), 0.040 (s, 3 H), 0.037 (s, 3 H), 0.03 (s, 3 H), −0.02 (s, 3 H); $^{13}C$ NMR (125 MHz, $CDCl_3$) d 173.3, 156.9, 133.6, 133.5, 132.4, 132.1, 131.9, 131.4, 129.8, 118.0, 80.5, 78.9, 74.9, 64.6, 44.2, 42.7, 37.8, 37.4, 36.0, 35.3, 35.2, 34.5, 34.2, 26.3, 26.2, 25.9, 25.7, 23.0, 18.5, 18.4, 18.1, 18.0, 17.5, 17.1, 16.44, 16.38, 14.1, 13.7, 10.1, −3.0, −3.4, −3.6, −4.4, −4.5, −4.8; high resolution mass spectrum (FAB, NBA) m/z 1072.7264 [(M+Na)$^+$; calcd for $C_{57}H_{111}NO_8Si_4Na$: 1072.7283].

(+)-Discodermolide [1].

Carbamate (+)-60 (202 mg, 0.191 mmol) was dissolved in MeOH (70 mL) and stirred for 15 min at room temperature. Aqueous hydrochloric acid (3N, 40 mL) was added in 2–4 mL portions over 4 hours at a rate which minimized precipitation (ca. 10 to 15 min intervals). An additional 20 mL of 3 N aq HCl was added over 1 h at 15 min intervals, and the sides of the flask/stir bar were rinsed with 8 mL of MeOH. After 8 h, an additional 20 mL of 3 N aq HCl was added in one portion, and the resulting solution was stirred for 2 h at rt, diluted with 350 mL of water and poured into 400 mL of EtOAc. The resulting layers were separated, and the aqueous layer was saturated with NaCl and extracted (3×EtOAc). The combined organic layers were washed with saturated aqueous $NaHCO_3$ (2×100 mL) and saturated brine, dried ($Na_2SO_4$), filtered, and concentrated. Flash chromatography (gradient elution; 5% MeOH/$CH_2Cl_2$ to 10% MeOH/$CH_2Cl_2$) gave 1 (107 mg, 93% yield) as a white amorphous solid. X-ray quality crystals were obtained by dissolving the amorphous solid in acetonitrile (0.1 M) at rt and allowing the solution to stand for several hours at rt: mp 108–111°; $[\alpha]^{23}{}_D$ +16° (c 0.033, MeOH); IR ($CHCl_3$) 3690, 3620, 3540, 3430, 1740 cm$^{-1}$; $^1H$ NMR (500 MHz, $CDCl_3$) δ 6.60 (dddd, J=16.8, 8.4, 8.4, 0.8 Hz, 1 H), 6.02 (apparent t, J=11.1 Hz, 1 H), 5.51 (dd, J=11.2, 7.9 Hz, 1 H), 5.42 (ddd, J=10.6, 10.6, 0.6 Hz, 1 H), 5.34 (apparent t, J=10.4 Hz, 1 H), 5.20 (dd, J=16.9, 1.9 Hz, 1 H), 5.16 (d, J=10.0 Hz, 1 H), 5.11 (d, J=10.1 Hz, 1 H), 4.77–4.69 (m, 1 H), 4.70 (dd, J=7.3, 4.2 Hz, 1 H), 4.60 (ddd, J=10.0, 10.0, 2.4 Hz, 1 H), 4.56 (br s, 2 H), 3.73 (m, 1 H), 3.28 (m, 1 H), 3.18 (dd, J=6.8, 4.8 Hz, 1 H), 2.98 (ddq, J=10.1, 6.9, 6.9 Hz, 1 H), 2.78 (ddq, J=9.8, 6.8, 6.8 Hz, 1 H), 2.66 (qd, J=7.3, 4.6 Hz, 1 H), 2.60–2.55 (m, 1 H), 2.10–1.80 (m, 10 H), 1.69 (ddd, J=14.4, 10.3, 3.1 Hz, 1 H), 1.64 (d, J=1.3 Hz, 3 H), 1.30 (d, J=7.4 Hz, 3 H), 1.06 (d, J=6.9 Hz, 3 H), 1.00 (d, J=6.8 Hz, 3 H), 0.99 (d, J=6.7 Hz, 3 H), 0.97 (d, J=6.8 Hz, 3 H), 0.94 (d, J=6.8 Hz, 3 H), 0.82 (d, J=6.3 Hz, 3 H); $^{13}C$ NMR (125 MHz, $CDCl_3$) d 173.6, 157.0, 134.4, 133.7, 133.4, 132.9, 132.2, 129.9, 129.8, 117.9, 79.1, 78.9, 77.2, 75.7, 73.2, 64.4, 43.1, 41.0, 37.4, 36.1, 36.0, 35.8, 35.3, 34.8, 33.1, 23.3, 18.4, 17.4, 15.6, 15.5, 13.7, 12.5, 9.0; high resolution mass spectrum (FAB, NBA) m/z 616.3840 [(M+Na)$^+$; calcd for $C_{33}H_{55}NO_8Na$: 616.3826].

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A process for forming a tetraene of formula:

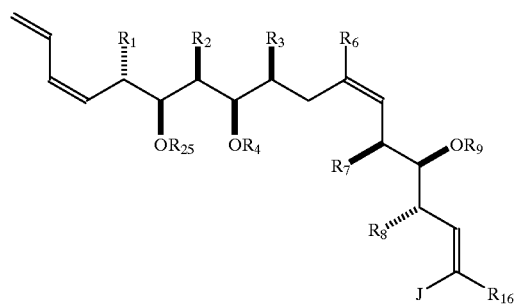

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl;

$R_4$ and $R_9$ are independently an acid labile hydroxyl protecting group;

$R_{25}$ is an oxidatively labile protecting group; and

J is selected from:

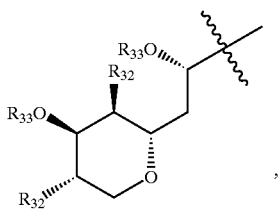
,

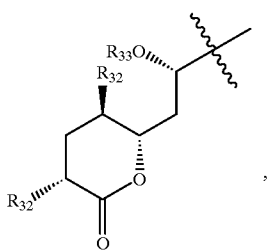
,

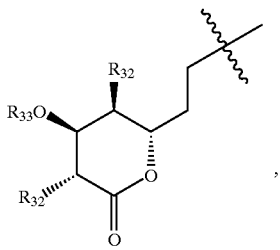
,

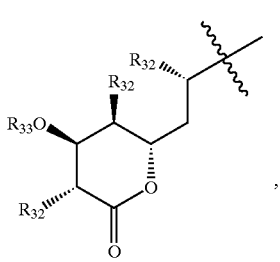
,

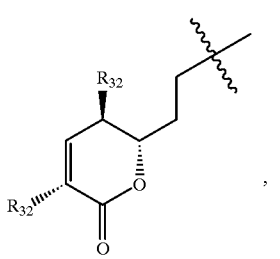
,

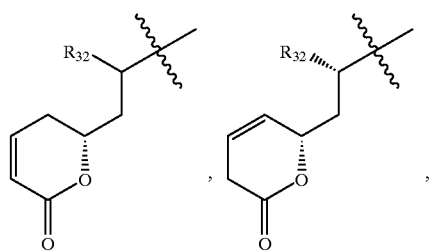
,

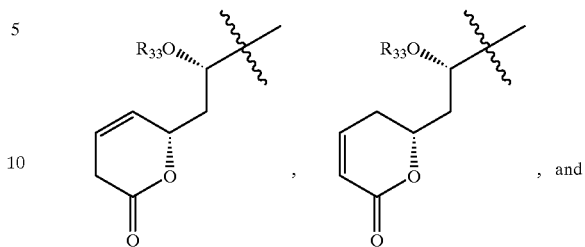
, and

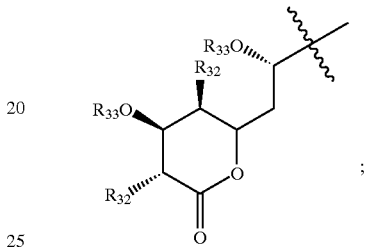
;

wherein $R_{32}$ is $C_1$–$C_6$ alkyl and $R_{33}$ is an acid labile hydroxyl protecting group;
the process comprising contacting a compound of the formula:

J—CHO with a phosphonium salt of the formula:

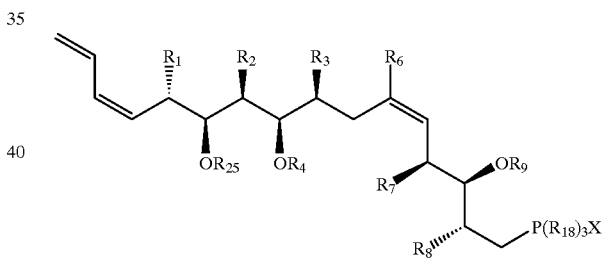

wherein $R_{18}$ is $C_6$–$C_{14}$ aryl, in the presence of a base for a time and under conditions effective to form the tetraene.

2. The process according to claim 1 wherein $R_1$, $R_2$, $R_7$, and $R_8$ are independently $C_1$–$C_4$ alkyl, $R_3$ and $R_6$ are independently selected from hydrogen and $C_1$–$C_4$ alkyl, and $R_{32}$ is $C_{1-4}$ alkyl.

3. A process for forming a tetraene of formula:

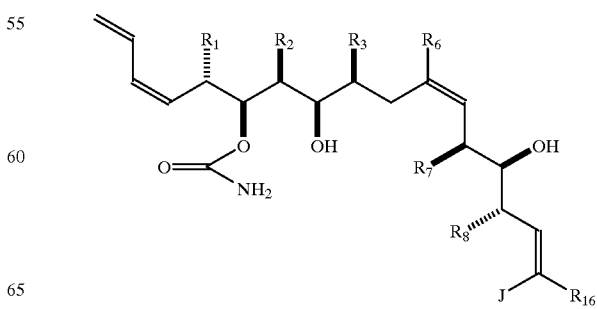

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl; and J is selected from:

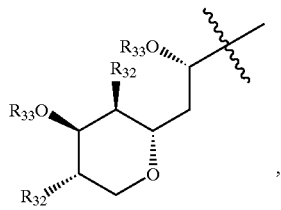
,
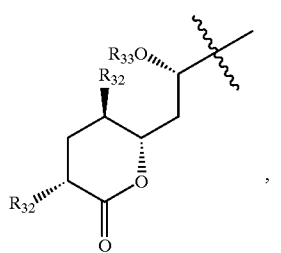
,
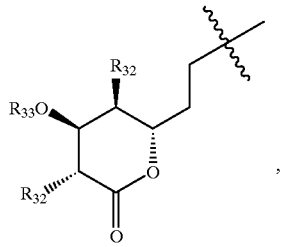
,
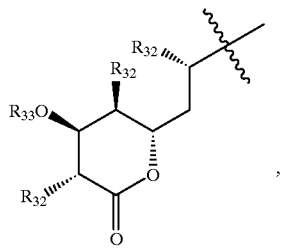
,
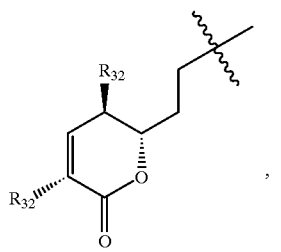
,
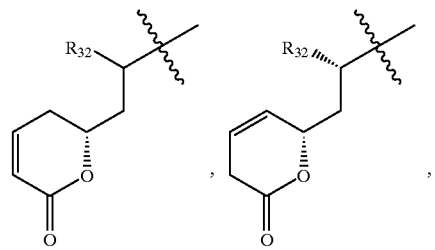
, -continued

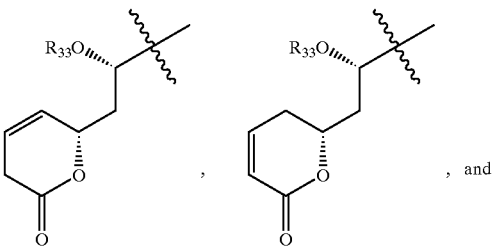
, and

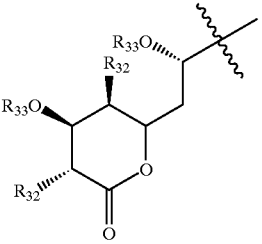
;

wherein $R_{32}$ is $C_1$–$C_6$ alkyl and $R_{33}$ is H;

the process comprising contacting an alcohol of formula:

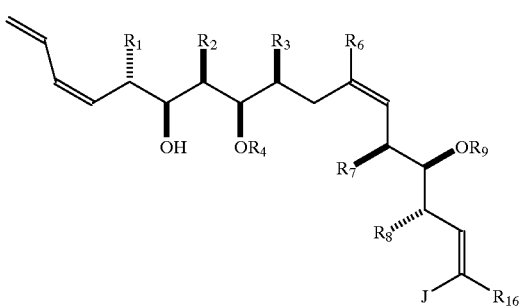

wherein $R_4$, $R_9$, and $R_{33}$ are acid labile hydroxyl protecting groups, with an isocyanate of the formula:

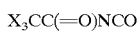

$X_3CC(=O)NCO$ wherein X is a halogen, to form a trichloroaceryl carbamate intermediate;

contacting the trichloroaceryl carbamate intermediate with neutral alumina to form a carbamate of formula:

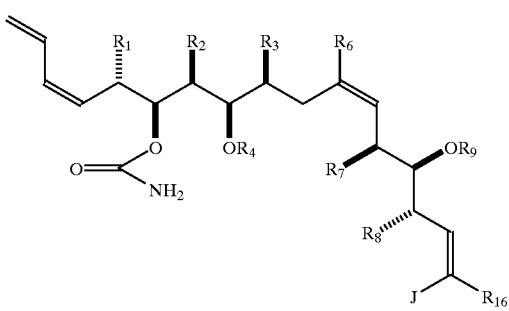

and;

removing the acid labile hydroxyl protecting groups by contacting the carbamate with acid in a protic solvent to form the tetraene.

4. The process according to claim 3 wherein the alcohol is formed by contacting a compound of formula:

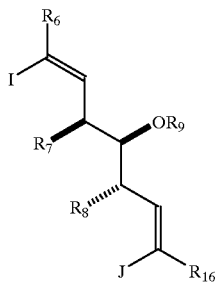

with a compound of formula:

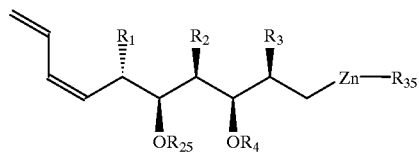

wherein $R_{25}$ is an oxidatively labile protecting group, and $R_{35}$ is selected from $C_4$ alkyl and a halogen, in the presence of a metal coupling catalyst for a time and under conditions effective to form a coupling product of formula:

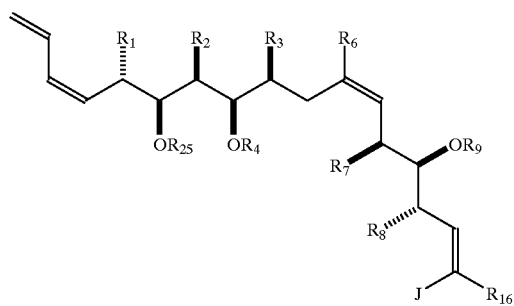

and deprotecting the coupling product to form the alcohol.

5. The process according to claim 3 wherein the alcohol is formed by contacting a compound of formula:

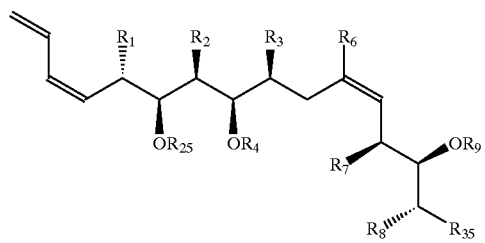

wherein:
$R_{25}$ is an oxidatively labile protecting group;
$R_{35}$ is selected from $CH_2$—$P(=O)Ph_2$, and

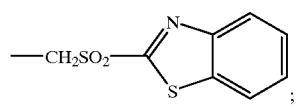

X is a halogen; and
$R_{18}$ is $C_{6-14}$ aryl;

with a compound of formula:

$$J—C(O)R^{16}$$

in the presence of a base to form a coupling product of formula:

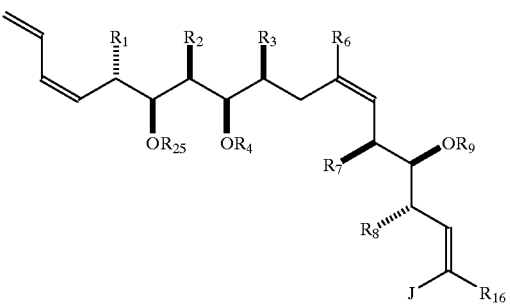

and deprotecting the coupling product to form the alcohol.

6. The process according to claim 3 wherein $R_1$, $R_2$, $R_7$, and $R_8$ are independently $C_1$–$C_4$ alkyl, $R_3$, $R_6$, and $R_{16}$ are independently selected from hydrogen and $C_1$–$C_4$ alkyl, J is:

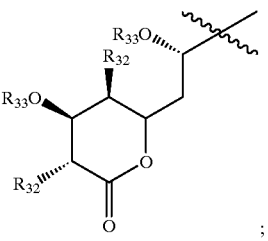

the isocyanate is $Cl_3CC(=O)NCO$, the acid is HCl, and the polar solvent is an alcohol selected from methanol, ethanol, and isopropanol.

7. The process according to claim 4 wherein $R_1$, $R_2$, $R_7$, and $R_8$ are independently $C_1$–$C_4$ alkyl, $R_3$, $R_6$, and $R_{16}$ are independently selected from hydrogen and $C_1$–$C_4$ alkyl, J is:

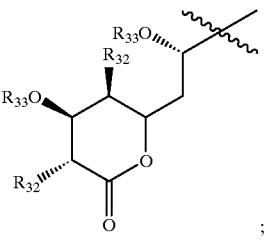

the isocyanate is $Cl_3CC(=O)NCO$, the acid is HCl, and the protic solvent is an alcohol selected from methanol, ethanol, and isopropanol.

8. The process according to claim 5 wherein $R_1$, $R_2$, $R_7$, and $R_8$ are independently $C_1$–$C_4$ alkyl, $R_3$, $R_6$, and $R_{16}$ are independently selected from hydrogen and $C_1$–$C_4$ alkyl, J is:

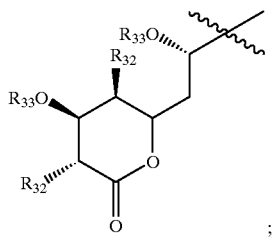

the isocyanate is $Cl_3CC(=O)NCO$, the acid is HCl, and the protic solvent is an alcohol selected from methanol, ethanol, and isopropanol.

9. A compound of formula:

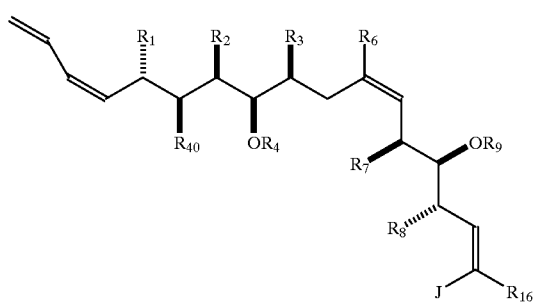

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl;

$R_4$, $R_9$, and $R_{14}$ are acid labile protecting groups;

$R_{40}$ is selected from $OR_{25}$ and $OC(=O)NH_2$;

$R_{25}$ is an oxidatively labile protecting group; and

J is selected from:

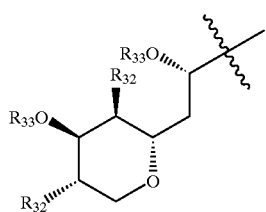

,

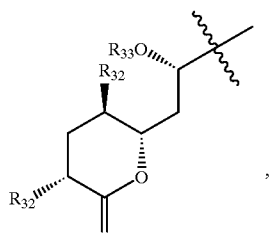

,

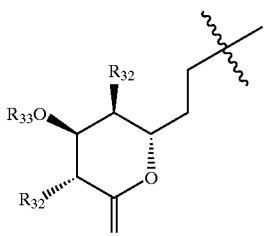

,

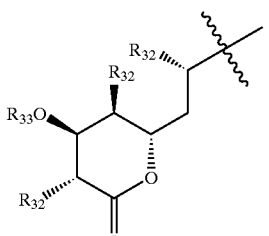

,

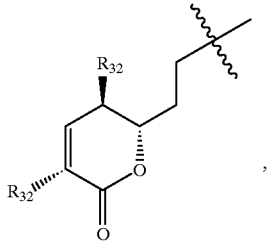

,

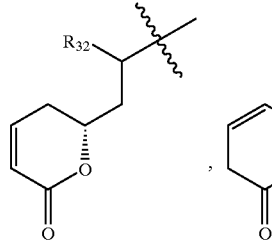

,

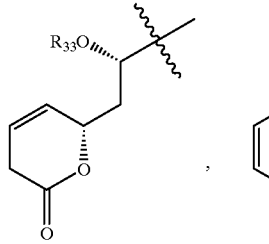

,

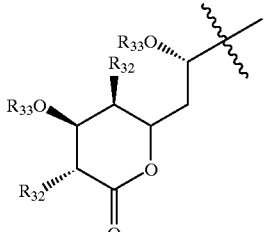

, and

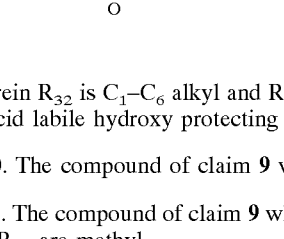

;

wherein $R_{32}$ is $C_1$–$C_6$ alkyl and $R_{33}$ is selected from H and an acid labile hydroxy protecting group.

10. The compound of claim 9 wherein $R_6$ is H.

11. The compound of claim 9 wherein $R_1$, $R_2$, $R_3$, $R_7$, $R_8$, and $R_{32}$ are methyl.

12. A compound having the formula:

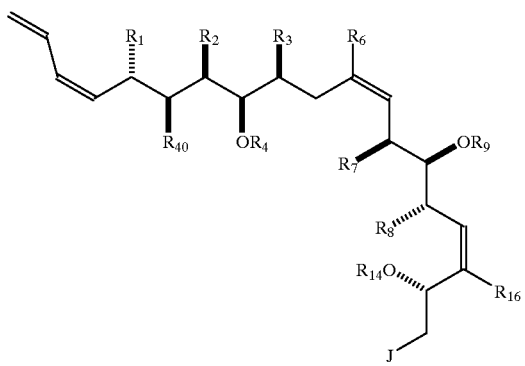

wherein:

$R_1$, $R_2$, $R_7$, and $R_8$ are independently $C_1$–$C_{10}$ alkyl;

$R_3$, $R_6$, and $R_{16}$ are independently selected from hydrogen and $C_1$–$C_6$ alkyl;

$R_4$, $R_9$, and $R_{14}$ are acid labile protecting groups;

$R_{40}$ is selected from $OR_{25}$ and $OC(=O)NH_2$;

$R_{25}$ is an oxidatively labile protecting group; and

J is aryl.

13. The compound of claim 12 wherein $R_6$ is H.

14. The compound of claim 12 wherein J is phenyl.

* * * * *

UNITED STATES PATENT AND TRADEMARK OFFICE
CERTIFICATE OF CORRECTION

PATENT NO.   : 6,242,616 B1
DATED        : June 5, 2001
INVENTOR(S)  : Smith, III et al.

It is certified that error appears in the above-identified patent and that said Letters Patent is hereby corrected as shown below:

Column 59,
Line 27, please delete "4 A" and insert therefore -- 4Å --;

Column 60,
Line 9, please delete "δ204.0" and insert therefore -- δ 204.0 --;

Column 61,
Line 42, please delete "CHC13" and insert therefore -- CHCl$_3$ --;

Column 62,
Line 44, please delete "I2" and insert therefore -- I$_2$ --;

Column 63,
Line 21, please delete "(LAB)" and insert therefore -- Δδ$_{AB}$ --;

Column 66,
Line 52, please delete "A5A" and insert therefore -- Δδ$_{AB}$ --;

Column 70,
Line 54, please delete "A5AB" and insert therefore -- Δδ$_{AB}$ --;

Column 71,
Line 10, please delete "/a=2:1" and insert therefore -- β/α=2:1 --;

Column 72,
Line 61, please delete "1$^3$C" and insert therefore -- $^{13}$C --;

Column 74,
Line 57, please delete "I2" and insert therefore -- I$_2$ --;

Column 77,
Line 34, please delete "-25.30º" and insert therefore -- 25.3º --;

Column 78,
Line 38, please delete "cm⁻;" and insert therefore -- cm$^{-1}$; --;

Column 113,
Line 47, please delete "67" and insert therefore -- δ --;

Column 115,
Line 3, please delete "comibined" and insert therefore -- combined --;

UNITED STATES PATENT AND TRADEMARK OFFICE
CERTIFICATE OF CORRECTION

PATENT NO.    : 6,242,616 B1
DATED         : June 5, 2001
INVENTOR(S)   : Smith, III et al.

It is certified that error appears in the above-identified patent and that said Letters Patent is hereby corrected as shown below:

Column 118,

Line 30, please delete "E" and insert therefore --AE--;

Column 121,

Line 8, please delete "E" and insert therefore --AE--;
Line 35, please delete "Chemselective" and insert therefore -- Chemoselective --;
Line 41, please delete "seperated" and insert therefore -- separated --;

Signed and Sealed this

Twelfth Day of August, 2003

JAMES E. ROGAN
*Director of the United States Patent and Trademark Office*